US012790316B2

(12) United States Patent

Komori et al.

(10) Patent No.: US 12,790,316 B2

(45) Date of Patent: Nov. 10, 2026

(54) 1, 4, 5, 6-TETRAHYDROPYRIMIDINE-2-AMINE DERIVATIVE

(71) Applicant: UBE Corporation, Yamaguchi (JP)

(72) Inventors: Ken-Ichi Komori, Yamaguchi (JP); Haruka Yamada, Yamaguchi (JP); Hayato Shimizu, Yamaguchi (JP); Yasuhiro Aga, Yamaguchi (JP); Ayumi Ogawa, Yamaguchi (JP); Toru Hasegawa, Yamaguchi (JP); Takashi Matsushita, Yamaguchi (JP); Yasunori Tokunaga, Yamaguchi (JP)

(73) Assignee: UBE Corporation, Yamaguchi (JP)

( * ) Notice: Subject to any disclaimer, the term of this patent is extended or adjusted under 35 U.S.C. 154(b) by 737 days.

(21) Appl. No.: 17/924,942

(22) PCT Filed: May 13, 2021

(86) PCT No.: PCT/JP2021/018252

§ 371 (c)(1),
(2) Date: Nov. 11, 2022

(87) PCT Pub. No.: WO2021/230325

PCT Pub. Date: Nov. 18, 2021

(65) Prior Publication Data

US 2023/0192661 A1 Jun. 22, 2023

(30) Foreign Application Priority Data

May 14, 2020 (JP) ................................ 2020-085420

(51) Int. Cl.

*C07D 403/12* (2006.01)
*A61P 19/04* (2006.01)
*C07D 403/14* (2006.01)

(52) U.S. Cl.

CPC ............ *C07D 403/12* (2013.01); *A61P 19/04* (2018.01); *C07D 403/14* (2013.01)

(58) Field of Classification Search

CPC ............................... C07D 403/12; A61P 19/04
See application file for complete search history.

(56) References Cited

U.S. PATENT DOCUMENTS

| | | | |
|---|---|---|---|
| 9,085,606 | B2 | 7/2015 | Ruminski et al. |
| 2002/0094956 | A1 | 7/2002 | Cosgrove |
| 2004/0127477 | A1 | 7/2004 | Chandrakumar et al. |
| 2005/0020505 | A1 | 1/2005 | Rogers et al. |
| 2014/0051715 | A1 | 2/2014 | Ruminski et al. |
| 2018/0072684 | A1 | 3/2018 | Ruminski et al. |

(Continued)

FOREIGN PATENT DOCUMENTS

| | | | |
|---|---|---|---|
| EP | 1079843 | B1 | 4/2007 |
| JP | 2002-511462 | A | 4/2002 |
| JP | 2002-516287 | A | 6/2002 |

(Continued)

OTHER PUBLICATIONS

McMahon et al. (2000).*
Pinedo et a. (2000).*
Office Action dated Jul. 24, 2024 for Russian Application No. 2022132230, filed May 13, 2021.
Hynes, R. O., "Integrins: Bidirectional Allosteric Signaling Machines" Cell (2002) 110(6):673-687.
Finney et al., "Integrin signaling in atherosclerosis" Cellular and Molecular Life Sciences (2017) 74(12), 2263-2282.
Zhou et al., "An integrin antagonist (MK-0429) decreases proteinuria and renal fibrosis in the ZSF 1 rat diabetic nephropathy model" Pharmacology Research and Perspectives (2017) 5(5):e00354.

(Continued)

*Primary Examiner* — Paul V Ward

(74) *Attorney, Agent, or Firm* — Knobbe, Martens, Olson & Bear, LLP

(57) ABSTRACT

Provided is a compound represented by the following general formula (I) or (II) or a pharmaceutically acceptable salt thereof, wherein A is a $C_6$-$C_{10}$ aryl group or a heteroaryl group, wherein at least one hydrogen atom of the aryl group or the heteroaryl group is optionally replaced with a substituent selected from a predetermined group, R is a hydrogen atom or a $C_1$-$C_6$ alkyl group, $R^1$ is a hydrogen atom or a halogen atom, and Y is a hydrogen atom, a fluorine atom or a hydroxy group.

(I)

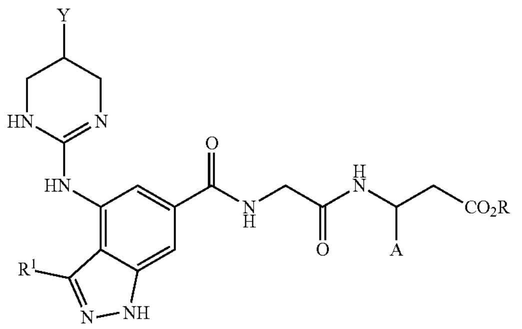

(II)

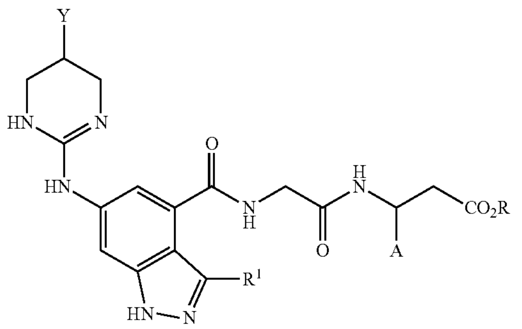

18 Claims, No Drawings

(56) References Cited

U.S. PATENT DOCUMENTS

2023/0192661 A1 6/2023 Komori et al.

FOREIGN PATENT DOCUMENTS

| | | | |
|---|---|---|---|
| JP | 2006-514050 | A | 4/2006 |
| JP | 2015-524412 | A | 8/2015 |
| JP | 2019-500355 | A | 1/2019 |
| RU | 2196769 | C2 | 1/2003 |
| RU | 2215746 | C2 | 11/2003 |
| WO | WO 1997/008145 | A1 | 3/1997 |
| WO | WO 1999/044994 | A1 | 9/1999 |
| WO | WO 1999/052896 | A1 | 10/1999 |
| WO | WO 2000/051686 | A1 | 9/2000 |
| WO | WO 2004/060376 | A1 | 7/2004 |
| WO | WO 2014/015054 | A1 | 1/2014 |
| WO | WO 2017/117538 | A1 | 7/2017 |
| WO | WO 2021/230325 | A1 | 11/2021 |

OTHER PUBLICATIONS

Wang et al., "αv integrins mediate beta-amyloid induced inhibition of long-term potentiation" Neurobiology of Aging (2008) 29(10):1485-1493.
Hatley et al., "An αv-RGD integrin inhibitor toolbox: drug discovery insight challenges and opportunities" Angewandte Chemie International Edition (2018) 57(13):3298-3321.
Felding-Habermann, B., "Integrin adhesion receptors in tumor metastasis" Clinical & Experimental Metastasis (2003) 20:203-213.
Morikawa et al., "TGF-β and the TGF-β family: context-dependent roles in cell and tissue physiology" Cold Spring Harbor Perspectives in Biology (2016) 8(5):a021873.
Munger et al., "Cross talk among TGF-β signaling pathways integrins and the extracellular matrix" Cold Spring Harbor Perspectives in Biology (2011) 3(11):a005017.
Reed et al., "The αvβ1 integrin plays a critical in vivo role in tissue fibrosis" Science Translational Medicine, (2015) 7 (288):288ra79.
Weiskirchen et al. "Organ and tissue fibrosis: Molecular signals, Molecular Aspects of Medicine" (2019) 65:2-15.
Meng et al., "TGF-β: the master regulator of fibrosis" Nature Reviews Nephrology (2016) 12 (6):325-338.
Popov et al., "Integrin αvβ6 is a marker of the progression of biliary and portal liver fibrosis and a novel target for antifibrotic therapies" Journal of Hepatology (2008) 48 (3):453-464.
Ma et al., "Transforming growth factor-β-dependent and-independent pathways of induction of tubulointerstitial fibrosis in β6—/— mice" American Journal of Pathology (2004) 163(4), 1261-1273.
Saini et al., "αvβ6 integrin may be a potential prognostic biomarker in interstitial lung disease" European Respiratory Journal (2015) 46(2):486-494.
Asano et al., "Increased Expression Levels of Integrin αvβ5 on Scleroderma Fibroblasts" American Journal of Pathology (2003) 163(4):1275-1292.
Munger et al., "The Integrin αvβ6 Binds and Activates Latent TGFβ1: A Mechanism for Regulating Pulmonary Inflammation and Fibrosis" Cell, (1999) 96 (3), 319-328.
Henderson et al., "Selective αv integrin depletion identifies a core, targetable molecular pathway that regulates fibrosis across sold organis" Nature Medicine (2013) 19(12):1617-1624.
Murray et al., "αv integrins on mesenchymal cells regulate skeletal and cardiac muscle fibrosis" Nature Communications (2017) 8(1):1118.
Hall et al., "Characterisation of a novel high affinity and selective αvβ6 integrin RGD-mimetic radioligand" Biochemical Pharmacology (2016) 117:88-96.
Office Action dated Mar. 11, 2025 for Russian Application No. 2022132230, filed May 13, 2021.
Office Action dated Aug. 12, 2023 issued for Chinese Application No. 202180034572.X, filed May 13, 2021.
International Search Report mailed Jun. 29, 2021 of PCT/JP2021/018252, filed May 13, 2021 in 3 pages.
Written Opinion mailed Jun. 29, 2021 of PCT/JP2021/018252, filed May 139, 2021 in 4 pages.
Extended European Search Report dated Mar. 25, 2024 for European Patent Application No. 21803967.5, filed May 13, 2021.
Badger et al., "Disease-modifying activity of SB 273005, an orally active, nonpeptide alphavbeta3 (vitronectin receptor) antagonist, in rat adjuvant-induced arthritis" Arthritis Rheum (2001) 44(1):128-37.
Brzozowska et al., "Integrin Alpha v Beta 6 (αvβ6) and Its Implications in Cancer Treatment" Int J Mol Sci. (2022) 15;23(20):12346.
Conroy, et al., "αv integrins: key regulators of tissue fibrosis" Cell Tissue Res. (2016) 365(3):511-519.
Dodagatta-Marri et al., "Integrin αvβ8 on T cells suppresses anti-tumor immunity in multiple models and is a promising target for tumor immunotherapy" Cell Rep. (2021) 36(1):109309.
Duong et al., "Integrins and signaling in osteoclast function" Matrix Biol. (2000) 19(2):97-105.
Engleman et al., "A peptidomimetic antagonist of the alpha(v)beta3 integrin inhibits bone resorption in vitro and prevents osteoporosis in vivo" J Clin Invest. (1997) May 1;99(9):2284-92.
Etich et al., "Signaling pathways affected by mutations causing osteogenesis imperfecta" Cell Signal. (2020) 76:109789.
Filla, et al., "The role of integrins in glaucoma" Exp Eye Res. (2017) 158:124-136.
Garlatti et al., "The Multiple Faces of Integrin-ECM Interactions in Inflammatory Bowel Disease" International Journal of Molecular Sciences (2021) 22(19):10439.
Krauss et al., "Improvement of outcome measures of dry eye by a noel integrin antagonist in the murine desiccating stress model" IOVS (2015) 56(10):5890-5895.
Li et al., "Integrins as attractive targets for cancer therapeutics" Acta Pharm Sin B. (2021) 11(9):2726-2737.
Liu et al., "Integrin alpha(v)beta(3)-Targeted Cancer Therapy" Drug Dev Res. (2008) 69(6):329-339.
Lowin et al., "Integrins and their ligands in rheumatoid arthritis" Arthritis Research & Therapy (2011) 13(5)244:1-8.
Morello, R., "Osteogenesis imperfecta and therapeutics" Matrix Biol. (2018) 71-72:294-312.
Pickarski et al., "Orally active αvβ3 integrin inhibitor MK-0429 reduces melanoma metastasis" Oncol Rep. (2015) J33(6):2737-45.
Seed et al., "A tumor-specific mechanism of $T_{reg}$ enrichment mediated by the integrin αvβ8" Sci Immunol. (2021) 6(57):eabf0558.
Song et al., "Targeting TGF-β for treatment of osteogenesis imperfecta" J Clin Invest. (2022) 132(7):e152571.
Sui, et al., "Inhibition of integrin α5β1 ameliorates VEGF-induced retinal neovascularization and leakage by suppressing NLRP3 inflammasome signaling in a mouse model" Graefe's Archive for Clinical and Experimental Ophthalmology (2018) 256:951-961.
Sun et al., "Irisin reduces bone fracture by facilitating osteogenesis and antagonizing TGF-β/Smad signaling in a growing mouse model of osteogenesis imperfecta" J Orthop Translat. (2022) 15;38:175-189.
Van Hove et al., "Targeting RGD-binding integrins as an integrative therapy for diabetic retinopathy and neovascular age-related macular degeneration" Prog Retin Eye Res. (2021) 85:100966.
Wang et al., "Alpha v integrins mediate beta-amyloid induced inhibition of long-term potentiation" Neurobiol Aging. (2008) 29(10):1485-93.
Office Action dated Sep. 12, 2025 for Mexican Application No. MX/a/2022/014200, filed May 13, 2021 in 6 pages.
Hahm et al., "αvβ6 Integrin Regulates Renal Fibrosis and Inflammation in Alport Mouse" The American Journal of Pathology (2007) 170(1):110-125.
The Japanese Society for Pediatric Nephrology, "Clinical Practice Guideline for Alport Syndrome" (2017).
International Search Report mailed Jan. 10, 2023 of PCT/JP2022/042070, filed Nov. 11, 2022 in 5 pages.
Written Opinion mailed Jan. 10, 2023 of PCT/JP2022/042070, filed Nov. 11, 2022 in 8 pages.
Extended European Search Report dated Sep. 10, 2025 for EP Application No. 22892894.1, filed Nov. 11, 2022 in 4 pages.
Canadian Office Action dated Jan. 26, 2026 issued to the Canadian Patent Application No. 3,182,964, filed May 13, 2021, in 7 pages.

(56) References Cited

OTHER PUBLICATIONS

Batt, et al., "Disubstituted Indazoles as Potent Antagonists of the Integrin $\alpha_v\beta_3$" J. Med. Chem (2000) 43:41-58.
Office Action dated Jan. 26, 2026 for Canadian Patent Application No. 3,182,964, filed May 13, 2021, in 7 pages.
Office Action dated Mar. 3, 2026 for Indian Patent Application No. 202217070110, filed May 13, 2021 in 9 pages.
Office Action dated May 5, 2026 for U.S. Appl. No. 18/709,010, filed May 9, 2024, in 10 pages.
Office Action dated Mar. 12, 2026 for Korean Patent Application No. 10-2022-7042726, filed Dec. 6, 2022, in 8 pages.
Office Action dated Mar. 16, 2026 for Australian Patent Application No. 2021270095, filed May 13, 2021, in 4 pages.
Hearing Notice dated Jun. 5, 2026 for Indian Patent Application No. 202217070110, filed Apr. 12, 2022, in 2 pages.
Office Action dated Jun. 12, 2026 for European Patent Application No. 22892894.1, filed May 24, 2024, in 5 pages.

* cited by examiner

1, 4, 5, 6-TETRAHYDROPYRIMIDINE-2-AMINE DERIVATIVE

This application is a national phase application under 35 U.S.C. § 371 of PCT Application No. PCT/JP2021/018252, filed May 13, 2021, which claims priority to JP Application No. 2020-085420, filed May 14, 2020, each of which are incorporated by reference in their entireties.

TECHNICAL FIELD

The present invention relates to a 1,4,5,6-tetrahydropyrimidin-2-amine derivative and a pharmaceutical composition containing the same and particularly relates to a 1,4,5,6-tetrahydropyrimidin-2-amine derivative for the prevention, alleviation and/or remedy of a disease related to integrin αv and a pharmaceutical composition containing the same.

BACKGROUND ART

In recent years, integrins have received attention in terms of possessing cell adhesion or intracellular signal transduction functions in response to extracellular matrix information. The integrins are proteins that are expressed on cell surface, and are composed of a heterodimer of two subunits α and β chains. 24 integrins form some subfamilies by combinations of 18 α chains and 8 β chains. RGD integrin, one of the major subfamilies, recognizes a ligand containing a RGD (arginine-glycine-aspartic acid) motif in a protein sequence. The RGD integrin includes 8 subtypes αvβ1, αvβ3, αvβ5, αvβ6, αvβ8, αIIbβ3, α5β1, and α8β1 (Non Patent Literature 1).

Integrin αv is known to participate in various diseases, and its inhibition is expected to have a therapeutic effect on, for example, cardiovascular disease, diabetic disease, neurodegenerative disease, cancer disease, tumor metastasis, eye disease, autoimmune disease, bone disease, and various fibroses (Non Patent Literatures 2 to 6).

Transforming growth factor β (TGF-β) is known to control cell proliferation, differentiation, or the like and to participate in diseases such as fibrosis, autoimmune disease, and cancer, and is secreted as an inactive complex with latency-associated protein (LAP) (Non Patent Literature 7). In research using cell, it has been reported that RGD integrin such as integrin αvβ1, αvβ3, αvβ5, αvβ6 and αvβ8 activates latent TGF-β (Non Patent Literatures 8 and 9).

Fibrosis, a pathological feature of many diseases, is caused by the dysfunction of body's original ability to repair injured tissues. Fibrosis brings about excessive scarring that surpasses the wound healing response of an important organ, and might cause unrecoverable injury and final organ failure (Non Patent Literature 10). In fibrosis, extracellular matrix is mainly produced by activated fibroblasts (myofibroblasts), and TGF-β is known to participate in the activation of the fibroblasts (Non Patent Literature 11).

The expression of integrins also participates in fibrosis. For example, the expression level of integrin β5 or β6 markedly increases after tissue injury and plays an important in vivo role in tissue fibrosis (Non Patent Literatures 12 and 13). The increased expression level of integrin β6 is also related to increase in the death rate of fibrosis patients (Non Patent Literature 14).

The inhibition of integrins is known to exhibit resistance to various fibroses. For example, integrin β6-knockout mice inhibit the activation of TGF-β and exhibit resistance to various fibroses (Non Patent Literatures 15 and 16). It has also been reported that fibroblast-specific deficiency in integrin αv similarly exhibits resistance to various fibroses (Non Patent Literatures 17 and 18).

For example, pirfenidone and nintedanib for idiopathic pulmonary fibrosis (IPF) are used as therapeutic drugs for fibrosis. However, any safe and established therapeutic drug for various organ fibroses has not yet been found. Thus, there is a demand for a therapeutic drug for fibrosis that is effective for various organs with reduced adverse reactions.

Research has been made so far on integrins involved in the functional control of various cells or their inhibitors (Patent Literatures 1 to 8 and Non Patent Literature 19).

CITATION LIST

Patent Literature

Patent Literature 1: WO 1997/008145
Patent Literature 2: WO 1999/044994
Patent Literature 3: WO 1999/052896
Patent Literature 4: WO 2000/051686
Patent Literature 5: WO 2004/060376
Patent Literature 6: WO 2014/015054
Patent Literature 7: US 2014/0051715
Patent Literature 8: WO 2017/117538

Non Patent Literature

Non Patent Literature 1: Cell, 2002, 110 (6), 673-687
Non Patent Literature 2: Cellular and Molecular Life Sciences, 2017, 74 (12), 2263-2282
Non Patent Literature 3: Pharmacology Research and Perspectives, 2017, 5 (5), e00354
Non Patent Literature 4: Neurobiology of Aging, 2008, 29 (10), 1485-1493
Non Patent Literature 5: Angewandte Chemie International Edition in English, 2018, 57 (13), 3298-3321
Non Patent Literature 6: Clinical & Experimental Metastasis, 2003, 20, 203-213
Non Patent Literature 7: Cold Spring Harbor Perspectives in Biology, 2016, 8 (5), a021873
Non Patent Literature 8: Cold Spring Harbor Perspectives in Biology, 2011, 3 (11), a005017
Non Patent Literature 9: Science Translational Medicine, 2015, 7 (288), 288ra79
Non Patent Literature 10: Molecular Aspects of Medicine, 2019, 65, 2-15
Non Patent Literature 11: Nature Reviews Nephrology, 2016, 12 (6), 325-338
Non Patent Literature 12: Journal of Hepatology, 2008, 48 (3), 453-464
Non Patent Literature 13: The American Journal of Pathology, 2004, 164 (4), 1275-1292
Non Patent Literature 14: European Respiratory Journal, 2015, 46 (2), 486-494
Non Patent Literature 15: The American Journal of Pathology, 2003, 163 (4), 1261-1273
Non Patent Literature 16: Cell, 1999, 96 (3), 319-328
Non Patent Literature 17: Nature Medicine, 2013, 19 (12), 1617-1624
Non Patent Literature 18: Nature Communications, 2017, 8 (1), 1118
Non Patent Literature 19: Biochemical Pharmacology, 2016, 117, 88-96

SUMMARY OF INVENTION

Technical Problem

The present invention relates to the provision of a novel compound useful in the prevention, alleviation and/or remedy of a disease related to integrin αv and a pharmaceutical composition containing the same.

Solution to Problem

The present inventors have conducted diligent studies on compounds having integrin αv inhibitory activity and consequently found that a series of 1,4,5,6-tetrahydropyrimidin-2-amine derivatives having an intramolecular indazole structure, or pharmaceutically acceptable salts thereof have excellent integrin αv (αvβ1, αvβ6, etc.) inhibitory activity, excellent pharmacokinetic characteristics or excellent safety. The 1,4,5,6-tetrahydropyrimidin-2-amine derivative according to the present invention or a pharmaceutically acceptable salt thereof can be useful in the prevention, alleviation and/or remedy of a disease related to integrin αv, preferably the prevention, alleviation and/or remedy of fibrosis.

Specifically, the present invention is as follows.

[1] A compound represented by the following general formula (I) or (II) or a pharmaceutically acceptable salt thereof:

(I)

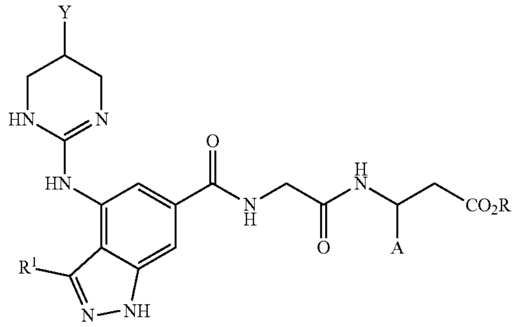

(II)

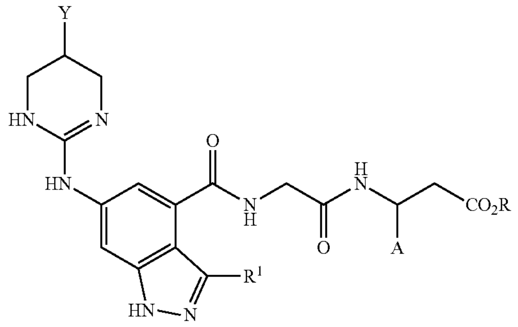

wherein

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

[2] A compound represented by the following general formula (I) or a pharmaceutically acceptable salt thereof:

(I)

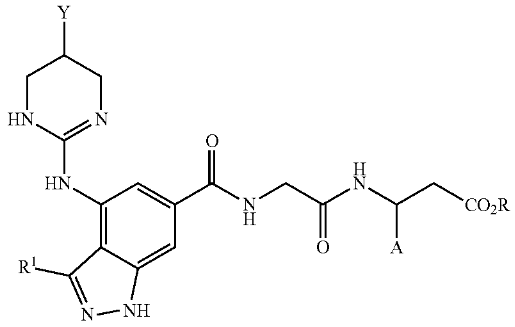

wherein

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

[3] A compound represented by the following general formula (II) or a pharmaceutically acceptable salt thereof:

(II)

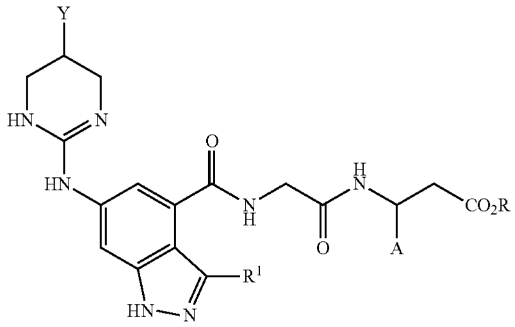

wherein

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

[4] The compound according to any one of [1] to [3] or a pharmaceutically acceptable salt thereof, wherein A is a phenyl group, wherein at least one hydrogen atom of the phenyl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group.

[5] The compound according to any one of [1] to [4] or a pharmaceutically acceptable salt thereof, wherein A is a phenyl group, wherein at least one hydrogen atom of the phenyl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group.

[6] The compound according to any one of [1] to [5] or a pharmaceutically acceptable salt thereof, wherein A is a phenyl group, wherein at least one hydrogen atom of the phenyl group is optionally replaced with a substituent selected from the group consisting of a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, and a heteroaryl group optionally substituted by a $C_1$-$C_6$ alkyl group.

[7] The compound according to any one of [1] to [6] or a pharmaceutically acceptable salt thereof, wherein Y is a fluorine atom.

[8] The compound according to any one of [1] to [7] or a pharmaceutically acceptable salt thereof, wherein A is a group represented by the following formula (i):

(i)

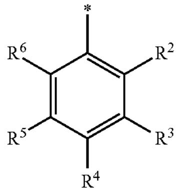

wherein $R^2$ is a hydrogen atom or a halogen atom, $R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group, $R^4$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group, $R^5$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group, and $R^6$ is a hydrogen atom or a halogen atom.

[9] The compound according to [8] or a pharmaceutically acceptable salt thereof, wherein $R^2$ is a hydrogen atom, $R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group, $R^4$ is a hydrogen atom or a halogen atom, $R^5$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group, and $R^6$ is a hydrogen atom or a halogen atom.

[10] The compound according to [1] or a pharmaceutically acceptable salt thereof, wherein the compound is selected from the group consisting of (3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(3-iodo-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-methyl-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-methoxy-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-fluoro-5-(trifluoromethyl)phenyl)propanoic acid, (3S)-3-(3,5-bis(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(1H-pyrazol-1-yl)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-3-(trifluoromethyl)phenyl)propanoic acid, (3S)-3-(2-chloro-3-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethyl)phenyl)propanoic acid, (3S)-3-(2-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(4-methyl-3-(trifluoromethyl)phenyl)propanoic acid, (3S)-3-(3-chloro-4-fluoro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-4-methoxyphenyl)-3-(2-(4-((5-fluoro-1,4,5,6-tetrahydropyrimidin-2-yl)amino)-1H-indazole-6-carboxamido)acetamido)propanoic acid, (3S)-3-(3,5-dichlorophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-chlorophenyl)-3-(2-(4-((5-fluoro-1,4,5,6-tetrahydropyrimidin-2-yl)amino)-1H-indazole-6-carboxamido)acetamido)propanoic acid, (3S)-3-(3,5-dibromophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-iodophenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-iodophenyl)-3-(2-(4-((5-fluoro-1,4,5,6-tetrahydropyrimidin-2-yl)amino)-1H-indazole-6-carboxamido)acetamido)propanoic acid, (3S)-3-(5-chloro-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(5-bromo-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-4-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(5-(difluoromethoxy)-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-5-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(3,5-bis(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethoxy)phenyl)propanoic acid, (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethoxy)phenyl)propanoic acid, (3S)-3-(2-(4-((5-fluoro-1,4,5,6-tetrahydropyrimidin-2-yl)amino)-1H-indazole-6-carboxamido)acetamido)-3-(3-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-(trifluoromethoxy)phenyl)propanoic acid, (3S)-3-(3-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-cyclopropylphenyl)-3-(2-(4-((5-fluoro-1,4,5,6-tetrahydropyrimidin-2-yl)amino)-1H-indazole-6-carboxamido)acetamido)propanoic acid, (3S)-3-(3-cyclopropoxyphenyl)-3-(2-(4-((5-fluoro-1,4,5,6-tetrahydropyrimidin-2-yl)amino)-1H-indazole-6-carboxamido)acetamido)propanoic acid, (3S)-3-(3-chlorophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromophenyl)-3-(2-(4-((5-fluoro-1,4,5,6-tetrahydropyrimidin-2-yl)amino)-1H-indazole-6-carboxamido)acetamido)propanoic acid, (3S)-3-(3-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(3,5-dimethyl-1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(3-morpholinophenyl)propanoic acid, (3S)-3-(4-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(4-(trifluoromethyl)phenyl)propanoic acid, (3S)-3-(3-chloro-5-(trifluoromethyl)phenyl)-3-(2-(3-fluoro-4-((5-fluoro-1,4,5,6-tetrahydropyrimidin-2-yl)amino)-1H-indazole-6-carboxamido)acetamido)propanoic acid, (3S)-3-(2-(3-chloro-4-((5-fluoro-1,4,5,6-tetrahydropyrimidin-2-yl)amino)-1H-indazole-6-carboxamido)acetamido)-3-(3-chloro-5-(trifluoromethyl)phenyl)propanoic acid, (3S)-3-(3-chloro-5-(trifluoromethyl)phenyl)-3-(2-(4-((5-hydroxy-1,4,5,6-tetrahydropyrimidin-2-yl)amino)-1H-indazole-6-carboxamido)acetamido)propanoic acid, (S)-3-(3-chloro-5-(trifluoromethyl)phenyl)-3-(2-(4-((1,4,5,6-tetrahydropyrimidin-2-yl)amino)-1H-indazole-6-carboxamido)acetamido)propanoic acid, (3S)-3-(3-chloro-5-(trifluoromethyl)phenyl)-3-(2-(6-((5-fluoro-1,4,5,6-tetrahydropyrimidin-2-yl)amino)-1H-indazole-4-carboxamido)acetamido)propanoic acid, (3S)-3-(3-bromo-5-(trifluoromethyl)phenyl)-3-(2-(6-((5-fluoro-1,4,5,6-tetrahydropyrimidin-2-yl)amino)-1H-indazole-4-carboxamido)acetamido)propanoic acid, (3S)-3-(2-(6-((5-fluoro-1,4,5,6-tetrahydropyrimidin-2-yl)amino)-1H-indazole-4-carboxamido)acetamido)-3-(3-iodo-5-(trifluoromethyl)phenyl)propanoic acid, (3S)-3-(2-(6-((5-fluoro-1,4,5,6-tetrahydropyrimidin-2-yl)amino)-1H-indazole-4-carboxamido)acetamido)-3-(4-fluoro-3-(trifluoromethyl)phenyl)propanoic acid, and (3S)-3-(2-(6-((5-fluoro-1,4,5,6-tetrahydropyrimidin-2-yl)amino)-1H-indazole-4-carboxamido)acetamido)-3-(3-(trifluoromethyl)phenyl)propanoic acid.

In another embodiment, the present invention relates to a pharmaceutical composition comprising a compound according to any one of [1] to [10] or a pharmaceutically acceptable salt thereof, and in an embodiment of the pharmaceutical composition, relates to a pharmaceutical composition for preventing, alleviating and/or treating a disease related to integrin αv or a disease that is improved by inhibiting integrin αv, or a pharmaceutical composition for treating fibrosis.

In an alternative embodiment, the present invention relates to a pharmaceutical composition, more preferably a pharmaceutical composition for the treatment of fibrosis, i.e., the prevention, alleviation and/or remedy of fibrosis, comprising a compound according to any one of [1] to [10] or a pharmaceutically acceptable salt thereof.

In an alternative embodiment, the present invention relates to a method for the treatment of a disease related to integrin αv or a disease that is improved by inhibiting integrin αv, for example, fibrosis, comprising administering a compound according to any one of [1] to [10] or a pharmaceutically acceptable salt thereof to a subject.

In an alternative embodiment, the present invention relates to use of a compound according to any one of [1] to [10] or a pharmaceutically acceptable salt thereof in the treatment of a disease related to integrin αv or a disease that is improved by inhibiting integrin αv, for example, fibrosis.

In an alternative embodiment, the present invention relates to the compound according to any one of [1] to [10] or a pharmaceutically acceptable salt thereof for use in the treatment of a disease related to integrin αv or a disease that is improved by inhibiting integrin αv, for example, fibrosis.

In an alternative embodiment, the present invention relates to use of a compound according to any one of [1] to [10] or a pharmaceutically acceptable salt thereof in the production of a medicament for the treatment of a disease related to integrin αv or a disease that is improved by inhibiting integrin αv, for example, fibrosis.

In an alternative embodiment, the present invention relates to an intermediate of a compound according to any one of [1] to [10] or a pharmaceutically acceptable salt thereof.

In an alternative embodiment, the present invention relates to a method for producing a compound according to any one of [1] to [10] or a pharmaceutically acceptable salt thereof.

Advantageous Effects of Invention

The present invention provides a novel compound and a method for synthesizing the compound. Another aspect of the present invention provides a pharmaceutical composition for the prevention, alleviation and/or remedy of a disease related to at least any integrin αv (e.g., fibrosis), comprising the compound, the compound for preventing, alleviating and/or treating the disease, or a method for preventing, alleviating and/or treating the disease with the compound. An alternative aspect of the present invention provides a novel intermediate for synthesizing the compound.

DESCRIPTION OF EMBODIMENTS

Definition

In the present specification, various substituents are as follows.

The "$C_6$-$C_{10}$ aryl group" means a monocyclic or dicyclic monovalent aromatic hydrocarbon group having 6 to 10 ring-forming carbon atoms. Examples of the aryl group include phenyl and naphthyl.

The "heteroaryl group" means a monovalent aromatic heterocyclic group containing at least one heteroatom selected from a nitrogen atom, an oxygen atom and a sulfur atom and is preferably a monovalent aromatic heterocyclic group having 5 to 10 ring-forming atoms. Examples of the heteroaryl group include: monocyclic heteroaryl groups such as pyrrolyl, furyl, thienyl, pyrazolyl, imidazolyl, oxazolyl, isoxazolyl, thiazolyl, isothiazolyl, triazolyl, oxadiazolyl, thiadiazolyl, tetrazolyl, pyranyl, pyridyl, pyridazinyl, pyrimidinyl, and pyrazinyl; and dicyclic heteroaryl groups such as indolyl, indazolyl, benzotriazolyl, benzofuranyl, benzimidazolyl, benzothiophenyl, benzisoxazolyl, benzopyranyl, benzothienyl, quinolyl, and isoquinolyl.

The "halogen" or the "halo" means a halogen atom. Examples thereof include a fluorine atom (fluoro), a chlorine atom (chloro), a bromine atom (bromo) and an iodine atom (iodo).

The "$C_1$-$C_6$ alkyl group" means an alkyl group having 1 to 6 carbon atoms, and the alkyl group may be a linear alkyl group or may be a branched alkyl group. Examples of the alkyl group include methyl, ethyl, n-propyl, isopropyl, n-butyl, isobutyl, sec-butyl, tert-butyl, n-pentyl, isopentyl, neopentyl, tert-pentyl, n-hexyl, isohexyl, neohexyl, and tert-hexyl. The alkyl group may be a $C_1$-$C_4$ alkyl group.

The "$C_1$-$C_6$ haloalkyl group" means a group in which at least one hydrogen of the "$C_1$-$C_6$ alkyl group" is replaced with a halogen atom. The haloalkyl group may be a linear haloalkyl group or may be a branched haloalkyl group. Examples of the haloalkyl group include fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 2-fluoroethyl, 2-chloroethyl, 2-bromoethyl, 2-iodoethyl, 2,2-difluoroethyl, 2,2-dichloroethyl, 2,2-dibromoethyl, 2,2-diiodoethyl, 2,2,2-trifluoroethyl, 2,2,2-trichloroethyl, 2,2,2-tribromoethyl, 2,2,2-triiodoethyl, 3-fluoropropyl, 3-chloropropyl, 3-bromopropyl, 3-iodopropyl, 4-fluorobutyl, 4-chlorobutyl, 4-bromobutyl, 4-iodobutyl, 5-fluoropentyl, 5-chloropentyl, 5-bromopentyl, 5-iodopentyl, 6-fluorohexyl, 6-chlorohexyl, 6-bromohexyl, and 6-iodohexyl. The haloalkyl group may be a $C_1$-$C_4$ haloalkyl group.

The "$C_2$-$C_6$ alkenyl group" means an alkenyl group having 2 to 6 carbon atoms, and the alkenyl group may be a linear alkenyl group or may be a branched alkenyl group. Examples of the alkenyl group include vinyl, allyl, 1-propenyl, 2-propenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-2-butenyl, 3-methyl-1-butenyl, 1-hexenyl, 2-hexenyl, 3-hexenyl, 4-hexenyl, 5-hexenyl, 1-methyl-2-pentenyl, and 3-methyl-1-pentenyl. The alkenyl group may be a $C_2$-$C_4$ alkenyl group.

The "$C_2$-$C_6$ alkynyl group" means an alkynyl group having 2 to 6 carbon atoms, and the alkynyl group may be a linear alkynyl group or may be a branched alkynyl group. Examples of the alkynyl group include ethynyl, 1-propynyl, 2-propynyl, 1-butynyl, 2-butynyl, 3-butynyl, 1-methyl-2-propynyl, 1,1-dimethyl-2-propynyl, 1-pentynyl, 2-pentynyl, 3-pentynyl, 4-pentynyl, 1-methyl-2-butynyl, 3-methyl-1-butynyl, 1-hexynyl, 2-hexynyl, 3-hexynyl, 4-hexynyl, 5-hexynyl, 1-methyl-2-pentynyl, and 3-methyl-1-pentynyl. The alkynyl group may be a $C_2$-$C_4$ alkynyl group.

The "$C_1$-$C_6$ alkoxy group" means a group in which the "$C_1$-$C_6$ alkyl group" is bonded via an oxygen atom. The alkoxy group may be a linear alkoxy group or may be a branched alkoxy group. Examples of the alkoxy group include methoxy, ethoxy, n-propoxy, isopropoxy, n-butoxy, isobutoxy, sec-butoxy, tert-butoxy, n-pentoxy, isopentoxy, neopentoxy, tert-pentoxy, n-hexoxy, isohexoxy, neohexoxy, and tert-hexoxy. The alkoxy group may be a $C_1$-$C_4$ alkoxy group.

The "$C_1$-$C_6$ haloalkoxy group" means a group in which at least one hydrogen of the "$C_1$-$C_6$ alkoxy group" is replaced with a halogen atom. The haloalkoxy group may be a linear haloalkoxy group or may be a branched haloalkoxy group. Examples of the haloalkoxy group include fluoromethoxy, chloromethoxy, bromomethoxy, iodomethoxy, difluoromethoxy, dichloromethoxy, dibromomethoxy, diiodomethoxy, trifluoromethoxy, trichloromethoxy, tribromomethoxy, triiodomethoxy, 2-fluoroethoxy, 2-chloroethoxy, 2-bromoethoxy, 2-iodoethoxy, 2,2-difluoroethoxy, 2,2-dichloroethoxy, 2,2-dibromoethoxy, 2,2-diiodoethoxy, 2,2,2-trifluoroethoxy, 2,2,2-trichloroethoxy, 2,2,2-tribromoethoxy, 2,2,2-triiodoethoxy, 3-fluoropropoxy, 3-chloropropoxy, 3-bromopropoxy, 3-iodopropoxy, 4-fluorobutoxy, 4-chlorobutoxy, 4-bromobutoxy, 4-iodobutoxy, 5-fluoropentoxy, 5-chloropentoxy, 5-bromopentoxy, 5-iodopentoxy, 6-fluorohexoxy, 6-chlorohexoxy, 6-bromohexoxy, and 6-iodohexoxy. The haloalkoxy group may be a $C_1$-$C_4$ haloalkoxy group.

The "$C_3$-$C_6$ cycloalkyl group" means an alicyclic saturated hydrocarbon group having 3 to 6 ring-forming carbon atoms. Examples of the cycloalkyl group include cyclopropyl, cyclobutyl, cyclopentyl, and cyclohexyl.

The "$C_3$-$C_6$ cycloalkenyl group" means an alicyclic unsaturated hydrocarbon group having 3 to 6 ring-forming carbon atoms and having at least one carbon-carbon double bond in the ring. Examples of the cycloalkenyl group include cyclopropenyl, cyclobutenyl, cyclopentenyl, and cyclohexenyl (2-cyclohexenyl and 3-cyclohexenyl).

The "$C_3$-$C_6$ cycloalkoxy group" means a group in which the "$C_3$-$C_6$ cycloalkyl group" is bonded via an oxygen atom. Examples of the cycloalkoxy group include cyclopropoxy, cyclobutoxy, cyclopentoxy, and cyclohexoxy.

The "heterocyclyl group" means a saturated monovalent heterocyclic group or a nonaromatic unsaturated monovalent heterocyclic group containing at least one heteroatom selected from a nitrogen atom, an oxygen atom and a sulfur atom, and is preferably a saturated monovalent heterocyclic group having 5 to 10 ring-forming atoms. Examples of the heterocyclyl group include azetidinyl, oxetanyl, thietanyl, pyrrolidinyl, piperidinyl, tetrahydrofuryl, tetrahydropyranyl, tetrahydrothienyl (i.e., thiolanyl), piperazinyl, and morpholinyl.

The "$C_1$-$C_6$ alkoxycarbonyl group" means a group in which the "$C_1$-$C_6$ alkoxy group" is bonded via a carbonyl group. The alkoxycarbonyl group may be a linear alkoxycarbonyl group or may be a branched alkoxycarbonyl group. Examples of the alkoxycarbonyl group include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentoxycarbonyl, isopentoxycarbonyl, neopentoxycarbonyl, tert-pentoxycarbonyl, n-hexoxycarbonyl, isohexoxycarbonyl, neohexoxycarbonyl, and tert-hexoxycarbonyl. The alkoxycarbonyl group may be a $C_1$-$C_4$ alkoxycarbonyl group.

The "$C_1$-$C_6$ alkylsulfanyl group" means a group in which the "$C_1$-$C_6$ alkyl group" is bonded via a sulfur atom. The alkylsulfanyl group may be a linear alkylsulfanyl group or may be a branched alkylsulfanyl group. Examples of the alkylsulfanyl group include methylsulfanyl, ethylsulfanyl, n-propylsulfanyl, isopropylsulfanyl, n-butylsulfanyl, isobutylsulfanyl, sec-butylsulfanyl, tert-butylsulfanyl, n-pentylsulfanyl, isopentylsulfanyl, neopentylsulfanyl, tert-pentylsulfanyl, n-hexylsulfanyl, isohexylsulfanyl, neohexylsulfanyl, and tert-hexylsulfanyl. The alkylsulfanyl group may be a $C_1$-$C_4$ alkylsulfanyl group.

The "$C_1$-$C_6$ alkylsulfonyl group" means a group in which the "$C_1$-$C_6$ alkyl group" is bonded via a sulfonyl group. The alkylsulfonyl group may be a linear alkylsulfonyl group or may be a branched alkylsulfonyl group. Examples of the alkylsulfonyl group include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, neohexylsulfonyl, and tert-hexylsulfonyl. The alkylsulfonyl group may be a $C_1$-$C_4$ alkylsulfonyl group.

In the present specification, the "pharmaceutically acceptable salt" includes a pharmaceutically acceptable acid-addition salt and a salt with a pharmaceutically acceptable acid (hereinafter, these are also collectively referred to as an "acid-addition salt, etc."), and a pharmaceutically acceptable base-addition salt and a salt with a pharmaceutically acceptable base (hereinafter, these are also collectively referred to as a "base-addition salt, etc.").

In the present specification, examples of the "acid-addition salt" or the "salt with an acid" (acid-addition salt, etc.) include hydrochloride, hydrobromide, sulfate, nitrate, phosphate, acetate, oxalate, malonate, fumarate, maleate, phthalate, trifluoroacetate, methanesulfonate, benzenesulfonate, p-toluenesulfonate, 2,4-dimethylbenzenesulfonate, 2,4,6-trimethylbenzenesulfonate, 4-ethylbenzenesulfonate, and naphthalenesulfonate.

In the present specification, the "base-addition salt" or the "salt with a base" (base-addition salt, etc.) includes, for example, a metal salt, an inorganic amine salt, an organic amine salt, and an amino acid salt. The metal salt may be, for example, an alkali metal salt such as sodium salt, potassium salt, or lithium salt; an alkaline earth metal salt such as calcium salt or magnesium salt; aluminum salt; iron salt; zinc salt; copper salt; nickel salt; or cobalt salt. The inorganic amine salt may be, for example, ammonium salt. The organic amine salt may be, for example, morpholine salt, glucosamine salt, ethylenediamine salt, guanidine salt, diethylamine salt, triethylamine salt, dicyclohexylamine salt, diethanolamine salt, piperazine salt, or tetramethylammonium salt. Examples of the amino acid salt include glycine salt, lysine salt, arginine salt, ornithine salt, glutamate, and aspartate.

In the present specification, the "disease related to integrin αv" is a disease involving integrin αv and is not particularly limited as long as its symptom is alleviated, improved, suppressed, or prevented by inhibiting integrin αv. Integrins are heterodimers composed of α and β chains. The integrin αv is an α chain. Integrins comprising integrin αv include integrins αvβ1, αvβ3, αvβ5, αvβ6 and αvβ8. The "disease related to integrin αv" may include a disease related to integrin αvβ1, αvβ3, αvβ5, αvβ6 or αvβ8 because these integrins comprise integrin αv. The "disease related to integrin αv" includes, for example, a "disease related to integrin αvβ1" or a "disease related to integrin αvβ6".

Examples of the disease related to integrin αv include inflammatory disease, fibrosis, cancer, neurodegenerative disease, eye disease, osteoporosis, and osteogenesis imperfecta. The inhibition of integrin αv includes decrease in the degree of signals mediated by integrin αv, as compared with a control, or decrease in the ability of integrin αv to bind to a ligand, as compared with a control.

In the present specification, the "inflammatory disease" refers to a disease, disorder, or a condition related to inflammation. Examples thereof include, but are not limited to, arthritis, rheumatoid arthritis, Crohn disease, irritable bowel disease, inflammatory bowel disease (IBD), systemic erythematosus, gum disease, psoriasis, acute hepatitis, chronic hepatitis, Alport's syndrome, inflammation caused by diabetes mellitus, joint arterial inflammation, large-cell arterial inflammation, Kawasaki disease, Takayasu arteritis, Churg-Strauss syndrome and Henoch-Schonlein purpura.

In the present specification, examples of the "fibrosis" include, but are not particularly limited to, fibroses in the lung, the liver, the kidney, the heart, vascular vessels, the skin, the pancreas, the bone marrow, and other organs or tissues. In the present invention, the fibrosis is preferably pulmonary fibrosis, hepatic fibrosis, renal fibrosis, cardiac fibrosis, vascular fibrosis, dermatofibrosis, pancreatic fibrosis, myelofibrosis or skeletal myofibrosis, more preferably pulmonary fibrosis, hepatic fibrosis, renal fibrosis or cardiac fibrosis.

The pulmonary fibrosis includes idiopathic pulmonary fibrosis (IPF), non-specific interstitial pneumonia (NSIP), cryptogenic organizing pneumonia (COP), acute interstitial pneumonia (AIP), interstitial lung disease, peribronchiolar fibrosis, peripheral airway disease (e.g., bronchiolitis obliterans), pulmonary emphysema, acute respiratory distress syndrome (ARDS), acute lung injury (ALI), postinfectious pulmonary fibrosis, drug-induced pulmonary fibrosis, airway fibrosis, diffuse alveolar damage, collagen-vascular disease-related pulmonary fibrosis, silicosis, radiation-induced fibrosis, bleomycin-induced fibrosis, influenza-induced fibrosis, asbestos-induced pulmonary fibrosis, desquamative interstitial pneumonia and chronic hypersensitivity pneumonitis.

The hepatic fibrosis includes primary biliary cholangitis (PBC), primary sclerosing cholangitis (PSC), infectious hepatic fibrosis (caused by HCV or a parasite such as blood fluke), alcoholic steatohepatitis (ASH), non-alcoholic fatty liver disease (NAFLD), non-alcoholic steatohepatitis (NASH), liver cirrhosis caused by every etiology, congenital hepatic fibrosis, Sjogren's syndrome, sarcoidosis, Wilson's disease, Gaucher's disease, hemochromatosis, and α1-antitrypsin deficiency.

The renal fibrosis includes chronic kidney disease (CKD), glomerulonephritis (GN) of every etiology, mesangial proliferative GN, immune GN, crescentic GN, tubulointerstitial injury, renal interstitial fibrosis, renal fibrosis brought about by complications of drug exposure (including the cyclosporine treatment of transplantation recipients), nephrogenic systemic fibrosis, HIV-related nephropathy, graft nephropathy, diabetic kidney disease (diabetic nephropathy), focal segmental glomerulosclerosis (FSGS), idiopathic retroperitoneal fibrosis, hypertensive nephrosclerosis and IgA nephropathy.

The cardiac fibrosis and the vascular fibrosis include cardiac fibrosis associated with myocardial infarction, vascular injury-induced fibrosis, cardiac stenosis, aortostenosis, atherosclerosis, thrombosis, arteriosclerosis, myocardial infarction, angina pectoris, cardiac valvular disease, renal arteriosclerosis, congestive heart failure, dilated cardiomyopathy, hypertrophic cardiomyopathy, restrictive cardiomyopathy, myocarditis, vascular stenosis cardiac fibrosis, post-infarction cardiac fibrosis, left ventricular hypertrophy, venous occlusion, restenosis, restenosis after angiogenesis, arteriovenous transplantation failure, hypertension, hypertensive heart disease, cardiomegaly, heart failure, aortic disease, hereditary hemorrhagic telangiectasia (HHT), arterial tortuosity syndrome, Raynaud syndrome and hypertriglyceridemia.

The dermatofibrosis includes generalized scleroderma, polymyositis, systemic lupus erythematosus, dermatomyositis, Dupuytren's contracture, postoperative adhesion, fibrosis caused by surgical incision or mechanical trauma, and excessive or hypertrophic scarring or keloid formation in the dermis during wound healing brought about from trauma or surgical wound.

The pancreatic fibrosis includes cystic fibrosis (CF), chronic pancreatitis, and autoimmune pancreatitis.

The myelofibrosis includes primary myelofibrosis, idiopathic myelofibrosis, secondary myelofibrosis, and myeloproliferative tumor.

The fibrosis in other organs or tissues includes skeletal myofibrosis, intestinal fibrosis, fibrosis after organ transplantation, induratio penis plastica (Peyronie disease), bladder fibrosis, Camurati-Engelmann disease, Loeys-Dietz syndrome, Marfan syndrome, premature ovarian failure, preeclampsia, mediastinal fibrosis, and intestinal stenosis.

In the present specification, the "cancer" includes tumor angiogenesis, carcinoma, sarcoma, lymphoma, leukemia, melanoma, mesothelioma, multiple myeloma, seminoma, and tumor metastasis. Examples of the tumor site that may be treated according to the present invention include the bladder, blood, bone, the brain, the breast, the central nervous system, the uterine cervix, the colon, the endometrium, the esophagus, the gallbladder, the genital organ, the genitourinary tract, the head, the kidney, the larynx, the liver, the lung, muscular tissues, the neck, oral or nasal mucosa, the ovary, the pancreas, the prostate, the skin, the spleen, the small intestine, the large intestine, the stomach, the testis, and the thyroid gland.

In the present specification, the "neurodegenerative disease" includes peripheral nerve disorder, Alzheimer's disease, Parkinson's disease, and multiple sclerosis.

In the present specification, the "eye disease" includes age-related macular degeneration (AMD), glaucoma, ocular fibrosis, retinal or corneal scarring, diabetic retinopathy, proliferative vitreoretinopathy (PVR), vitreoretinopathy of arbitrary etiology, fibrosis related to ophthalmic surgery, retinal reattachment surgery, cataract extraction, or an arbitrary type of drainage treatment, scarring in the cornea and the conjunctiva, corneal endothelial fibrosis, alkaline burn (e.g., alkaline burn in the cornea), capsulolenticular fibrosis after cataract operation, excessive scarring in tissues surrounding extraocular muscle in strabismus operation, anterior subcapsular cataract and posterior capsule opacification, anterior eye fibrosis, corneal stromal fibrosis, fibrosis related to corneal clouding, trabecular meshwork fibrosis, fibrosis related to glaucoma, posterior eye fibrosis, fibrovascular scarring, fibrosis in the retinal blood vessel or choroid blood vessel of the eye, retinal fibrosis, epiretinal fibrosis, retinal gliosis, subretinal fibrosis, fibrosis related to retinal operation and glaucoma operation, retinal traction detachment related to tissue contraction in diabetic retinopathy, scarring of cicatricial pemphigoid glaucoma filtration surgery, retinopathy of prematurity (ROP) and familial exudative vitreoretinopathy (FEVR).

In the present specification, the "subject" is a human, a monkey, a bovine, a horse, sheep, a goat, a rabbit, a dog, a cat, a mouse, a rat, a guinea pig or a transgenic species thereof. In the present specification, the subject is an individual in need of the treatment of the disease.

In the present specification, the "treatment" includes at least one of prevention, alleviation and remedy and also encompasses reduction of a symptom of the disease, suppression of the progression of a symptom of the disease, removal of a symptom of the disease, improvement in the prognosis of the disease, prevention of the recurrence of the disease, and prevention of the disease. In one aspect of the present invention, the treatment is remedy.

Compound of Present Invention

In one embodiment, the present invention relates to a compound represented by the following general formula (I) or (II) or a pharmaceutically acceptable salt thereof:

(I)

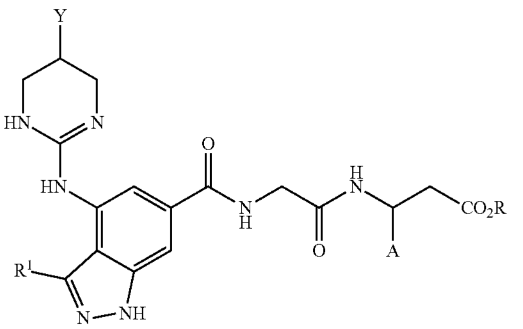

(II)

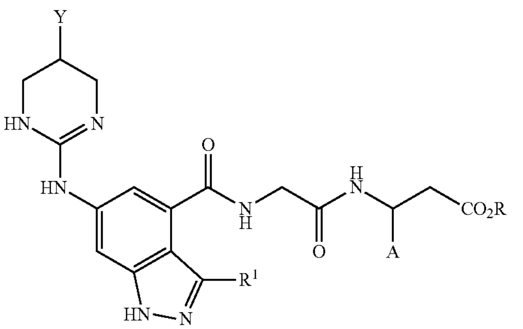

wherein

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

In the present specification, the compound represented by the general formula (I) is also simply referred to as a "compound (I)" and the compound represented by the general formula (II) is also simply referred to as a "compound (II)".

In one embodiment of the present invention, A in the compound (I) or (II) is preferably a phenyl group.

At least one hydrogen atom of the phenyl group that may be selected as A is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group.

At least one hydrogen atom of the phenyl group that may be selected as A is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group.

In another embodiment of the present invention, at least one hydrogen atom of the phenyl group that may be selected as A is optionally replaced with a substituent selected from the group consisting of a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, and a heteroaryl group optionally substituted by a $C_1$-$C_6$ alkyl group.

In an alternative embodiment of the present invention, A in the compound (I) or (II) may be a group represented by the following formula (i):

(i)

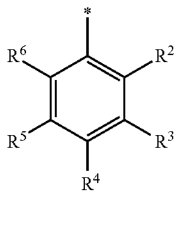

In the formula (i), $R^2$ is a hydrogen atom or a halogen atom.

In another embodiment, $R^2$ is a hydrogen atom, a fluorine atom or a chlorine atom.

In an alternative embodiment, $R^2$ is a hydrogen atom.

$R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In another embodiment, $R^3$ is a hydrogen atom, a halogen atom, a $C_1$-$C_6$ haloalkyl group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_4$ alkyl group.

In an alternative embodiment, $R^3$ is a hydrogen atom, a halogen atom, a $C_1$-$C_4$ haloalkyl group, a $C_1$-$C_4$ haloalkoxy group, a $C_3$-$C_6$ cycloalkyl group, a $C_3$-$C_6$ cycloalkoxy group, a heterocyclyl group, or a heteroaryl group.

In an alternative embodiment, $R^3$ is a hydrogen atom, a halogen atom, a difluoromethyl group, a trifluoromethyl group, a difluoromethoxy group, a trifluoromethoxy group, a cyclopropyl group, a cyclopropoxy group, a morpholinyl group, or a pyrazolinyl group.

In an alternative embodiment, $R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group.

In an alternative embodiment, $R^3$ is a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, or a heteroaryl group optionally substituted by a $C_1$-$C_4$ alkyl group.

In an alternative embodiment, $R^3$ is a halogen atom, a methyl group, a difluoromethyl group, a trifluoromethyl group, a methoxy group, a difluoromethoxy group, a trifluoromethoxy group, or a pyrazolinyl group optionally substituted by a methyl group.

In an alternative embodiment, $R^3$ is a halogen atom, a trifluoromethyl group, a difluoromethoxy group, a trifluoromethoxy group, or a pyrazolinyl group.

$R^4$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group.

In another embodiment, $R^4$ is a hydrogen atom, a halogen atom, a $C_1$-$C_4$ alkyl group, a $C_1$-$C_4$ haloalkyl group, a $C_1$-$C_4$ alkoxy group, or a $C_1$-$C_4$ haloalkoxy group.

In an alternative embodiment, $R^4$ is a hydrogen atom, a halogen atom, a methyl group, a trifluoromethyl group, a methoxy group, or a difluoromethoxy group.

In an alternative embodiment, $R^4$ is a hydrogen atom or a halogen atom.

In an alternative embodiment, $R^4$ is a hydrogen atom or a fluorine atom.

$R^5$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group.

In another embodiment, $R^5$ is a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, or a pyrazolinyl group.

In an alternative embodiment, $R^5$ is a hydrogen atom, a halogen atom, a methyl group, a trifluoromethyl group, a methoxy group, a difluoromethoxy group, or a pyrazolinyl group.

In an alternative embodiment, $R^5$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group.

In an alternative embodiment, $R^5$ is a hydrogen atom, a halogen atom, a $C_1$-$C_4$ alkyl group, a $C_1$-$C_4$ haloalkyl group, a $C_1$-$C_4$ alkoxy group, or a $C_1$-$C_4$ haloalkoxy group.

In an alternative embodiment, $R^5$ is a hydrogen atom, a halogen atom, a methyl group, a difluoromethyl group, a trifluoromethyl group, a methoxy group, a difluoromethoxy group, or a trifluoromethoxy group.

In an alternative embodiment, $R^5$ is a halogen atom, a methyl group, a trifluoromethyl group, a difluoromethoxy group, or a trifluoromethoxy group.

$R^6$ is a hydrogen atom or a halogen atom.

In another embodiment, $R^6$ is a hydrogen atom, a fluorine atom or a chlorine atom.

In an alternative embodiment, $R^6$ is a hydrogen atom or a fluorine atom.

In an alternative embodiment, for example, in the formula (i), $R^2$ may be a hydrogen atom, $R^3$ may be a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group, $R^4$ may be a hydrogen atom or a halogen atom, $R^5$ may be a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group, and $R^6$ may be a hydrogen atom or a halogen atom.

In an alternative embodiment, in the formula (i), $R^2$ may be a hydrogen atom, $R^3$ may be a hydrogen atom, a halogen atom, a $C_1$-$C_6$ haloalkyl group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_4$ alkyl group, $R^4$ may be a hydrogen atom or a halogen atom, $R^5$ may be a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group, and $R^6$ may be a hydrogen atom or a halogen atom.

In an alternative embodiment of the present invention, A in the compound (I) or (II) may be a group represented by any of the following formulas (i)-a to (i)-g:

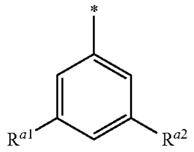

(i)-a

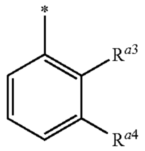

(i)-b

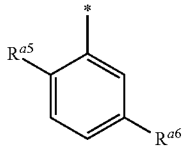

(i)-c

-continued (i)-d

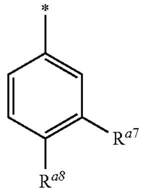

(i)-e

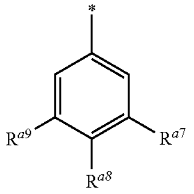

(i)-f

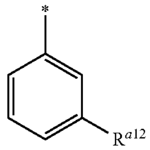

(i)-g

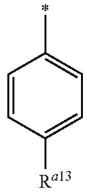

wherein * represents a binding position, and $R^{a1}$ to $R^{a13}$ are each independently a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group.

In the embodiment, $R^{a1}$ to $R^{a13}$ may each independently be a substituent selected from the group consisting of a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, and a heteroaryl group optionally substituted by a $C_1$-$C_6$ alkyl group.

In an alternative embodiment of the present invention, when A in the compound (I) or (II) is a group represented by the formula (i)-a, one of $R^{a1}$ and $R^{a2}$ may be a halogen atom, a $C_1$-$C_6$ haloalkyl group, or a $C_1$-$C_6$ haloalkoxy group, and the other moiety may be a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-a, one of $R^{a1}$ and $R^{a2}$ may be a halogen atom, a trifluoromethyl group, a difluoromethoxy group, or a trifluoromethoxy group, and the other moiety may be a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-a, one of $R^{a1}$ and $R^{a2}$ may be a halogen atom, a difluoromethyl group, a trifluoromethyl group, a difluoromethoxy group, or a trifluoromethoxy group, and the other moiety may be a halogen atom, a methyl group, a difluoromethyl group, a trifluoromethyl group, a methoxy group, a difluoromethoxy group, a trifluoromethoxy group, a cyclopropyl group, a cyclopropoxy group, a morpholinyl group, or a pyrazolinyl group.

In an alternative embodiment of the present invention, when A in the compound (I) or (II) is a group represented by the formula (i)-b, $R^{a3}$ may be a halogen atom, and $R^{a4}$ may be a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-b, $R^{a3}$ may be a halogen atom, and $R^{a4}$ may be a halogen atom, a $C_1$-$C_6$ haloalkyl group, or a $C_1$-$C_6$ haloalkoxy group.

In an alternative embodiment of the present invention, when A in the compound (I) or (II) is a group represented by the formula (i)-b, $R^{a3}$ may be a halogen atom, and $R^{a4}$ may be a $C_1$-$C_6$ haloalkyl group.

In an alternative embodiment of the present invention, when A in the compound (I) or (II) is a group represented by the formula (i)-c, $R^{a5}$ may be a halogen atom, and $R^{a6}$ may be a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-c, $R^{a5}$ may be a halogen atom, and $R^{a6}$ may be a halogen atom, a $C_1$-$C_6$ haloalkyl group, or a $C_1$-$C_6$ haloalkoxy group.

In an alternative embodiment of the present invention, when A in the compound (I) or (II) is a group represented by the formula (i)-c, $R^{a5}$ may be a halogen atom, and $R^{a6}$ may be a halogen atom, a trifluoromethyl group, or a trifluoromethoxy group.

In an alternative embodiment of the present invention, when A in the compound (I) or (II) is a group represented by the formula (i)-d, one of $R^{a7}$ and $R^{a8}$ may be a halogen atom, a $C_1$-$C_6$ haloalkyl group, or a $C_1$-$C_6$ haloalkoxy group, and the other moiety may be a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-d, one of $R^{a7}$ and $R^{a8}$ may be a halogen atom, a $C_1$-$C_6$ haloalkyl group, or a $C_1$-$C_6$ haloalkoxy group, and the other moiety may be a halogen atom, a $C_1$-$C_6$ alkyl group, a $C_1$-$C_6$ haloalkyl group, a $C_1$-$C_6$ alkoxy group, or a $C_1$-$C_6$ haloalkoxy group.

In an alternative embodiment of the present invention, when A in the compound (I) or (II) is a group represented by the formula (i)-d, one of $R^{a7}$ and $R^{a8}$ may be a halogen atom, a trifluoromethyl group, or a trifluoromethoxy group, and the other moiety may be a halogen atom, a methyl group, a difluoromethyl group, a trifluoromethyl group, a methoxy group, a difluoromethoxy group, or a trifluoromethoxy group.

In an alternative embodiment of the present invention, when A in the compound (I) or (II) is a group represented by the formula (i)-e, at least one of $R^{a9}$, $R^{a10}$ and $R^{a11}$ may be a halogen atom, a $C_1$-$C_6$ haloalkyl group, or a $C_1$-$C_6$ haloalkoxy group, and the remaining moieties may each individually be a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-e, $R^{a9}$, $R^{a10}$ and $R^{a11}$ may each individually be a halogen atom, a $C_1$-$C_6$ haloalkyl group, or a $C_1$-$C_6$ haloalkoxy group.

In an alternative embodiment of the present invention, when A in the compound (I) or (II) is a group represented by the formula (i)-f, $R^{a12}$ may be a halogen atom, a $C_1$-$C_6$ haloalkyl group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-f, $R^{a12}$ may be a halogen atom, a difluoromethyl group, a trifluoromethyl group, a difluoromethoxy group, a trifluoromethoxy group, a cyclopropyl group, a cyclopropoxy group, a morpholinyl group, or a pyrazolinyl group optionally substituted by a methyl group.

In an alternative embodiment of the present invention, when A in the compound (I) or (II) is a group represented by the formula (i)-g, $R^{a13}$ may be a halogen atom, a $C_1$-$C_6$ haloalkyl group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group.

In an alternative embodiment of the present invention, when A in the compound (I) or (II) is a group represented by the formula (i)-f, $R^{a13}$ may be a halogen atom, a difluoromethyl group, a trifluoromethyl group, a difluoromethoxy group, a trifluoromethoxy group, a cyclopropyl group, a cyclopropoxy group, a morpholinyl group, or a pyrazolinyl group optionally substituted by a methyl group.

In an alternative embodiment of the present invention, when A in the compound (I) or (II) is a group represented by the formula (i)-f, $R^{a13}$ may be a $C_1$-$C_6$ haloalkyl group or a $C_1$-$C_6$ haloalkoxy group.

Alternatively, $R^{a13}$ may be a difluoromethyl group, a trifluoromethyl group, a difluoromethoxy group, or a trifluoromethoxy group.

In one embodiment, R in the compound (I) or (II) is a hydrogen atom or a $C_1$-$C_6$ alkyl group.

In another embodiment, R in the compound (I) or (II) is a hydrogen atom or a $C_1$-$C_4$ alkyl group.

In an alternative embodiment, R in the compound (I) or (II) is a hydrogen atom or a methyl group.

In an alternative embodiment, R in the compound (I) or (II) is a hydrogen atom.

In one embodiment, $R^1$ in the compound (I) or (II) is a hydrogen atom or a halogen atom.

In another embodiment, $R^1$ in the compound (I) or (II) is a hydrogen atom, a fluorine atom or a chlorine atom.

In an alternative embodiment, $R^1$ in the compound (I) or (II) is a hydrogen atom.

In one embodiment, Y in the compound (I) or (II) is a hydrogen atom, a fluorine atom or a hydroxy group.

In an alternative embodiment, Y in the compound (I) or (II) is a fluorine atom.

In an alternative embodiment, the present invention provides a compound selected from the following group or a pharmaceutically acceptable salt thereof:

(3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid (3S)-3-(2-(4-((5-fluoro-1,4,5,6-tetrahydropyrimidin-2-yl)amino)-1H-indazole-6-carboxamido)acetamido)-3-(3-iodo-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-methyl-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-methoxy-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-fluoro-5-(trifluoromethyl)phenyl)propanoic acid, (3S)-3-(3,5-bis(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(1H-pyrazol-1-yl)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-3-(trifluoromethyl)phenyl)propanoic acid, (3S)-3-(2-chloro-3-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethyl)phenyl)propanoic acid, (3S)-3-(2-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(4-methyl-3-(trifluoromethyl)phenyl)propanoic acid, (3S)-3-(3-chloro-4-fluoro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-4-methoxyphenyl)-3-(2-(4-((5-fluoro-1,4,5,6-tetrahydropyrimidin-2-yl)amino)-1H-indazole-6-carboxamido)acetamido)propanoic acid, (3S)-3-(3,5-dichlorophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-chlorophenyl)-3-(2-(4-((5-fluoro-1,4,5,6-tetrahydropyrimidin-2-yl)amino)-1H-indazole-6-carboxamido)acetamido)propanoic acid, (3S)-3-(3,5-dibromophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-iodophenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-iodophenyl)-3-(2-(4-((5-fluoro-1,4,5,6-tetrahydropyrimidin-2-yl)amino)-1H-indazole-6-carboxamido)acetamido)propanoic acid, (3S)-3-(5-chloro-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(5-bromo-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-4-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(5-(difluoromethoxy)-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-5-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(3,5-bis(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethoxy)phenyl)propanoic acid, (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethoxy)phenyl)propanoic acid, (3S)-3-(2-(4-((5-fluoro-1,4,5,6-tetrahydropyrimidin-2-yl)amino)-1H-indazole-6-carboxamido)acetamido)-3-(3-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-(trifluoromethoxy)phenyl)propanoic acid, (3S)-3-(3-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-cyclopropylphenyl)-3-(2-(4-((5-fluoro-1,4,5,6-tetrahydropyrimidin-2-yl)amino)-1H-indazole-6-carboxamido)acetamido)propanoic acid, (3S)-3-(3-cyclopropoxyphenyl)-3-(2-(4-((5-fluoro-1,4,5,6-tetrahydropyrimidin-2-yl)amino)-1H-indazole-6-carboxamido)acetamido)propanoic acid, (3S)-3-(3-chlorophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromophenyl)-3-(2-(4-((5-fluoro-1,4,5,6-tetrahydropyrimidin-2-yl)amino)-1H-indazole-6-carboxamido)acetamido)propanoic acid, (3S)-3-(3-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(3,5-dimethyl-1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(3-morpholinophenyl)propanoic acid, (3S)-3-(4-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(4-(trifluoromethyl)phenyl)propanoic acid, (3S)-3-(3-chloro-5-(trifluoromethyl)phenyl)-3-(2-(3-fluoro-4-((5-fluoro-1,4,5,6-tetrahydropyrimidin-2-yl)amino)-1H-indazole-6-carboxamido)acetamido)propanoic acid, (3S)-3-(2-(3-chloro-4-((5-fluoro-1,4,5,6-tetrahydropyrimidin-2-yl)amino)-1H-indazole-6-carboxamido)acetamido)-3-(3-chloro-5-(trifluoromethyl)phenyl)propanoic acid, (3S)-3-(3-chloro-5-(trifluoromethyl)phenyl)-3-(2-(4-((5-hydroxy-1,4,5,6-tetrahydropyrimidin-2-yl)amino)-1H-indazole-6-carboxamido)acetamido)propanoic acid, (S)-3-(3-chloro-5-(trifluoromethyl)phenyl)-3-(2-(4-((1,4,5,6-tetrahydropyrimidin-2-yl)amino)-1H-indazole-6-carboxamido)acetamido)propanoic acid, (3S)-3-(3-chloro-5-(trifluoromethyl)phenyl)-3-(2-(6-((5-fluoro-1,4,5,6-tetrahydropyrimidin-2-yl)amino)-1H-indazole-4-carboxamido)acetamido)propanoic acid, (3S)-3-(3-bromo-5-(trifluoromethyl)phenyl)-3-(2-(6-((5-fluoro-1,4,5,6-tetrahydropyrimidin-2-yl)amino)-1H-indazole-4-carboxamido)acetamido)propanoic acid, (3S)-3-(2-(6-((5-fluoro-1,4,5,6-tetrahydropyrimidin-2-yl)amino)-1H-indazole-4-carboxamido)acetamido)-3-(3-iodo-5-(trifluoromethyl)phenyl)propanoic acid, (3S)-3-(2-(6-((5-fluoro-1,4,5,6-tetrahydropyrimidin-2-yl)amino)-1H-indazole-4-carboxamido)acetamido)-3-(4-fluoro-3-(trifluoromethyl)phenyl)propanoic acid, and (3S)-3-(2-(6-((5-fluoro-1,4,5,6-tetrahydropyrimidin-2-yl)amino)-1H-indazole-4-carboxamido)acetamido)-3-(3-(trifluoromethyl)phenyl)propanoic acid.

The compound represented by the general formula (I) or (II) of the present invention or a pharmaceutically acceptable salt thereof can form a hydrate or a solvate, and each individual or a mixture thereof is encompassed by the present invention.

When the compound represented by the general formula (I) or (II) of the present invention or a pharmaceutically acceptable salt thereof has one or more asymmetric centers, carbon-carbon double bonds, axial chirality, or the like, optical isomers (including enantiomers and diastereomers), geometrical isomers, tautomers, and rotational isomers may exist. These isomers and mixtures thereof are represented by a single formula such as the formula (I) or (II). The present invention encompasses each of these isomers and mixtures (including racemates) thereof at arbitrary ratios.

In an embodiment, the compound (I) of the present invention has both the following absolute configurations:

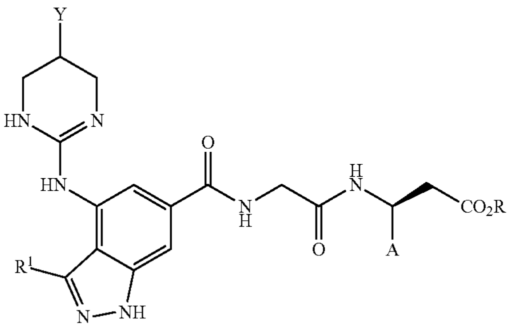

and

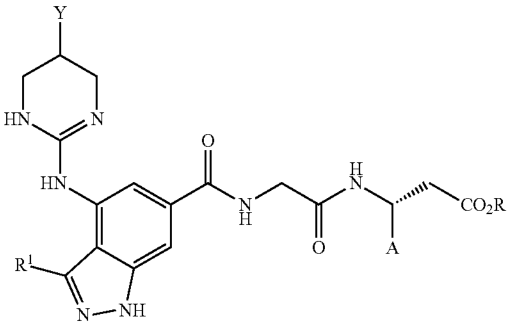

In an embodiment, the compound (I) of the present invention has the following absolute configuration:

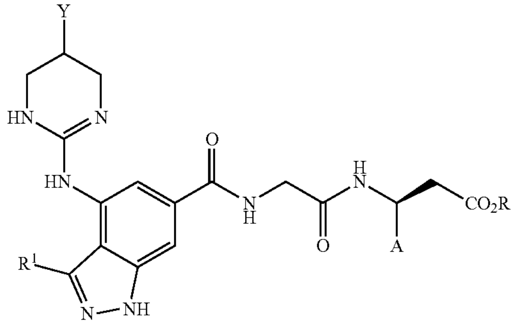

In an embodiment, the compound (I) of the present invention has the following absolute configuration:

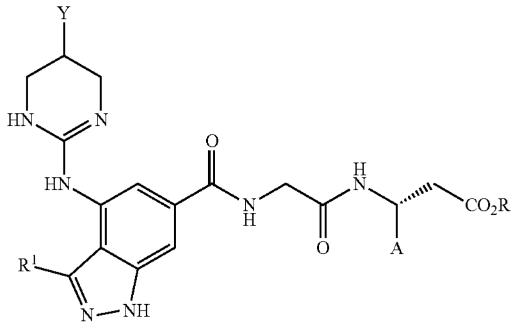

Likewise, in an embodiment, the compound (II) of the present invention has both the following absolute configurations:

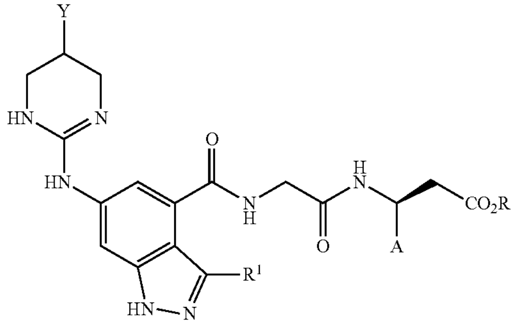

and

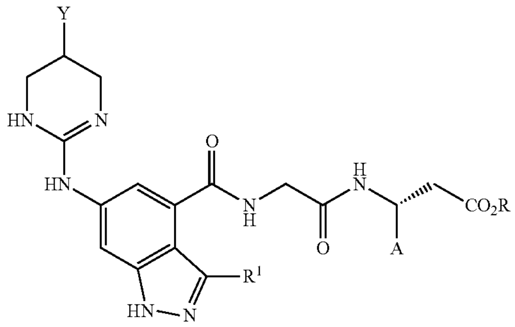

In an embodiment, the compound (II) of the present invention has the following absolute configuration:

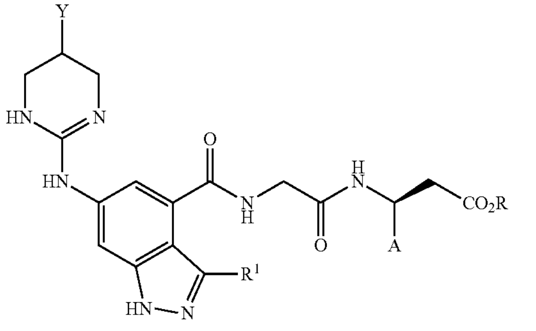

In an embodiment, the compound (II) of the present invention has the following absolute configuration:

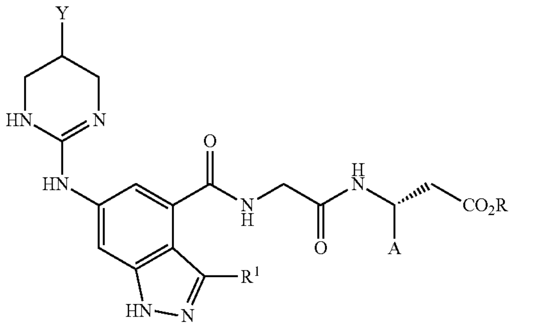

A racemate can be resolved into optical enantiomers by a method known in the art, for example, separation of a diastereoisomeric salt thereof with an optically active acid, and release of an optically active amine compound by treatment with a base. Another method for resolving a racemic compound into optical enantiomers is based on chromatography of optically active matrix. The compound of the present invention may also be resolved by the formation of a diastereoisomeric derivative. A further method for resolving optical isomers known to those skilled in the art, such as J. Jaques, A. Collet and S. Wilen et al., "Enantiomers, Racemates, and Resolutions", John Wiley and Sons, New York (1981) can be used. An optically active compound can also be produced from an optically active starting material.

The compound represented by the general formula (I) or (II) of the present invention can form an acid-addition salt, etc., and such an acid-addition salt, etc. is encompassed by the pharmaceutically acceptable salt of the present invention.

The compound represented by the general formula (I) or (II) of the present invention can form an acid-addition salt with an acid at an arbitrary ratio, and each individual (e.g., monohydrochloride or dihydrochloride) or a mixture thereof is encompassed by the present invention. When R in the general formula (I) or (II) is, for example, a hydrogen atom, such a compound can form a base-addition salt, etc., and such a base-addition salt, etc. is also encompassed by the pharmaceutically acceptable salt of the present invention.

The compound represented by the general formula (I) or (II) of the present invention, when having a group capable of forming an ester group, such as a hydroxy group or a carboxy group, can be converted to a pharmaceutically acceptable ester, and such a pharmaceutically acceptable ester is encompassed by the present invention. The pharmaceutically acceptable ester of the compound represented by the general formula (I) or (II) is capable of serving as a prodrug of the compound represented by the general formula (I) or (II) and can be hydrolyzed in a metabolic process (e.g., hydrolysis), when administered in vivo to a subject, to form the compound represented by the general formula (I) or (II).

The compound represented by the general formula (I) or (II) of the present invention or a pharmaceutically acceptable salt thereof can form an isotope compound in which one or more atoms constituting the compound or the salt are replaced with isotope atoms at a non-natural ratio. The isotope atom may be radioactive or nonradioactive and includes, for example, heavy hydrogen ($^{2}H$; D), tritium ($^{3}H$; T), carbon-14 ($^{14}C$), and iodine-125 ($^{125}I$). The radioactive or nonradioactive isotope compound may be used as a medicament for the remedy or prevention of a disease, a reagent for research (e.g., a reagent for assay), a diagnostic drug (e.g., a diagnostic imaging drug), or the like. The present invention encompasses such a radioactive or nonradioactive isotope compound.

The compound represented by the general formula (I) or (II) of the present invention or a pharmaceutically acceptable salt thereof is capable of inhibiting the binding of integrin αv to its ligand.

In an alternative embodiment, the compound represented by the general formula (I) or (II) of the present invention or a pharmaceutically acceptable salt thereof is capable of inhibiting the activation of TGF-β. TGF-β participates in the differentiation, survival, proliferation, and the like of cells and plays an important role in development, immunity, wound healing, and the like and therefore, is deeply involved in diseases such as inflammation, fibrosis and cancer. TGF-β is known to have three types of isoforms in mammals, and TGF-β1 is known as a master regulator for tissue repair, inflammation, and fibrosis (Seminars in Cell and Developmental Biology, 2020, 101, 123-139). TGF-β is secreted as an inactive form (latent form) and activated by various methods so as to exhibit physiological activity. RGD integrin including αvβ1 and αvβ6 is known to play an important role in the activation of TGF-β1. For example, an αvβ1 integrin inhibitor (Non Patent Literature 8: Science Translational Medicine, 2015, 7 (288), 288ra79) or an αvβ6 integrin inhibitor (Cancer Research, 2008, 68 (2), 561-570) inhibits the activation of TGF-β1. Thus, the compound represented by the general formula (I) or (II) of the present invention or a pharmaceutically acceptable salt thereof can be useful in the prevention, alleviation and/or remedy of diseases such as inflammatory disease, fibrosis, cancer, neurodegenerative disease, eye disease, osteoporosis and osteogenesis imperfecta.

In an alternative embodiment, the compound represented by the general formula (I) or (II) of the present invention or a pharmaceutically acceptable salt thereof is capable of inducing the dedifferentiation of activated human hepatic stellate cells. Stellate cells or fibroblasts differentiate into active stellate cells or myofibroblasts expressing α-smooth muscle actin (α-SMA, ACTA2) through TGF-β1 or the like, and enhance collagen production, etc. For example, it has been reported that in integrin αv-knockout stellate cells, the expression of α-SMA was suppressed and further the production of collagen or the like was also suppressed, because TGF-β1 is not activated (Non Patent Literature 16: Nature Medicine, 2013, 19 (12), 1617-1624). Such enhanced collagen production is seen in diseases such as inflammation, fibrosis and cancer. Thus, the compound represented by the general formula (I) or (II) of the present invention or a pharmaceutically acceptable salt thereof can be useful in the prevention, alleviation and/or remedy of diseases such as inflammatory disease, fibrosis, cancer, neurodegenerative disease, eye disease, osteoporosis and osteogenesis imperfecta.

In an alternative embodiment, the compound represented by the general formula (I) or (II) of the present invention or a pharmaceutically acceptable salt thereof is capable of suppressing increase in hydroxyproline (HYP) level which is an index for fibrosis in non-alcoholic steatohepatitis (NASH) model animals. Thus, the compound represented by the general formula (I) or (II) of the present invention or a pharmaceutically acceptable salt thereof can be useful in the prevention, alleviation and/or remedy of non-alcoholic steatohepatitis (NASH).

In an alternative embodiment, the compound represented by the general formula (I) or (II) of the present invention or a pharmaceutically acceptable salt thereof has excellent pharmacokinetic characteristics. The compound represented by the general formula (I) or (II) of the present invention or a pharmaceutically acceptable salt thereof is capable of exhibiting excellent transcellular permeability, for example, in a membrane permeability test using Caco2 cells. The transcellular permeability in a membrane permeability test using Caco2 cells reportedly correlates with the rate of intestinal absorption.

In an alternative embodiment, the compound represented by the general formula (I) or (II) of the present invention or a pharmaceutically acceptable salt thereof has excellent safety. The compound represented by the general formula (I) or (II) of the present invention or a pharmaceutically acceptable salt thereof is shown to form no or few reactive metabolites through metabolism in liver microsomes, for example.

<Pharmaceutical Composition of Present Invention>

In one embodiment, the present invention relates to a pharmaceutical composition comprising the compound represented by the general formula (I) or (II) of the present invention or a pharmaceutically acceptable salt thereof.

In one embodiment, the pharmaceutical composition of the present invention can be used for the treatment of a disease related to integrin αv.

In one embodiment, the present invention relates to use of the compound represented by the general formula (I) or (II) of the present invention or a pharmaceutically acceptable salt thereof for a disease related to integrin αv.

In one embodiment, the present invention relates to the compound represented by the general formula (I) or (II) of the present invention or a pharmaceutically acceptable salt thereof for use in the treatment of a disease related to integrin αv.

In one embodiment, the present invention relates to use of the compound represented by the general formula (I) or (II) of the present invention or a pharmaceutically acceptable salt thereof for producing a medicament for the treatment of a disease related to integrin αv.

In one embodiment, the present invention relates to a method for the treatment of a disease related to integrin αv, comprising administering the compound represented by the general formula (I) or (II) of the present invention or a pharmaceutically acceptable salt thereof in an amount effective for prevention, alleviation and/or remedy to a subject.

In one embodiment of the present invention, examples of the disease related to integrin αv can include inflammatory disease, fibrosis, cancer, neurodegenerative disease, eye disease, osteoporosis, and osteogenesis imperfecta.

In an alternative embodiment, the disease related to integrin αv is fibrosis.

In one embodiment, the fibrosis can be selected from fibroses in the lung, the liver, the kidney, the heart, vascular vessels, the skin, the pancreas, the bone marrow, and other organs or tissues.

In another embodiment, the fibrosis can be selected from pulmonary fibrosis, hepatic fibrosis, renal fibrosis, cardiac fibrosis, vascular fibrosis, dermatofibrosis, pancreatic fibrosis, myelofibrosis and skeletal myofibrosis.

In an alternative embodiment, the fibrosis can be selected from pulmonary fibrosis, hepatic fibrosis, renal fibrosis and cardiac fibrosis.

In one embodiment, the disease related to integrin αv is idiopathic pulmonary fibrosis (IPF).

In another embodiment, the disease related to integrin αv is non-alcoholic fatty liver disease (NAFLD).

In an alternative embodiment, the disease related to integrin αv is non-alcoholic steatohepatitis (NASH).

In an alternative embodiment, the disease related to integrin αv is primary biliary cholangitis (PBC).

In an alternative embodiment, the disease related to integrin αv is primary sclerosing cholangitis (PSC).

In an alternative embodiment, the disease related to integrin αv is alcoholic steatohepatitis.

In an alternative embodiment, the disease related to integrin αv is chronic kidney disease (CKD).

In an alternative embodiment, the disease related to integrin αv is diabetic kidney disease (diabetic nephropathy).

In an alternative embodiment, the disease related to integrin αv is cardiac fibrosis associated with myocardial infarction.

The subject to which the compound represented by the general formula (I) or (II) of the present invention or a pharmaceutically acceptable salt thereof or the pharmaceutical composition of the present invention is administered is a mammal. The mammal includes, for example, a human, a monkey, a bovine, a horse, sheep, a goat, a rabbit, a dog, a cat, a mouse, a rat, a guinea pig or a transgenic species thereof. The compound represented by the general formula (I) or (II) of the present invention or a pharmaceutically acceptable salt thereof or the pharmaceutical composition of the present invention is preferably administered to a human.

The dose, i.e., the amount effective for prevention, alleviation and/or remedy, of the compound represented by the general formula (I) or (II) of the present invention or a pharmaceutically acceptable salt thereof may vary depending on the frequency and method of administration, the animal species, sex, age, body weight and general condition of a recipient, the severity of the disease, etc., and can be appropriately set by those skilled in the art. For oral administration as to an adult human (60 kg), for example, 0.01 to 3000 mg, preferably 0.1 to 600 mg, is appropriate as the dose per day of the compound of the present invention and can be administered once to several times a day, for example, in one portion or two, three or four divided portions. For parenteral administration to an adult human, for example, 0.001 to 1000 mg, preferably 0.01 to 300 mg, is appropriate as the dose of the compound of the present invention and can be administered once to several times a day, for example, in one portion or two, three or four divided portions. For parenteral administration, the compound of the present invention can be used at a concentration of, for example, 0.00001% (w/v) to 10% (w/v), preferably 0.001% (w/v) to 5% (w/v).

As for a parenteral route of intravenous, intrathecal, intramuscular or similar administration, etc., the dosage is typically smaller than an amount that is used for oral administration.

The compound represented by the general formula (I) or (II) of the present invention or a pharmaceutically acceptable salt thereof may be administered by single administration or multiple administration, either singly as a pure compound or in combination with a pharmaceutically acceptable carrier. A pharmaceutical composition formed by combining the compound of the present invention with a pharmaceutically acceptable carrier may be administered in various dosage forms suitable for administration routes. The pharmaceutical composition according to the present invention may be formulated together with a pharmaceutically acceptable carrier in accordance with a conventional approach disclosed in, for example, Remington: The Science and Practice of Pharmacy, 19 Edition, Gennaro, Ed., Mack Publishing Co., Easton, Pa., 1995.

The pharmaceutical composition of the present invention can be administered orally or parenterally. The parenteral route may include, for example, rectal, transnasal, pulmonary, transdermal, intracerebral, intraperitoneal, vaginal, subcutaneous, intramuscular, intrathecal, intravenous and intradermal routes. The pharmaceutical composition of the present invention may be specified and formulated for administration through an arbitrary appropriate route. A preferred route may be selected depending on the general condition and age of a recipient, the properties of a condition to receive a treatment, and an active ingredient selected.

The pharmaceutical composition for oral administration includes solid preparations such as capsules, tablets, sugar-coated tablets, pills, lozenges, powders and granules. Such solid preparations can be prepared in a coated form, if appropriate. Nonsolid preparations for oral administrations include solutions (including solutions for inhalations), emulsions, suspensions, syrups and elixirs.

The pharmaceutical composition for parenteral administration includes, for example, injections, suppositories, sprays, ointments, creams, gels, inhalants, skin patches, and implants. The injection is particularly suitable for intravenous, intramuscular, subcutaneous and intraperitoneal administration. Every sterile aqueous medium used is readily available by a standard approach known to those skilled in the art.

In the case of preparing an oral solid preparation, a carrier, for example, an excipient, and optionally a binder, a disintegrant, a lubricant, a colorant, a corrigent, and the like can be added to a principal agent, followed by a routine method to prepare tablets, coated tablets, granules, fine granules, powders, capsules, or the like. An oral nonsolid preparation such as a syrup can also be appropriately prepared.

For example, lactose, sucrose, corn starch, saccharose, glucose, sorbitol, crystalline cellulose, or silicon dioxide is used as the excipient. For example, polyvinyl alcohol, ethylcellulose, methylcellulose, gum arabic, hydroxypropylcellulose, or hydroxypropylmethylcellulose is used as the binder. For example, magnesium stearate, talc, or silica is used as the lubricant. An agent that is acceptable for addition to medicaments is used as the colorant. For example, cacao powder, menthol, aromatic acid, mint oil, kapur, or powdered cinnamon bark is used as the corrigent. Such tablets or granules may be appropriately coated, if necessary, with sugar, gelatin, or the like as a matter of course.

In the case of preparing an injection, a carrier, for example, a pH adjuster, a buffer, a suspending agent, a solubilizer, a stabilizer, a tonicity agent, or a preservative can be added, if necessary, to a principal agent, followed by a routine method to prepare an intravenous injection, a subcutaneous injection, an intramuscular injection, or an intravenous drip infusion agent. In this respect, a freeze-dried product may be prepared by a routine method, if necessary.

Examples of the suspending agent can include methylcellulose, polysorbate 80, hydroxyethylcellulose, gum arabic, powdered tragacanth, sodium carboxymethylcellulose, and polyoxyethylene sorbitan monolaurate.

Examples of the solubilizer can include polyoxyethylene hydrogenated castor oil, polysorbate 80, nicotinamide, polyoxyethylene sorbitan monolaurate, macrogol, castor oil fatty acid ethyl ester, and cyclodextrin.

Examples of the stabilizer can include sodium sulfite and sodium metasulfite. Examples of the preservative can include methyl p-hydroxybenzoate, ethyl p-hydroxybenzoate, sorbic acid, phenol, cresol, and chlorocresol.

Synthesis Method

The compound represented by the general formula (I) or (II) of the present invention can be produced by a method summarized in any of reaction processes 1 to 2 given below. A modification or an alteration that is known per se to chemists in the art or can be obvious to those skilled in the art may be used in the methods described below.

In the following description about production methods, A, R, $R^1$ and Y are as defined above, unless otherwise specified.

Process 1

A compound (I) or (II) wherein R is a $C_1$-$C_6$ alkyl group can be produced through step 1 of the following process 1.

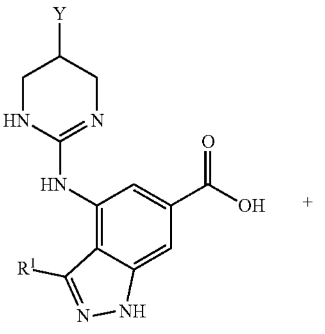

(1A)

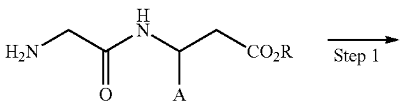

(3)

-continued

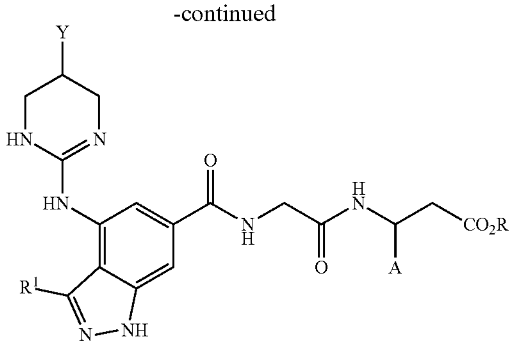

(I)

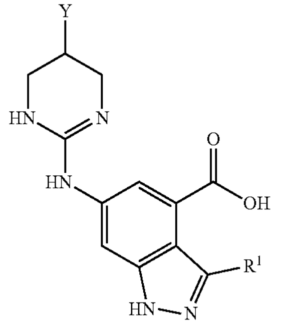

(2A)

+

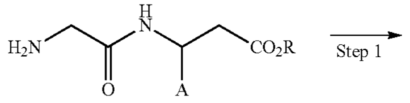

(3)

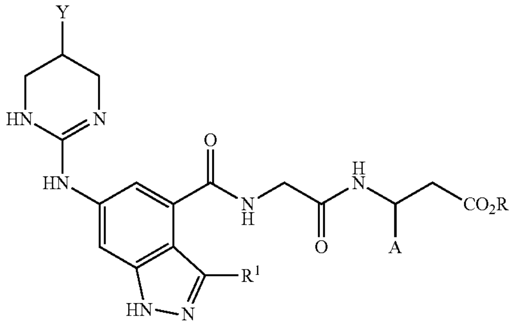

(II)

Step 1 of process 1 is the step of condensing a compound (1A) or (2A) and a compound (3) in a solvent using a dehydration-condensation agent to produce the compound (I) or (II) of the present invention.

The compound (1A) or (2A) can be produced in accordance with syntheses 1 and 2 mentioned later and the description of Examples of the present specification. The compound (1A) or (2A) may be an acid-addition salt, etc. Examples of the acid-addition salt, etc. include hydrochloride, sulfate, and acetate.

The compound (3) can also be produced in accordance with synthesis 6 mentioned later and the description of Examples of the present specification.

The compound (3) may be an acid-addition salt, etc. Examples of the acid-addition salt, etc. include hydrochloride, sulfate, and acetate.

Examples of the dehydration-condensation agent for use in step 1 of process 1 include dicyclohexylcarbodiimide (DCC), N,N'-diisopropylcarbodiimide (DIC), 1-(3-dimethylaminopropyl)-3-ethylcarbodiimide or hydrochloride thereof (EDC, EDAC), N,N-dicyclohexylamide, carbonyldiimidazole, 1H-benzotriazol-1-yloxytris(dimethylamino) phosphonium hexafluorophosphate, and O-(7-azabenzotriazol-1-yl)-1,1,3,3-tetramethyluronium hexafluorophosphate. N,N'-Diisopropylcarbodiimide or dicyclohexylcarbodiimide is preferred.

Step 1 of process 1 may be performed, if necessary, in the presence of an activator such as 1-hydroxybenzotriazole (HOBt), 1-hydroxy-7-azabenzotriazole (HOAt), N-hydroxysuccinimide (HOSu), or 4-dimethylaminopyridine.

Step 1 of process 1 may be performed, if necessary, in the presence of a base such as N,N-diisopropylethylamine, N-methylmorpholine, or triethylamine.

The solvent for use in step 1 of process 1 is not particularly limited as long as the solvent dissolves the starting materials to some extent without inhibiting the reaction. Examples thereof include: amides such as N,N-dimethylformamide (DMF), N,N-dimethylacetamide, and N-methylpyrrolidone; halogenated hydrocarbons such as dichloromethane (DCM); esters such as ethyl acetate; hydrocarbons such as dichlorohexane and n-hexane; aromatic hydrocarbons such as toluene; ethers such as tetrahydrofuran, diethyl ether, cyclopentyl methyl ether, 1,4-dioxane, and tert-butyl methyl ether; sulfur solvents such as dimethyl sulfoxide (DMSO); and arbitrary mixed solvents thereof. An aprotic polar solvent is preferred, and N,N-dimethylformamide, dimethyl sulfoxide, or a mixed solvent prepared by mixing them is more preferred.

The reaction temperature differs depending on the types, usages, etc. of the starting materials, the solvent, and the like, and is usually −20 °C to 100 °C, preferably 0 °C to 50 °C.

The reaction time differs depending on the reaction temperature, etc., and is usually 10 minutes to 120 hours, preferably 30 minutes to 48 hours.

Process 2

A compound (I') or (II') which is a compound (I) or (II) wherein R is a hydrogen atom can be produced by subjecting the compound (I) or (II) produced by the process 1 to step 2 of the following process 2.

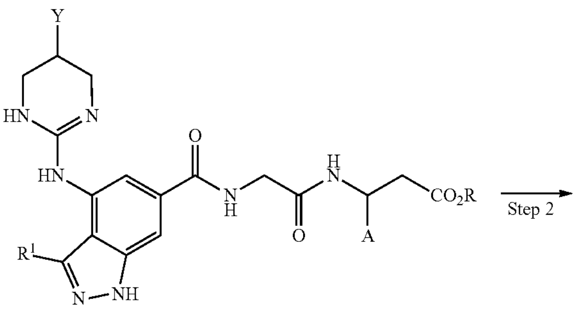

(I)

-continued

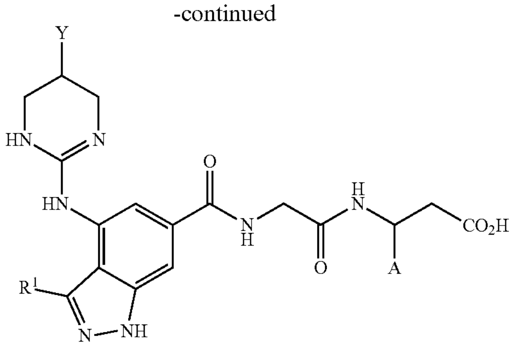

(I')

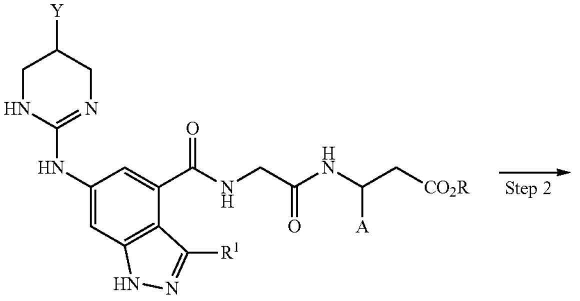

(II)

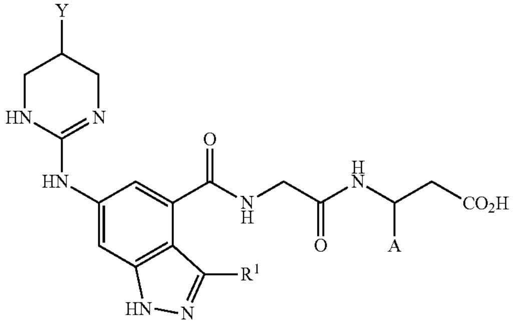

(II')

Step 2 of process 2 is the step of hydrolyzing the ester moiety of the compound (I) or (II) or an acid-addition salt, etc. thereof in a solvent, for example, through reaction with a base to produce a compound (I') or (II').

Examples of the base for use in step 2 of process 2 include alkali metal hydroxide such as lithium hydroxide, sodium hydroxide, and potassium hydroxide, and alkaline earth metal hydroxide such as calcium hydroxide and magnesium hydroxide. Alkali metal hydroxide is preferred, and lithium hydroxide or sodium hydroxide is more preferred. These bases may each be used singly or may be used in combination of two or more thereof. A method for adding the base may involve adding the base in the form of a solution containing the base dissolved in a solvent mentioned later.

The solvent for use in step 2 of process 2 is not particularly limited as long as the solvent dissolves the starting materials to some extent without inhibiting the reaction. Examples thereof include: water; amides such as N,N-dimethylformamide, N,N-dimethylacetamide, and N-methylpyrrolidone; halogenated hydrocarbons such as dichloromethane; hydrocarbons such as dichlorohexane and n-hexane; aromatic hydrocarbons such as toluene; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Water, acetonitrile, tetrahydrofuran, N,N-dimethylformamide, methanol, ethanol, or a mixed solvent prepared by mixing two or more of them is preferred.

The reaction temperature differs depending on the types, usages, etc. of the starting materials, the solvent, and the like, and is usually −20 °C to 100 °C, preferably 0 °C to 50 °C.

The reaction time differs depending on the reaction temperature, etc., and is usually 1 minute to 48 hours, preferably 10 minutes to 30 hours.

Synthesis 1

The compounds (1A) and (2A) for use as starting materials in the process 1 mentioned above can be produced through each step of the following synthesis 1.

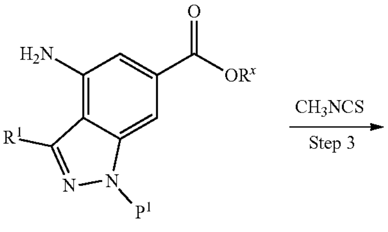

(1A)-1

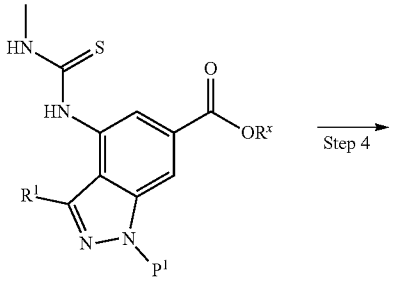

(1A)-2

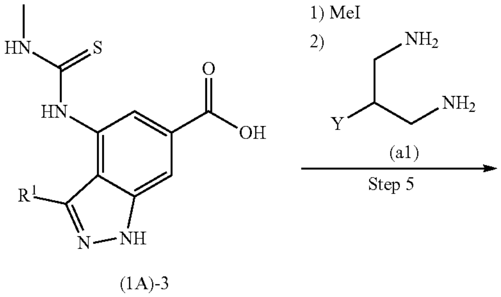

(1A)-3

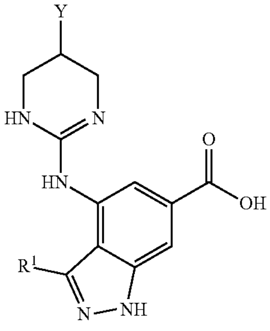

(1A)

-continued

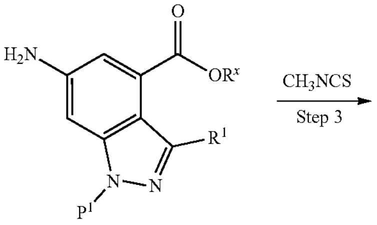

(2A)-1

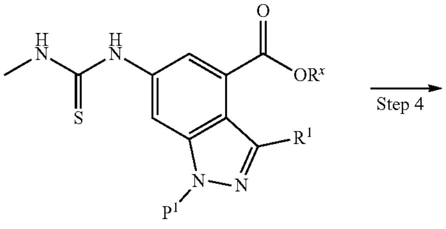

(2A)-2

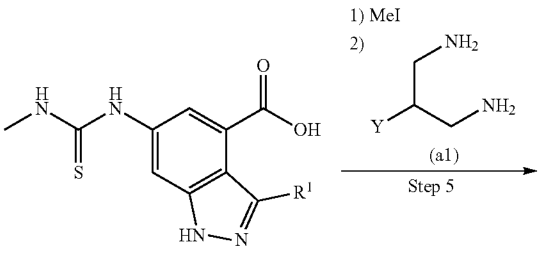

(2A)-3

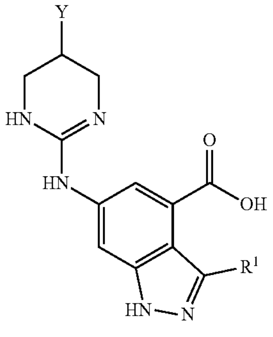

(2A)

In the formulas, $P^1$ represents a protective group such as a tetrahydropyranyl (THP) group.

In the formulas, $R^x$ is a hydrocarbon group having 1 to 6 carbon atoms, specifically, preferably a $C_1$-$C_6$ alkyl group.

In the following description about production methods, $P^1$ and $R^x$ are as defined above unless otherwise specified.

Step 3 of synthesis 1 is the step of reacting a compound (1A)-1 or (2A)-1 with methyl isothiocyanate in a solvent to obtain a compound (1A)-2 or (2A)-2.

The compound (1A)-1 or (2A)-1 is known in the art or may be produced from another compound known in the art. The compound can be produced, for example, in accordance with syntheses 3 and 4 mentioned later and the description of Examples of the present specification.

The solvent for use in step 3 of synthesis 1 is not particularly limited as long as the solvent dissolves the starting materials to some extent without inhibiting the reaction. Examples thereof include: amides such as N,N-dimethylformamide, N,N-dimethylacetamide, and N-methylpyrrolidone; halogenated hydrocarbons such as dichloromethane; esters such as ethyl acetate; hydrocarbons such as dichlorohexane and n-hexane; aromatic hydrocarbons such as toluene; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. N,N-Dimethylformamide, N-methylpyrrolidone, or methanol is preferred.

Step 3 of synthesis 1 may be performed, if necessary, in the presence of acetic acid.

The reaction temperature differs depending on the types, usages, etc. of the starting materials, the solvent, and the like, and is usually 0 °C to 150 °C, preferably 20 °C to 120 °C.

The reaction time differs depending on the reaction temperature, etc., and is usually 10 minutes to 72 hours, preferably 30 minutes to 48 hours.

Step 4 of synthesis 1 is the step of eliminating the protective group $P^1$ and the substituent $R^x$ in the compound (1A)-2 or (2A)-2 in a solvent to obtain a compound (1A)-3 or (2A)-3.

In step 4 of synthesis 1, the protective group $P^1$ may be eliminated first, or the substituent $R^x$ may be eliminated first.

When the protective group $P^1$ is, for example, a tetrahydropyranyl group, this group can be eliminated by preparing an acidic solution by the addition of an acid to a solution containing the compound (1A)-2 or (2A)-2.

Examples of the acid for use in the elimination of the protective group $P^1$ in step 4 of synthesis 1 include, but are not particularly limited to, hydrochloric acid, sulfuric acid, nitric acid, and trifluoroacetic acid (TFA). These acids may each be used singly or may be used in combination of two or more thereof. A method for adding the acid may involve adding the acid in the form of a solution containing the acid dissolved in a solvent mentioned later.

The solvent for use in the elimination of the protective group $P^1$ in step 4 of synthesis 1 is not particularly limited as long as the solvent dissolves the starting materials to some extent without inhibiting the reaction. Examples thereof include: water; amides such as N,N-dimethylformamide, N,N-dimethylacetamide, and N-methylpyrrolidone; halogenated hydrocarbons such as dichloromethane; aromatic hydrocarbons such as toluene; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Water, tetrahydrofuran, dichloromethane, 1,4-dioxane, methanol, or a mixed solvent prepared by mixing two or more of them is preferred.

The reaction temperature differs depending on the types, usages, etc. of the starting materials, the solvent, and the like, and is usually −20 °C to 150 °C, preferably 0 °C to 100 °C.

The reaction time differs depending on the reaction temperature, etc., and is usually 10 minutes to 24 hours, preferably 30 minutes to 10 hours.

The substituent $R^x$ can be eliminated by adding a base to a solution containing the compound (1A)-2 or (2A)-2.

Examples of the base for use in the elimination of the substituent $R^x$ in step 4 of synthesis 1 include alkali metal hydroxide such as lithium hydroxide, sodium hydroxide, and potassium hydroxide, and alkaline earth metal hydroxide such as calcium hydroxide and magnesium hydroxide. Alkali metal hydroxide is preferred, and lithium hydroxide or sodium hydroxide is more preferred. These bases may each be used singly or may be used in combination of two or more thereof. A method for adding the base may involve adding the base in the form of a solution containing the base dissolved in a solvent mentioned later.

The solvent for use in the elimination of the substituent $R^x$ in step 4 of synthesis 1 is not particularly limited as long as the solvent dissolves the starting materials to some extent without inhibiting the reaction. Examples thereof include: water; amides such as N,N-dimethylformamide, N,N-dimethylacetamide, and N-methylpyrrolidone; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Water, tetrahydrofuran, methanol, or a mixed solvent prepared by mixing two or more of them is preferred.

The reaction temperature differs depending on the types, usages, etc. of the starting materials, the solvent, and the like, and is usually −20 °C to 100 °C, preferably 0 °C to 50 °C.

The reaction time differs depending on the reaction temperature, etc., and is usually 10 minutes to 24 hours, preferably 30 minutes to 10 hours.

Step 5 of synthesis 1 is the step of reacting the compound (1A)-3 or (2A)-3 with methyl iodide (iodomethane) which is a methylating agent in reaction of the first stage and with diamine of the compound (a1) or an acid-addition salt, etc. thereof in reaction of the second stage in a solvent to obtain a compound (1A) or (2A).

The solvent for use at the first stage in step 5 of synthesis 1 is not particularly limited as long as the solvent dissolves the starting materials to some extent without inhibiting the reaction. Examples thereof include: amides such as N,N-dimethylformamide, N,N-dimethylacetamide, and N-methylpyrrolidone; halogenated hydrocarbons such as dichloromethane; esters such as ethyl acetate; hydrocarbons such as dichlorohexane and n-hexane; aromatic hydrocarbons such as toluene; ethers such as tetrahydrofuran, diethyl ether, cyclopentyl methyl ether, 1,4-dioxane, and tert-butyl methyl ether; and arbitrary mixed solvents thereof. N,N-Dimethylformamide or N-methylpyrrolidone is preferred.

The reaction temperature differs depending on the types, usages, etc. of the starting materials, the solvent, and the like, and is usually 0 °C to 150 °C, preferably 10 °C to 120 °C, more preferably 20 °C to 50 °C.

The reaction time differs depending on the reaction temperature, etc., and is usually 1 minute to 48 hours, preferably 10 minutes to 24 hours.

At the second stage in step 5 of synthesis 1, a compound (1A) or (2A) is produced through reaction with diamine of the compound (a1) or an acid-addition salt, etc. thereof in the presence or absence of water. The compound (a1) may be an acid-addition salt, etc. Examples of the acid-addition salt, etc. include hydrochloride, sulfate, and acetate.

The reaction temperature differs depending on the types, usages, etc. of the starting materials, the solvent, and the like, and is usually 0 °C to 150 °C, preferably 20 °C to 120 °C.

The reaction time differs depending on the reaction temperature, etc., and is usually 10 minutes to 48 hours, preferably 30 minutes to 24 hours.

Both the protective group $P^1$ and the substituent $R^x$ in the compound (1A)-2 or (2A)-2 are eliminated in a solvent in step 4 of synthesis 1, and then, step 5 is performed to produce a compound (1A) or (2A). Alternatively, as shown below, the substituent $R^x$ in the compound (1A)-2 may be eliminated to prepare a compound (1A)-3' (step 4a), followed by the step 5 mentioned above to prepare a compound (1A)-4, and then, the protective group $P^1$ can be eliminated to produce a compound (1A) (step 4b). The compound (2A) can also be produced by the same scheme as described below.

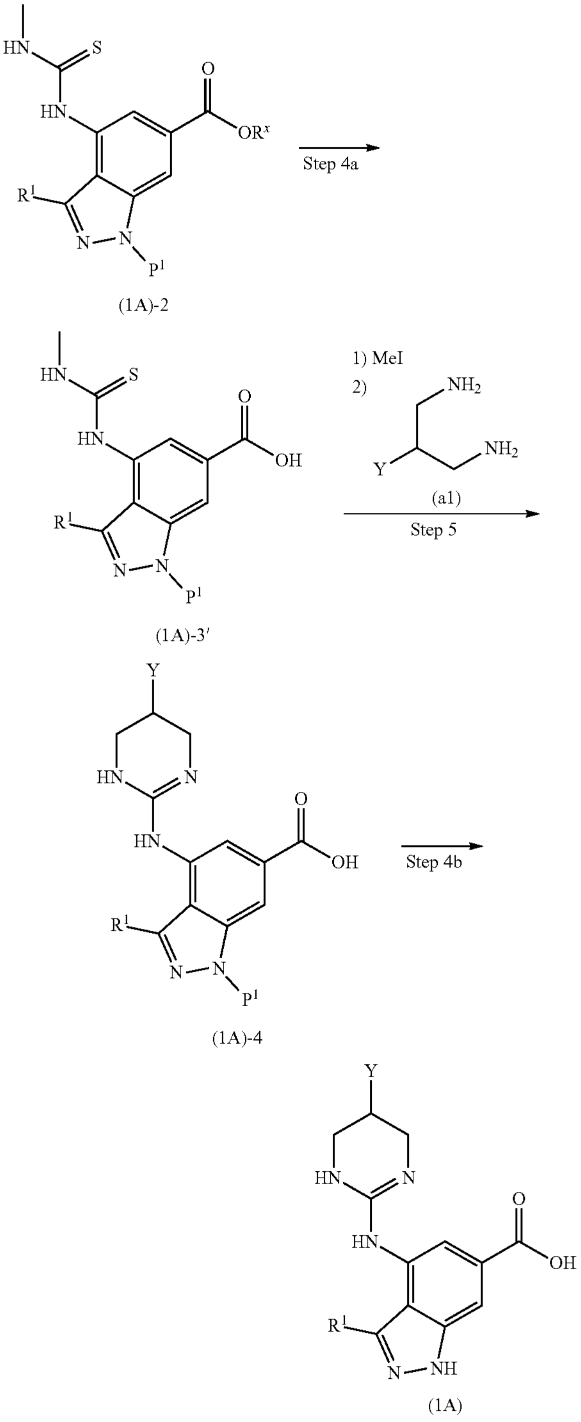

(1A)-2

(1A)-3'

(a1)

(1A)-4

(1A)

In the scheme, the same methods as in step 4 can be applied to a method for eliminating the substituent $R^x$ in step 4a, and a method for eliminating the protective group $P^1$ in step 4b.

Synthesis 2

In synthesis 1, the compound (1A) or (2A) is produced using the compound (1A)-1 or (2A)-1 in which the amino group of the 5-membered heterocyclic ring is protected with the protective group $P^1$. This compound may be produced using a compound that is not protected with the protective group $P^1$.

For example, the compound (1A) may be produced through each step of synthesis 2 given below using a compound (1A)-1'. The compound (2A) can also be produced by the same scheme as in the following synthesis 2.

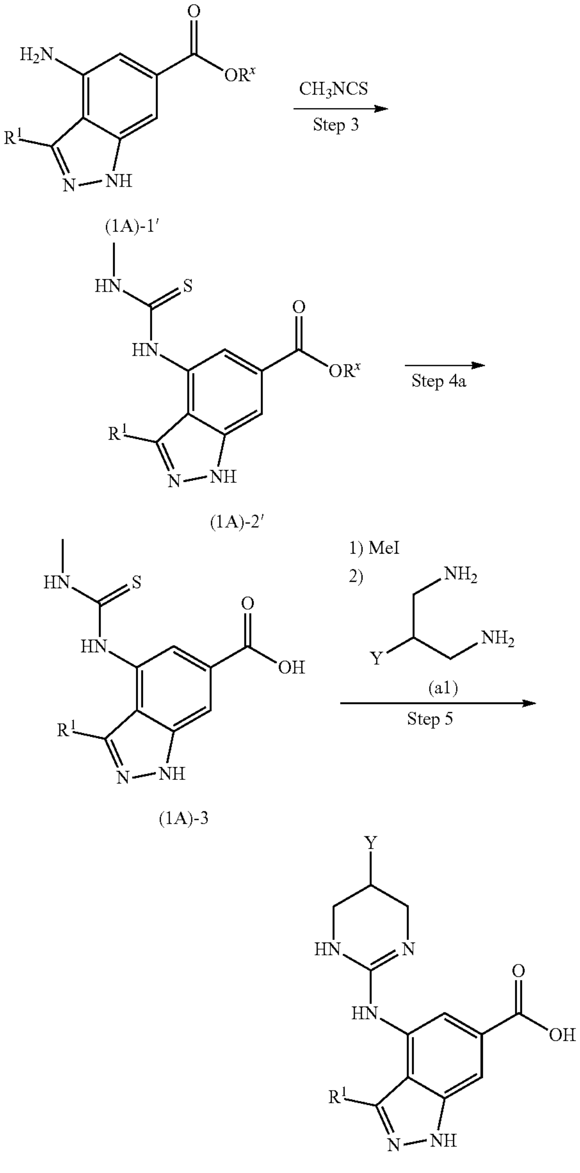

(1A)-1'

(1A)-2'

(1A)-3

(1A)

Step 3 and step 5 of synthesis 2 are the same as step 3 and step 5 of synthesis 1.

Step 4a of synthesis 2 is the step of eliminating the substituent $R^x$ in the compound (1A)-2' or (2A)-2' in a solvent to obtain a compound (1A)-3 or (2A)-3. Unlike step 4 of synthesis 1, only the operation of eliminating the substituent $R^x$ is performed in step 4a of synthesis 2.

The substituent $R^x$ can be eliminated by adding a base, as in the method for eliminating the substituent $R^x$ in step 4 of the synthesis 1 mentioned above. The type of the base for use in step 4a of synthesis 2 and a method for adding the base are the same as in the method for eliminating the substituent $R^x$ in step 4 of the synthesis 1 mentioned above.

Synthesis 3

The compound (1A)-1 for use as a starting material in the synthesis 1 mentioned above can be produced through steps 6 to 8 of synthesis 3 given below. The compound (2A)-1 can also be produced by the same scheme as in the following synthesis 3.

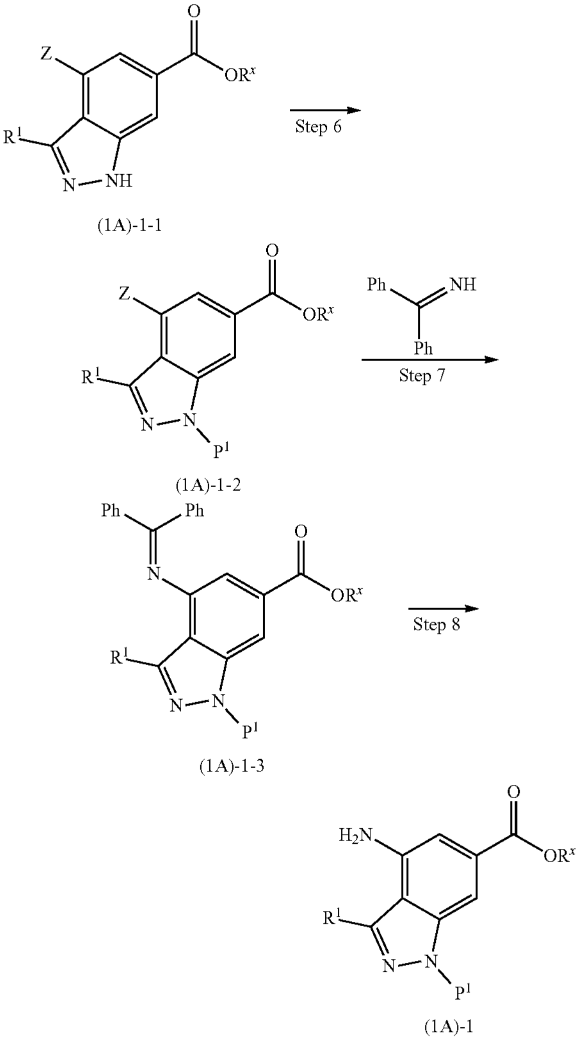

(1A)-1-1

(1A)-1-2

(1A)-1-3

(1A)-1

In the formulas, Z is a chlorine atom, a bromine atom, or an iodine atom.

Step 6 of synthesis 3 is the step of introducing the protective group $P^1$ to the amino structure moiety of the 5-membered heterocyclic ring of a compound (1A)-1-1 in a solvent to obtain a compound (1A)-1-2. The compound (1A)-1-1 is known in the art or may be produced from another compound known in the art.

A method known in the art can be used as a method for introducing the protective group $P^1$. The method can be performed in accordance with, for example, a method described in Org. Biomol. Chem., 2017, 15, 8614-8626, or J. Org. Chem., 2015, 80, 7713-7726. Specifically, the protective group can be introduced to the amino structure moiety using a compound corresponding to the protective group to be introduced.

When the protective group $P^1$ is, for example, a tetrahydropyranyl group, the tetrahydropyranyl group can be introduced to the amino structure moiety of the 5-membered heterocyclic ring through reaction with dihydropyran (DHP) in the presence of an acid catalyst (p-toluenesulfonic acid, etc.).

The solvent for use in step 6 of synthesis 3 is not particularly limited as long as the solvent dissolves the starting materials to some extent without inhibiting the reaction. Examples thereof include: amides such as N,N-dimethylformamide, N,N-dimethylacetamide, and N-methylpyrrolidone; halogenated hydrocarbons such as dichloromethane; esters such as ethyl acetate; hydrocarbons such as dichlorohexane and n-hexane; aromatic hydrocarbons such as toluene and xylene; ethers such as tetrahydrofuran, diethyl ether, cyclopentyl methyl ether, 1,4-dioxane, and tert-butyl methyl ether; and arbitrary mixed solvents thereof. Dichloromethane, toluene, xylene, or tetrahydrofuran is preferred.

The reaction temperature differs depending on the types, usages, etc. of the starting materials, the solvent, and the like, and is usually 0 °C to 150 °C, preferably 0 °C to 50 °C.

The reaction time differs depending on the reaction temperature, etc., and is usually 10 minutes to 48 hours, preferably 30 minutes to 24 hours.

Step 7 of synthesis 3 is the step of reacting the compound (1A)-1-2 with benzophenone imine in the presence of a catalyst in a solvent under a stream of an inert gas to obtain a compound (1A)-1-3.

Examples of the catalyst for use in step 7 of synthesis 3 include organic palladium complexes such as tris(dibenzylideneacetone)dipalladium and palladium acetate.

In step 7 of synthesis 3, the reaction may be performed in the presence of a ligand or may be performed in the absence of a ligand.

Examples of the ligand for use in step 7 of synthesis 3 include 4,5'-bis(diphenylphosphino)-9,9'-dimethylxanthene (Xantphos) and 2,2'-bis(diphenylphosphino)-1,1'-binaphthyl (BINAP).

In step 7 of synthesis 3, the reaction may be performed in the presence of a base or may be performed in the absence of a base.

Examples of the base for use in step 7 of synthesis 3 include: alkali metal carbonate such as cesium carbonate, potassium carbonate, sodium carbonate, and sodium bicarbonate; alkali metal phosphate such as tribasic potassium phosphate, sodium phosphate, and sodium biphosphate; alkali metal fluoride such as cesium fluoride and potassium fluoride; alkylamines such as triethylamine and N,N-diisopropylethylamine; pyridines such as pyridine and 4-dimethylaminopyridine; and 1,8-diazabicyclo[5.4.0]-7-undecene. Alkali metal carbonate is preferred, and cesium carbonate is more preferred. These bases may each be used singly or may be used in combination of two or more thereof. A method for adding the base may involve adding the base in the form of a solution containing the base dissolved in a solvent mentioned later.

The solvent for use in step 7 of synthesis 3 is not particularly limited as long as the solvent dissolves the starting materials to some extent without inhibiting the reaction. Examples thereof include: water; amides such as N,N-dimethylformamide, N,N-dimethylacetamide, and N-methylpyrrolidone; halogenated hydrocarbons such as dichloromethane; esters such as ethyl acetate; hydrocarbons such as dichlorohexane and n-hexane; aromatic hydrocarbons such as toluene and xylene; ethers such as tetrahydrofuran, diethyl ether, cyclopentyl methyl ether, 1,4-dioxane, and tert-butyl methyl ether; and arbitrary mixed solvents thereof. Toluene, xylene, or 1,4-dioxane is preferred.

Examples of the inert gas used include nitrogen gas and argon gas.

The reaction temperature differs depending on the types, usages, etc. of the starting materials, the solvent, and the like, and is usually 50 °C to 250 °C, preferably 70 °C to 200 °C.

The reaction time differs depending on the reaction temperature, etc., and is usually 1 hour to 48 hours, preferably 3 hours to 24 hours.

Step 8 of synthesis 3 is the step of obtaining a compound (1A)-1 from the compound (1A)-1-3.

A method for obtaining the compound (1A)-1 in step 8 can involve obtaining the compound (1A)-1 through the reductive reaction of the compound (1A)-1-3 in the presence of a metal catalyst and in the presence of hydrogen gas in a solvent.

Examples of the metal catalyst for use in step 8 of synthesis 3 include inhomogeneous catalysts such as Pd—C catalysts, palladium hydroxide catalysts, Pt—C catalysts, and platinum oxide catalysts.

The solvent for use in step 8 of synthesis 3 is not particularly limited as long as the solvent dissolves the starting materials to some extent without inhibiting the reaction. Examples thereof include: water; acetic acid; amides such as N,N-dimethylformamide, N,N-dimethylacetamide, and N-methylpyrrolidone; esters such as ethyl acetate; hydrocarbons such as dichlorohexane and n-hexane; aromatic hydrocarbons such as toluene and xylene; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Ethyl acetate, tetrahydrofuran, or methanol is preferred.

The reaction temperature differs depending on the types, usages, etc. of the starting materials, the solvent, and the like, and is usually 0 °C to 150 °C, preferably 20 °C to 100 °C.

The reaction time differs depending on the reaction temperature, etc., and is usually 10 minutes to 120 hours, preferably 30 minutes to 48 hours.

In step 8, the compound (1A)-1 may be obtained by hydrolyzing the compound (1A)-1-3 by the addition of an acid (e.g., citric acid) solution to a solution containing the compound (1A)-1-3.

The solvent for use in step 8 of synthesis 3 is not particularly limited as long as the solvent dissolves the starting materials to some extent without inhibiting the reaction. Examples thereof include: water; amides such as N,N-dimethylformamide, N,N-dimethylacetamide, and N-methylpyrrolidone; esters such as ethyl acetate; hydrocarbons such as dichlorohexane and n-hexane; aromatic hydrocarbons such as toluene and xylene; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Tetrahydrofuran is preferred.

The reaction temperature differs depending on the types, usages, etc. of the starting materials, the solvent, and the like, and is usually 0 °C to 200 °C, preferably 0 °C to 100 °C.

The reaction time differs depending on the reaction temperature, etc., and is usually 10 minutes to 120 hours, preferably 30 minutes to 48 hours.

Synthesis 4

The compound (1A)-1 for use as a starting material in the synthesis 1 mentioned above may be produced through each step of synthesis 4 given below using a compound (1A)-1-4 given below, in addition to the synthesis 3 mentioned above. The compound (2A)-1 can also be produced by the same scheme as in the following synthesis 4.

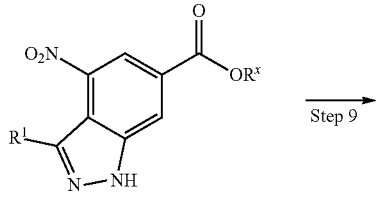

(1A)-1-4

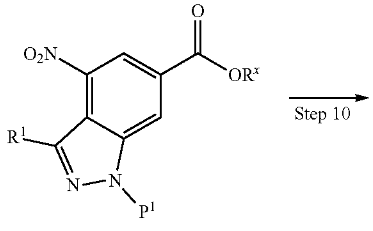

(1A)-1-2

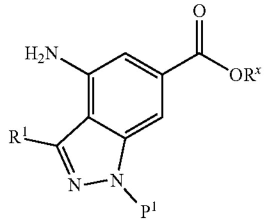
(1A)-1

Step 9 of synthesis 4 is the step of introducing the protective group $P^1$ to the amino structure moiety of the 5-membered heterocyclic ring of a compound (1A)-1-4 in a solvent to obtain a compound (1A)-1-5. The compound (1A)-1-4 is known in the art or may be produced from another compound known in the art. The same method as in step 6 of the synthesis 3 mentioned above can be adopted as a method for introducing the protective group $P^1$ in step 9. The solvent used is also the same as that used in step 6 of synthesis 3.

Step 10 of synthesis 4 is the step of reducing the nitro group of the compound (1A)-1-5 into an amino group to obtain a compound (1A)-1.

In step 10 of synthesis 4, a method for reducing the nitro group of the compound (1A)-1-5 into an amino group to obtain a compound (1A)-1 can involve reducing the nitro group of the compound (1A)-1-5 into an amino group through the reductive reaction of the compound (1A)-1-5 in the presence of a reducing agent such as sodium dithionite in a solvent to obtain a compound (1A)-1.

The solvent for use in step 10 of synthesis 4 using a reducing agent is not particularly limited as long as the solvent dissolves the starting materials to some extent without inhibiting the reaction. Examples thereof include: water; acetic acid; amides such as N,N-dimethylformamide, N,N-dimethylacetamide, and N-methylpyrrolidone; esters such as ethyl acetate; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Water or ethanol is preferred.

The reaction temperature differs depending on the types, usages, etc. of the starting materials, the solvent, and the like, and is usually 0 °C to 200 °C, preferably 50 °C to 150 °C.

The reaction time differs depending on the reaction temperature, etc., and is usually 10 minutes to 48 hours, preferably 30 minutes to 24 hours.

In step 10, the compound (1A)-1 may be obtained by reducing the nitro group of compound (1A)-1-5 into an amino group through the reductive reaction of the compound (1A)-1-5 in the presence of a metal catalyst and in the presence of hydrogen gas in a solvent.

In this case, examples of the metal catalyst used include inhomogeneous catalysts such as Pd—C catalysts, palladium hydroxide catalysts, Pt—C catalysts, and platinum oxide catalysts.

The solvent for use in step 10 of synthesis 4 using a metal catalyst is not particularly limited as long as the solvent dissolves the starting materials to some extent without inhibiting the reaction. Examples thereof include: water; acetic acid; amides such as N,N-dimethylformamide, N,N-dimethylacetamide, and N-methylpyrrolidone; esters such as ethyl acetate; ethers such as tetrahydrofuran, diethyl ether, cyclopentyl methyl ether, 1,4-dioxane, and tert-butyl methyl ether; alcohols such as methanol, ethanol, n-propanol, and isopropanol; nitriles such as acetonitrile and propionitrile; and arbitrary mixed solvents thereof. Acetic acid or tetrahydrofuran is preferred.

The reaction temperature differs depending on the types, usages, etc. of the starting materials, the solvent, and the like, and is usually 0 °C to 200 °C, preferably 20 °C to 100 °C.

The reaction time differs depending on the reaction temperature, etc., and is usually 10 minutes to 48 hours, preferably 30 minutes to 24 hours.

Synthesis 5

A compound (4)-S which is an S form of the compound (4) for use as a starting material in the process 1 mentioned above, wherein R is a $C_1$-$C_6$ alkyl group can be produced through steps 11 to 13 of synthesis 5 given below. The compound (4)-S is included in the compound (4).

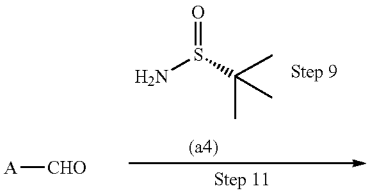

(4)-1

-continued

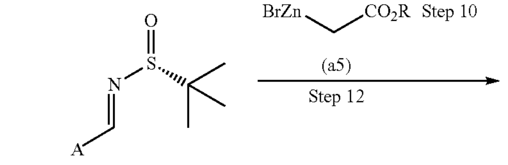

(4)-S-1

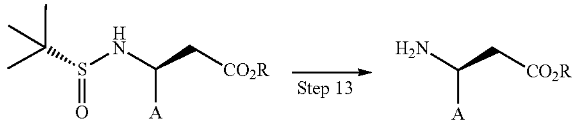

(4)-S-2 (4)-S

Step 11 of synthesis 5 is the step of reacting a compound (4)-1 with (R)-2-methylpropane-2-sulfinamide of a compound (a4) in the presence of pyrrolidine and a molecular sieve (4 angstroms) in a solvent to obtain a compound (4)-S-1.

The solvent for use in step 11 of synthesis 5 is not particularly limited as long as the solvent dissolves the starting materials to some extent without inhibiting the reaction. Examples thereof include: halogenated hydrocarbons such as dichloromethane (DCM); aromatic hydrocarbons such as toluene and xylene; ethers such as tetrahydrofuran, diethyl ether, cyclopentyl methyl ether, 1,4-dioxane, and tert-butyl methyl ether; and arbitrary mixed solvents thereof. Toluene or tetrahydrofuran is preferred.

The reaction temperature differs depending on the types, usages, etc. of the starting materials, the solvent, and the like, and is usually −20 °C to 150 °C, preferably 0 °C to 120 °C.

The reaction time differs depending on the reaction temperature, etc., and is usually 10 minutes to 48 hours, preferably 30 minutes to 24 hours.

Step 12 of synthesis 5 is the step of reacting the compound (4)-S-1 with a compound (a5) in a solvent to obtain a compound (4)-S-2.

The compound (a5) used is a compound corresponding to R of the compound (4)-S of interest. The compound (a5) is known in the art, or can be produced from a compound known in the art in accordance with the description of Examples of the present specification mentioned later.

Specific examples of the compound (a5) include (2-methoxy-2-oxoethyl)zinc(II) bromide, (2-ethoxy-2-oxoethyl)zinc(II) bromide, (2-isopropoxy-2-oxoethyl)zinc(II) bromide, and [2-(tert-butoxy)-2-oxoethyl]zinc(II) bromide.

The solvent for use in step 12 of synthesis 5 is not particularly limited as long as the solvent dissolves the starting materials to some extent without inhibiting the reaction. Examples thereof include: halogenated hydrocarbons such as dichloromethane (DCM); aromatic hydrocarbons such as toluene; ethers such as tetrahydrofuran, diethyl ether, cyclopentyl methyl ether, 1,4-dioxane, and tert-butyl methyl ether; and arbitrary mixed solvents thereof. Tetrahydrofuran is preferred.

The reaction temperature differs depending on the types, usages, etc. of the starting materials, the solvent, and the like, and is usually −78 °C to 100 °C, preferably −20 °C to 50 °C.

The reaction time differs depending on the reaction temperature, etc., and is usually 10 minutes to 48 hours, preferably 30 minutes to 24 hours.

Step 13 of synthesis 5 is the step of reacting the compound (4)-S-2 with an acid in a solvent to obtain a compound (4)-S.

Examples of the acid for use in step 13 of synthesis 5 include: organic acids such as acetic acid, formic acid, trifluoroacetic acid, and p-toluenesulfonic acid; and inorganic acids such as hydrochloric acid, hydrobromic acid, and sulfuric acid. Hydrochloric acid is preferred. These acids may each be used singly or may be used in combination of two or more thereof. A method for adding the acid may involve adding the acid in the form of a solution containing the acid dissolved in a solvent mentioned later.

The solvent for use in step 13 of synthesis 5 is not particularly limited as long as the solvent dissolves the starting materials to some extent without inhibiting the reaction. Examples thereof include: water; alcohols such as methanol and ethanol; halogenated hydrocarbons such as dichloromethane (DCM); aromatic hydrocarbons such as toluene; ethers such as tetrahydrofuran, diethyl ether, cyclopentyl methyl ether, 1,4-dioxane, and tert-butyl methyl ether; and arbitrary mixed solvents thereof. An ether, an alcohol or an arbitrary mixed solvent thereof is preferred.

The reaction temperature differs depending on the types, usages, etc. of the starting materials, the solvent, and the like, and is usually −20 °C to 100 °C, preferably 0 °C to 50 °C.

The reaction time differs depending on the reaction temperature, etc., and is usually 1 minute to 48 hours, preferably 10 minutes to 24 hours.

The compound (4)-S thus obtained may be an acid-addition salt, etc. Examples of the acid-addition salt, etc. include hydrochloride, sulfate, and acetate.

As described above, the compound (4)-S can be synthesized through steps 11 to 13 of synthesis 5. An asymmetric compound opposite to the compound (4)-S can be synthesized through steps 11 to 13 using, for example, (S)-2-methylpropane-2-sulfinamide, instead of the compound (a4). Further, a racemate of the compound (4)-S can be synthesized through steps 11 to 13 using, for example, racemic 2-methylpropane-2-sulfinamide, instead of the compound (a4).

Synthesis 6

The compound (3) for use as a starting material in the process 1 mentioned above, wherein R is a $C_1$-$C_6$ alkyl group can be produced through steps 14 and 15 of the following synthesis 6.

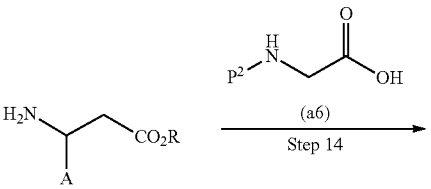

(4)

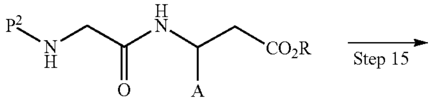

(3)-1

-continued

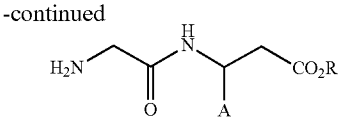

(3)

Step 14 of synthesis 6 is the step of reacting the compound (4) obtained by a method such as synthesis 5 or an acid-addition salt, etc. thereof with a compound (a6) in the presence of a dehydration-condensation agent in a solvent to obtain a compound (3)-1.

In the formulas, $P^2$ represents a protective group such as a t-butoxycarbonyl group (Boc).

Examples of the dehydration-condensation agent for use in step 14 of synthesis 6 include dicyclohexylcarbodiimide (DCC), N,N'-diisopropylcarbodiimide (DIC), 1-(3-dimethylaminopropyl)-3-ethylcarbodiimide or hydrochloride thereof (EDC, EDAC), N,N-dicyclohexylamide, 1-hydroxybenzotriazole, carbonyldiimidazole, 1H-benzotriazol-1-yloxytris(dimethylamino)phosphonium hexafluorophosphate, and Q-(7-azabenzotriazol-1-yl)-1,1,3,3-tetramethyluronium hexafluorophosphate. 1-(3-Dimethylaminopropyl)-3-ethylcarbodiimide or hydrochloride thereof (EDC, EDAC) is preferred.

In step 14 of synthesis 6, the reaction may be performed in the presence of a base or may be performed in the absence of a base.

Examples of the base for use in step 14 of synthesis 6 include N,N-diisopropylethylamine, N-methylmorpholine, triethylamine, 4-(N,N-dimethylamino)pyridine, and N-ethyl-N-isopropylpropan-2-amine. N,N-Diisopropylethylamine or triethylamine is preferred. These bases may each be used singly or may be used in combination of two or more thereof. A method for adding the base may involve adding the base in the form of a solution containing the base dissolved in a solvent mentioned later.

The solvent for use in step 14 of synthesis 6 is not particularly limited as long as the solvent dissolves the starting materials to some extent without inhibiting the reaction. Examples thereof include: amides such as N,N-dimethylformamide (DMF), N,N-dimethylacetamide, and N-methylpyrrolidone; halogenated hydrocarbons such as dichloromethane (DCM); esters such as ethyl acetate; hydrocarbons such as dichlorohexane and n-hexane; aromatic hydrocarbons such as toluene; ethers such as tetrahydrofuran, diethyl ether, cyclopentyl methyl ether, 1,4-dioxane, and tert-butyl methyl ether; and arbitrary mixed solvents thereof. Dichloromethane is preferred.

The reaction temperature differs depending on the types, usages, etc. of the starting materials, the solvent, and the like, and is usually −20 °C to 100 °C, preferably 0 °C to 50 °C.

The reaction time differs depending on the reaction temperature, etc., and is usually 10 minutes to 72 hours, preferably 30 minutes to 48 hours.

Step 15 of synthesis 6 is the step of deprotecting the protective group $P^2$ from the compound (3)-1 using an acid in a solvent to obtain a compound (3).

Examples of the acid for use in step 15 of synthesis 6 include: organic acids such as acetic acid, formic acid, trifluoroacetic acid, and p-toluenesulfonic acid; and inorganic acids such as hydrochloric acid, hydrobromic acid, and sulfuric acid. Hydrochloric acid is preferred. These acids may each be used singly or may be used in combination of two or more thereof. A method for adding the acid may involve adding the acid in the form of a solution containing the acid dissolved in a solvent mentioned later.

The solvent for use in step 15 of synthesis 6 is not particularly limited as long as the solvent dissolves the starting materials to some extent without inhibiting the reaction. Examples thereof include: water; alcohols such as methanol and ethanol; halogenated hydrocarbons such as dichloromethane (DCM); aromatic hydrocarbons such as benzene, toluene, and xylene; ethers such as tetrahydrofuran, diethyl ether, cyclopentyl methyl ether, 1,4-dioxane, and tert-butyl methyl ether; nitriles such as acetonitrile and propionitrile; and arbitrary mixed solvents thereof. An ether, an alcohol or an arbitrary mixed solvent thereof is preferred.

The reaction temperature differs depending on the types, usages, etc. of the starting materials, the solvent, and the like, and is usually −20 °C to 100 °C, preferably 0 °C to 50 °C.

The reaction time differs depending on the reaction temperature, etc., and is usually 10 minutes to 72 hours, preferably 30 minutes to 48 hours.

The compound (3) thus obtained may be an acid-addition salt, etc. Examples of the acid-addition salt, etc. include hydrochloride, sulfate, and acetate.

In the present specification, the obtained compound in each step may be isolated or purified by an approach known in the art or may be subjected directly to a subsequent step. The isolation or the purification can be carried out by use of a usual operation, for example, filtration, extraction, crystallization, or each column chromatography.

Intermediate of Present Invention

In one embodiment of the present invention, compounds given below which are intermediates of the compound (I) or (II) or a pharmaceutically acceptable salt thereof are also included in the present invention.

In one embodiment, examples of the intermediate of the present invention include compounds represented by the following general formula (X-1) or (X-2) and salts thereof:

(X-1)

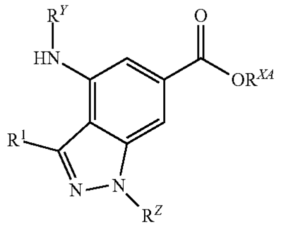

(X-2)

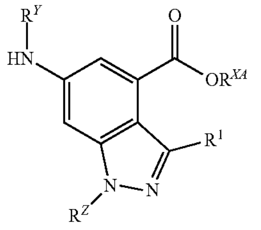

In the formulas (X-1) and (X-2), RY is a group represented by the following formula (x)-i or (x)-ii:

(x)-i

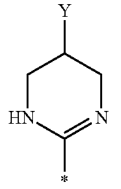

(x)-ii

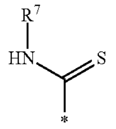

wherein Y is a hydrogen atom, a fluorine atom or a hydroxy group, as in the general formulas (I) and (II), $R^7$ is a $C_1$-$C_6$ alkyl group, and * represents a binding position.

$R^1$ is a hydrogen atom or a halogen atom, as in the general formulas (I) and (II).

$R^{XA}$ is a hydrogen atom or a hydrocarbon group having 1 to 6 carbon atoms and is preferably a hydrogen atom or a $C_1$-$C_6$ alkyl group.

$R^Z$ is a hydrogen atom or $P^1$ (wherein $P^1$ represents, as mentioned above, a protective group such as a tetrahydropyranyl (THP) group).

In one embodiment, RY in the general formula (X-1) is a group represented by the formula (x)-i.

In one embodiment, RY in the general formula (X-1) is a group represented by the formula (x)-ii.

In one embodiment, RY in the general formula (X-2) is a group represented by the formula (x)-i.

In one embodiment, RY in the general formula (X-2) is a group represented by the formula (x)-ii.

In one embodiment, examples of the intermediate of the present invention include compounds represented by the following general formula (X-1-1) or (X-2-1) and salts thereof:

(X-1-1)

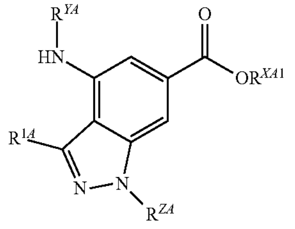

(X-2-1)

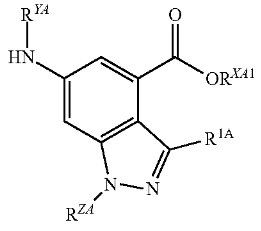

In the formulas (X-1-1) and (X-2-1), $R^{YA}$ is a group represented by the following formula (x)-i-1, (x)-i-2, (x)-i-3, or (x)-ii-1:

(x)-i-1

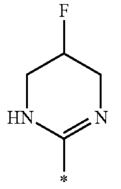

(x)-i-2

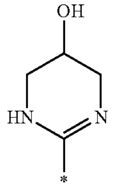

(x)-i-3

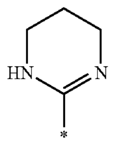

(x)-ii-1

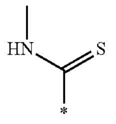

wherein * represents a binding position.

$R^{1A}$ is a hydrogen atom, a fluorine atom, or a chlorine atom.

$R^{XA1}$ is a hydrogen atom or a methyl group.

$R^{ZA}$ is a hydrogen atom or a tetrahydropyranyl (THP) group.

In one embodiment, $R^{YA}$ in the general formula (X-1-1) is a group represented by the formula (x)-i-1, the formula (x)-i-2, or the formula (x)-i-3.

In one embodiment, $R^{YA}$ in the general formula (X-1-1) is a group represented by the formula (x)-ii-1.

In one embodiment, $R^{YA}$ in the general formula (X-2-1) is a group represented by the formula (x)-i-1, the formula (x)-i-2, or the formula (x)-i-3.

In one embodiment, $R^{YA}$ in the general formula (X-2-1) is a group represented by the formula (x)-ii-1.

In one embodiment, examples of the intermediate of the present invention include compounds selected from the following group and salts thereof:

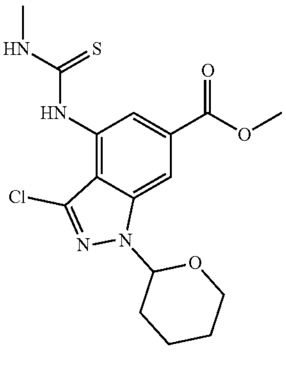

-continued
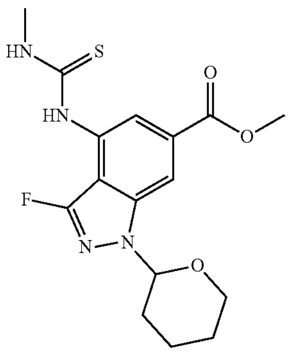
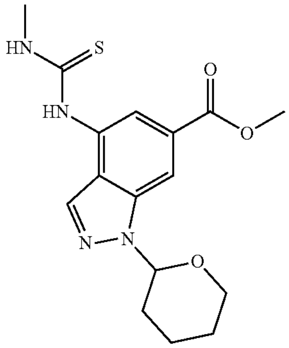
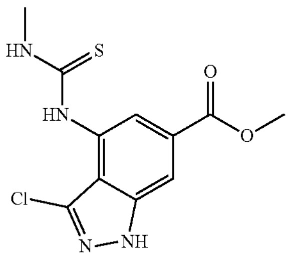
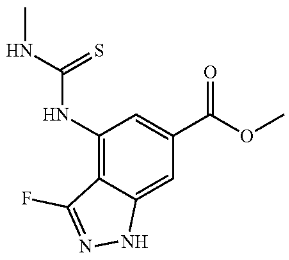
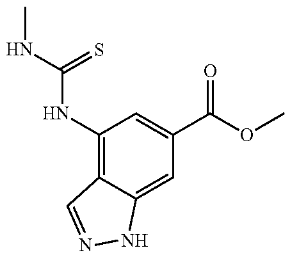
-continued
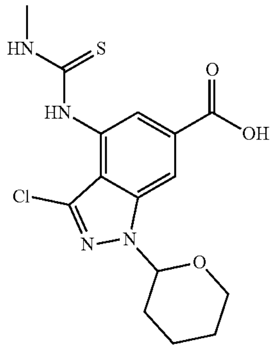
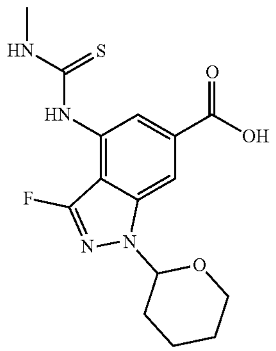
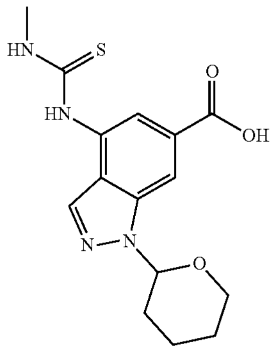
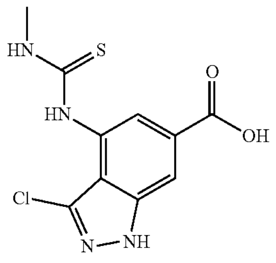
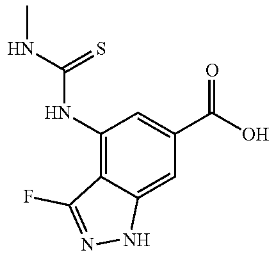

-continued
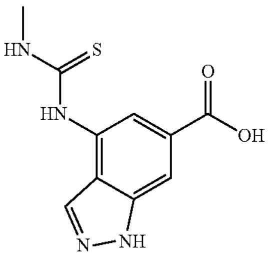
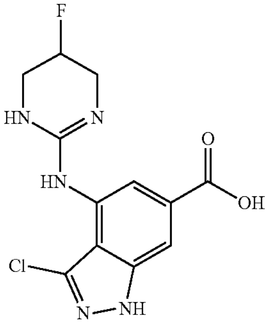
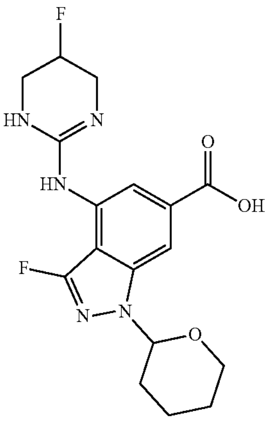
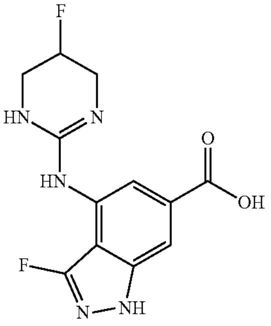
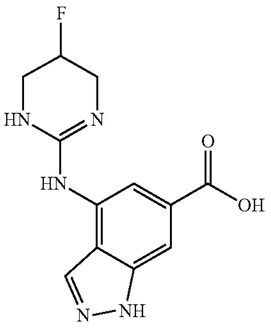
-continued
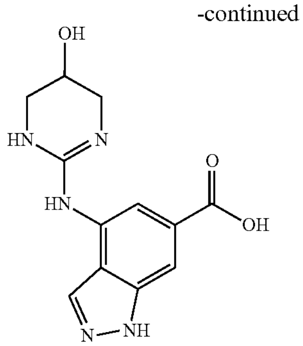
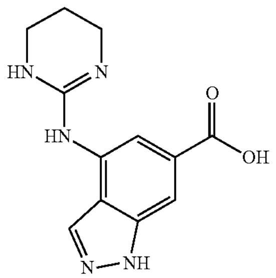
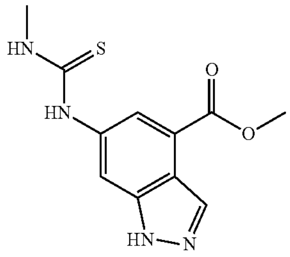
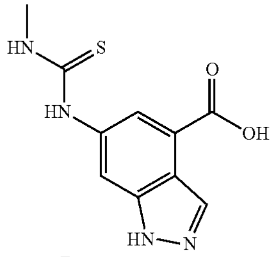
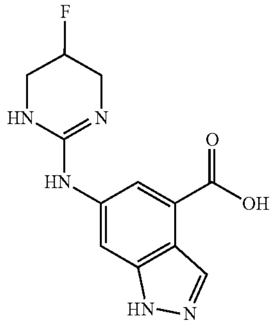
In one embodiment, the intermediate of the present invention is a compound selected from the following group or a salt thereof:

-continued
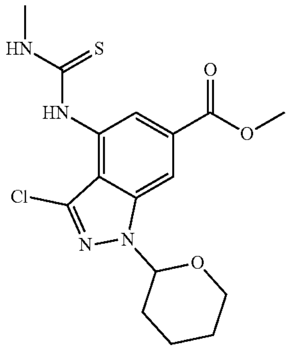
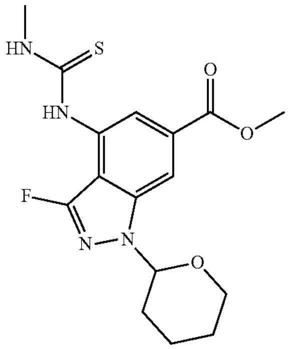
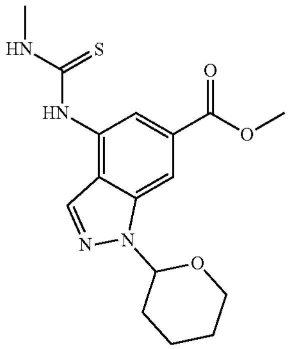
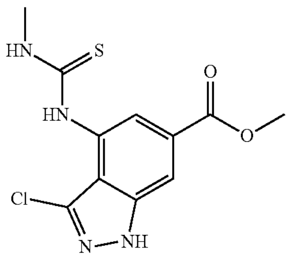
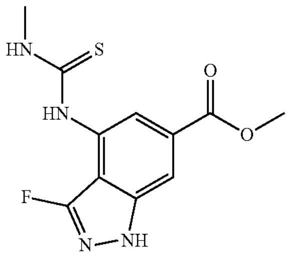
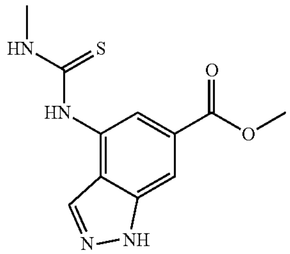
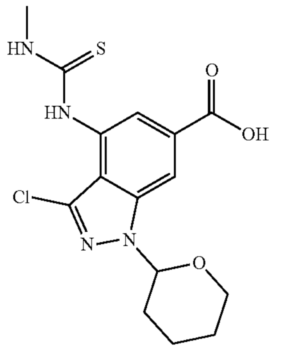
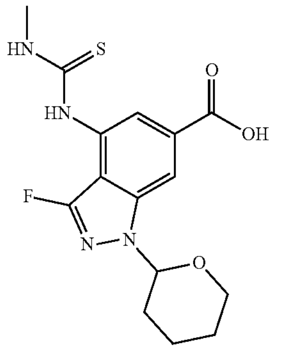
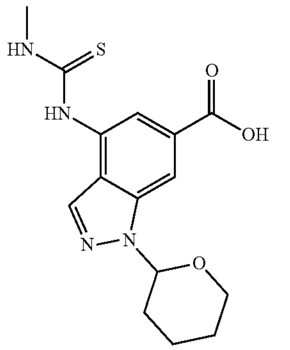
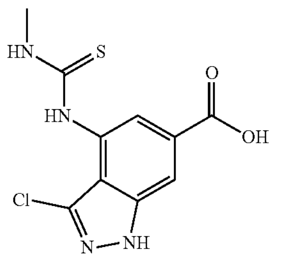

-continued
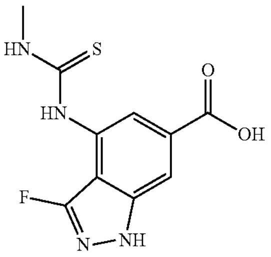
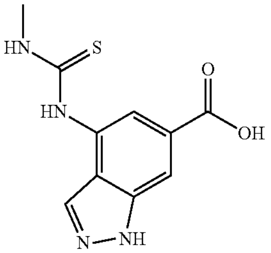
In one embodiment, the intermediate of the present invention is a compound selected from the following group or a salt thereof:
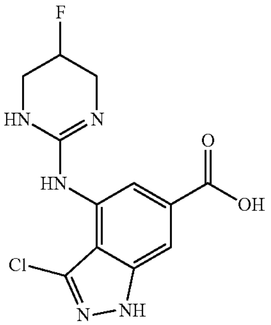
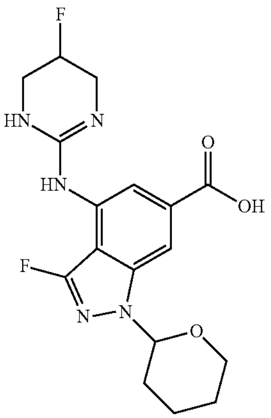
-continued
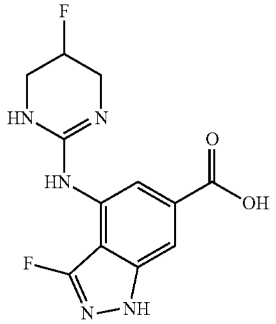
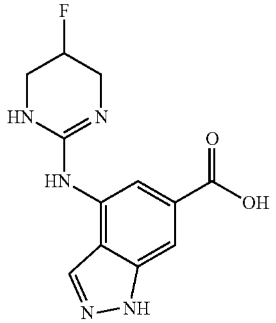
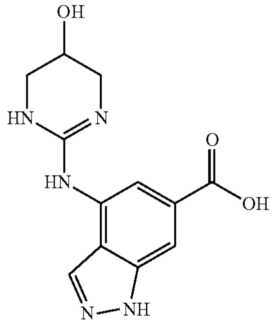
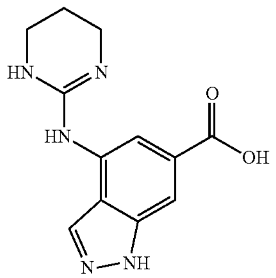
In one embodiment, the intermediate of the present invention is a compound selected from the following group or a salt thereof:
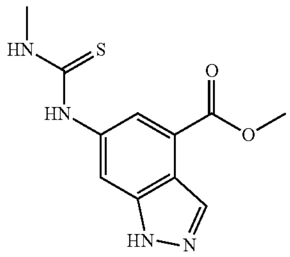

-continued

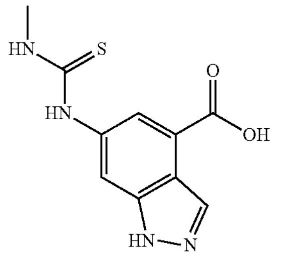

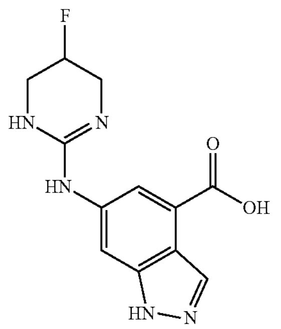

In another embodiment, examples of the intermediate of the present invention include compounds represented by the following general formula (X-3) and salts thereof:

(X-3)

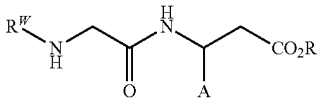

In the formula (X-3), A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, as in the general formulas (I) and (II).

R is a hydrogen atom or a $C_1$-$C_6$ alkyl group, as in the general formulas (I) and (II).

$R^W$ is a hydrogen atom or $P^2$, wherein $P^2$ represents, as mentioned above, a protective group such as a t-butoxycarbonyl group (Boc).

In one embodiment, examples of the intermediate of the present invention include compounds represented by the following general formula (X-3-1) and salts thereof:

(X-3-1)

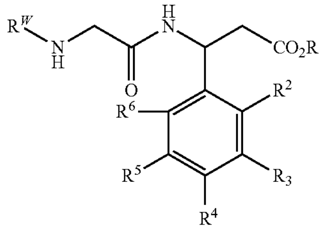

In the formula (X-3-1),

- $R^2$ is a hydrogen atom or a halogen atom,
- $R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group,
- $R^4$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group,
- $R^5$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group,
- $R^6$ is a hydrogen atom or a halogen atom,
- R is a hydrogen atom or a $C_1$-$C_6$ alkyl group, as in the general formulas (I) and (II), and
- $R^W$ is a hydrogen atom or $P^2$ (wherein $P^2$ represents, as mentioned above, a protective group such as a t-butoxycarbonyl group (Boc)).

In one embodiment, examples of the intermediate of the present invention include compounds represented by the following general formula (X-3-2) and salts thereof:

(X-3-2)

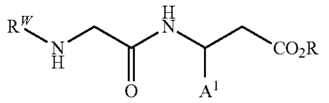

R is a hydrogen atom or a $C_1$-$C_6$ alkyl group, as in the general formulas (I) and (II).

$R^W$ is a hydrogen atom or $P^2$ (wherein $P^2$ represents, as mentioned above, a protective group such as a t-butoxycarbonyl group (Boc)).

$A^1$ is a group selected from the group given below. In the following formulas, * represents a binding position.

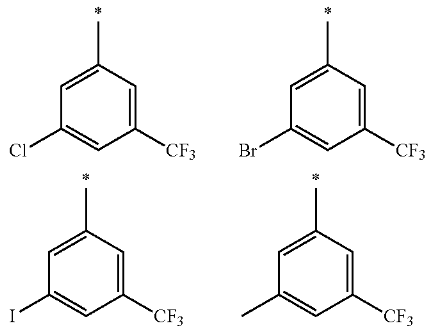

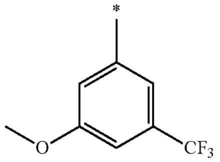
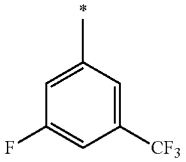
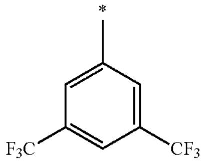
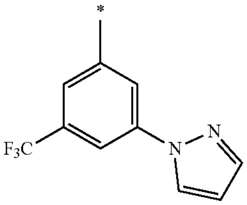
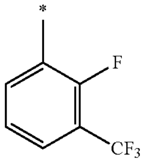
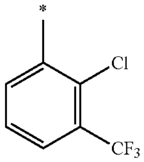
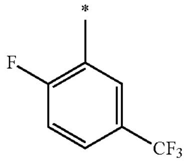
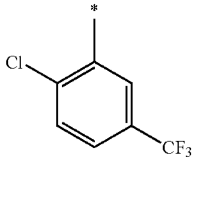
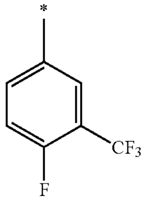
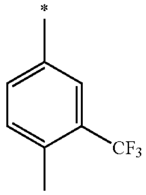
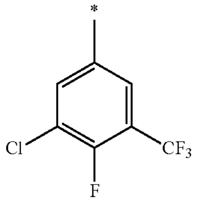
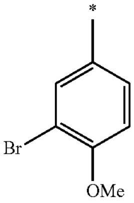
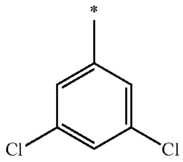
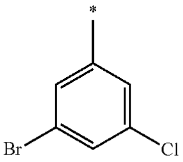
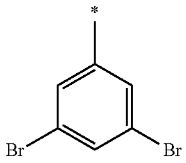
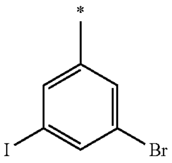
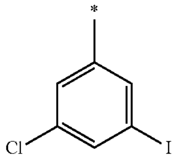
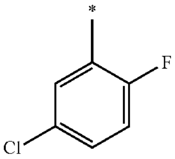
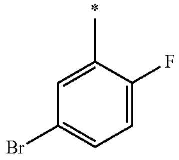
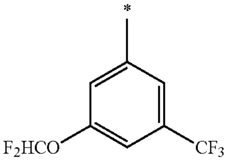
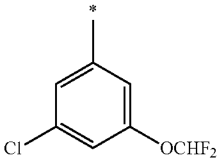
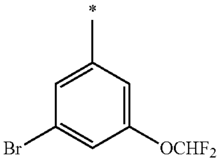
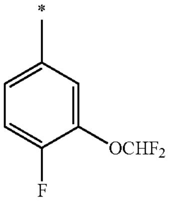
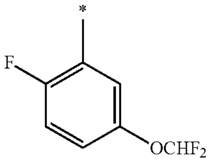
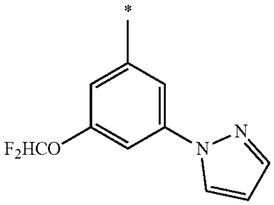
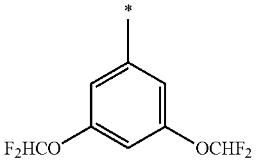
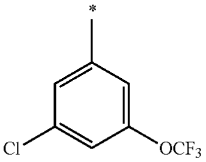
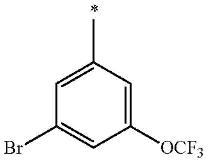
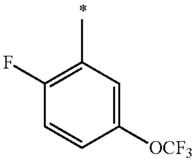
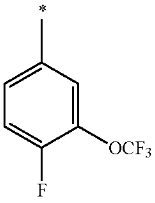
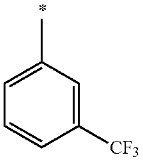
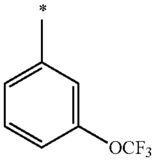
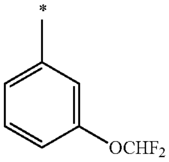
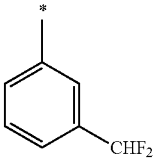
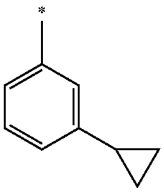
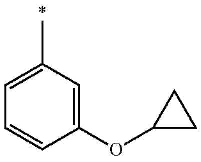
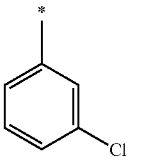
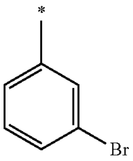
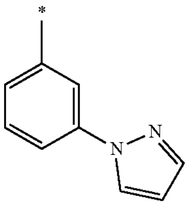

-continued

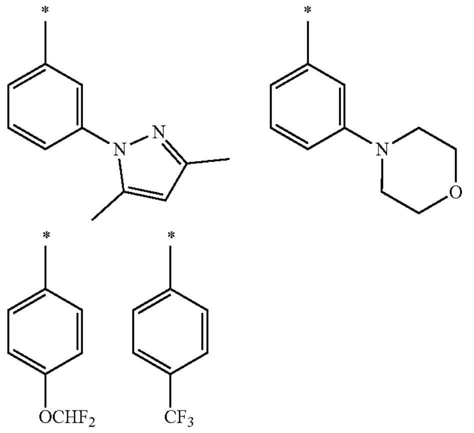

In one embodiment, the intermediate of the present invention may be a salt of the compound represented by any of the formulas (X-1) to (X-3), the formula (X-1-1), the formula (X-2-1), the formula (X-3-1) and the formula (X-2-3). Examples of the salt include, but are not particularly limited to, the "acid-addition salt, etc." and the "base-addition salt, etc." listed as examples of the "pharmaceutically acceptable salt" mentioned above.

All references including publications, patent applications and patents cited herein are incorporated herein by reference in their entirety.

EXAMPLES

Hereinafter, the present invention will be described in more detail with reference to Reference Examples, Examples and Test Examples. However, the scope of the present invention is not limited by these examples. The names Reference Examples, Examples and Test Examples are merely given for the sake of convenience in order to discriminate among experimental examples and do not mean that any of these examples are not included in the present invention.

DUIS in the ionization mode of a mass spectrum is a mixed mode of ESI and APCI.

In the present specification, $^1$H-NMR is indicated by chemical shift (δ) with tetramethylsilane as an internal standard (0 ppm), and a coupling constant (J value) is indicated by Hz unit, unless otherwise specified. The abbreviation of the splitting pattern of each peak means the following: s: singlet, d: doublet, dd: double doublet, ddd: double double doublet, t: triplet, tt: triple triplet, quin: quintet, and m: multiplet.

Abbreviations described in Reference Examples, Examples, Test Examples and chemical structural formulas are typically used in meanings that are generally used in the field of organic chemistry or pharmaceuticals, and specifically, should be understood as the abbreviations of the following terms by those skilled in the art.

Me: methyl group
DMSO: dimethyl sulfoxide
tert: tertiary
N: normal
M: molar concentration
ESI: electrospray ionization
APCI: atmospheric pressure chemical ionization
EI: electronic ionization
CI: chemical ionization

Reference Example 1-(a)

Production of (R,E)-N-(3-chloro-5-(trifluoromethyl) benzylidene)-2-methylpropane-2-sulfinamide

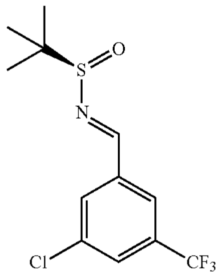 [SMILES: CC(C)(C)[S@@](=O)/N=C/c1cc(Cl)cc(C(F)(F)F)c1]

To a solution of 3.82 g of 3-chloro-5-(trifluoromethyl) benzaldehyde in toluene (20 ml), 2.35 g of (R)-2-methylpropane-2-sulfinamide (manufactured by Combi-Blocks Inc.), 0.079 ml of pyrrolidine, and 4 g of a molecular sieve (4 angstroms) were added at room temperature under a stream of argon, and the mixture was stirred at 70 °C for 2.5 hours.

After the completion of reaction, the reaction mixture was filtered through celite and concentrated under reduced pressure. Hexane was added to the concentration residue, and the mixture was stirred at room temperature for 30 minutes. A deposited solid was collected by filtration, washed with hexane, and then dried under reduced pressure at 60 °C to obtain 2.22 g of the title compound as a white solid.

Mass spectrum (ESI, m/z): 312 $[M+H]^+$.

Reference Example 2-(a), Etc.

Corresponding starting compounds were treated in the same manner as in Reference Example 1-(a) to obtain compounds described in the following Tables 1-1 to 1-8.

TABLE 1-1

| Reference Example | Structural formula | Mass spectrum |
|---|---|---|
| Reference Example 2-(a) | 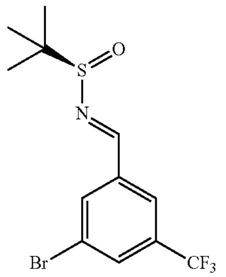 [SMILES: CC(C)(C)[S@@](=O)/N=C/c1cc(Br)cc(C(F)(F)F)c1] | (Cl, m/z): 356, 358 $[M + H]^+$ |
| Reference Example 3-(a) | 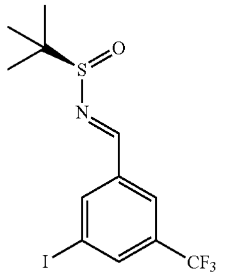 [SMILES: CC(C)(C)[S@@](=O)/N=C/c1cc(I)cc(C(F)(F)F)c1] | (ESI, m/z): 404 $[M + H]^+$ |

TABLE 1-1-continued

| Reference Example | Structural formula | Mass spectrum |
|---|---|---|
| Reference Example 4-(a) | 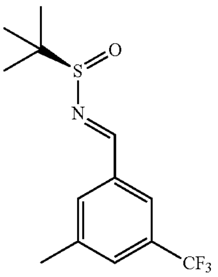 [SMILES: Cc1cc(/C=N/[S@](=O)C(C)(C)C)cc(C(F)(F)F)c1] | (DUIS, m/z): 292 [M + H]$^+$ |
| Reference Example 5-(a) | 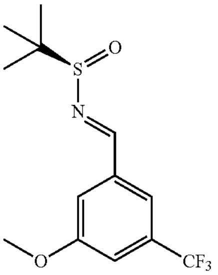 [SMILES: COc1cc(/C=N/[S@](=O)C(C)(C)C)cc(C(F)(F)F)c1] | (ESI, m/z): 308 [M + H]$^+$ |
| Reference Example 6-(a) | 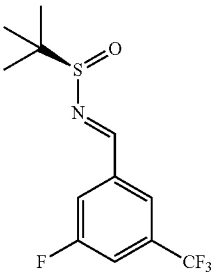 [SMILES: CC(C)(C)[S@@](=O)/N=C/c1cc(F)cc(C(F)(F)F)c1] | (ESI, m/z): 296 [M + H]$^+$ |
| Reference Example 7-(a) | 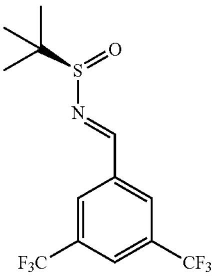 [SMILES: CC(C)(C)[S@@](=O)/N=C/c1cc(C(F)(F)F)cc(C(F)(F)F)c1] | (ESI, m/z): 346 [M + H]$^+$ |

TABLE 1-2

| Reference Example | Structural formula | Mass spectrum |
|---|---|---|
| Reference Example 9-(a) | 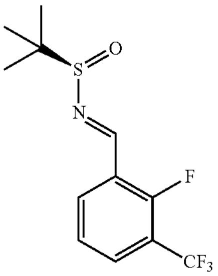 [SMILES: CC(C)(C)[S@@](=O)/N=C/c1cccc(C(F)(F)F)c1F] | (ESI, m/z): 296 [M + H]$^+$ |

TABLE 1-2-continued

| Reference Example | Structural formula | Mass spectrum |
|---|---|---|
| Reference Example 10-(a) | 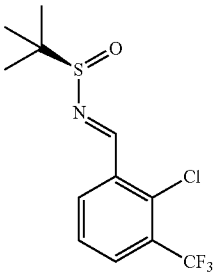 [SMILES: CC(C)(C)[S@@](=O)/N=C/c1cccc(C(F)(F)F)c1Cl] | (ESI, m/z): 312 [M + H]$^+$ |
| Reference Example 11-(a) | 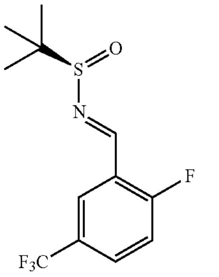 [SMILES: CC(C)(C)[S@@](=O)/N=C/c1cc(C(F)(F)F)ccc1F] | (ESI, m/z): 296 [M + H]$^+$ |
| Reference Example 12-(a) | 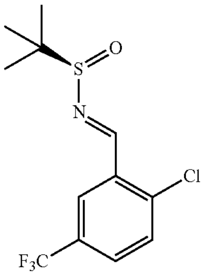 [SMILES: CC(C)(C)[S@@](=O)/N=C/c1cc(C(F)(F)F)ccc1Cl] | (ESI, m/z): 312 [M + H]$^+$ |
| Reference Example 13-(a) | 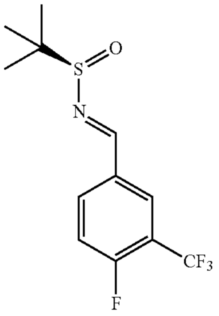 [SMILES: CC(C)(C)[S@@](=O)/N=C/c1ccc(F)c(C(F)(F)F)c1] | (ESI, m/z): 296 [M + H]$^+$ |
| Reference Example 14-(a) | 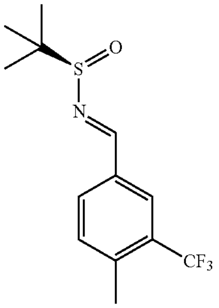 [SMILES: Cc1ccc(/C=N/[S@](=O)C(C)(C)C)cc1C(F)(F)F] | (ESI, m/z): 292 [M + H]$^+$ |

TABLE 1-3

| Reference Example | Structural formula | Mass spectrum |
|---|---|---|
| Reference Example 15-(c) | 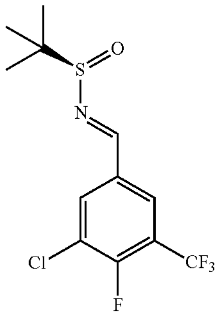 [SMILES: CC(C)(C)[S@@](=O)/N=C/c1cc(Cl)c(F)c(C(F)(F)F)c1] | (ESI, m/z): 330 [M + H]$^+$. |
| Reference Example 16-(a) | 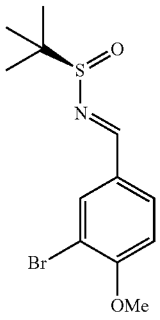 [SMILES: COc1ccc(/C=N/[S@](=O)C(C)(C)C)cc1Br] | (ESI, m/z): 318, 320 [M + H]$^+$ |
| Reference Example 17-(a) | 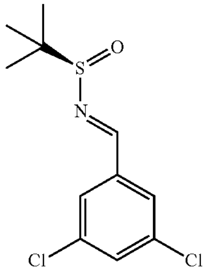 [SMILES: CC(C)(C)[S@@](=O)/N=C/c1cc(Cl)cc(Cl)c1] | (DUIS, m/z): 278 [M + H]$^+$ |
| Reference Example 18-(a) | 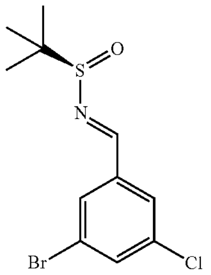 [SMILES: CC(C)(C)[S@@](=O)/N=C/c1cc(Cl)cc(Br)c1] | (ESI, m/z): 322, 324 [M + H]$^+$ |
| Reference Example 19-(a) | 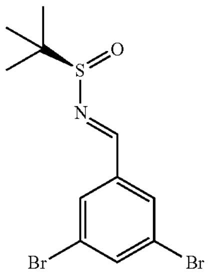 [SMILES: CC(C)(C)[S@@](=O)/N=C/c1cc(Br)cc(Br)c1] | (ESI, m/z): 368 [M + H]$^+$ |

TABLE 1-3-continued

| Reference Example | Structural formula | Mass spectrum |
|---|---|---|
| Reference Example 20-(a) | 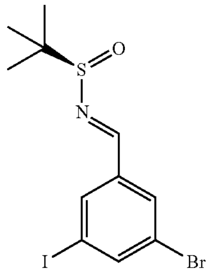 [SMILES: CC(C)(C)[S@@](=O)/N=C/c1cc(Br)cc(I)c1] | (ESI, m/z): 414, 416 [M + H]$^+$ |

TABLE 1-4

| Reference Example | Structural formula | Mass spectrum |
|---|---|---|
| Reference Example 21-(c) | 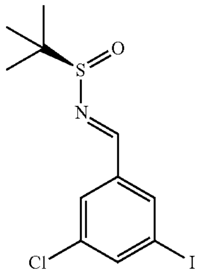 [SMILES: CC(C)(C)[S@@](=O)/N=C/c1cc(Cl)cc(I)c1] | (ESI, m/z): 370 [M + H]$^+$ |
| Reference Example 22-(a) | 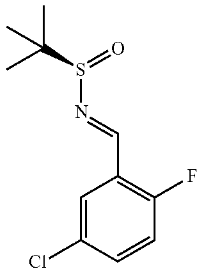 [SMILES: CC(C)(C)[S@@](=O)/N=C/c1cc(Cl)ccc1F] | (ESI, m/z): 262 [M + H]$^+$ |
| Reference Example 23-(a) | 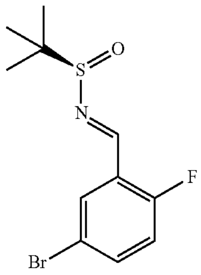 [SMILES: CC(C)(C)[S@@](=O)/N=C/c1cc(Br)ccc1F] | (ESI, m/z): 306, 308 [M + H]$^+$ |
| Reference Example 24-(b) | 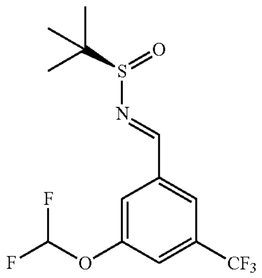 [SMILES: CC(C)(C)[S@@](=O)/N=C/c1cc(OC(F)F)cc(C(F)(F)F)c1] | (ESI, m/z): 344 [M + H]$^+$ |

TABLE 1-4-continued

| Reference Example | Structural formula | Mass spectrum |
|---|---|---|
| Reference Example 25-(b) | 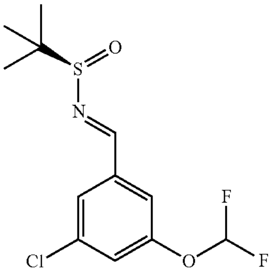 [SMILES: CC(C)(C)[S@@](=O)/N=C/c1cc(Cl)cc(OC(F)F)c1] | (ESI, m/z): 310 [M + H]$^+$ |
| Reference Example 26-(b) | 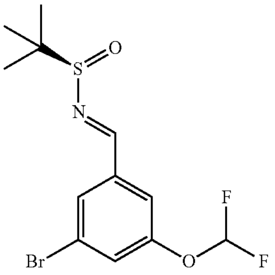 [SMILES: CC(C)(C)[S@@](=O)/N=C/c1cc(Br)cc(OC(F)F)c1] | (ESI, m/z): 354, 356 [M + H]$^+$ |

TABLE 1-5

| Reference Example | Structural formula | Mass spectrum |
|---|---|---|
| Reference Example 27-(b) | 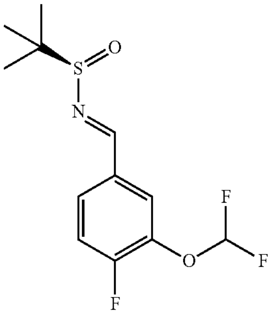 [SMILES: CC(C)(C)[S@@](=O)/N=C/c1ccc(F)c(OC(F)F)c1] | (ESI, m/z): 294 [M + H]$^+$ |
| Reference Example 28-(b) | 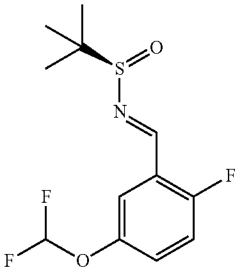 [SMILES: CC(C)(C)[S@@](=O)/N=C/c1cc(OC(F)F)ccc1F] | (ESI, m/z): 294 [M + H]$^+$ |
| Reference Example 30-(c) | 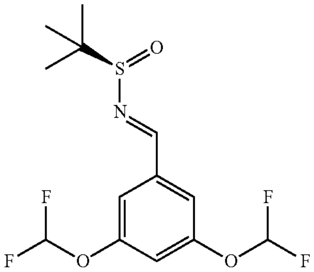 [SMILES: CC(C)(C)[S@@](=O)/N=C/c1cc(OC(F)F)cc(OC(F)F)c1] | (Cl, m/z): 342 [M + H]$^+$ |

TABLE 1-5-continued

| Reference Example | Structural formula | Mass spectrum |
|---|---|---|
| Reference Example 31-(a) | 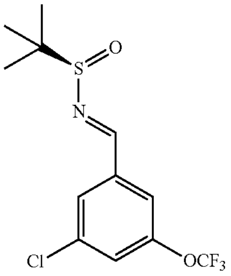 [SMILES: CC(C)(C)[S@@](=O)/N=C/c1cc(Cl)cc(OC(F)(F)F)c1] | (ESI, m/z): 328 [M + H]$^+$ |
| Reference Example 32-(a) | 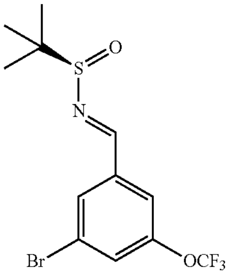 [SMILES: CC(C)(C)[S@@](=O)/N=C/c1cc(Br)cc(OC(F)(F)F)c1] | (ESI, m/z): 372, 374 [M + H]$^+$ |
| Reference Example 33-(a) | 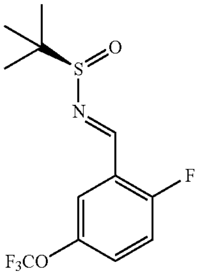 [SMILES: CC(C)(C)[S@@](=O)/N=C/c1cc(OC(F)(F)F)ccc1F] | (ESI, m/z): 312 [M + H]$^+$ |

TABLE 1-6

| Reference Example | Structural formula | Mass spectrum |
|---|---|---|
| Reference Example 34-(a) | 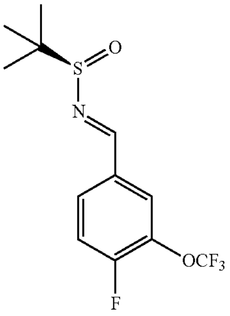 [SMILES: CC(C)(C)[S@@](=O)/N=C/c1ccc(F)c(OC(F)(F)F)c1] | (ESI, m/z): 312 [M + H]$^+$. |
| Reference Example 35-(a) | 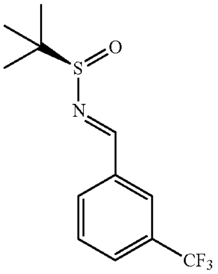 [SMILES: CC(C)(C)[S@@](=O)/N=C/c1cccc(C(F)(F)F)c1] | (ESI, m/z): 278 [M + H]$^+$ |

TABLE 1-6-continued

| Reference Example | Structural formula | Mass spectrum |
|---|---|---|
| Reference Example 36-(a) | 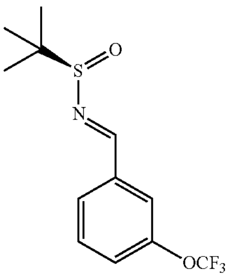 [SMILES: CC(C)(C)[S@@](=O)/N=C/c1cccc(OC(F)(F)F)c1] | (ESI, m/z): 294 [M + H]+ |
| Reference Example 37-(a) | 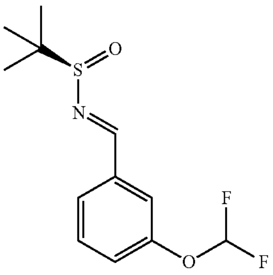 [SMILES: CC(C)(C)[S@@](=O)/N=C/c1cccc(OC(F)F)c1] | (ESI, m/z): 276 [M + H]+ |
| Reference Example 38-(a) | 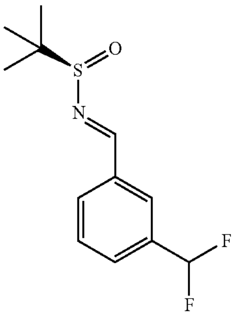 [SMILES: CC(C)(C)[S@@](=O)/N=C/c1cccc(C(F)F)c1] | (ESI, m/z): 260 [M + H]+ |
| Reference Example 39-(a) | 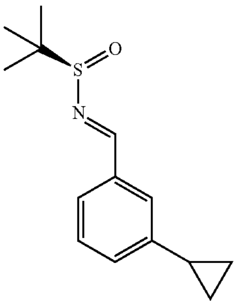 [SMILES: CC(C)(C)[S@@](=O)/N=C/c1cccc(C2CC2)c1] | (ESI, m/z): 250 [M + H]+ |

TABLE 1-7

| Reference Example | Structural formula | Mass spectrum |
|---|---|---|
| Reference Example 40-(a) | 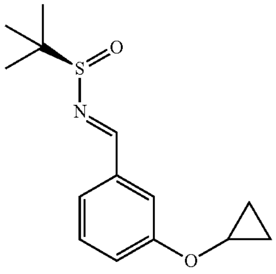 [SMILES: CC(C)(C)[S@@](=O)/N=C/c1cccc(OC2CC2)c1] | (ESI, m/z): 266 [M + H]+ |
| Reference Example 41-(a) | 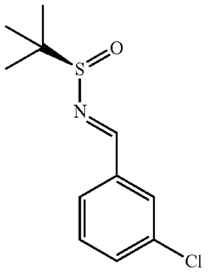 | (ESI, m/z): 244 [M + H]+ |
| Reference Example 42-(a) | 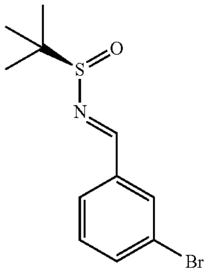 | (ESI, m/z): 288, 290 [M + H]+ |
| Reference Example 43-(a) | 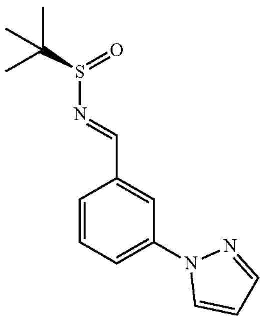 [SMILES: CC(C)(C)[S@@](=O)/N=C/c1cccc(-n2cccn2)c1] | (ESI, m/z): 276 [M + H]+ |
| Reference Example 44-(a) | 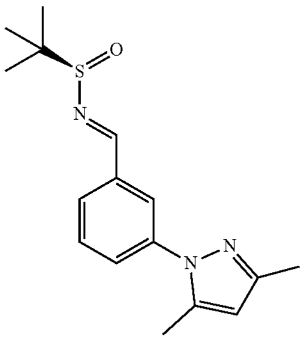 [SMILES: Cc1cc(C)n(-c2cccc(/C=N/[S@](=O)C(C)(C)C)c2)n1] | (ESI, m/z): 304 [M + H]+ |

TABLE 1-7-continued

| Reference Example | Structural formula | Mass spectrum |
|---|---|---|
| Reference Example 45-(a) | 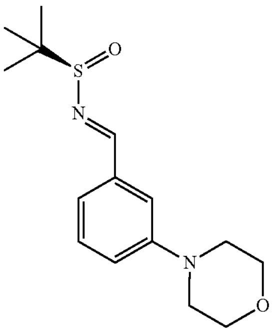 [SMILES: CC(C)(C)[S@@](=O)/N=C/c1cccc(N2CCOCC2)c1] | (ESI, m/z): 295 [M + H]$^+$ |

TABLE 1-8

| Reference Example | Structural formula | Mass spectrum |
|---|---|---|
| Reference Example 46-(a) | 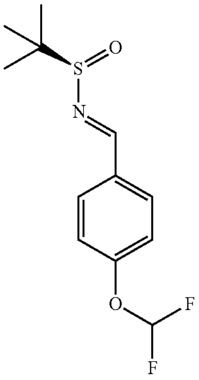 [SMILES: CC(C)(C)[S@@](=O)/N=C/c1ccc(OC(F)F)cc1] | (ESI, m/z): 276 [M + H]$^+$ |
| Reference Example 47-(a) | 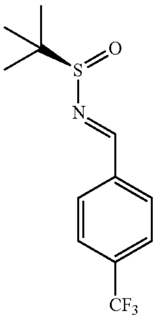 [SMILES: CC(C)(C)[S@@](=O)/N=C/c1ccc(C(F)(F)F)cc1] | (ESI, m/z): 278 [M + H]$^+$ |

Reference Example 1-(b)

Production of methyl (S)-3-(((R)-tert-butylsulfinyl) amino)-3-(3-chloro-5-(trifluoromethyl)phenyl)propanoate

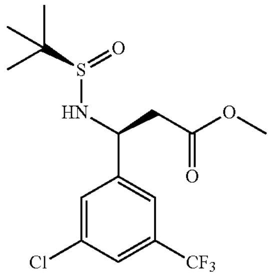 [SMILES: COC(=O)C[C@H](N[S@](=O)C(C)(C)C)c1cc(Cl)cc(C(F)(F)F)c1]

To 33.3 g of zinc, 5.05 g of copper(I) chloride was added with stirring under a stream of argon, followed by deaeration under reduced pressure at a bath temperature of 70 °C for 15 minutes. After purging with argon, 45 ml of tetrahydrofuran was added thereto under a stream of argon, and the mixture was stirred at 70 °C for 1 hour. Then, the bath temperature was lowered to 40 °C, and 10.4 ml of methyl bromoacetate was added dropwise thereto at an internal temperature of 30 °C to 37 °C. After the completion of addition, the mixture was stirred at a bath temperature of 50 °C for 1 hour. The reaction mixture was brought back to room temperature and then cooled in an ice salt bath. A solution of 5.00 g of (R,E)-N-(3-chloro-5-(trifluoromethyl)benzylidene)-2-methylpropane-2-sulfinamide synthesized in the same manner as in Reference Example 1-(a) in tetrahydrofuran (22.5 ml) was added dropwise thereto at an internal temperature of −5 °C or lower under a stream of argon, and the mixture was further washed repeatedly with 7.50 ml of tetrahydrofuran. After the completion of dropwise addition, the mixture was cooled in an ice bath and stirred for 2 hours.

After the completion of reaction, the reaction mixture was filtered through celite (545) and washed with ethyl acetate. Then, a saturated aqueous solution of ammonium chloride was added to the filtrate, and the mixture was stirred. This mixed solution was filtered, and the filtrate was separated into organic and aqueous layers. The organic layer was washed with saturated saline, dried over anhydrous magnesium sulfate, filtered, and concentrated under reduced pressure. The obtained concentration residue was purified by medium-pressure preparative chromatography (silica gel, eluting solvent: hexane:ethyl acetate) to obtain 4.82 g of the title compound as a pale yellow oil.

Mass spectrum (ESI, m/z): 386 [M+H]$^+$.

Reference Example 2-(b), Etc.

Corresponding starting compounds were treated in the same manner as in Reference Example 1-(b) to obtain compounds described in the following Tables 2-1 to 2-8.

TABLE 2-1

| Reference Example | Structural formula | Mass spectrum |
|---|---|---|
| Reference Example 2-(b) | 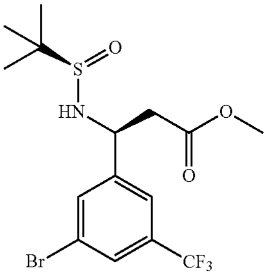 | (Cl, m/z): 430, 432 [M + H]+ |
| Reference Example 3-(b) | 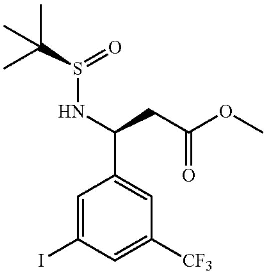 [SMILES: COC(=O)C[C@H](N[S@](=O)C(C)(C)C)c1cc(I)cc(C(F)(F)F)c1] | (ESI, m/z): 478 [M + H]+ |
| Reference Example 4-(b) | 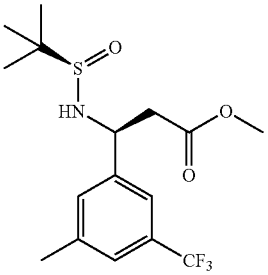 [SMILES: COC(=O)C[C@H](N[S@](=O)C(C)(C)C)c1cc(C)cc(C(F)(F)F)c1] | (ESI, m/z): 366 [M + H]+ |
| Reference Example 5-(b) | 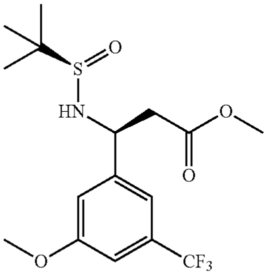 [SMILES: COC(=O)C[C@H](N[S@](=O)C(C)(C)C)c1cc(OC)cc(C(F)(F)F)c1] | (ESI, m/z): 382 [M + H]+ |
| Reference Example 6-(b) | 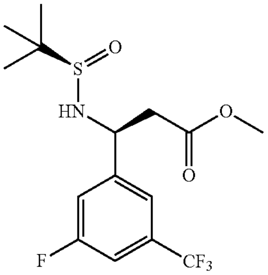 | (ESI, m/z): 370 [M + H]+ |

TABLE 2-1-continued

| Reference Example | Structural formula | Mass spectrum |
|---|---|---|
| Reference Example 7-(b) | 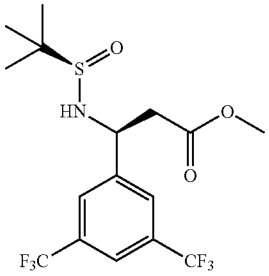 [SMILES: COC(=O)C[C@H](N[S@](=O)C(C)(C)C)c1cc(C(F)(F)F)cc(C(F)(F)F)c1] | (ESI, m/z): 420 [M + H]+ |

TABLE 2-2

| Reference Example | Structural formula | Mass spectrum |
|---|---|---|
| Reference Example 9-(b) | 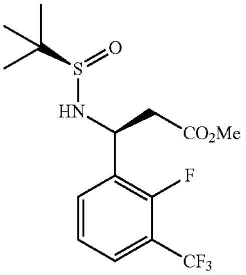 [SMILES: COC(=O)C[C@H](N[S@](=O)C(C)(C)C)c1cccc(C(F)(F)F)c1F] | (ESI, m/z): 370 [M + H]+ |
| Reference Example 10-(b) | 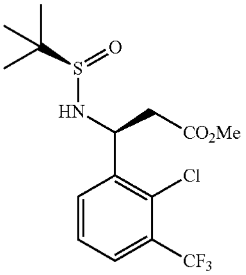 [SMILES: COC(=O)C[C@H](N[S@](=O)C(C)(C)C)c1cccc(C(F)(F)F)c1Cl] | (ESI, m/z): 386 [M + H]+ |
| Reference Example 11-(b) | 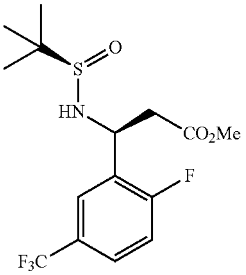 [SMILES: COC(=O)C[C@H](N[S@](=O)C(C)(C)C)c1cc(C(F)(F)F)ccc1F] | (ESI, m/z): 370 [M + H]+ |
| Reference Example 12-(b) | 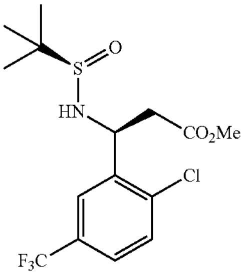 [SMILES: COC(=O)C[C@H](N[S@](=O)C(C)(C)C)c1cc(C(F)(F)F)ccc1Cl] | (ESI, m/z): 386 [M + H]+ |

TABLE 2-2-continued

| Reference Example | Structural formula | Mass spectrum |
|---|---|---|
| Reference Example 13-(b) | 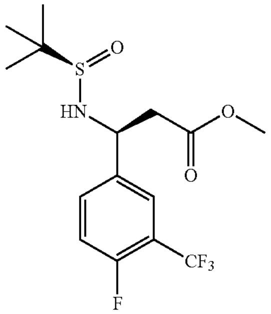 [SMILES: COC(=O)C[C@H](N[S@](=O)C(C)(C)C)c1ccc(F)c(C(F)(F)F)c1] | (ESI, m/z): 370 [M + H]$^+$ |
| Reference Example 14-(b) | 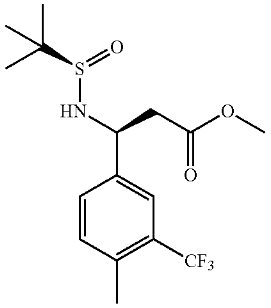 [SMILES: COC(=O)C[C@H](N[S@](=O)C(C)(C)C)c1ccc(C)c(C(F)(F)F)c1] | (ESI, m/z): 366 [M + H]$^+$ |

TABLE 2-3

| Reference Example | Structural formula | Mass spectrum |
|---|---|---|
| Reference Example 15-(d) | 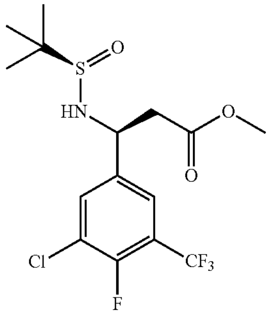 [SMILES: COC(=O)C[C@H](N[S@](=O)C(C)(C)C)c1cc(Cl)c(F)c(C(F)(F)F)c1] | (ESI, m/z): 404 [M + H]$^+$ |
| Reference Example 16-(b) | 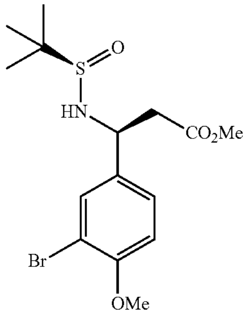 [SMILES: COC(=O)C[C@H](N[S@](=O)C(C)(C)C)c1ccc(OC)c(Br)c1] | (ESI, m/z): 392, 394 [M + H]$^+$ |

TABLE 2-3-continued

| Reference Example | Structural formula | Mass spectrum |
|---|---|---|
| Reference Example 17-(b) | 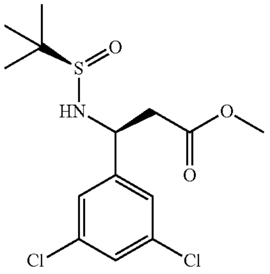 [SMILES: COC(=O)C[C@H](N[S@](=O)C(C)(C)C)c1cc(Cl)cc(Cl)c1] | (ESI, m/z): 352 [M + H]$^+$ |
| Reference Example 18-(b) | 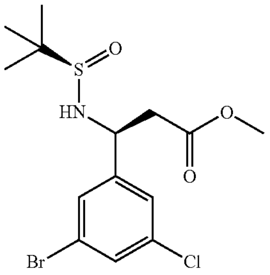 [SMILES: COC(=O)C[C@H](N[S@](=O)C(C)(C)C)c1cc(Cl)cc(Br)c1] | (ESI, m/z): 396, 398 [M + H]$^+$ |
| Reference Example 19-(b) | 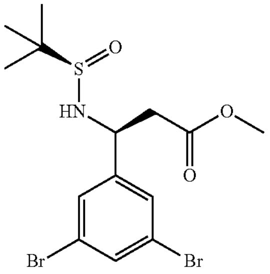 [SMILES: COC(=O)C[C@H](N[S@](=O)C(C)(C)C)c1cc(Br)cc(Br)c1] | (ESI, m/z): 442 [M + H]$^+$ |
| Reference Example 20-(b) | 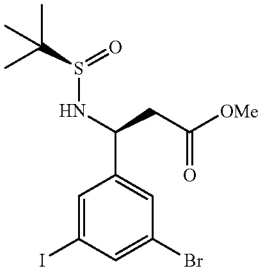 [SMILES: COC(=O)C[C@H](N[S@](=O)C(C)(C)C)c1cc(Br)cc(I)c1] | (ESI, m/z): 488, 490 [M + H]$^+$ |

TABLE 2-4

| Reference Example | Structural formula | Mass spectrum |
|---|---|---|
| Reference Example 21-(d) | 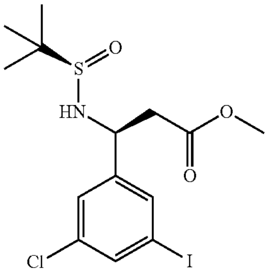 [SMILES: COC(=O)C[C@H](N[S@](=O)C(C)(C)C)c1cc(Cl)cc(I)c1] | (ESI, m/z): 444 [M + H]$^+$ |

TABLE 2-4-continued

| Reference Example | Structural formula | Mass spectrum |
|---|---|---|
| Reference Example 22-(b) | 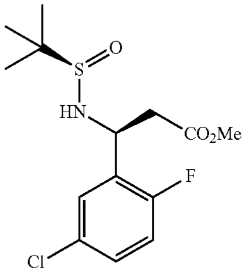 [SMILES: COC(=O)C[C@H](N[S@](=O)C(C)(C)C)c1cc(Cl)ccc1F] | (ESI, m/z): 336 [M + H]$^+$ |
| Reference Example 23-(b) | 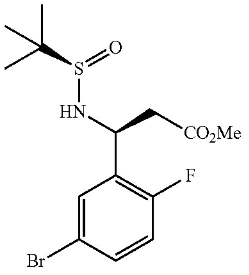 [SMILES: COC(=O)C[C@H](N[S@](=O)C(C)(C)C)c1cc(Br)ccc1F] | (ESI, m/z): 380, 382 [M + H]$^+$ |
| Reference Example 24-(c) | 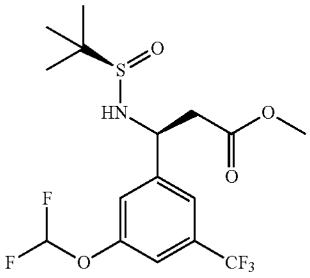 [SMILES: COC(=O)C[C@H](N[S@](=O)C(C)(C)C)c1cc(OC(F)F)cc(C(F)(F)F)c1] | (ESI, m/z): 418 [M + H]$^+$ |
| Reference Example 25-(c) | 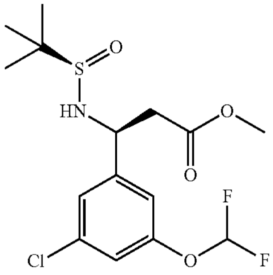 [SMILES: COC(=O)C[C@H](N[S@](=O)C(C)(C)C)c1cc(Cl)cc(OC(F)F)c1] | (ESI, m/z): 384 [M + H]$^+$ |
| Reference Example 26-(c) | 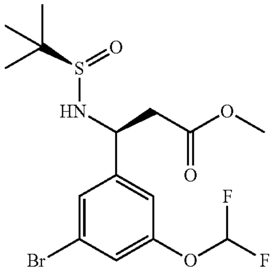 [SMILES: COC(=O)C[C@H](N[S@](=O)C(C)(C)C)c1cc(Br)cc(OC(F)F)c1] | (ESI, m/z): 428, 430 [M + H]$^+$ |

TABLE 2-5

| Reference Example | Structural formula | Mass spectrum |
|---|---|---|
| Reference Example 27-(c) | 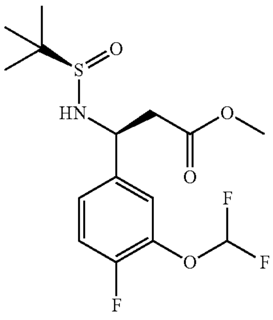 [SMILES: COC(=O)C[C@H](N[S@](=O)C(C)(C)C)c1ccc(F)c(OC(F)F)c1] | (ESI, m/z): 368 [M + H]$^+$ |
| Reference Example 28-(c) | 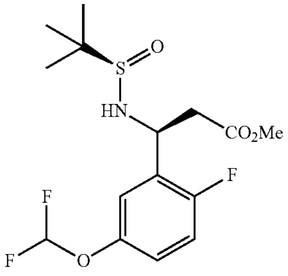 [SMILES: COC(=O)C[C@H](N[S@](=O)C(C)(C)C)c1cc(OC(F)F)ccc1F] | (ESI, m/z): 368 [M + H]$^+$ |
| Reference Example 30-(d) | 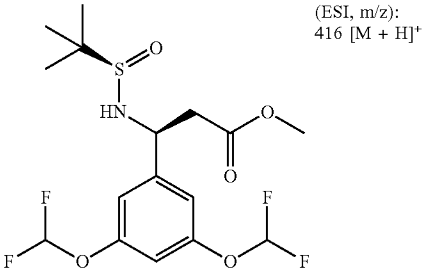 | (ESI, m/z): 416 [M + H]$^+$ |
| Reference Example 31-(b) | 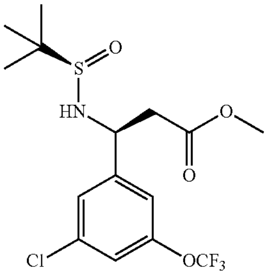 | (ESI, m/z): 402 [M + H]$^+$ |
| Reference Example 32-(b) | 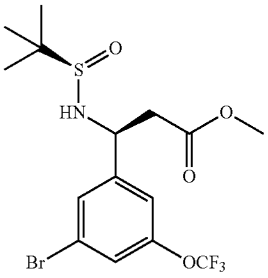 | (ESI, m/z): 446, 448 [M + H]$^+$ |

TABLE 2-5-continued

| Reference Example | Structural formula | Mass spectrum |
|---|---|---|
| Reference Example 33-(b) | 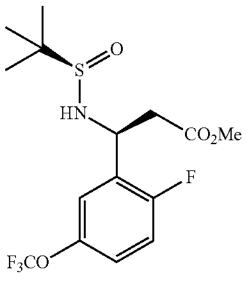 [SMILES: COC(=O)C[C@H](N[S@](=O)C(C)(C)C)c1cc(OC(F)(F)F)ccc1F] | (ESI, m/z): 386 [M + H]$^+$ |

TABLE 2-6

| Reference Example | Structural formula | Mass spectrum |
|---|---|---|
| Reference Example 34-(b) | 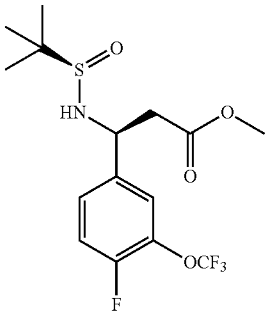 | (ESI, m/z): 386 [M + H]$^+$ |
| Reference Example 35-(b) | 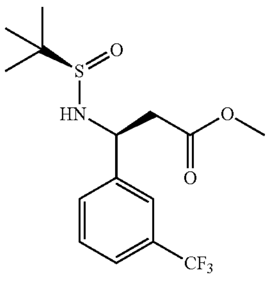 | (ESI, m/z): 352 [M + H]$^+$ |
| Reference Example 36-(b) | 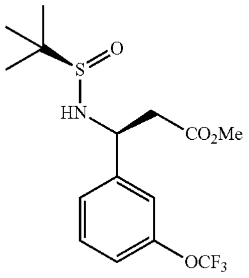 [SMILES: COC(=O)C[C@H](N[S@](=O)C(C)(C)C)c1cccc(OC(F)(F)F)c1] | (ESI, m/z): 368 [M + H]$^+$ |

TABLE 2-6-continued

| Reference Example | Structural formula | Mass spectrum |
|---|---|---|
| Reference Example 37-(b) | 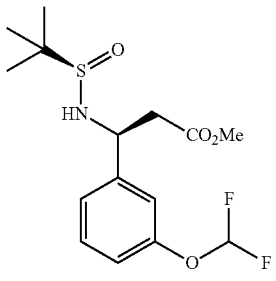 [SMILES: COC(=O)C[C@H](N[S@](=O)C(C)(C)C)c1cccc(OC(F)F)c1] | (ESI, m/z): 350 [M + H]$^+$ |
| Reference Example 38-(b) | 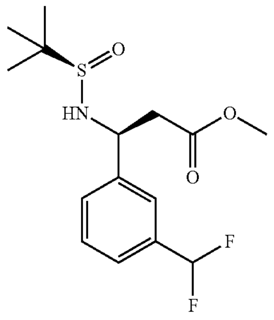 [SMILES: COC(=O)C[C@H](N[S@](=O)C(C)(C)C)c1cccc(C(F)F)c1] | (ESI, m/z): 334 [M + H]$^+$ |
| Reference Example 39-(b) | 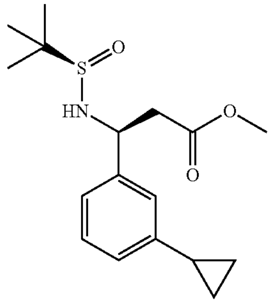 [SMILES: COC(=O)C[C@H](N[S@](=O)C(C)(C)C)c1cccc(C2CC2)c1] | (ESI, m/z): 324 [M + H]$^+$ |

TABLE 2-7

| Reference Example | Structural formula | Mass spectrum |
|---|---|---|
| Reference Example 40-(b) | 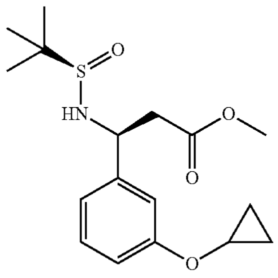 [SMILES: COC(=O)C[C@H](N[S@](=O)C(C)(C)C)c1cccc(OC2CC2)c1] | (ESI, m/z): 340 [M + H]$^+$ |

TABLE 2-7-continued

| Reference Example | Structural formula | Mass spectrum |
|---|---|---|
| Reference Example 41-(b) | 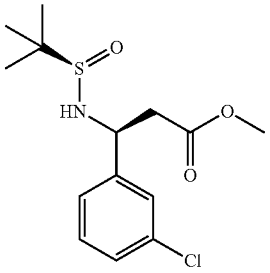 [SMILES: COC(=O)C[C@H](N[S@](=O)C(C)(C)C)c1cccc(Cl)c1] | (ESI, m/z): 318 [M + H]$^+$ |
| Reference Example 42-(b) | 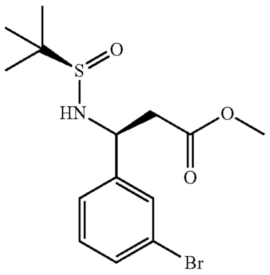 [SMILES: COC(=O)C[C@H](N[S@](=O)C(C)(C)C)c1cccc(Br)c1] | (ESI, m/z): 362, 364 [M + H]$^+$ |
| Reference Example 43-(b) | 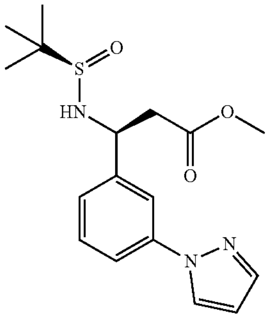 [SMILES: COC(=O)C[C@H](N[S@](=O)C(C)(C)C)c1cccc(-n2cccn2)c1] | (ESI, m/z): 350 [M + H]$^+$ |
| Reference Example 44-(b) | 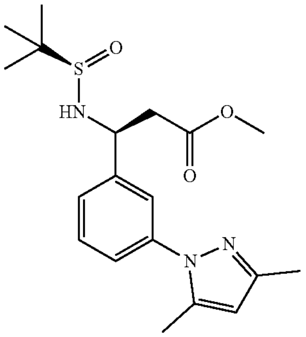 [SMILES: COC(=O)C[C@H](N[S@](=O)C(C)(C)C)c1cccc(-n2nc(C)cc2C)c1] | (ESI, m/z): 378 [M + H]$^+$ |
| Reference Example 45-(b) | 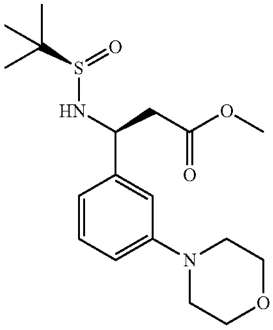 [SMILES: COC(=O)C[C@H](N[S@](=O)C(C)(C)C)c1cccc(N2CCOCC2)c1] | (ESI, m/z): 369 [M + H]$^+$ |

TABLE 2-8

| Reference Example | Structural formula | Mass spectrum |
|---|---|---|
| Reference Example 46-(b) | 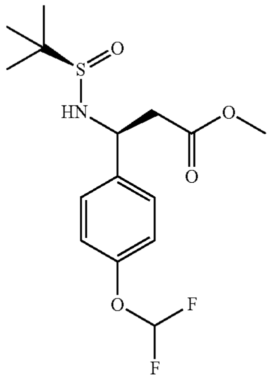 [SMILES: COC(=O)C[C@H](N[S@](=O)C(C)(C)C)c1ccc(OC(F)F)cc1] | (ESI, m/z): 350 [M + H]$^+$ |
| Reference Example 47-(b) | 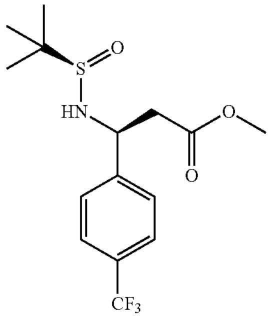 [SMILES: COC(=O)C[C@H](N[S@](=O)C(C)(C)C)c1ccc(C(F)(F)F)cc1] | (ESI, m/z): 352 [M + H]$^+$ |

Reference Example 1-(c)

Production of methyl (S)-3-amino-3-(3-chloro-5-(trifluoromethyl)phenyl)propanoate hydrochloride

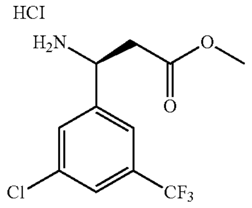 [SMILES: "HCI" ; COC(=O)C[C@H](N)c1cc(Cl)cc(C(F)(F)F)c1]

To a solution of 24.6 g of methyl (S)-3-(((R)-tert-butylsulfinyl)amino)-3-(3-chloro-5-(trifluoromethyl)phenyl) propanoate synthesized in the same manner as in Reference Example 1-(b) in cyclopentyl methyl ether (270 ml), 2.52 ml of methanol and 34.2 ml of a 4 M solution of hydrogen chloride in cyclopentyl methyl ether were added at room temperature under a stream of argon, and the mixture was stirred at room temperature for 1 hour.

After the completion of reaction, the reaction mixture was concentrated under reduced pressure. 50 ml of cyclopentyl methyl ether and 600 ml of hexane were added to the concentration residue, and the mixture was stirred at room temperature for 1 hour. A deposited solid was collected by filtration, washed with hexane, and then dried under reduced pressure at 50 °C to obtain 17.5 g of the title compound as a white solid.

Mass spectrum (ESI, m/z): 282 [M+H]$^+$.

Reference Example 2-(c), Etc.

Corresponding starting compounds were treated in the same manner as in Reference Example 1-(c) to obtain compounds described in the following Tables 3-1 to 3-7.

TABLE 3-1

| Reference Example | Structural formula | Mass spectrum |
|---|---|---|
| Reference Example 2-(c) | HCl 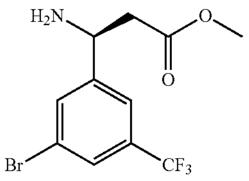 | (CI, m/z): 326, 328 $[M + H]^+$ |
| Reference Example 3-(c) | HCl 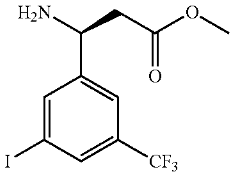 | (ESI, m/z): 374 $[M + H]^+$ |
| Reference Example 4-(c) | HCl 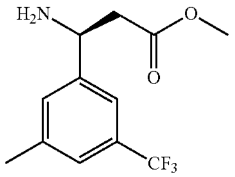 | (DUIS, m/z): 262 $[M + H]^+$ |
| Reference Example 5-(c) | HCl 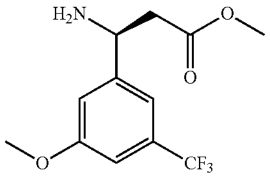 | (ESI, m/z): 278 $[M + H]^+$ |
| Reference Example 6-(c) | HCl 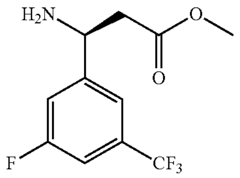 | (ESI, m/z): 266 $[M + H]^+$ |
| Reference Example 9-(c) | HCl 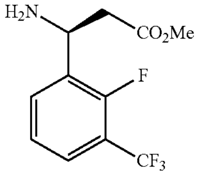 | (ESI, m/z): 266 $[M + H]^+$ |

TABLE 3-2

| Reference Example | Structural formula | Mass spectrum |
|---|---|---|
| Reference Example 10-(c) | HCl 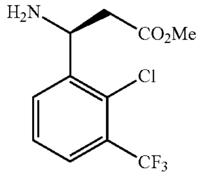 | (ESI, m/z): 282 $[M + H]^+$ |
| Reference Example 11-(c) | HCl 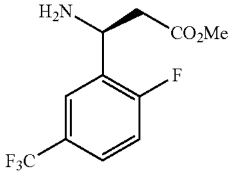 | (ESI, m/z): 266 $[M + H]^+$ |
| Reference Example 12-(c) | HCl 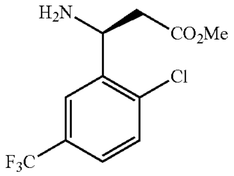 | (ESI, m/z): 282 $[M + H]^+$ |
| Reference Example 13-(c) | HCl 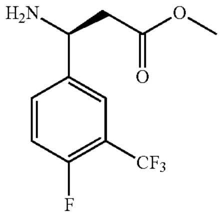 | (ESI, m/z): 266 $[M + H]^+$ |
| Reference Example 15-(e) | HCl 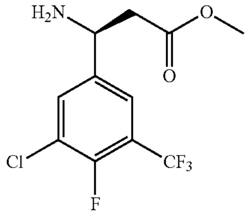 | (ESI, m/z): 300 $[M + H]^+$ |
| Reference Example 16-(c) | HCl 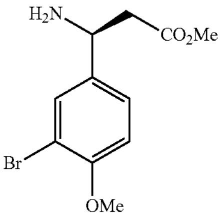 | (ESI, m/z): 288, 290 $[M + H]^+$ |

TABLE 3-3

| Reference Example | Structural formula | Mass spectrum |
|---|---|---|
| Reference Example 17-(c) | HCl 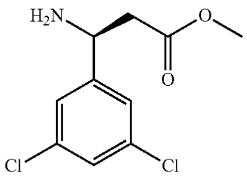 | (DUIS, m/z): 248 $[M + H]^+$ |
| Reference Example 19-(c) | HCl 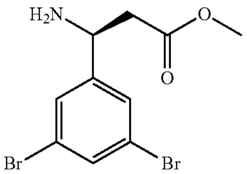 | (ESI, m/z): 338 $[M + H]^+$ |
| Reference Example 20-(c) | HCl 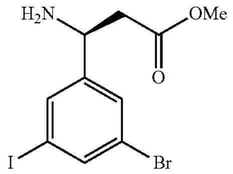 | (ESI, m/z): 384, 386 $[M + H]^+$ |
| Reference Example 21-(e) | HCl 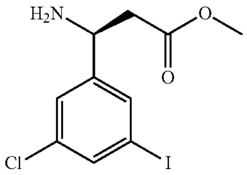 | (ESI, m/z): 340 $[M + H]^+$ |
| Reference Example 22-(c) | HCl 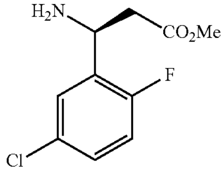 | (ESI, m/z): 232 $[M + H]^+$ |
| Reference Example 23-(c) | 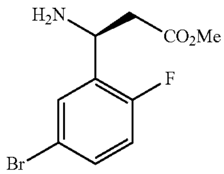 [SMILES: COC(=O)C[C@H](N)c1cc(Br)ccc1F] | (ESI, m/z): 276, 278 $[M + H]^+$ |

TABLE 3-4

| Reference Example | Structural formula | Mass spectrum |
|---|---|---|
| Reference Example 24-(d) | HCl 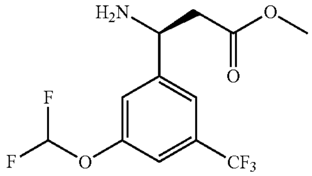 | (ESI, m/z): 314 $[M + H]^+$ |
| Reference Example 25-(d) | HCl 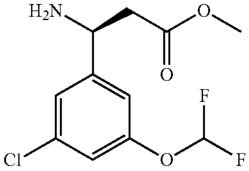 | (ESI, m/z): 280 $[M + H]^+$ |
| Reference Example 26-(d) | HCl 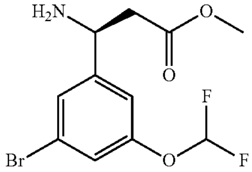 | (ESI, m/z): 324, 326 $[M + H]^+$ |
| Reference Example 27-(d) | HCl 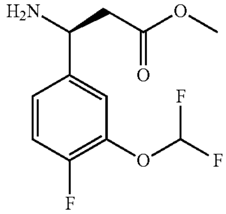 | (ESI, m/z): 264 $[M + H]^+$ |
| Reference Example 28-(d) | 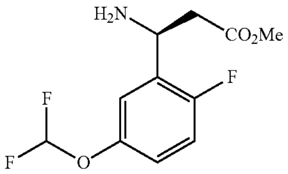 [SMILES: COC(=O)C[C@H](N)c1cc(OC(F)F)ccc1F] | (ESI, m/z): 264 $[M + H]^+$ |
| Reference Example 30-(e) | HCl 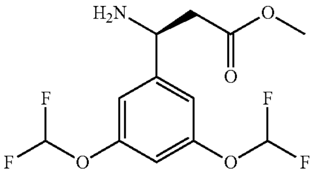 | (ESI, m/z): 312 $[M + H]^+$ |

TABLE 3-5

| Reference Example | Structural formula | Mass spectrum |
|---|---|---|
| Reference Example 31-(c) | 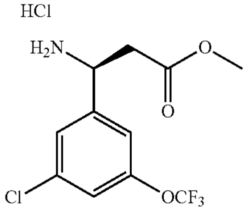 [SMILES: Cl ; COC(=O)C[C@H](N)c1cc(Cl)cc(OC(F)(F)F)c1] | (ESI, m/z): 298 [M + H]$^+$ |
| Reference Example 32-(c) | 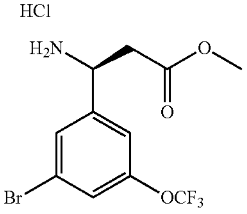 [SMILES: Cl ; COC(=O)C[C@H](N)c1cc(Br)cc(OC(F)(F)F)c1] | (ESI, m/z): 342, 344 [M + H]$^+$ |
| Reference Example 33-(c) | 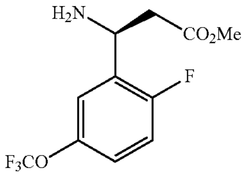 | (ESI, m/z): 282 [M + H]$^+$ |
| Reference Example 35-(c) | 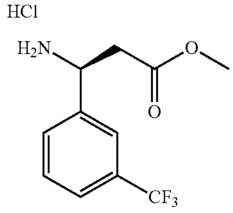 [SMILES: Cl ; COC(=O)C[C@H](N)c1cccc(C(F)(F)F)c1] | (ESI, m/z): 248 [M + H]$^+$ |
| Reference Example 36-(c) | 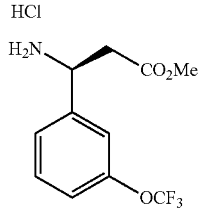 [SMILES: Cl ; COC(=O)C[C@H](N)c1cccc(OC(F)(F)F)c1] | (ESI, m/z): 264 [M + H]$^+$ |
| Reference Example 37-(c) | 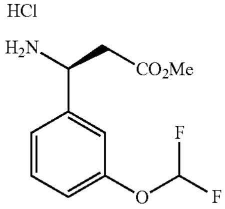 [SMILES: Cl ; COC(=O)C[C@H](N)c1cccc(OC(F)F)c1] | (ESI, m/z): 246 [M + H]$^+$ |

TABLE 3-6

| Reference Example | Structural formula | Mass spectrum |
|---|---|---|
| Reference Example 38-(c) | 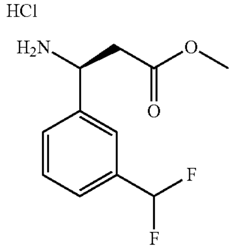 [SMILES: Cl ; COC(=O)C[C@H](N)c1cccc(C(F)F)c1] | (ESI, m/z): 230 [M + H]$^+$ |
| Reference Example 39-(c) | 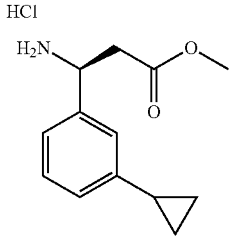 [SMILES: Cl ; COC(=O)C[C@H](N)c1cccc(C2CC2)c1] | (ESI, m/z): 220 [M + H]$^+$ |
| Reference Example 40-(c) | 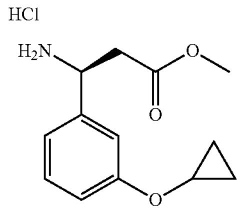 [SMILES: Cl ; COC(=O)C[C@H](N)c1cccc(OC2CC2)c1] | (ESI, m/z): 236 [M + H]$^+$ |
| Reference Example 43-(c) | 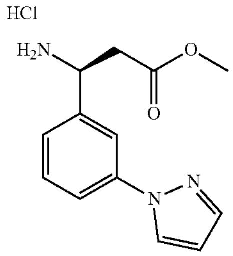 [SMILES: Cl ; COC(=O)C[C@H](N)c1cccc(-n2cccn2)c1] | (ESI, m/z): 246 [M + H]$^+$ |
| Reference Example 44-(c) | 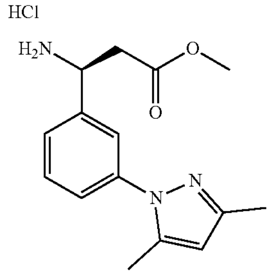 [SMILES: Cl ; COC(=O)C[C@H](N)c1cccc(-n2nc(C)cc2C)c1] | (ESI, m/z): 274 [M + H]$^+$ |
| Reference Example 45-(c) | 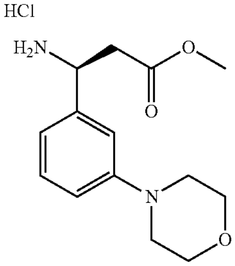 [SMILES: Cl ; COC(=O)C[C@H](N)c1cccc(N2CCOCC2)c1] | (ESI, m/z): 265 [M + H]$^+$ |

TABLE 3-7

| Reference Example | Structural formula | Mass spectrum |
|---|---|---|
| Reference Example 46-(c) | HCl 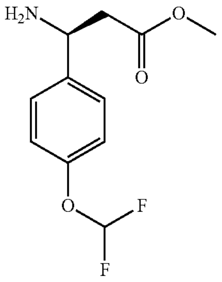 | (ESI, m/z): 246 [M + H]$^+$ |
| Reference Example 47-(c) | HCl 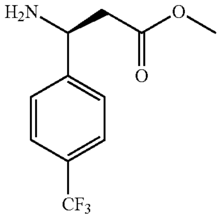 | (ESI, m/z): 248 [M + H]$^+$ |

Reference Example 1-(d)

Production of methyl (S)-3-(2-((tert-butoxycarbonyl)amino)acetamido)-3-(3-chloro-5-(trifluoromethyl)phenyl)propanoate

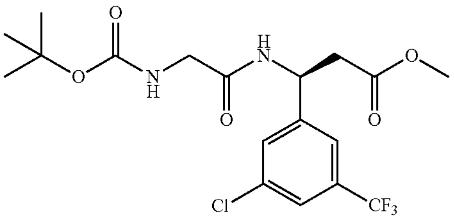

To a solution of 2.23 g of methyl (S)-3-amino-3-(3-chloro-5-(trifluoromethyl)phenyl)propanoate hydrochloride synthesized in Reference Example 1-(c), and 0.977 ml of triethylamine in dichloromethane (20 ml), 1.36 g of (tert-butoxycarbonyl)glycine and 1.61 g of 1-(3-dimethylaminopropyl)-3-ethylcarbodiimide hydrochloride were added at room temperature under a stream of argon, and the mixture was stirred at room temperature for 30 minutes.

After the completion of reaction, a saturated aqueous solution of ammonium chloride was added to the reaction mixture, and the mixed solution was subjected to extraction with dichloromethane. The organic layer was washed with saturated saline, dried over anhydrous sodium sulfate, filtered, and concentrated under reduced pressure. The concentration residue was purified by medium-pressure preparative chromatography (silica gel, eluting solvent: hexane: ethyl acetate) to obtain 2.92 g of the title compound as a colorless oil.

Mass spectrum (ESI, m/z): 439 [M+H]$^+$.

Reference Example 2-(d), Etc.

Corresponding starting compounds were treated in the same manner as in Reference Example 1-(d) to obtain compounds described in the following Tables 4-1 to 4-8.

TABLE 4-1

| Reference Example | Structural formula | Mass spectrum |
|---|---|---|
| Reference Example 2-(d) | 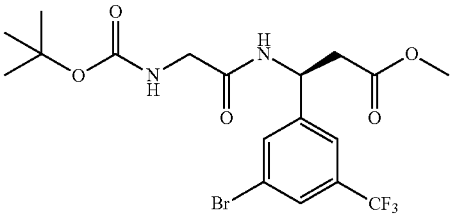 [SMILES: COC(=O)C[C@H](NC(=O)CNC(=O)OC(C)(C)C)c1cc(Br)cc(C(F)(F)F)c1] | (Cl, m/z): 483, 485 [M + H]$^+$ |
| Reference Example 3-(d) | 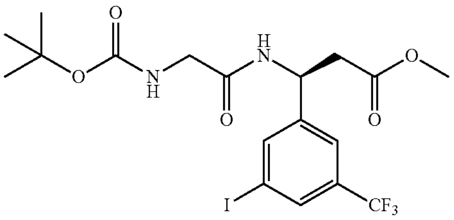 | (ESI, m/z): 531 [M + H]$^+$ |

TABLE 4-1-continued
| Reference Example | Structural formula | Mass spectrum |
|---|---|---|
| Reference Example 4-(d) | 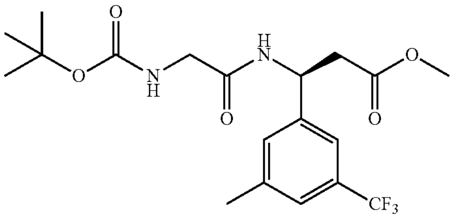 | (ESI, m/z): 419 [M + H]$^+$ |
| Reference Example 5-(d) | 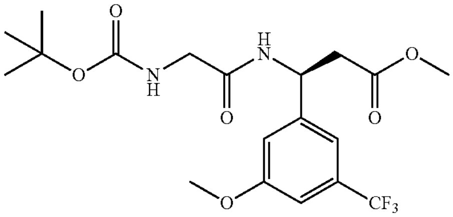 [SMILES: COC(=O)C[C@H](NC(=O)CNC(=O)OC(C)(C)C)c1cc(OC)cc(C(F)(F)F)c1] | (ESI, m/z): 435 [M + H]$^+$ |
| Reference Example 6-(d) | 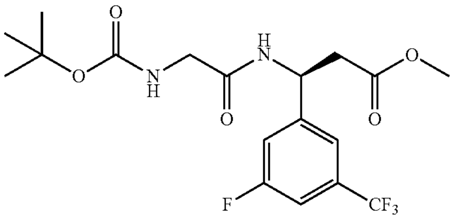 [SMILES: COC(=O)C[C@H](NC(=O)CNC(=O)OC(C)(C)C)c1cc(F)cc(C(F)(F)F)c1] | (ESI, m/z): 423 [M + H]$^+$ |
| Reference Example 7-(d) | 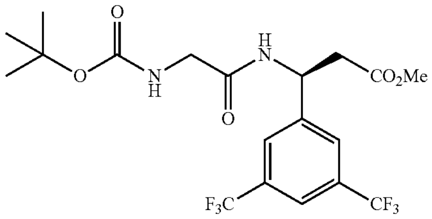 [SMILES: COC(=O)C[C@H](NC(=O)CNC(=O)OC(C)(C)C)c1cc(C(F)(F)F)cc(C(F)(F)F)c1] | (ESI, m/z): 473 [M + H]$^+$ |
TABLE 4-2
| Reference Example | Structural formula | Mass spectrum |
|---|---|---|
| Reference Example 9-(d) | 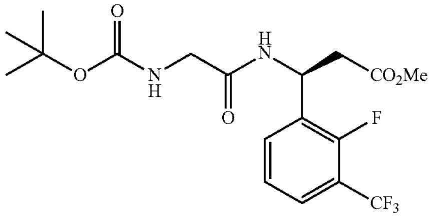 [SMILES: COC(=O)C[C@H](NC(=O)CNC(=O)OC(C)(C)C)c1cccc(C(F)(F)F)c1F] | (ESI, m/z): 445 [M + Na]$^+$ |
| Reference Example 10-(d) | 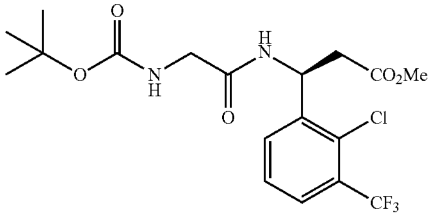 | (ESI, m/z): 461 [M + Na]$^+$ |

TABLE 4-2-continued
| Reference Example | Structural formula | Mass spectrum |
|---|---|---|
| Reference Example 11-(d) | 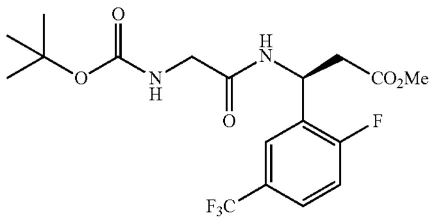 [SMILES: COC(=O)C[C@H](NC(=O)CNC(=O)OC(C)(C)C)c1cc(C(F)(F)F)ccc1Cl] | (ESI, m/z): 445 [M + Na]$^+$ |
| Reference Example 12-(d) | 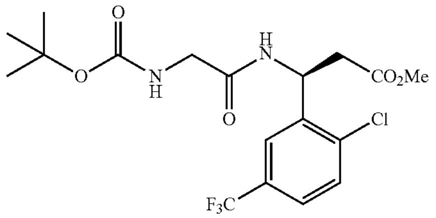 | (ESI, m/z): 461 [M + Na]$^+$ |
| Reference Example 13-(d) | 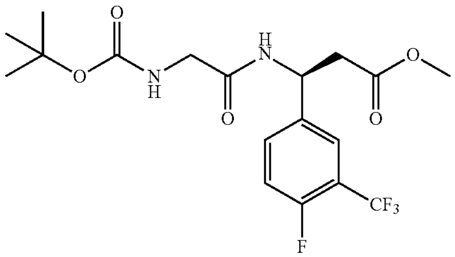 [SMILES: COC(=O)C[C@H](NC(=O)CNC(=O)OC(C)(C)C)c1ccc(F)c(C(F)(F)F)c1] | (ESI, m/z): 423 [M + H]$^+$ |
| Reference Example 14-(d) | 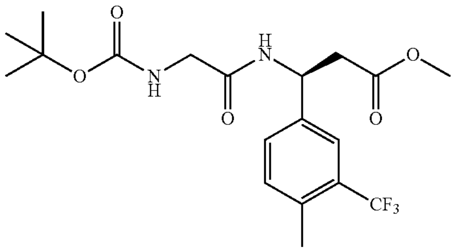 [SMILES: COC(=O)C[C@H](NC(=O)CNC(=O)OC(C)(C)C)c1ccc(C)c(C(F)(F)F)c1] | (ESI, m/z): 419 [M + H]$^+$ |
TABLE 4-3
| Reference Example | Structural formula | Mass spectrum |
|---|---|---|
| Reference Example 15-(f) | 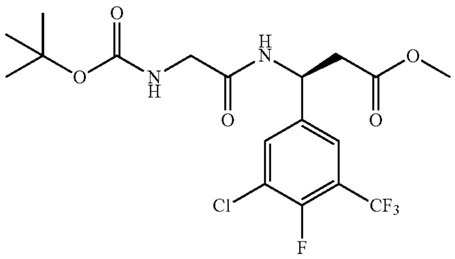 [SMILES: COC(=O)C[C@H](NC(=O)CNC(=O)OC(C)(C)C)c1cc(Cl)c(F)c(C(F)(F)F)c1] | (ESI, m/z): 457 [M + H]$^+$ |

TABLE 4-3-continued
| Reference Example | Structural formula | Mass spectrum |
| --- | --- | --- |
| Reference Example 16-(d) | 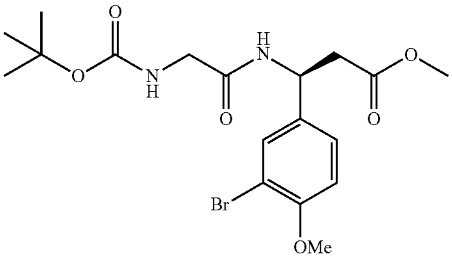 [SMILES: COC(=O)C[C@H](NC(=O)CNC(=O)OC(C)(C)C)c1ccc(OC)c(Br)c1] | (ESI, m/z): 445, 447 [M + H]+ |
| Reference Example 17-(d) | 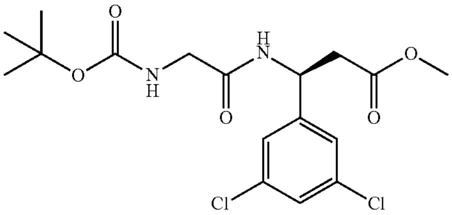 [SMILES: COC(=O)C[C@H](NC(=O)CNC(=O)OC(C)(C)C)c1cc(Cl)cc(Cl)c1] | (ESI, m/z): 427 [M + Na]+ |
| Reference Example 18-(d) | 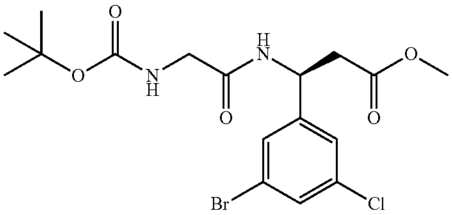 | (ESI, m/z): 449, 451 [M + H]+ |
| Reference Example 19-(d) | 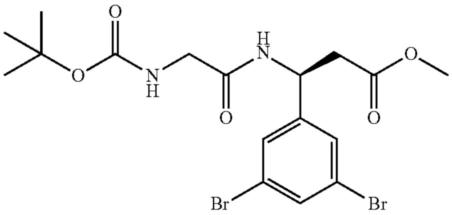 [SMILES: COC(=O)C[C@H](NC(=O)CNC(=O)OC(C)(C)C)c1cc(Br)cc(Br)c1] | (DUIS, m/z): 493 [M − H]− |
| Reference Example 20-(d) | 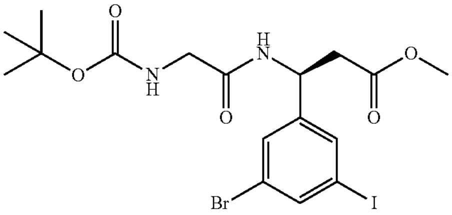 [SMILES: COC(=O)C[C@H](NC(=O)CNC(=O)OC(C)(C)C)c1cc(Br)cc(I)c1] | (ESI, m/z): 541, 543 [M + H]+ |
TABLE 4-4
| Reference Example | Structural formula | Mass spectrum |
| --- | --- | --- |
| Reference Example 21-(f) | 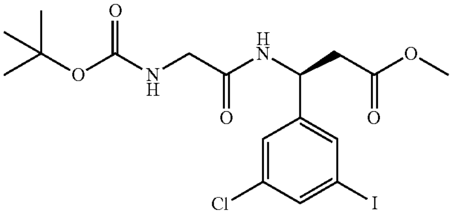 [SMILES: COC(=O)C[C@H](NC(=O)CNC(=O)OC(C)(C)C)c1cc(Cl)cc(I)c1] | (ESI, m/z): 497 [M + H]+ |

TABLE 4-4-continued
| Reference Example | Structural formula | Mass spectrum |
|---|---|---|
| Reference Example 22-(d) | 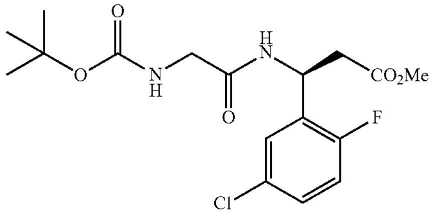 [SMILES: COC(=O)C[C@H](NC(=O)CNC(=O)OC(C)(C)C)c1cc(Cl)ccc1F] | (ESI, m/z): 389 [M + H]+ |
| Reference Example 23-(d) | 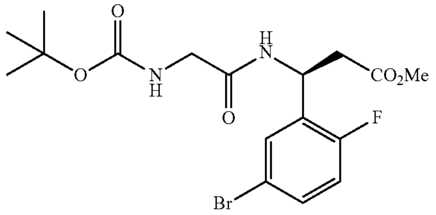 [SMILES: COC(=O)C[C@H](NC(=O)CNC(=O)OC(C)(C)C)c1cc(Br)ccc1F] | (ESI, m/z): 433, 435 [M + H]+ |
| Reference Example 24-(e) | 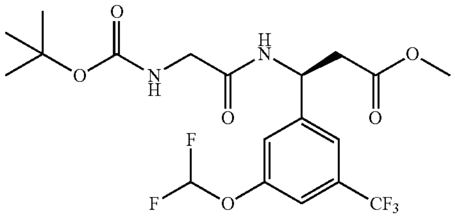 [SMILES: COC(=O)C[C@H](NC(=O)CNC(=O)OC(C)(C)C)c1cc(OC(F)F)cc(C(F)(F)F)c1] | (ESI, m/z): 471 [M + H]+ |
| Reference Example 25-(e) | 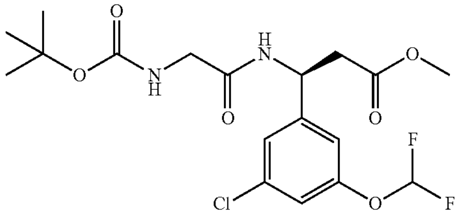 [SMILES: COC(=O)C[C@H](NC(=O)CNC(=O)OC(C)(C)C)c1cc(Cl)cc(OC(F)F)c1] | (ESI, m/z): 437 [M + H]+ |
| Reference Example 26-(e) | 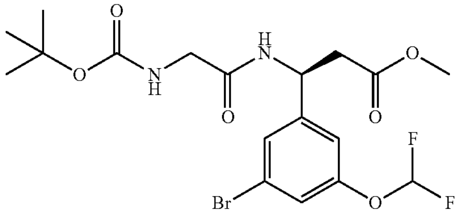 [SMILES: COC(=O)C[C@H](NC(=O)CNC(=O)OC(C)(C)C)c1cc(Br)cc(OC(F)F)c1] | (ESI, m/z): 481, 483 [M + H]+ |
TABLE 4-5
| Reference Example | Structural formula | Mass spectrum |
|---|---|---|
| Reference Example 27-(e) | 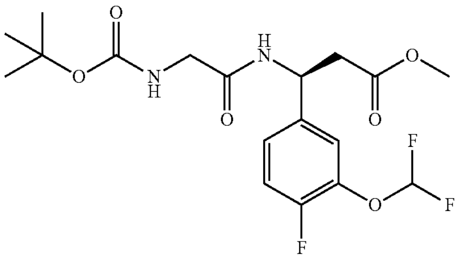 [SMILES: COC(=O)C[C@H](NC(=O)CNC(=O)OC(C)(C)C)c1ccc(F)c(OC(F)F)c1] | (ESI, m/z): 421 [M + H]+ |

TABLE 4-5-continued
| Reference Example | Structural formula | Mass spectrum |
|---|---|---|
| Reference Example 28-(e) | 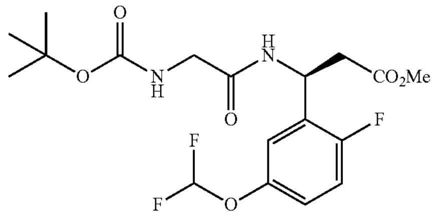 [SMILES: COC(=O)C[C@H](NC(=O)CNC(=O)OC(C)(C)C)c1cc(OC(F)F)ccc1F] | (ESI, m/z): 421 [M + H]$^+$ |
| Reference Example 30-(f) | 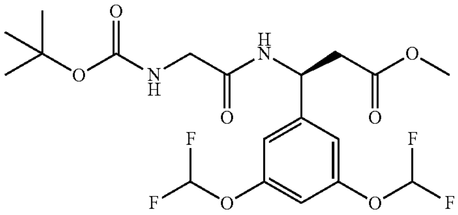 [SMILES: COC(=O)C[C@H](NC(=O)CNC(=O)OC(C)(C)C)c1cc(OC(F)F)cc(OC(F)F)c1] | (ESI, m/z): 469 [M + H]$^+$ |
| Reference Example 31-(d) | 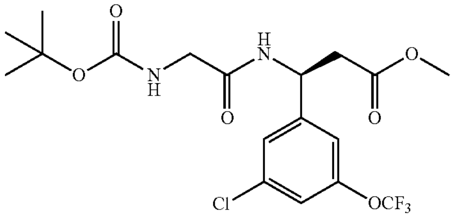 [SMILES: COC(=O)C[C@H](NC(=O)CNC(=O)OC(C)(C)C)c1cc(Cl)cc(OC(F)(F)F)c1] | (ESI, m/z): 455 [M + H]$^+$ |
| Reference Example 32-(d) | 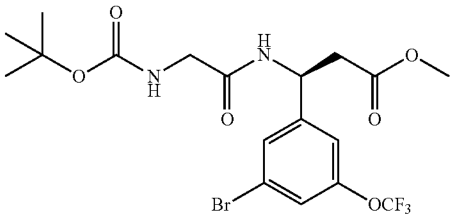 | (ESI, m/z): 499, 501 [M + H]$^+$ |
| Reference Example 33-(d) | 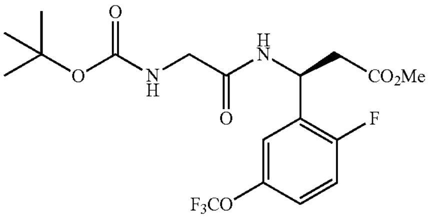 | (ESI, m/z): 439 [M + H]$^+$ |
TABLE 4-6
| Reference Example | Structural formula | Mass spectrum |
|---|---|---|
| Reference Example 34-(d) | 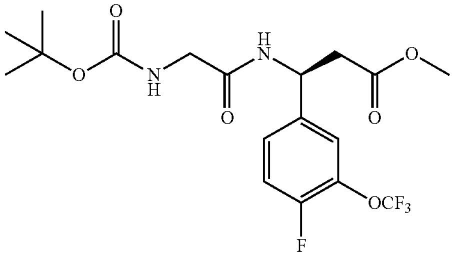 [SMILES: COC(=O)C[C@H](NC(=O)CNC(=O)OC(C)(C)C)c1ccc(F)c(OC(F)(F)F)c1] | (ESI, m/z): 439 [M + H]$^+$ |

TABLE 4-6-continued
| Reference Example | Structural formula | Mass spectrum |
|---|---|---|
| Reference Example 35-(d) | 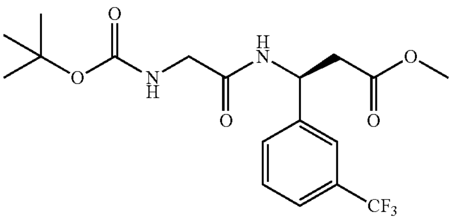 [SMILES: COC(=O)C[C@H](NC(=O)CNC(=O)OC(C)(C)C)c1cccc(C(F)(F)F)c1] | (ESI, m/z): 405 [M + H]+ |
| Reference Example 36-(d) | 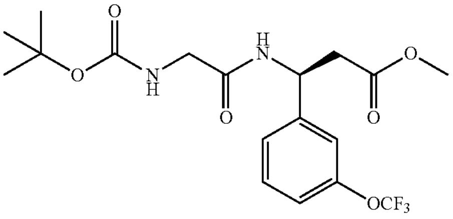 [SMILES: COC(=O)C[C@H](NC(=O)CNC(=O)OC(C)(C)C)c1cccc(OC(F)(F)F)c1] | (ESI, m/z): 443 [M + Na]+ |
| Reference Example 37-(d) | 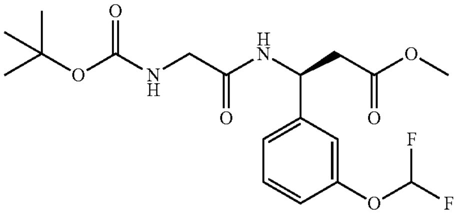 [SMILES: COC(=O)C[C@H](NC(=O)CNC(=O)OC(C)(C)C)c1cccc(OC(F)F)c1] | (ESI, m/z): 403 [M + H]+ |
| Reference Example 38-(d) | 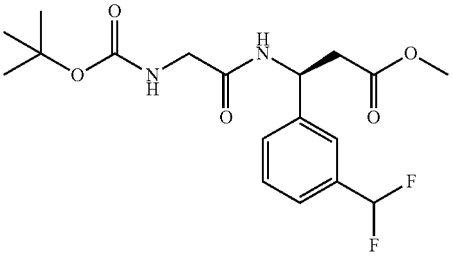 [SMILES: COC(=O)C[C@H](NC(=O)CNC(=O)OC(C)(C)C)c1cccc(C(F)F)c1] | (ESI, m/z): 409 [M + Na]+ |
| Reference Example 39-(d) | 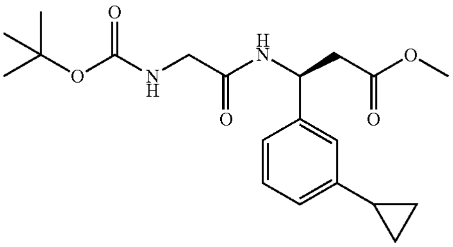 [SMILES: COC(=O)C[C@H](NC(=O)CNC(=O)OC(C)(C)C)c1cccc(C2CC2)c1] | (ESI, m/z): 377 [M + H]+ |
TABLE 4-7
| Reference Example | Structural formula | Mass spectrum |
|---|---|---|
| Reference Example 40-(d) | 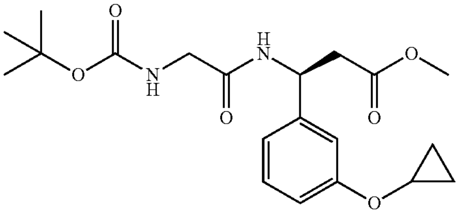 [SMILES: COC(=O)C[C@H](NC(=O)CNC(=O)OC(C)(C)C)c1cccc(OC2CC2)c1] | (ESI, m/z): 393 [M + H]+ |

TABLE 4-7-continued
| Reference Example | Structural formula | Mass spectrum |
|---|---|---|
| Reference Example 41-(d) | 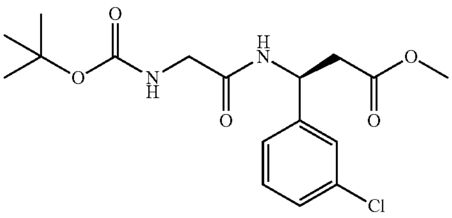 [SMILES: COC(=O)C[C@H](NC(=O)CNC(=O)OC(C)(C)C)c1cccc(Cl)c1] | (ESI, m/z): 371 $[M + H]^+$ |
| Reference Example 42-(d) | 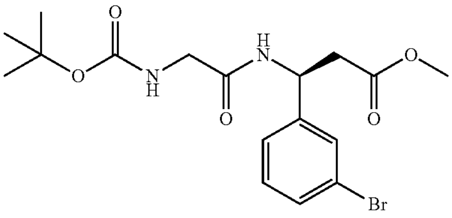 [SMILES: COC(=O)C[C@H](NC(=O)CNC(=O)OC(C)(C)C)c1cccc(Br)c1] | (ESI, m/z): 415, 417 $[M + H]^+$ |
| Reference Example 43-(d) | 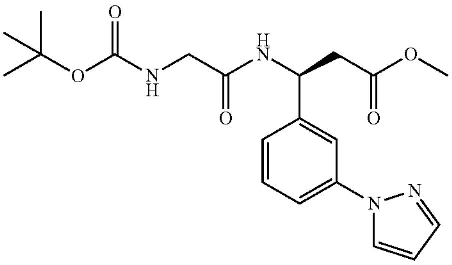 [SMILES: COC(=O)C[C@H](NC(=O)CNC(=O)OC(C)(C)C)c1cccc(-n2cccn2)c1] | (ESI, m/z): 403 $[M + H]^+$ |
| Reference Example 44-(d) | 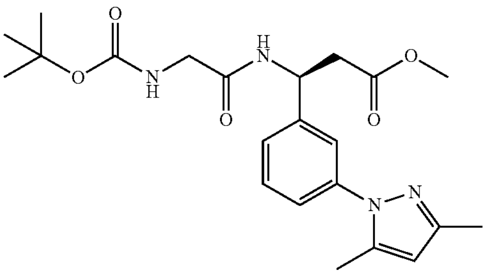 [SMILES: COC(=O)C[C@H](NC(=O)CNC(=O)OC(C)(C)C)c1cccc(-n2nc(C)cc2C)c1] | (ESI, m/z): 431 $[M + H]^+$ |
| Reference Example 45-(d) | 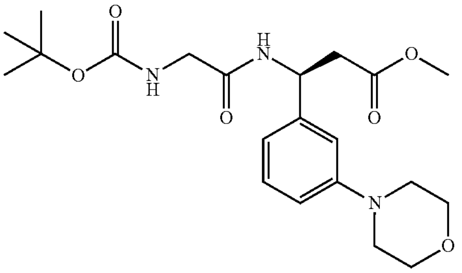 [SMILES: COC(=O)C[C@H](NC(=O)CNC(=O)OC(C)(C)C)c1cccc(N2CCOCC2)c1] | (ESI, m/z): 422 $[M + H]^+$ |

TABLE 4-8

| Reference Example | Structural formula | Mass spectrum |
|---|---|---|
| Reference Example 46-(d) | 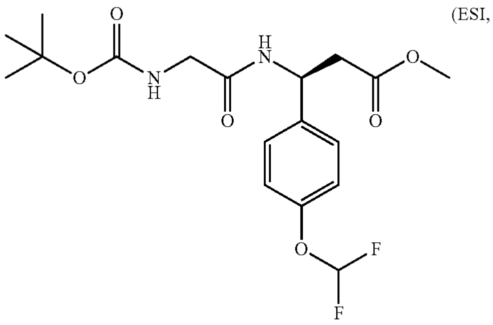 | (ESI, m/z): 425 [M + Na]$^+$ |
| Reference Example 47-(d) | 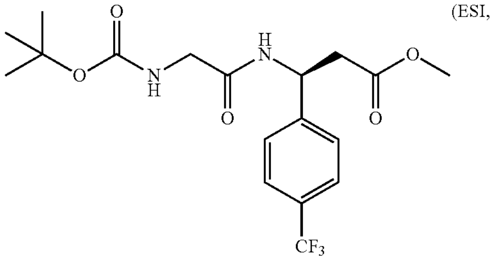 | (ESI, m/z): 427 [M + Na]$^+$ |

Reference Example 1-(e)

Production of methyl (S)-3-(2-aminoacetamido)-3-(3-chloro-5-(trifluoromethyl)phenyl)propanoate hydrochloride

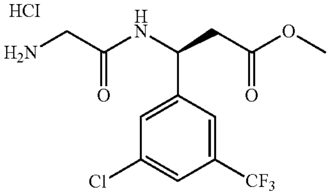

To a solution of 27.8 g of methyl (S)-3-(2-((tert-butoxycarbonyl)amino)acetamido)-3-(3-chloro-5-(trifluoromethyl)phenyl)propanoate synthesized in the same manner as in Reference Example 1-(d) in cyclopentyl methyl ether (190 ml), 60 ml of a 4 M solution of hydrogen chloride in cyclopentyl methyl ether was added at room temperature under a stream of argon, and the mixture was stirred at room temperature for 7 hours.

After the completion of reaction, the reaction mixture was concentrated under reduced pressure to obtain 21.5 g of the title compound as a pale yellow oil.

Mass spectrum (ESI, m/z): 339 [M+H]$^+$.

Reference Example 2-(e), Etc.

Corresponding starting compounds were treated in the same manner as in Reference Example 1-(e) to obtain compounds described in the following Tables 5-1 to 5-8.

TABLE 5-1

| Reference Example | Structural formula | Mass spectrum |
|---|---|---|
| Reference Example 2-(e) | 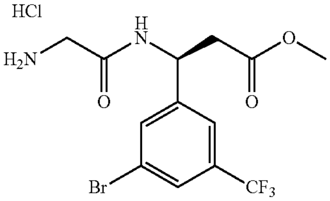 [SMILES: Cl ; COC(=O)C[C@H](NC(=O)CN)c1cc(Br)cc(C(F)(F)F)c1] | (CI, m/z): 383, 385 [M + H]$^+$ |
| Reference Example 3-(e) | 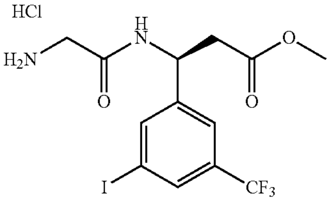 [SMILES: Cl ; COC(=O)C[C@H](NC(=O)CN)c1cc(I)cc(C(F)(F)F)c1] | (ESI, m/z): 431 [M + H]$^+$ |

TABLE 5-1-continued

| Reference Example | Structural formula | Mass spectrum |
| --- | --- | --- |
| Reference Example 4-(e) | HCl 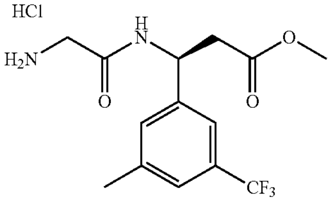 | (ESI, m/z): 319 [M + H]$^+$ |
| Reference Example 5-(e) | HCl 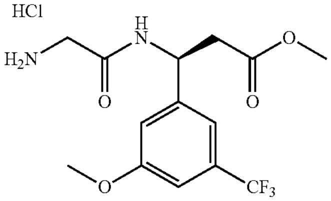 [SMILES: Cl ; COC(=O)C[C@H](NC(=O)CN)c1cc(OC)cc(C(F)(F)F)c1] | (ESI, m/z): 335 [M + H]$^+$ |
| Reference Example 6-(e) | HCl 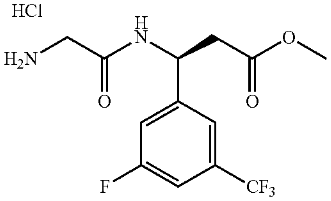 [SMILES: Cl ; COC(=O)C[C@H](NC(=O)CN)c1cc(F)cc(C(F)(F)F)c1] | (ESI, m/z): 323 [M + H]$^+$ |
| Reference Example 7-(e) | HCl 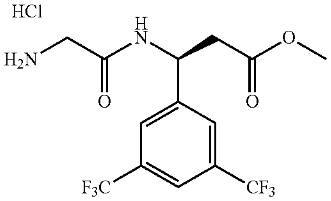 [SMILES: Cl ; COC(=O)C[C@H](NC(=O)CN)c1cc(C(F)(F)F)cc(C(F)(F)F)c1] | (ESI, m/z): 373 [M + H]$^+$ |

TABLE 5-2

| Reference Example | Structural formula | Mass spectrum |
| --- | --- | --- |
| Reference Example 8-(b) | HCl 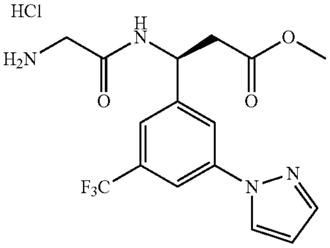 | (ESI, m/z): 371 [M + H]$^+$ |
| Reference Example 9-(e) | HCl 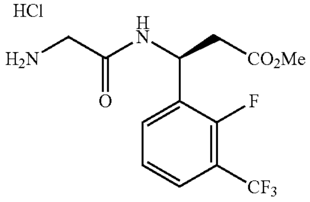 [SMILES: Cl ; COC(=O)C[C@H](NC(=O)CN)c1cccc(C(F)(F)F)c1F] | (ESI, m/z): 323 [M + H]$^+$ |

TABLE 5-2-continued
| Reference Example | Structural formula | Mass spectrum |
| --- | --- | --- |
| Reference Example 10-(e) | 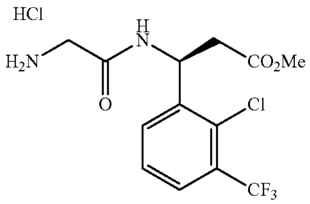 | (ESI, m/z): 339 [M + H]$^+$ |
| Reference Example 11-(e) | 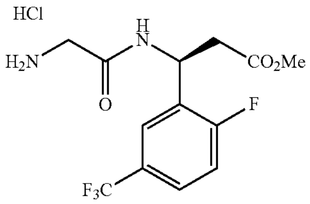 [SMILES: Cl ; COC(=O)C[C@H](NC(=O)CN)c1cc(C(F)(F)F)ccc1F] | (ESI, m/z): 323 [M + H]$^+$ |
| Reference Example 12-(e) | 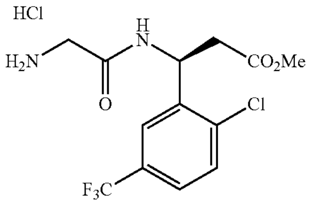 [SMILES: Cl ; COC(=O)C[C@H](NC(=O)CN)c1cc(C(F)(F)F)ccc1Cl] | (ESI, m/z): 339 [M + H]$^+$ |
| Reference Example 13-(e) | 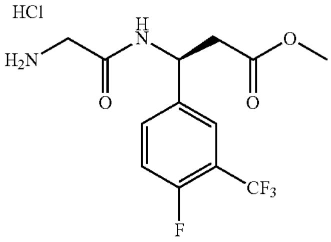 [SMILES: Cl ; COC(=O)C[C@H](NC(=O)CN)c1ccc(F)c(C(F)(F)F)c1] | (ESI, m/z): 323 [M + H]$^+$ |
TABLE 5-3
| Reference Example | Structural formula | Mass spectrum |
| --- | --- | --- |
| Reference Example 15-(g) | 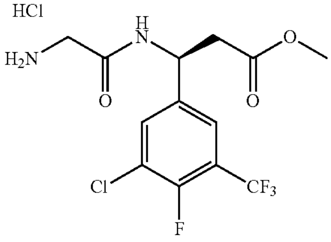 [SMILES: Cl ; COC(=O)C[C@H](NC(=O)CN)c1cc(Cl)c(F)c(C(F)(F)F)c1] | (ESI, m/z): 357 [M + H]$^+$ |
| Reference Example 16-(e) | 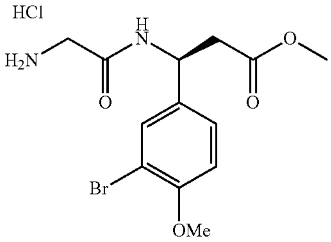 [SMILES: Cl ; COC(=O)C[C@H](NC(=O)CN)c1ccc(OC)c(Br)c1] | (ESI, m/z): 345, 347 [M + H]$^+$ |

TABLE 5-3-continued

| Reference Example | Structural formula | Mass spectrum |
| --- | --- | --- |
| Reference Example 17(e) | HCl 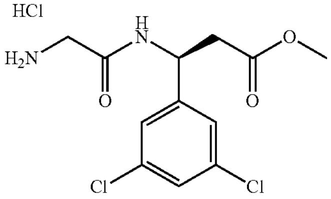 | (ESI, m/z): 305 $[M + H]^+$ |
| Reference Example 18-(e) | HCl 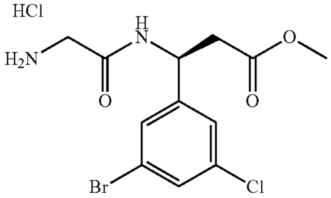 | (ESI, m/z): 349, 351 $[M + H]^+$ |
| Reference Example 19-(e) | HCl 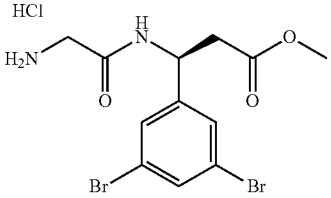 | (ESI, m/z): 395 $[M + H]^+$ |
| Reference Example 20-(e) | HCl 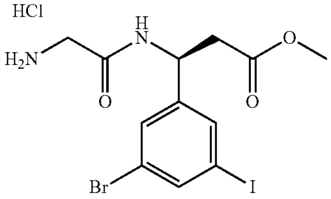 [SMILES: Cl ; COC(=O)C[C@H](NC(=O)CN)c1cc(Br)cc(I)c1] | (ESI, m/z): 441, 443 $[M + H]^+$ |

TABLE 5-4

| Reference Example | Structural formula | Mass spectrum |
| --- | --- | --- |
| Reference Example 21-(g) | HCl 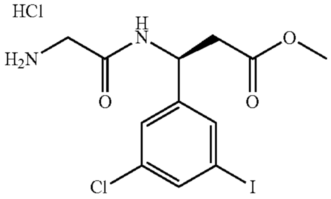 [SMILES: Cl ; COC(=O)C[C@H](NC(=O)CN)c1cc(Cl)cc(I)c1] | (ESI, m/z): 397 $[M + H]^+$ |
| Reference Example 22-(e) | HCl 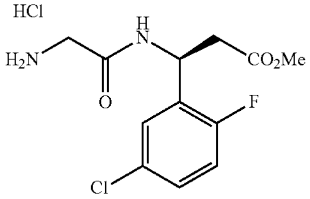 [SMILES: Cl ; COC(=O)C[C@H](NC(=O)CN)c1cc(Cl)ccc1F] | (ESI, m/z): 289 $[M + H]^+$ |

TABLE 5-4-continued
| Reference Example | Structural formula | Mass spectrum |
|---|---|---|
| Reference Example 23-(e) | HCl 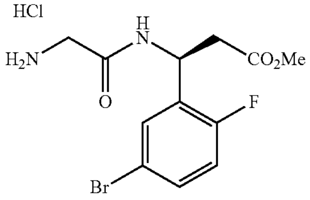 [SMILES: Cl ; COC(=O)C[C@H](NC(=O)CN)c1cc(Br)ccc1F] | (ESI, m/z): 333, 335 [M + H]+ |
| Reference Example 24-(f) | HCl 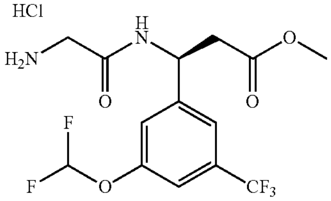 [SMILES: Cl ; COC(=O)C[C@H](NC(=O)CN)c1cc(OC(F)F)cc(C(F)(F)F)c1] | (ESI, m/z): 371 [M + H]+ |
| Reference Example 25-(f) | HCl 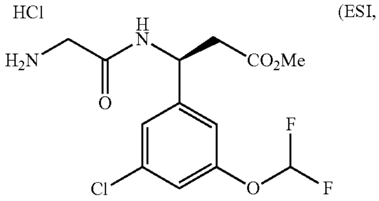 | (ESI, m/z): 337 [M + H]+ |
| Reference Example 26-(f) | HCl 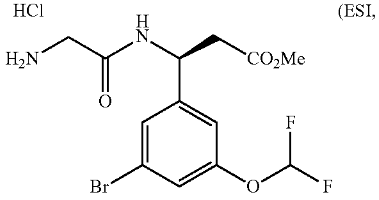 | (ESI, m/z): 381, 383 [M + H]+ |
TABLE 5-5
| Reference Example | Structural formula | Mass spectrum |
|---|---|---|
| Reference Example 27-(f) | HCl 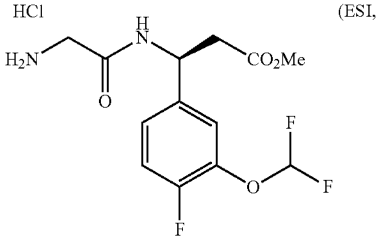 | (ESI, m/z): 321 [M + H]+ |
| Reference Example 28-(f) | HCl 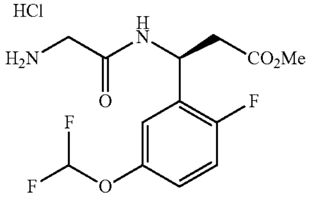 [SMILES: Cl ; COC(=O)C[C@H](NC(=O)CN)c1cc(OC(F)F)ccc1F] | (ESI, m/z): 321 [M + H]+ |

TABLE 5-5-continued

| Reference Example | Structural formula | Mass spectrum |
|---|---|---|
| Reference Example 29-(b) | HCl 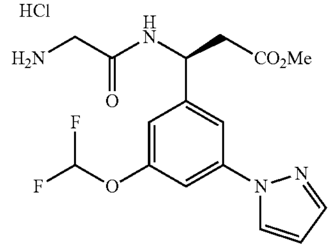 [SMILES: Cl ; COC(=O)C[C@H](NC(=O)CN)c1cc(OC(F)F)cc(-n2cccn2)c1] | (ESI, m/z): 369 [M + H]$^+$ |
| Reference Example 30-(g) | HCl 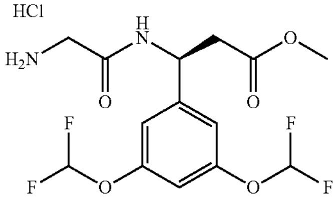 [SMILES: Cl ; COC(=O)C[C@H](NC(=O)CN)c1cc(OC(F)F)cc(OC(F)F)c1] | (ESI, m/z): 369 [M + H]$^+$ |
| Reference Example 31-(e) | HCl 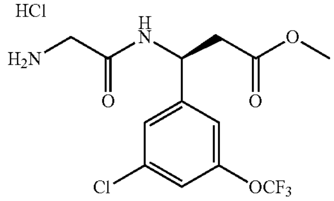 | (ESI, m/z): 355 [M + H]$^+$ |
| Reference Example 32-(e) | HCl 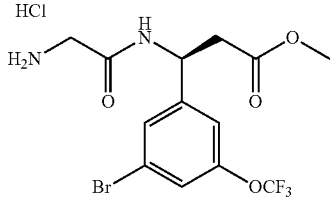 [SMILES: Cl ; COC(=O)C[C@H](NC(=O)CN)c1cc(Br)cc(OC(F)(F)F)c1] | (ESI, m/z): 399, 401 [M + H]$^+$ |

TABLE 5-6

| Reference Example | Structural formula | Mass spectrum |
|---|---|---|
| Reference Example 33-(e) | HCl 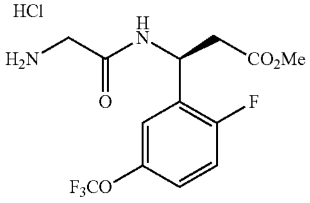 [SMILES: Cl ; COC(=O)C[C@H](NC(=O)CN)c1cc(OC(F)(F)F)ccc1F] | (ESI, m/z): 339 [M + H]$^+$ |
| Reference Example 34-(e) | HCl 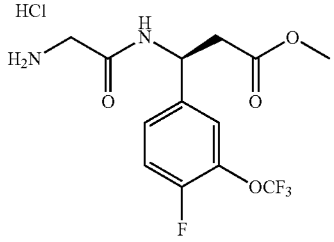 [SMILES: Cl ; COC(=O)C[C@H](NC(=O)CN)c1ccc(F)c(OC(F)(F)F)c1] | (ESI, m/z): 339 [M + H]$^+$ |

TABLE 5-6-continued

| Reference Example | Structural formula | Mass spectrum |
| --- | --- | --- |
| Reference Example 35-(e) | HCl 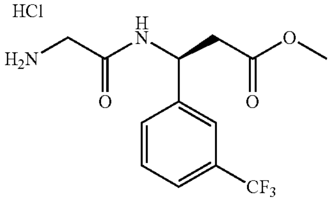 | (ESI, m/z): 305 [M + H]$^+$ |
| Reference Example 36-(e) | HCl 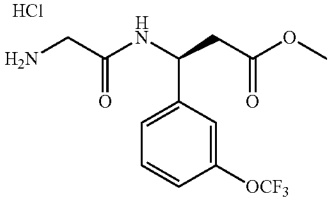 [SMILES: Cl ; COC(=O)C[C@H](NC(=O)CN)c1cccc(OC(F)(F)F)c1] | (ESI, m/z): 321 [M + H]$^+$ |
| Reference Example 37-e) | HCl 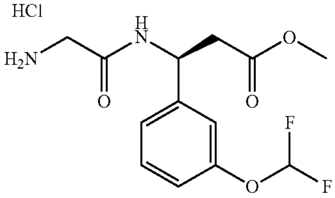 [SMILES: Cl ; COC(=O)C[C@H](NC(=O)CN)c1cccc(OC(F)F)c1] | (ESI, m/z): 303 [M + H]$^+$ |
| Reference Example 38-(e) | HCl 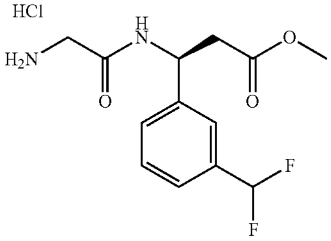 [SMILES: Cl ; COC(=O)C[C@H](NC(=O)CN)c1cccc(C(F)F)c1] | (ESI, m/z): 287 [M + H]$^+$ |

TABLE 5-7

| Reference Example | Structural formula | Mass spectrum |
| --- | --- | --- |
| Reference Example 39-(e) | HCl 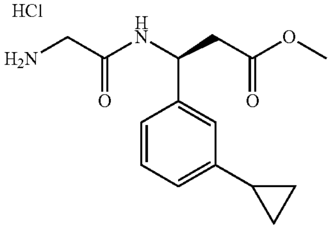 [SMILES: Cl ; COC(=O)C[C@H](NC(=O)CN)c1cccc(C2CC2)c1] | (ESI, m/z): 277 [M + H]$^+$ |
| Reference Example 40-(e) | HCl 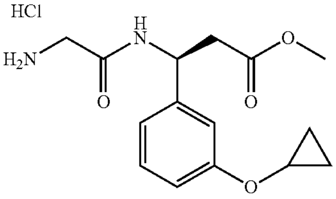 [SMILES: Cl ; COC(=O)C[C@H](NC(=O)CN)c1cccc(OC2CC2)c1] | (ESI, m/z): 293 [M + H]$^+$ |

TABLE 5-7-continued
| Reference Example | Structural formula | Mass spectrum |
|---|---|---|
| Reference Example 41-(e) | HCl 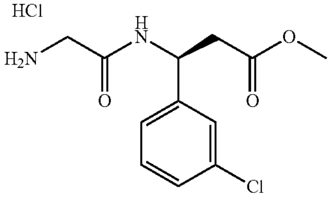 [SMILES: Cl ; COC(=O)C[C@H](NC(=O)CN)c1cccc(Cl)c1] | (ESI, m/z): 271 [M + H]$^+$ |
| Reference Example 42-(e) | HCl 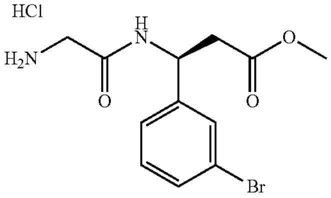 | (ESI, m/z): 315, 317 [M + H]$^+$ |
| Reference Example 43-(e) | HCl 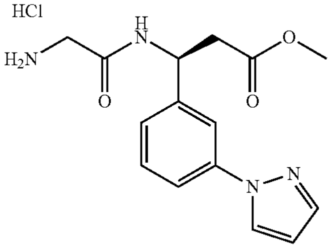 [SMILES: Cl ; COC(=O)C[C@H](NC(=O)CN)c1cccc(-n2cccn2)c1] | (ESI, m/z): 303 [M + H]$^+$ |
| Reference Example 44-(e) | HCl 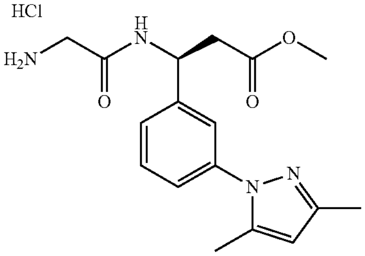 [SMILES: Cl ; COC(=O)C[C@H](NC(=O)CN)c1cccc(-n2nc(C)cc2C)c1] | (ESI, m/z): 331 [M + H]$^+$ |
TABLE 5-8
| Reference Example | Structural formula | Mass spectrum |
|---|---|---|
| Reference Example 45-(e) | HCl 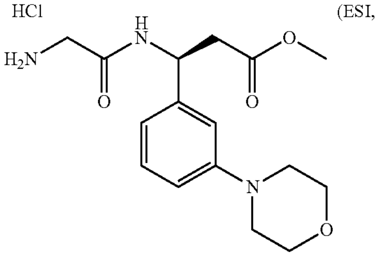 | (ESI, m/z): 322 [M + H]$^+$ |

TABLE 5-8-continued

| Reference Example | Structural formula | Mass spectrum |
| --- | --- | --- |
| Reference Example 46-(e) | 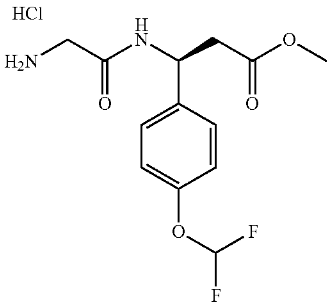 [SMILES: Cl ; COC(=O)C[C@H](NC(=O)CN)c1ccc(OC(F)F)cc1] | (ESI, m/z): 303 [M + H]$^+$ |
| Reference Example 47-(e) | 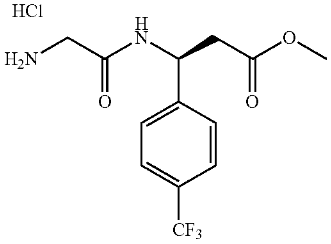 [SMILES: Cl ; COC(=O)C[C@H](NC(=O)CN)c1ccc(C(F)(F)F)cc1] | (ESI, m/z): 305 [M + H]$^+$ |

Reference Example 18-(c)

Production of methyl (S)-3-amino-3-(3-bromo-5-chlorophenyl)propanoate hydrochloride

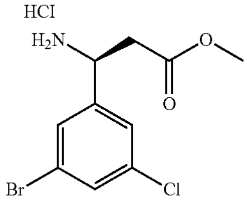

To a solution of 2.26 g of methyl (S)-3-(3-bromo-5-chlorophenyl)-3-(((R)-tert-butylsulfinyl)amino)propanoate synthesized in Reference Example 18-(b) in 1,4-dioxane (20 ml), 0.23 ml of methanol and 4.1 ml of a 4 M solution of hydrogen chloride in 1,4-dioxane were added at room temperature under a stream of argon, and the mixture was stirred at room temperature for 18 hours.

After the completion of reaction, 60 ml of hexane was added to the reaction mixture, and the mixture was stirred at room temperature for 1 hour. The reaction mixture was concentrated under reduced pressure. 10 ml of tert-butyl methyl ether was added to the concentration residue, and the mixture was stirred at room temperature for 3 hours. A solid was collected by filtration and dried under reduced pressure to obtain 1.07 g of the title compound as a white solid.

Mass spectrum (ESI, m/z): 292, 294 [M+H]$^+$.

Reference Example 7-(c), Etc.

Corresponding starting compounds were treated in the same manner as in Reference Example 18-(c) to obtain compounds described in the following Table 6.

TABLE 6

| Reference Example | Structural formula | Mass spectrum |
| --- | --- | --- |
| Reference Example 7-(c) | 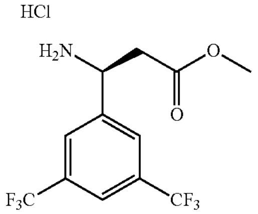 [SMILES: Cl ; COC(=O)C[C@H](N)c1cc(C(F)(F)F)cc(C(F)(F)F)c1] | |

TABLE 6-continued

| Reference Example | Structural formula | Mass spectrum |
|---|---|---|
| Reference Example 14-(c) | HCl 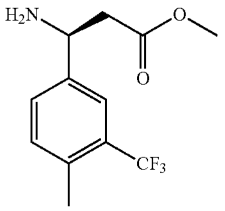 | (ESI, m/z): 262 [M + H]$^+$ |
| Reference Example 34-(c) | HCl 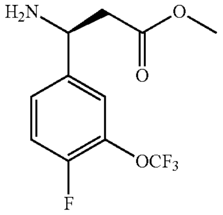 | |
| Reference Example 41-(c) | HCl 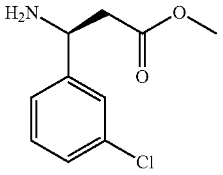 | (ESI, m/z): 214 [M + H]$^+$ |
| Reference Example 42-(c) | HCl 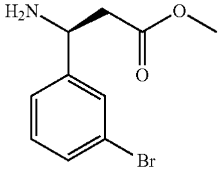 | (ESI, m/z): 258, 260 [M + H]$^+$ |

Reference Example 8-(a)

Production of methyl (S)-3-(3-(1H-pyrazol-1-yl)-5-(trifluoromethyl)phenyl)-3-(2-((tert-butoxycarbonyl)amino)acetamido)propanoate

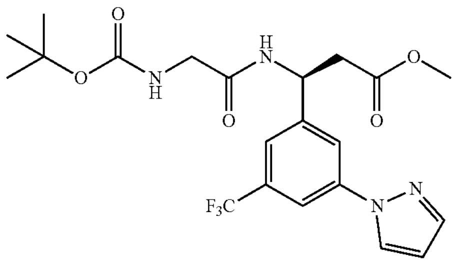 [SMILES: COC(=O)C[C@H](NC(=O)CNC(=O)OC(C)(C)C)c1cc(-n2cccn2)cc(C(F)(F)F)c1]

To a solution of 300 mg of methyl (S)-3-(2-((tert-butoxycarbonyl)amino)acetamido)-3-(3-bromo-5-(trifluoromethyl)phenyl)propanoate synthesized in the same manner as in Reference Example 2-(d) in N,N-dimethylformamide (3 ml), 51 mg of pyrazole, 392 μl of trans-N,N'-dimethylcyclohexane-1,2-diamine, and 345 mg of potassium carbonate were added at room temperature under a stream of argon, and the mixture was stirred at room temperature for 10 minutes under argon bubbling. Subsequently, 236 mg of copper(I) iodide was added thereto at room temperature, and the mixture was stirred at 90 °C for 3 hours.

After the completion of reaction, water was added to the reaction mixture, and the mixed solution was subjected to extraction with ethyl acetate. The organic layer was washed with a saturated aqueous solution of ammonium chloride and saturated saline, dried over anhydrous magnesium sulfate, filtered, and concentrated under reduced pressure. The obtained residue was purified by medium-pressure preparative chromatography (silica gel, eluting solvent: hexane: ethyl acetate) to obtain 81 mg of the title compound as a colorless oil.

Mass spectrum (ESI, m/z): 471 [M+H]$^+$.

Reference Example 29-(a)

A corresponding starting compound was treated in the same manner as in Reference Example 8-(a) to obtain a compound described in the following Table 7.

TABLE 7

| Reference Example | Structural formula | Mass spectrum |
|---|---|---|
| Reference Example 29-(a) | 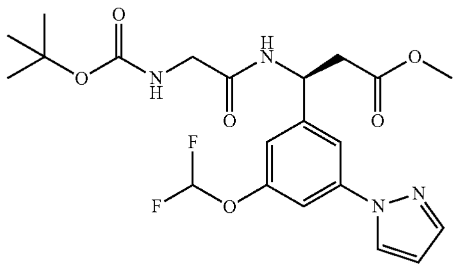 [SMILES: COC(=O)C[C@H](NC(=O)CNC(=O)OC(C)(C)C)c1cc(OC(F)F)cc(-n2cccn2)c1] | (ESI, m/z): 469 [M + H]$^+$ |

Reference Example 14-(e)

Production of methyl (S)-3-(2-aminoacetamido)-3-(4-methyl-3-(trifluoromethyl)phenyl)propanoate hydrochloride

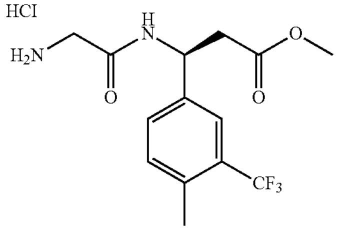 [SMILES: "HCI" ; COC(=O)C[C@H](NC(=O)CN)c1ccc(C)c(C(F)(F)F)c1]

To 293 mg of methyl (S)-3-(2-((tert-butoxycarbonyl)amino)acetamido)-3-(4-methyl-3-(trifluoromethyl)phenyl)propanoate synthesized in Reference Example 14-(d), 3.2 ml of tert-butyl methyl ether and 0.657 ml of a 4 M solution of hydrogen chloride in 1,4-dioxane were added in a nitrogen atmosphere, and the mixture was stirred at room temperature for 3 hours. 0.657 ml of a 4 M solution of hydrogen chloride in 1,4-dioxane was further added thereto, and the mixture was stirred at room temperature for 3 hours. 0.657 ml of a 4 M solution of hydrogen chloride in 1,4-dioxane was further added thereto, and the mixture was stirred at room temperature for 2 hours. After the completion of reaction, the reaction mixture was concentrated under reduced pressure to obtain 259 mg of the title compound.

Mass spectrum (ESI, m/z): 319 [M+H]$^+$.

Reference Example 15-(a)

Production of (3-chloro-4-fluoro-5-(trifluoromethyl)phenyl)methanol

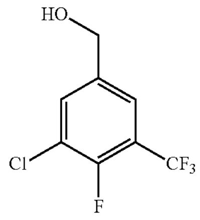 [SMILES: OCc1cc(Cl)c(F)c(C(F)(F)F)c1]

To a solution of 1.00 g of 3-chloro-4-fluoro-5-(trifluoromethyl)benzoic acid in tetrahydrofuran (20 ml), 9.16 ml of a 0.9 M solution of a borane-tetrahydrofuran complex in tetrahydrofuran was added in an ice bath under a stream of argon, and the mixture was stirred at room temperature for 20 hours.

After the completion of reaction, 2 M hydrochloric acid was added to the reaction mixture, and the mixed solution was subjected to extraction with ethyl acetate. The organic layer was washed with a saturated aqueous solution of sodium bicarbonate, dried over anhydrous magnesium sulfate, filtered, and concentrated under reduced pressure. The obtained residue was purified by medium-pressure preparative chromatography (silica gel, eluting solvent: hexane: ethyl acetate) to obtain 1.06 g of the title compound as a colorless oil.

Mass spectrum (EI, m/z): 228 [M]$^+$.

Reference Example 21-(a), Etc.

Corresponding starting compounds were treated in the same manner as in Reference Example 15-(a) to obtain compounds described in the following Table 8.

TABLE 8

| Reference Example | Structural formula | Mass spectrum |
|---|---|---|
| Reference Example 21-(a) | 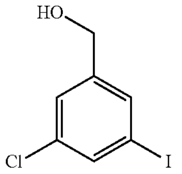 | (EI, m/z): 268 [M]$^+$ |

TABLE 8-continued

| Reference Example | Structural formula | Mass spectrum |
|---|---|---|
| Reference Example 30-(a) | 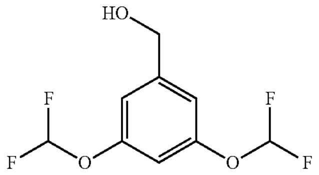 [SMILES: OCc1cc(OC(F)F)cc(OC(F)F)c1] | (EI, m/z): 240 [M]$^+$ |

Reference Example 21-(b)

Production of 3-chloro-5-iodobenzaldehyde

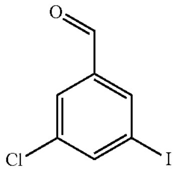

To a solution of 2.04 g of (3-chloro-5-iodophenyl)methanol synthesized in Reference Example 21-(a) in dichloromethane (40 ml), 4.83 g of Dess-Martin periodinane was added at room temperature with stirring under a stream of argon, and the mixture was stirred at room temperature for 10 minutes.

After the completion of reaction, a saturated aqueous solution of sodium bicarbonate supplemented with sodium thiosulfate was added to the reaction solution, and the mixed solution was subjected to extraction with methylene chloride. The organic layer was washed with saturated saline, dried over anhydrous magnesium sulfate, filtered, and concentrated under reduced pressure. The obtained residue was purified by medium-pressure preparative chromatography (silica gel, eluting solvent: hexane:ethyl acetate) to obtain 1.66 g of the title compound as a colorless oil.

Mass spectrum (EI, m/z): 266 [M]$^+$.

Reference Example 15-(b), Etc.

Corresponding starting compounds were treated in the same manner as in Reference Example 21-(b) to obtain compounds described in the following Table 9.

TABLE 9

| Reference Example | Structural formula | Mass spectrum |
|---|---|---|
| Reference Example 15-(b) | 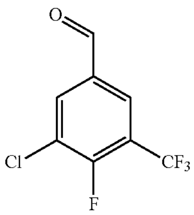 [SMILES: O=Cc1cc(Cl)c(F)c(C(F)(F)F)c1] | (CI, m/z): 227 [M + H]$^+$ |

TABLE 9-continued

| Reference Example | Structural formula | Mass spectrum |
|---|---|---|
| Reference Example 30-(b) | 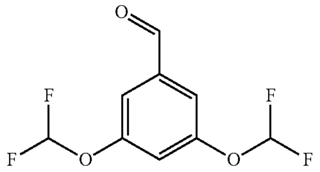 [SMILES: O=Cc1cc(OC(F)F)cc(OC(F)F)c1] | |

Reference Example 24-(a)

Production of 3-(difluoromethoxy)-5-(trifluoromethyl)benzaldehyde

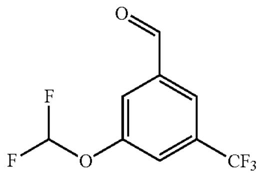

To a suspension of 4.36 g of potassium carbonate in N,N-dimethylformamide (16 ml), a solution of 6.42 g of sodium chlorodifluoroacetate and 4.00 g of 3-hydroxy-5-(trifluoromethyl)benzaldehyde in N,N-dimethylformamide (20 ml) was added dropwise at 95 °C under a stream of argon, and the mixture was stirred at 95 °C for 30 minutes.

After the completion of reaction, water was added to the reaction mixture, and the mixed solution was subjected to extraction with tert-butyl methyl ether. The organic layer was washed with saturated saline, dried over anhydrous magnesium sulfate, filtered, and concentrated under reduced pressure. The obtained residue was purified by medium-pressure preparative chromatography (silica gel, eluting solvent: hexane:ethyl acetate) to obtain 1.48 g of the title compound as a colorless oil.

Mass spectrum (EI, m/z): 240 [M]$^+$.

Reference Example 25-(a), Etc.

Corresponding starting compounds were treated in the same manner as in Reference Example 24-(a) to obtain compounds described in the following Table 10.

TABLE 10

| Reference Example | Structural formula | Mass spectrum |
|---|---|---|
| Reference Example 25-(a) | 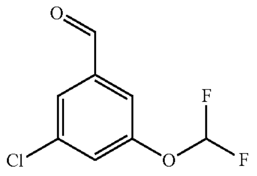 [SMILES: O=Cc1cc(Cl)cc(OC(F)F)c1] | (EI, m/z): 206 $[M]^+$ |
| Reference Example 26-(a) | 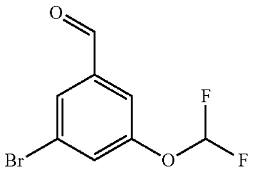 [SMILES: O=Cc1cc(Br)cc(OC(F)F)c1] | (EI, m/z): 250, 252 $[M]^+$ |
| Reference Example 27-(a) | 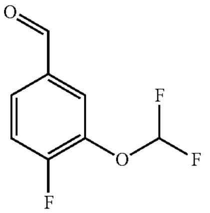 [SMILES: O=Cc1ccc(F)c(OC(F)F)c1] | (EI, m/z): 190 $[M]^+$ |
| Reference Example 28-(a) | 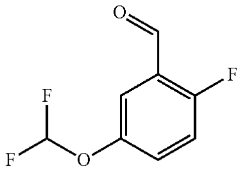 [SMILES: O=Cc1cc(OC(F)F)ccc1F] | (EI, m/z): 190 $[M]^+$ |

Reference Example 1-(f)

Production of 2-fluoromalonamide

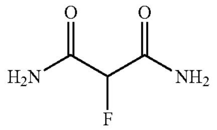

To a solution of 25.0 g of diethyl 2-fluoromalonate in methanol (100 ml), 80 ml of a 7 N solution of ammonia in methanol was added at room temperature under a stream of argon, and the mixture was stirred at room temperature for 4 hours.

After the completion of reaction, a solid was collected by filtration, washed with methanol, and then dried under reduced pressure at 50 °C to obtain 15.91 g of the title compound as a white solid.

$^1$H-NMR spectrum (400 MHz, DMSO-$d_6$) δ: 7.78-7.48 (m, 4H), 5.16 (d, J=48.9 Hz, 1H).

Reference Example 1-(g)

Production of 2-fluoropropane-1,3-diamine hydrochloride

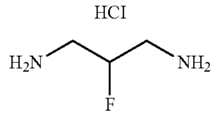

To 400 ml of a 0.9 M solution of a borane-tetrahydrofuran complex in tetrahydrofuran, 7.20 g of 2-fluoromalonamide synthesized in Reference Example 1-(f) was added in divided portions at room temperature under a stream of argon, and the mixture was stirred at room temperature for 20 hours.

After the completion of reaction, the reaction mixture was cooled to 0 °C, and 73 ml of methanol was added dropwise thereto at 20 °C or lower. The mixture was stirred at room temperature for 1 hour and concentrated under reduced pressure. 40 ml of ethanol was added to the concentration residue, then 60 ml of a 2 M solution of hydrogen chloride in ethanol was added thereto at 0 °C, and the mixture was stirred at room temperature for 3 hours. A deposited solid was collected by filtration, and the solid was dissolved in methanol and concentrated under reduced pressure. To the obtained solution of 6.91 g of the solid in methanol (200 ml), 70 g of Amberlite (IRA478RF CL) sequentially washed with 200 ml of water and 200 ml of methanol was added at room temperature, and the mixture was stirred at room temperature for 30 minutes. The reaction mixture was filtered, and the filtrate was concentrated under reduced pressure to obtain 4.55 g of the title compound as a white solid.

$^1$H-NMR spectrum (400 MHz, DMSO-$d_6$+$D_2O$) δ: 4.77-4.53 (m, 1H), 3.01-2.79 (m, 4H).

Reference Example 48-(a)

Production of methyl 4-bromo-3-fluoro-1-(tetrahydropyran-2-yl)-1H-indazole-6-carboxylate

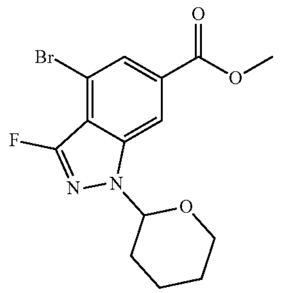 [SMILES: COC(=O)c1cc(Br)c2c(F)nn(C3CCCCO3)c2c1]

To a suspension of 200 mg of methyl 4-bromo-1H-indazole-6-carboxylate in acetonitrile (8 ml), 333 mg of 1-chloromethyl-4-fluoro-1,4-diazoniabicyclo[2.2.2]octane bis(tetrafluoroborate) was added at room temperature under a stream of argon, and the mixture was stirred at 100 °C for 4 hours.

After the completion of reaction, water was added to the reaction mixture, and the mixed solution was subjected to extraction with ethyl acetate. The organic layer was washed with saturated saline, dried over anhydrous sodium sulfate, filtered, and concentrated under reduced pressure.

To a suspension of the obtained concentration residue in dichloromethane (8 ml), 143 μl of 3,4-dihydro-2H-pyran and 15 mg of p-toluenesulfonic acid monohydrate were added at room temperature under a stream of argon, and the mixture was stirred at room temperature for 4 hours.

After the completion of reaction, a saturated aqueous solution of sodium bicarbonate was added to the reaction mixture, and the mixed solution was subjected to extraction with dichloromethane. The organic layer was washed with water, dried over anhydrous magnesium sulfate, filtered, and concentrated under reduced pressure. The obtained residue was subjected to medium-pressure preparative chromatography (silica gel, eluting solvent: hexane:ethyl acetate), and a fraction containing the compound of interest was concentrated under reduced pressure.

The obtained residue was purified by gel permeation chromatography (column: YMC-GPC T30000, YMC-GPC T4000, and YMC-GPC T2000, eluting solvent: ethyl acetate) to obtain 32 mg of the title compound as a white solid.

Mass spectrum (ESI, m/z): 357, 359 $[M+H]^+$.

Reference Example 49-(a)

Production of methyl 3-chloro-4-nitro-1H-indazole-6-carboxylate

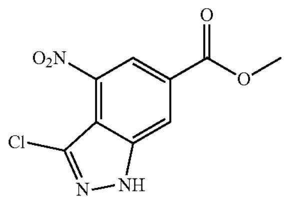 [SMILES: COC(=O)c1cc([N+](=O)[O-])c2c(Cl)n[nH]c2c1]

To a suspension of 300 mg of methyl 4-nitro-1H-indazole-6-carboxylate in acetonitrile (8 ml), 217 mg of N-chlorosuccinimide was added at room temperature under a stream of argon, and the mixture was stirred at 80 °C for 2 hours. Next, 145 mg of N-chlorosuccinimide was further added thereto at 80 °C, and the mixture was stirred at 80 °C for 2 hours.

After the completion of reaction, the reaction mixture was poured to a saturated aqueous solution of sodium bicarbonate, and the mixed solution was subjected to extraction with ethyl acetate. The organic layer was washed with saturated saline, dried over anhydrous magnesium sulfate, filtered, and concentrated under reduced pressure to obtain 347 mg of the title compound as a pale yellow solid.

Mass spectrum (ESI, m/z): 254 $[M-H]^-$.

Reference Example 1-(h)

Production of methyl 4-bromo-1-(tetrahydropyran-2-yl)-1H-indazole-6-carboxylate

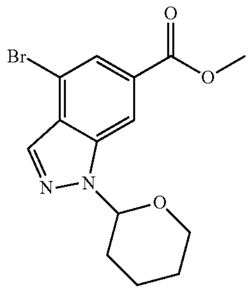 [SMILES: COC(=O)c1cc(Br)c2cnn(C3CCCCO3)c2c1]

To a suspension of 1.00 g of methyl 4-bromo-1H-indazole-6-carboxylate in dichloromethane (10 ml), 717 μl of 3,4-dihydro-2H-pyran and 82 mg of p-toluenesulfonic acid monohydrate were added at room temperature under a stream of argon, and the mixture was stirred at room temperature for 1 hour.

After the completion of reaction, a saturated aqueous solution of sodium bicarbonate was added to the reaction mixture, and the mixed solution was subjected to extraction with dichloromethane. The organic layer was washed with water, dried over anhydrous magnesium sulfate, filtered, and concentrated under reduced pressure. The obtained residue was purified by medium-pressure preparative chromatography (silica gel, eluting solvent: hexane:ethyl acetate) to obtain 1.13 g of the title compound as a pale yellow solid.

Mass spectrum (ESI, m/z): 339, 341 $[M+H]^+$.

Reference Example 49-(b)

A corresponding starting compound was treated in the same manner as in Reference Example 1-(h) to obtain a compound described in the following Table 11.

TABLE 11

| Reference Example | Structural formula | Mass spectrum |
|---|---|---|
| Reference Example 49-(b) | 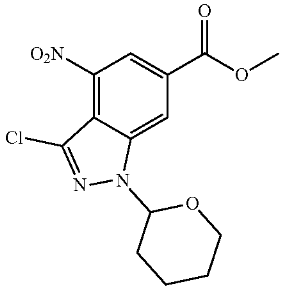 [SMILES: COC(=O)c1cc([N+](=O)[O-])c2c(Cl)nn(C3CCCCO3)c2c1] | (ESI, m/z): 340 $[M + H]^+$ |

Reference Example 1-(i)

Production of methyl 4-((diphenylmethylene) amino)-1-(tetrahydropyran-2-yl)-1H-indazole-6-carboxylate

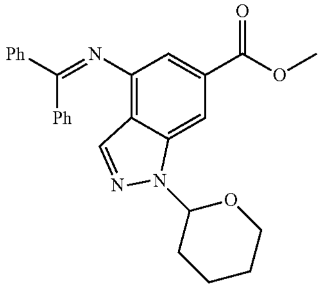 [SMILES: COC(=O)c1cc(N=C(c2ccccc2)c2ccccc2)c2cnn(C3CCCCO3)c2c1]

To a solution of 1.13 g of methyl 4-bromo-1-(tetrahydropyran-2-yl)-1H-indazole-6-carboxylate synthesized in Reference Example 1-(h) in xylene (20 ml), 1.11 ml of benzophenone imine, 305 mg of tris(dibenzylideneacetone) dipalladium(0), 771 mg of 4,5-bis(diphenylphosphino)-9,9-dimethylxanthene, and 3.26 g of cesium carbonate were added at room temperature under a stream of argon. After purging with an argon atmosphere, the mixture was stirred at 150 °C for 6 hours under a stream of argon.

After the completion of reaction, a saturated aqueous solution of ammonium chloride was added to the reaction mixture, and the mixed solution was subjected to extraction with toluene. The organic layer was washed with saturated saline, dried over anhydrous sodium sulfate, filtered, and concentrated under reduced pressure. The obtained residue was subjected to medium-pressure preparative chromatography (silica gel, eluting solvent: hexane:ethyl acetate), and a fraction containing the compound of interest was concentrated under reduced pressure. 20 mL of tert-butyl methyl ether was added to the obtained residue at room temperature, and the mixture was stirred at room temperature for 1 hour. A solid was collected by filtration to obtain 1.09 g of the title compound as a yellow solid.

$^1$H-NMR spectrum (400 MHz, DMSO-$d_6$) δ: 8.09 (d, J=0.8 Hz, 1H), 7.90-7.87 (m, 1H), 7.78-7.70 (m, 2H), 7.62-7.46 (m, 3H), 7.28-7.17 (m, 5H), 6.91 (d, J=1.1 Hz, 1H), 5.91 (dd, J=2.3, 9.5 Hz, 1H), 3.89-3.72 (m, 5H), 2.40-2.29 (m, 1H), 2.04-1.92 (m, 2H), 1.80-1.68 (m, 1H), 1.61-1.49 (m, 2H).

Reference Example 48-(b)

A corresponding starting compound was treated in the same manner as in Reference Example 1-(i) to obtain a compound described in the following Table 12.

TABLE 12

| Reference Example | Structural formula | Mass spectrum |
|---|---|---|
| Reference Example 48-(b) | 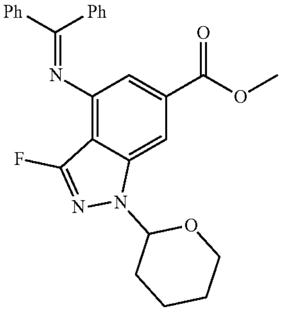 [SMILES: COC(=O)c1cc(N=C(c2ccccc2)c2ccccc2)c2c(F)nn(C3CCCCO3)c2c1] | (ESI, m/z): 458 [M + H]$^+$ |

Reference Example 1-(j)

Production of methyl 4-amino-1-(tetrahydropyran-2-yl)-1H-indazole-6-carboxylate

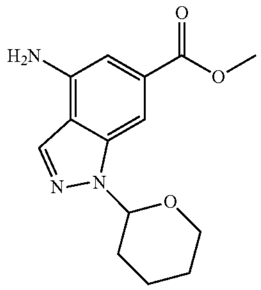 [SMILES: COC(=O)c1cc(N)c2cnn(C3CCCCO3)c2c1]

To a solution of 890 mg of methyl 4-((diphenylmethylene)amino)-1-(tetrahydropyran-2-yl)-1H-indazole-6-carboxylate synthesized in Reference Example 1-(i) in tetrahydrofuran (30 ml), 970 mg of 5% palladium carbon (containing 50.57% water, AER-type manufactured by N.E. Chemcat Corp.) was added at room temperature under a stream of argon. After purging with a hydrogen atmosphere, the mixture was stirred at room temperature for 1.5 hours.

After the completion of reaction, the reaction mixture was filtered through celite and washed with ethyl acetate, and the filtrate was concentrated under reduced pressure. The obtained residue was purified by medium-pressure preparative chromatography (silica gel, eluting solvent: hexane: ethyl acetate) to obtain 523 mg of the title compound as a white solid.

Mass spectrum (ESI, m/z): 276 [M+H]$^+$.

Reference Example 48-(c)

Production of methyl 4-amino-3-fluoro-1-(tetrahydropyran-2-yl)-1H-indazole-6-carboxylate

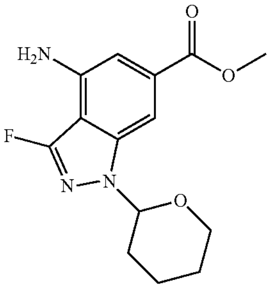 [SMILES: COC(=O)c1cc(N)c2c(F)nn(C3CCCCO3)c2c1]

To a solution of 100 mg of methyl 4-((diphenylmethylene)amino)-3-fluoro-1-(tetrahydropyran-2-yl)-1H-indazole-6-carboxylate synthesized in Reference Example 48-(b) in tetrahydrofuran (0.4 ml), 0.8 ml of a 10% aqueous citric acid solution was added at room temperature under a stream of argon, and the mixture was stirred at 70 °C for 18 hours.

After the completion of reaction, a saturated aqueous solution of sodium bicarbonate was added to the reaction mixture, and the mixed solution was subjected to extraction with ethyl acetate. The organic layer was washed with saturated saline, dried over anhydrous sodium sulfate, filtered, and concentrated under reduced pressure. The obtained residue was purified by medium-pressure preparative chromatography (silica gel, eluting solvent: hexane: ethyl acetate) to obtain 53 mg of the title compound as a yellow solid.

Mass spectrum (ESI, m/z): 294 $[M+H]^+$.

Reference Example 49-(c)

Production of methyl 4-amino-3-chloro-1-(tetrahydropyran-2-yl)-1H-indazole-6-carboxylate

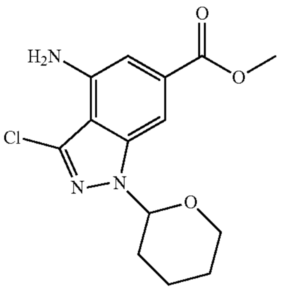 [SMILES: COC(=O)c1cc(N)c2c(Cl)nn(C3CCCCO3)c2c1]

To a suspension of 304 mg of methyl 3-chloro-4-nitro-1-(tetrahydropyran-2-yl)-1H-indazole-6-carboxylate synthesized in Reference Example 49-(b) in ethanol (3 ml) and water (1.5 ml), 779 mg of sodium dithionite was added at room temperature under a stream of argon, and the mixture was stirred at 90 °C for 1 hour.

After the completion of reaction, the reaction mixture was poured to water, and the mixed solution was subjected to extraction with ethyl acetate. The organic layer was washed with a saturated aqueous solution of sodium bicarbonate, dried over anhydrous magnesium sulfate, filtered, and concentrated under reduced pressure. The obtained residue was purified by medium-pressure preparative chromatography (silica gel, eluting solvent: hexane:ethyl acetate) to obtain 131 mg of the title compound as a pale yellow solid.

Mass spectrum (ESI, m/z): 310 $[M+H]^+$.

Reference Example 1-(k)

Production of methyl 4-(3-methylthioureido)-1-(tetrahydropyran-2-yl)-1H-indazole-6-carboxylate

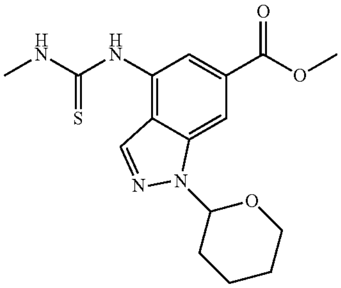

To a solution of 200 mg of methyl 4-amino-1-(tetrahydropyran-2-yl)-1H-indazole-6-carboxylate synthesized in the same manner as in Reference Example 1-(j) in N-methylpyrrolidone (2 ml), 133 mg of methyl isothiocyanate and 200 μl of acetic acid were added at room temperature under a stream of argon, and the mixture was stirred at 100 °C for 9 hours.

After the completion of reaction, water was added to the reaction mixture, and the mixed solution was subjected to extraction with ethyl acetate. The organic layer was washed with saturated saline, dried over anhydrous magnesium sulfate, filtered, and concentrated under reduced pressure. The obtained residue was purified by medium-pressure preparative chromatography (silica gel, eluting solvent: hexane:ethyl acetate) to obtain 184 mg of the title compound as a white solid.

Mass spectrum (ESI, m/z): 349 $[M+H]^+$.

Reference Example 48-(d), Etc.

Corresponding starting compounds were treated in the same manner as in Reference Example 1-(k) to obtain compounds described in the following Table 13.

TABLE 13

| Reference Example | Structural formula | Mass spectrum |
|---|---|---|
| Reference Example 48-(d) | 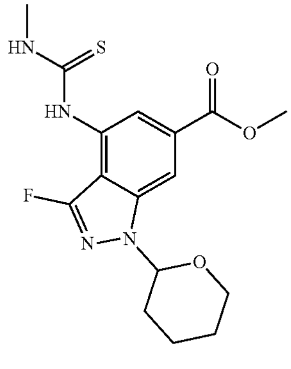 [SMILES: CNC(=S)Nc1cc(C(=O)OC)cc2c1c(F)nn2C1CCCCO1] | (ESI, m/z): 367 $[M + H]^+$ |

TABLE 13-continued

| Reference Example | Structural formula | Mass spectrum |
|---|---|---|
| Reference Example 49-(d) | 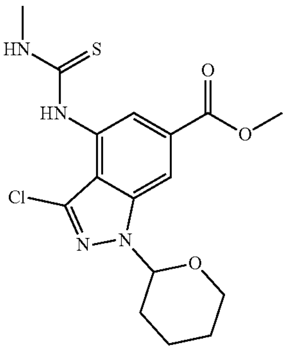 [SMILES: CNC(=S)Nc1cc(C(=O)OC)cc2c1c(Cl)nn2C1CCCCO1] | (ESI, m/z): 383 [M + H]$^+$ |

Reference Example 52-(a)

Production of methyl 6-(3-methylthioureido)-1H-indazole-4-carboxylate

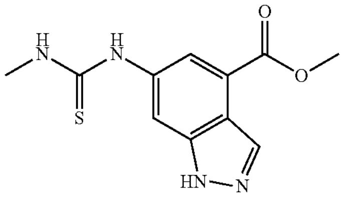

To a solution of 500 mg of methyl 6-amino-1H-indazole-4-carboxylate in N-methylpyrrolidone (2.5 ml), 233 mg of methyl isothiocyanate was added at room temperature under a stream of argon, and the mixture was stirred at room temperature for 2 hours, left standing at room temperature for 84 hours, and stirred at 70 °C for 7 hours.

After the completion of reaction, water was added to the reaction mixture, and the mixture was stirred at room temperature for 15 minutes. A deposited solid was collected by filtration, washed with water, and then dried under reduced pressure at 60 °C to obtain 408 mg of the title compound as a pale yellow solid.

Mass spectrum (ESI, m/z): 265 [M+H]$^+$.

Reference Example 1-(l)

Production of 4-(3-methylthioureido)-1H-indazole-6-carboxylic acid

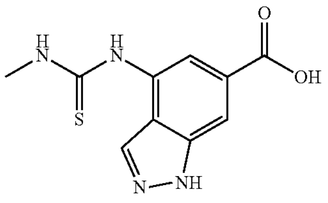 [SMILES: CNC(=S)Nc1cc(C(=O)O)cc2[nH]ncc12]

To a suspension of 4.81 g of methyl 4-(3-methylthioureido)-1-(tetrahydropyran-2-yl)-1H-indazole-6-carboxylate synthesized in the same manner as in Reference Example 1-(k) in methanol (69.2 ml), 17.3 ml of a 4 M solution of hydrogen chloride in 1,4-dioxane was added at room temperature under a stream of argon, and the mixture was stirred at room temperature for 6 hours.

After the completion of reaction, the reaction mixture was concentrated under reduced pressure, subjected to azeotropy with 30 ml of tert-butyl methyl ether, and dried under reduced pressure at 50 °C.

To a suspension of the obtained residue in methanol (41.4 ml), 41.4 ml of a 1 M aqueous sodium hydroxide solution was added at room temperature under a stream of argon, and the mixture was stirred at room temperature for 3 hours.

After the completion of reaction, the reaction mixture was adjusted to pH 4.0 by the addition of 2 M hydrochloric acid, and the mixture was stirred at room temperature for 1 hour. A deposited solid was collected by filtration, washed with water, and then dried under reduced pressure at 60 °C to obtain 2.80 g of the title compound as a pale yellow solid.

Mass spectrum (ESI, m/z): 251 [M+H]$^+$.

Reference Example 49-(e)

Production of methyl 3-chloro-4-(3-methylthioureido)-1H-indazole-6-carboxylate

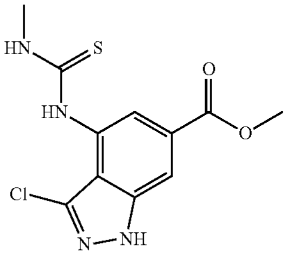 [SMILES: CNC(=S)Nc1cc(C(=O)OC)cc2[nH]nc(Cl)c12]

To a suspension of 840 mg of methyl 3-chloro-4-(3-methylthioureido)-1-(tetrahydropyran-2-yl)-1H-indazole-6-carboxylate synthesized in the same manner as in Reference Example 49-(d) in dichloromethane (5 ml), 2.52 ml of trifluoroacetic acid was added dropwise at room temperature under a stream of argon, and the mixture was stirred at room temperature for 10 hours.

After the completion of reaction, the reaction mixture was concentrated under reduced pressure. The obtained residue was purified by medium-pressure preparative chromatography (silica gel, eluting solvent: hexane:ethyl acetate) to obtain 375 mg of the title compound as a pale yellow solid.

Mass spectrum (ESI, m/z): 299 [M+H]$^+$.

Reference Example 48-(e)

Production of 3-fluoro-4-(3-methylthioureido)-1-(tetrahydropyran-2-yl)-1H-indazole-6-carboxylic acid

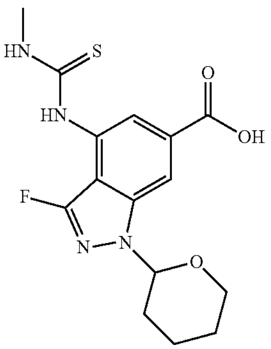 [SMILES: CNC(=S)Nc1cc(C(=O)O)cc2c1c(F)nn2C1CCCCO1]

To a suspension of 245 mg of methyl 3-fluoro-4-(3-methylthioureido)-1-(tetrahydropyran-2-yl)-1H-indazole-6-carboxylate synthesized in the same manner as in Reference Example 48-(d) in methanol (2 ml), 2 ml of a 1 M aqueous sodium hydroxide solution and 3 ml of tetrahydrofuran were added at room temperature under a stream of argon, and the mixture was stirred at room temperature for 2 hours.

After the completion of reaction, the reaction mixture was adjusted to pH 4.0 by the addition of 1 M hydrochloric acid, and the mixture was stirred at room temperature for 1 hour. The reaction mixture was concentrated under reduced pressure, and tetrahydrofuran was distilled off under reduced pressure. The residue was stirred at room temperature for 15 hours. A deposited solid was collected by filtration, washed with water, and then dried under reduced pressure at 60 °C to obtain 202 mg of the title compound as a white solid.

Mass spectrum (ESI, m/z): 353 $[M+H]^+$.

Reference Example 49-(f)

Production of 3-chloro-4-(3-methylthioureido)-1H-indazole-6-carboxylic acid

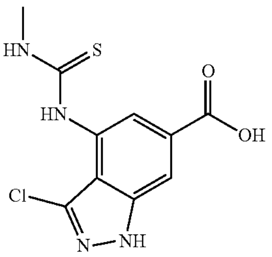 [SMILES: CNC(=S)Nc1cc(C(=O)O)cc2[nH]nc(Cl)c12]

To a suspension of 337 mg of methyl 3-chloro-4-(3-methylthioureido)-1H-indazole-6-carboxylate synthesized in Reference Example 49-(e) in methanol (4.2 ml), 1.69 ml of a 2 M aqueous sodium hydroxide solution was added dropwise at room temperature, and the mixture was stirred at room temperature for 5 hours.

After the completion of reaction, the reaction mixture was adjusted to pH 4 by the addition of 2 M hydrochloric acid, and the mixture was stirred at room temperature for 0.5 hours. A deposited solid was collected by filtration and dried under reduced pressure to obtain 110 mg of the title compound as a pale yellow solid.

Mass spectrum (ESI, m/z): 285 $[M+H]^+$.

Reference Example 52-(b)

A corresponding starting compound was treated in the same manner as in Reference Example 49-(f) to obtain a compound described in the following Table 14.

TABLE 14

| Reference Example | Structural formula | Mass spectrum |
|---|---|---|
| Reference Example 52-(b) | 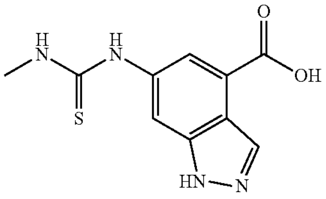 [SMILES: CNC(=S)Nc1cc(C(=O)O)c2cn[nH]c2c1] | (ESI, m/z): 251 $[M + H]^+$ |

Reference Example 1-(m)

Production of 4-((5-fluoro-1,4,5,6-tetrahydropyrimidin-2-yl)amino)-1H-indazole-6-carboxylic acid

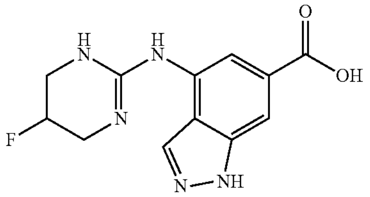 [SMILES: O=C(O)c1cc(NC2=NCC(F)CN2)c2cn[nH]c2c1]

To a solution of 10.00 g of 4-(3-methylthioureido)-1H-indazole-6-carboxylic acid synthesized in the same manner as in Reference Example 1-(1) in N-methylpyrrolidone (100 ml), 3.00 ml of iodomethane was added at room temperature under a stream of argon, and the mixture was stirred at room temperature for 16 hours. The pressure of the reaction mixture was reduced, and excess iodomethane was removed. 10.27 g of 2-fluoropropane-1,3-diamine hydrochloride synthesized in the same manner as in Reference Example 1-(g) and 17 ml of water were added to the obtained solution at room temperature, and the mixture was stirred at 110 °C for 8 hours, stirred at room temperature for 13 hours, stirred at 110 °C for 11 hours, stirred at room temperature for 13 hours, and stirred at 110 °C for 9 hours.

After the completion of reaction, 283 ml of water was added to the reaction mixture, and the mixture was stirred at room temperature for 15 hours. A deposited solid was collected by filtration, washed with water, and then dried under reduced pressure at 60 °C to obtain 7.40 g of the title compound as a white solid.

Mass spectrum (ESI, m/z): 278 $[M+H]^+$.

Reference Example 48-(f), Etc.

Corresponding starting compounds were treated in the same manner as in Reference Example 1-(m) to obtain compounds described in the following Table 15.

TABLE 15

| Reference Example | Structural formula | Mass spectrum |
|---|---|---|
| Reference Example 48-(f) | 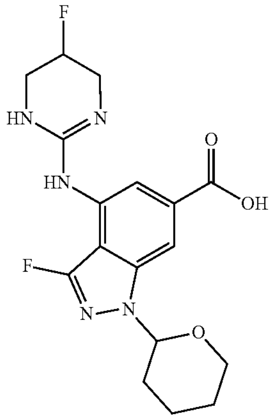 [SMILES: O=C(O)c1cc(NC2=NCC(F)CN2)c2c(F)nn(C3CCCCO3)c2c1] | (ESI, m/z): 380 $[M + H]^+$ |
| Reference Example 49-(g) | 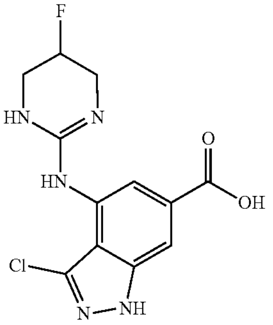 [SMILES: O=C(O)c1cc(NC2=NCC(F)CN2)c2c(Cl)n[nH]c2c1] | (ESI, m/z): 312 $[M + H]^+$ |
| Reference Example 52-(c) | 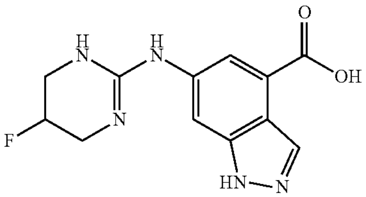 [SMILES: O=C(O)c1cc(NC2=NCC(F)CN2)cc2[nH]ncc12] | (ESI, m/z): 278 $[M + H]^+$ |

Reference Example 50-(a)

Production of 4-((5-hydroxy-1,4,5,6-tetrahydropyrimidin-2-yl)amino)-1H-indazole-6-carboxylic acid

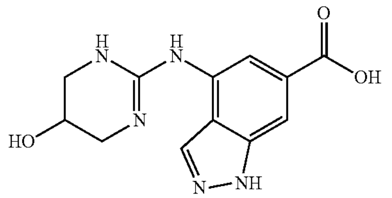 [SMILES: O=C(O)c1cc(NC2=NCC(O)CN2)c2cn[nH]c2c1]

To a solution of 1.00 g of 4-(3-methylthioureido)-1H-indazole-6-carboxylic acid synthesized in the same manner as in Reference Example 1-(l) in N-methylpyrrolidone (10 ml), 0.30 ml of iodomethane was added at room temperature under a stream of argon, and the mixture was stirred at room temperature for 2 hours. The pressure of the reaction mixture was reduced, and excess iodomethane was removed. 1.08 g of 1,3-diaminopropan-2-ol was added to the obtained solution at room temperature, and the mixture was stirred at 110 °C for 6 hours.

After the completion of reaction, the reaction mixture was cooled to room temperature and stirred at room temperature for 17 hours. 10 ml of water was added thereto, and the mixture was stirred at room temperature for 4 hours. A deposited solid was collected by filtration, washed with water, and then dried under reduced pressure to obtain 915 mg of the title compound as a white solid.

Mass spectrum (ESI, m/z): 276 $[M+H]^+$.

Reference Example 51-(a)

A corresponding starting compound was treated in the same manner as in Reference Example 50-(a) to obtain a compound described in the following Table 16.

TABLE 16

| Reference Example | Structural formula | Mass spectrum |
| --- | --- | --- |
| Reference Example 51-(a) | 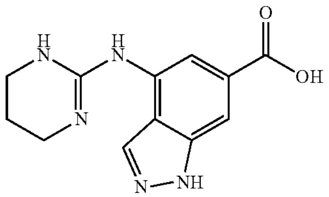 [SMILES: O=C(O)c1cc(NC2=NCCCN2)c2cn[nH]c2c1] | (ESI, m/z): 260 $[M + H]^+$ |

Reference Example 48-(g)

Production of 3-fluoro-4-((5-fluoro-1,4,5,6-tetrahydropyrimidin-2-yl)amino)-1H-indazole-6-carboxylic acid

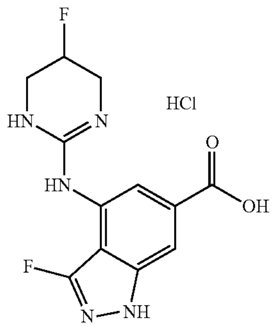 [SMILES: O=C(O)c1cc(NC2=NCC(F)CN2)c2c(F)n[nH]c2c1 ; Cl]

To 110 mg of 3-fluoro-4-((5-fluoro-1,4,5,6-tetrahydropyrimidin-2-yl)amino)-1-(tetrahydropyran-2-yl)-1H-indazole-6-carboxylic acid synthesized in the same manner as in Reference Example 48-(f), 2.9 ml of 1 M hydrochloric acid was added at room temperature under a stream of argon, and the mixture was stirred at 60 °C for 11 hours and stirred at room temperature for 13 hours. Subsequently, 1.45 ml of 1 M hydrochloric acid was added thereto at room temperature, and the mixture was stirred at 70 °C for 9 hours and stirred at room temperature for 18 hours.

After the completion of reaction, a solid was collected by filtration, washed with water, and then dried under reduced pressure at 60 °C to obtain 74 mg of the title compound as a white solid.

Mass spectrum (ESI, m/z): 296 $[M+H]^+$.

Example 1-(a)

Production of methyl (3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate

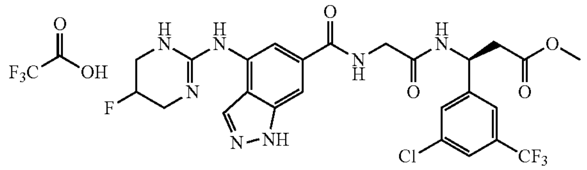

To a suspension of 80 mg of methyl (S)-3-(2-aminoacetamido)-3-(3-chloro-5-(trifluoromethyl)phenyl)propanoate hydrochloride synthesized in the same manner as in Reference Example 1-(e) and 65 mg of 4-((5-fluoro-1,4,5,6-tetrahydropyrimidin-2-yl)amino)-1H-indazole-6-carboxylic acid synthesized in the same manner as in Reference Example 1-(m) in N,N-dimethylformamide (1 ml), 38 mg of 1-hydroxybenzotriazole was added at room temperature under a stream of argon, and the mixture was stirred at room temperature for 10 minutes. Subsequently, 0.043 ml of N,N'-diisopropylcarbodiimide was added thereto at room temperature, and the mixture was stirred at room temperature for 5 hours.

After the completion of reaction, the reaction mixture was purified by medium-pressure preparative chromatography (ODS, eluting solvent: 0.1% aqueous trifluoroacetic acid solution: 0.1% solution of trifluoroacetic acid in acetonitrile) to obtain 132 mg of the title compound as a pale yellow solid.

Mass spectrum (ESI, m/z): 598 $[M+H]^+$.

Example 2-(a), Etc.

Corresponding starting compounds were treated in the same manner as in Example 1-(a) to obtain compounds described in the following Tables 17-1 to 17-7.

TABLE 17-1

| Example | Structural formula | Mass spectrum |
|---|---|---|
| Example 2-(a) | 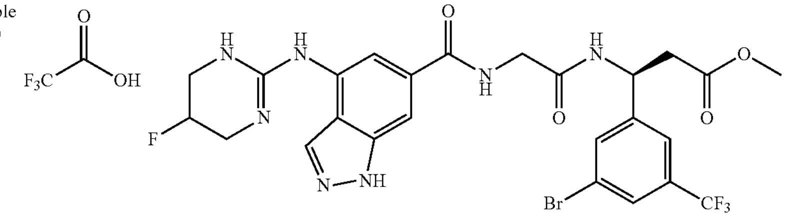 | (ESI, m/z): 642, 644 $[M + H]^+$ |
| Example 3-(a) | 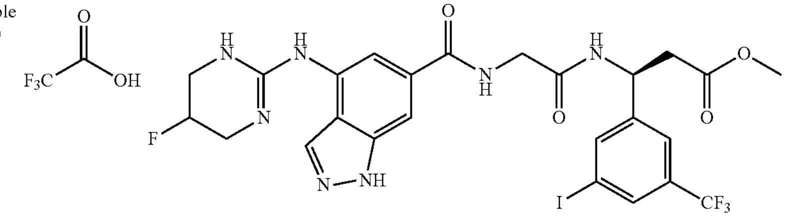 | (ESI, m/z): 690 $[M + H]^+$ |
| Example 4-(a) | 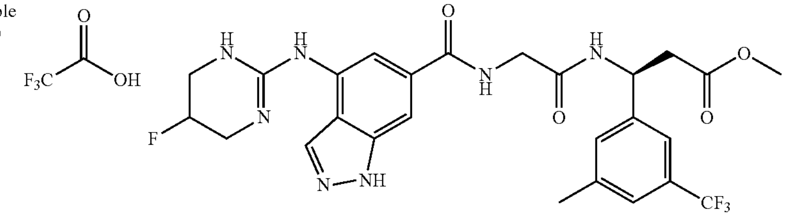 | (ESI, m/z): 578 $[M + H]^+$ |
| Example 5-(a) | 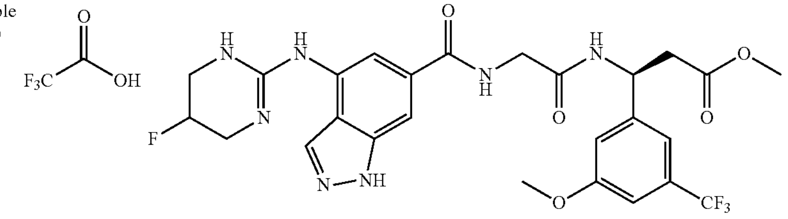 | (ESI, m/z): 594 $[M + H]^+$ |

TABLE 17-1-continued
| Example | Structural formula | Mass spectrum |
| --- | --- | --- |
| Example 6-(a) | 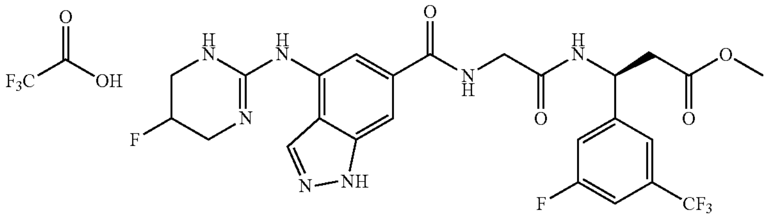 [SMILES: O=C(O)C(F)(F)F ; COC(=O)C[C@H](NC(=O)CNC(=O)c1cc(NC2=NCC(F)CN2)c2cn[nH]c2c1)c1cc(I)cc(C(F)(F)F)c1] | (ESI, m/z): 582 [M + H]$^+$ |
| Example 7-(a) | 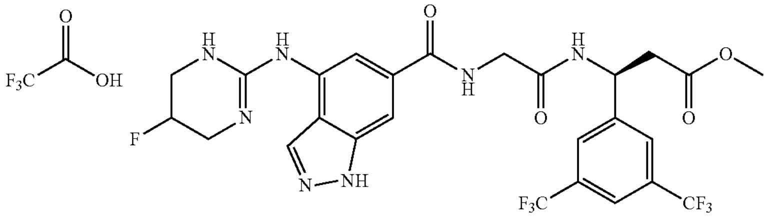 [SMILES: O=C(O)C(F)(F)F ; COC(=O)C[C@H](NC(=O)CNC(=O)c1cc(NC2=NCC(F)CN2)c2cn[nH]c2c1)c1cc(C(F)(F)F)cc(C(F)(F)F)c1] | (ESI, m/z): 632 [M + H]$^+$ |
| Example 8-(a) | 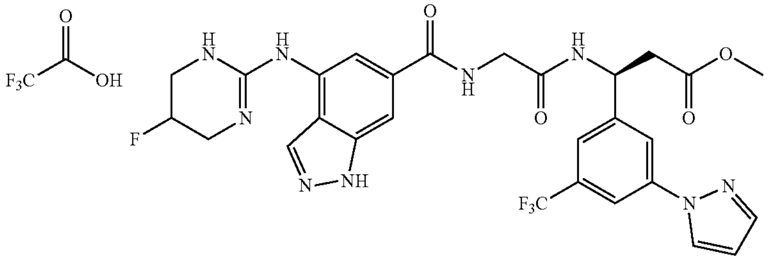 [SMILES: O=C(O)C(F)(F)F ; COC(=O)C[C@H](NC(=O)CNC(=O)c1cc(NC2=NCC(F)CN2)c2cn[nH]c2c1)c1cc(-n2cccn2)cc(C(F)(F)F)c1] | (ESI, m/z): 630 [M + H]$^+$ |
| Example 9-(a) | 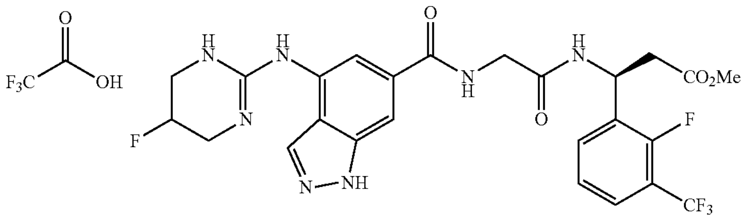 [SMILES: O=C(O)C(F)(F)F ; COC(=O)C[C@H](NC(=O)CNC(=O)c1cc(NC2=NCC(F)CN2)c2cn[nH]c2c1)c1cccc(C(F)(F)F)c1F] | (ESI, m/z): 582 [M + H]$^+$ |
TABLE 17-2
| Example | Structural formula | Mass spectrum |
| --- | --- | --- |
| Example 10-(a) | 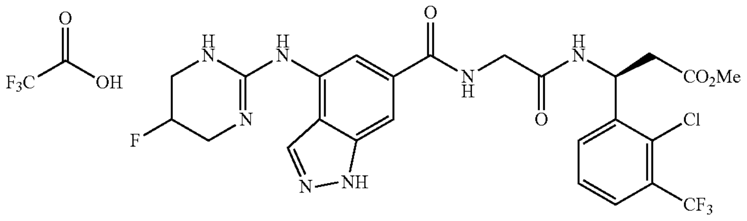 [SMILES: O=C(O)C(F)(F)F ; COC(=O)C[C@H](NC(=O)CNC(=O)c1cc(NC2=NCC(F)CN2)c2cn[nH]c2c1)c1cccc(C(F)(F)F)c1Cl] | (ESI, m/z): 598 [M + H]$^+$ |
| Example 11-(a) | 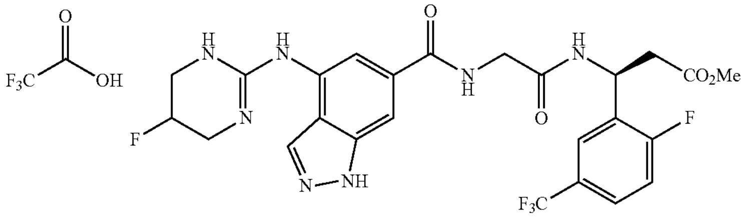 [SMILES: O=C(O)C(F)(F)F ; COC(=O)C[C@H](NC(=O)CNC(=O)c1cc(NC2=NCC(F)CN2)c2cn[nH]c2c1)c1cc(C(F)(F)F)ccc1F] | (ESI, m/z): 582 [M + H]$^+$ |

TABLE 17-2-continued
| Example | Structural formula | Mass spectrum |
|---|---|---|
| Example 12-(a) | 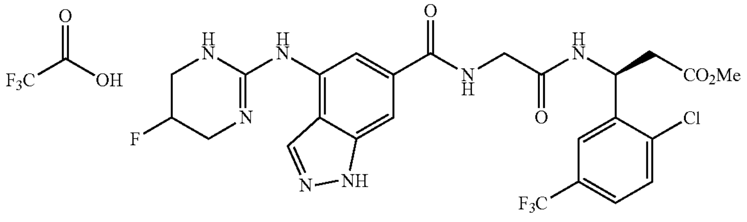 [SMILES: O=C(O)C(F)(F)F ; COC(=O)C[C@H](NC(=O)CNC(=O)c1cc(NC2=NCC(F)CN2)c2cn[nH]c2c1)c1cc(C(F)(F)F)ccc1Cl] | (ESI, m/z): 598 $[M + H]^+$ |
| Example 13-(a) | 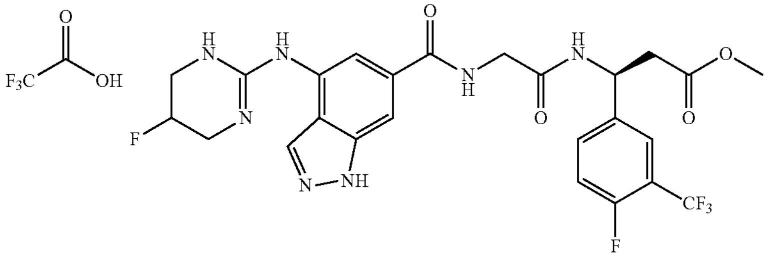 [SMILES: O=C(O)C(F)(F)F ; COC(=O)C[C@H](NC(=O)CNC(=O)c1cc(NC2=NCC(F)CN2)c2cn[nH]c2c1)c1ccc(F)c(C(F)(F)F)c1] | (ESI, m/z): 582 $[M + H]^+$ |
| Example 14-(a) | 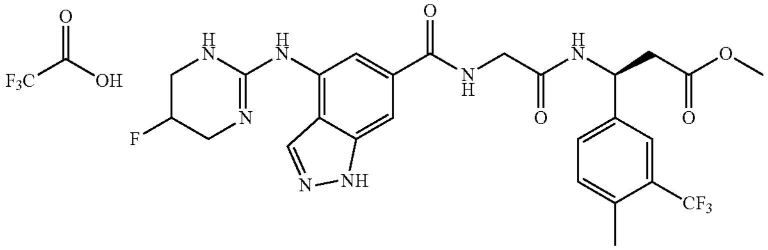 [SMILES: O=C(O)C(F)(F)F ; COC(=O)C[C@H](NC(=O)CNC(=O)c1cc(NC2=NCC(F)CN2)c2cn[nH]c2c1)c1ccc(C)c(C(F)(F)F)c1] | (ESI, m/z): 578 $[M + H]^+$ |
| Example 15-(a) | 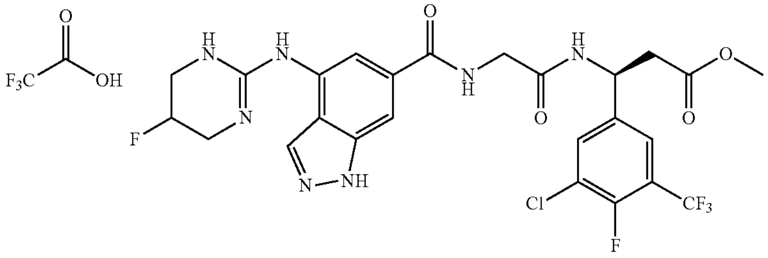 [SMILES: O=C(O)C(F)(F)F ; COC(=O)C[C@H](NC(=O)CNC(=O)c1cc(NC2=NCC(F)CN2)c2cn[nH]c2c1)c1cc(Cl)c(F)c(C(F)(F)F)c1] | (ESI, m/z): 616 $[M + H]^+$ |
| Example 16-(a) | 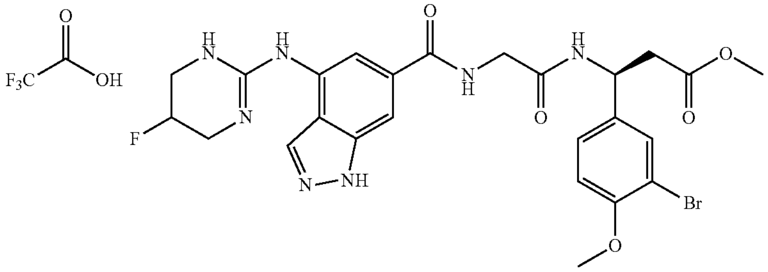 [SMILES: O=C(O)C(F)(F)F ; COC(=O)C[C@H](NC(=O)CNC(=O)c1cc(NC2=NCC(F)CN2)c2cn[nH]c2c1)c1ccc(OC)c(Br)c1] | (ESI, m/z): 604, 606 $[M + H]^+$ |
| Example 17-(a) | 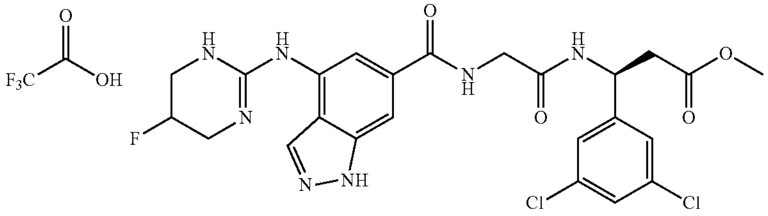 [SMILES: O=C(O)C(F)(F)F ; COC(=O)C[C@H](NC(=O)CNC(=O)c1cc(NC2=NCC(F)CN2)c2cn[nH]c2c1)c1cc(Cl)cc(Cl)c1] | (ESI, m/z): 564 $[M + H]^+$ |

TABLE 17-3
| Example | Structural formula | Mass spectrum |
|---|---|---|
| Example 18-(a) | 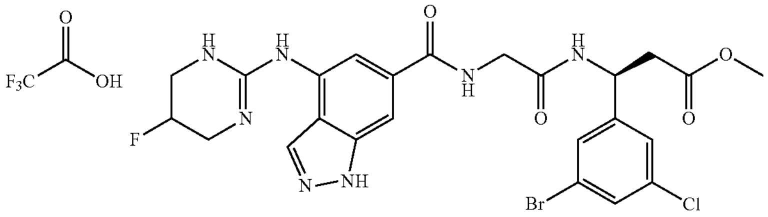 [SMILES: O=C(O)C(F)(F)F ; COC(=O)C[C@H](NC(=O)CNC(=O)c1cc(NC2=NCC(F)CN2)c2cn[nH]c2c1)c1cc(Cl)cc(Br)c1] | (ESI, m/z): 608, 610 $[M + H]^+$ |
| Example 19-(a) | 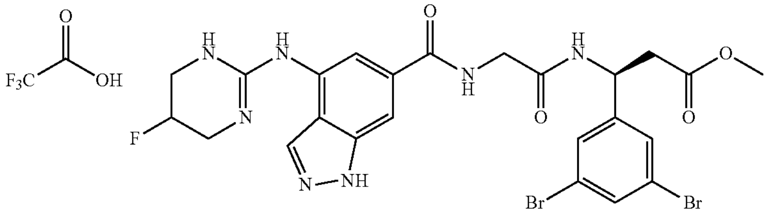 [SMILES: O=C(O)C(F)(F)F ; COC(=O)C[C@H](NC(=O)CNC(=O)c1cc(NC2=NCC(F)CN2)c2cn[nH]c2c1)c1cc(Br)cc(Br)c1] | (ESI, m/z): 654 $[M + H]^+$ |
| Example 20-(a) | 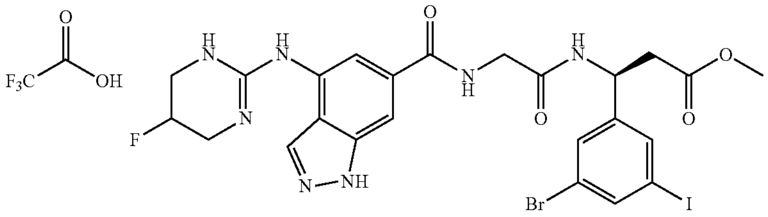 | (ESI, m/z): 700, 702 $[M + H]^+$ |
| Example 21-(a) | 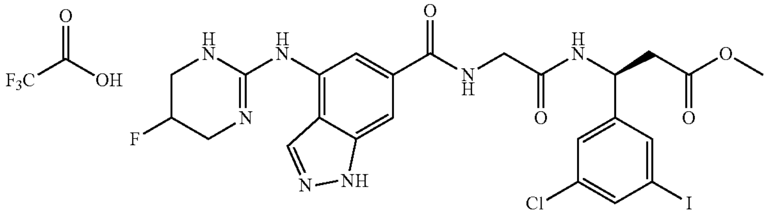 [SMILES: O=C(O)C(F)(F)F ; COC(=O)C[C@H](NC(=O)CNC(=O)c1cc(NC2=NCC(F)CN2)c2cn[nH]c2c1)c1cc(Cl)cc(I)c1] | (ESI, m/z): 656 $[M + H]^+$ |
| Example 22-(a) | 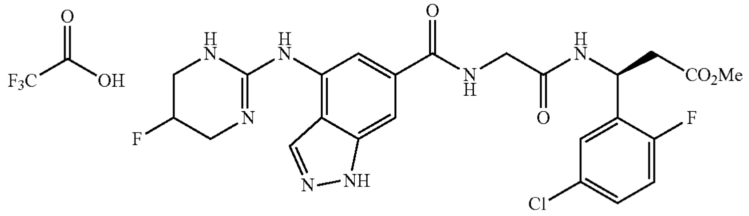 | (ESI, m/z): 548 $[M + H]^+$ |
| Example 23-(a) | 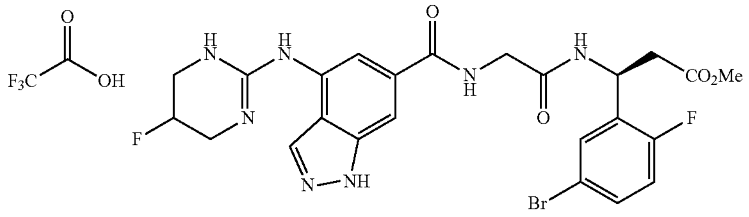 [SMILES: O=C(O)C(F)(F)F ; COC(=O)C[C@H](NC(=O)CNC(=O)c1cc(NC2=NCC(F)CN2)c2cn[nH]c2c1)c1cc(Cl)ccc1F] | (ESI, m/z): 592, 594 $[M + H]^+$ |
| Example 24-(a) | 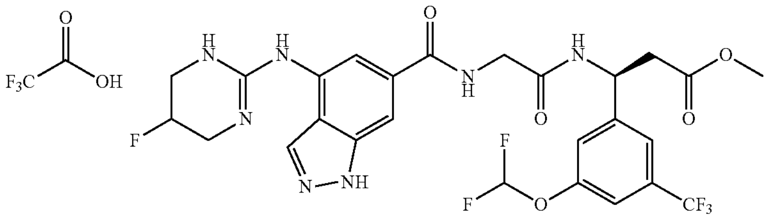 [SMILES: O=C(O)C(F)(F)F ; COC(=O)C[C@H](NC(=O)CNC(=O)c1cc(NC2=NCC(F)CN2)c2cn[nH]c2c1)c1cc(OC(F)F)cc(C(F)(F)F)c1] | (ESI, m/z): 630 $[M + H]^+$ |

TABLE 17-3-continued
| Example | Structural formula | Mass spectrum |
|---|---|---|
| Example 25-(a) | 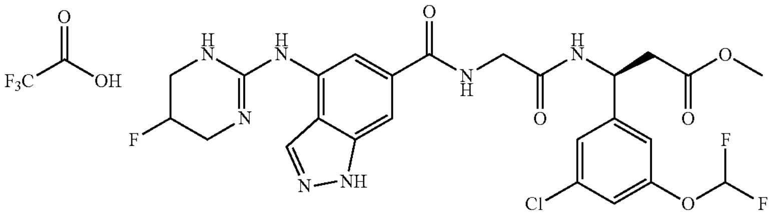 [SMILES: O=C(O)C(F)(F)F ; COC(=O)C[C@H](NC(=O)CNC(=O)c1cc(NC2=NCC(F)CN2)c2cn[nH]c2c1)c1cc(Cl)cc(OC(F)F)c1] | (ESI, m/z): 596 [M + H]+ |
TABLE 17-4
| Example | Structural formula | Mass spectrum |
|---|---|---|
| Example 26-(a) | 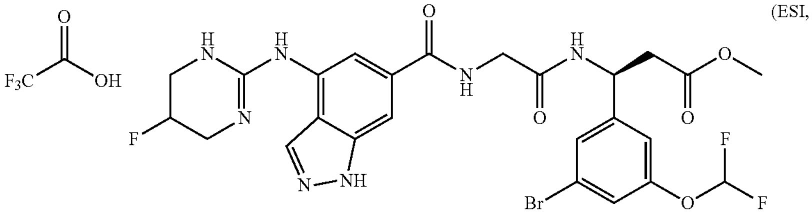 | (ESI, m/z): 640, 642 [M + H]+ |
| Example 27-(a) | 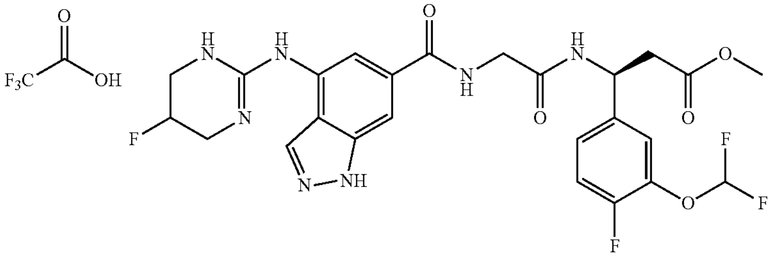 [SMILES: O=C(O)C(F)(F)F ; COC(=O)C[C@H](NC(=O)CNC(=O)c1cc(NC2=NCC(F)CN2)c2cn[nH]c2c1)c1ccc(F)c(OC(F)F)c1] | (ESI, m/z): 580 [M + H]+ |
| Example 28-(a) | 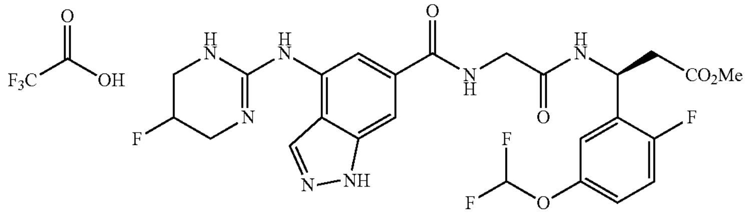 [SMILES: O=C(O)C(F)(F)F ; COC(=O)C[C@H](NC(=O)CNC(=O)c1cc(NC2=NCC(F)CN2)c2cn[nH]c2c1)c1cc(OC(F)F)ccc1F] | (ESI, m/z): 580 [M + H]+ |
| Example 29-(a) | 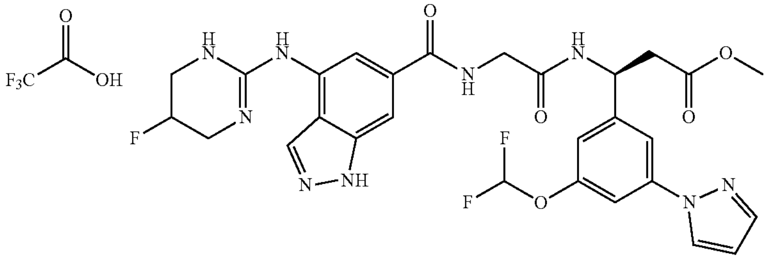 [SMILES: O=C(O)C(F)(F)F ; COC(=O)C[C@H](NC(=O)CNC(=O)c1cc(NC2=NCC(F)CN2)c2cn[nH]c2c1)c1cc(OC(F)F)cc(-n2cccn2)c1] | (ESI, m/z): 628 [M + H]+ |
| Example 30-(a) | 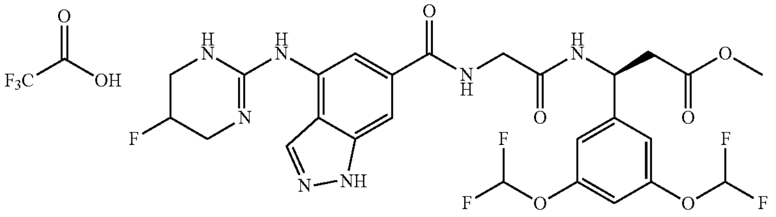 [SMILES: O=C(O)C(F)(F)F ; COC(=O)C[C@H](NC(=O)CNC(=O)c1cc(NC2=NCC(F)CN2)c2cn[nH]c2c1)c1cc(OC(F)F)cc(OC(F)F)c1] | (ESI, m/z): 628 [M + H]+ |

TABLE 17-4-continued
| Example | Structural formula | Mass spectrum |
| --- | --- | --- |
| Example 31-(a) | 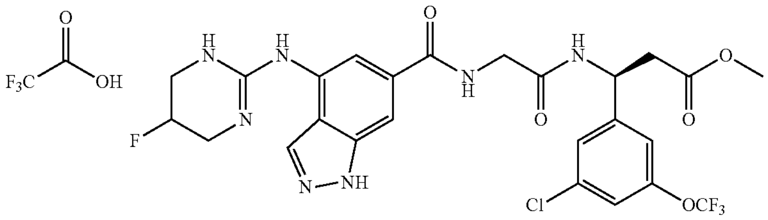 [SMILES: O=C(O)C(F)(F)F ; COC(=O)C[C@H](NC(=O)CNC(=O)c1cc(NC2=NCC(F)CN2)c2cn[nH]c2c1)c1cc(Cl)cc(OC(F)(F)F)c1] | (ESI, m/z): 614 [M + H]$^+$ |
| Example 32-(a) | 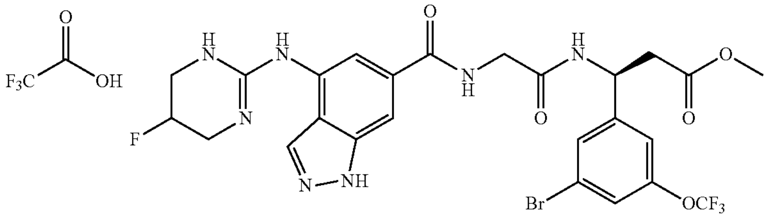 [SMILES: O=C(O)C(F)(F)F ; COC(=O)C[C@H](NC(=O)CNC(=O)c1cc(NC2=NCC(F)CN2)c2cn[nH]c2c1)c1cc(Br)cc(OC(F)(F)F)c1] | (ESI, m/z): 658, 660 [M + H]$^+$ |
| Example 33-(a) | 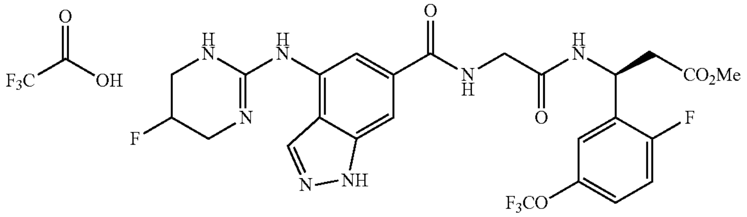 [SMILES: O=C(O)C(F)(F)F ; COC(=O)C[C@H](NC(=O)CNC(=O)c1cc(NC2=NCC(F)CN2)c2cn[nH]c2c1)c1cc(OC(F)(F)F)ccc1F] | (ESI, m/z): 598 [M + H]$^+$ |
TABLE 17-5
| Example | Structural formula | Mass spectrum |
| --- | --- | --- |
| Example 34-(a) | 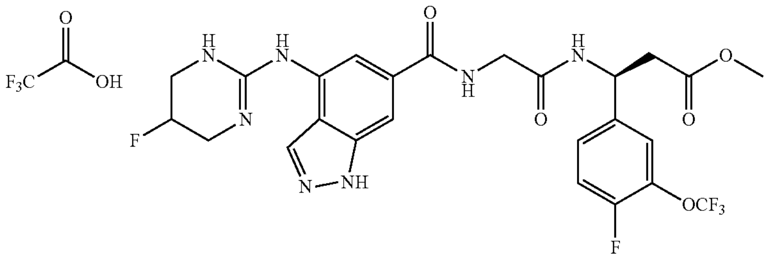 [SMILES: O=C(O)C(F)(F)F ; COC(=O)C[C@H](NC(=O)CNC(=O)c1cc(NC2=NCC(F)CN2)c2cn[nH]c2c1)c1ccc(F)c(OC(F)(F)F)c1] | (ESI, m/z): 598 [M + H]$^+$ |
| Example 35-(a) | 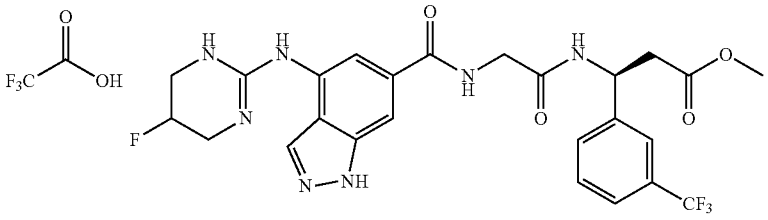 [SMILES: O=C(O)C(F)(F)F ; COC(=O)C[C@H](NC(=O)CNC(=O)c1cc(NC2=NCC(F)CN2)c2cn[nH]c2c1)c1cccc(C(F)(F)F)c1] | (ESI, m/z): 564 [M + H]$^+$ |
| Example 36-(a) | 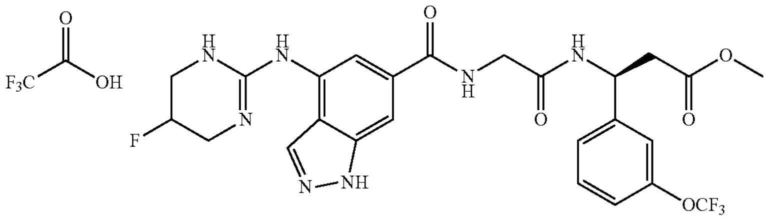 [SMILES: O=C(O)C(F)(F)F ; COC(=O)C[C@H](NC(=O)CNC(=O)c1cc(NC2=NCC(F)CN2)c2cn[nH]c2c1)c1cccc(OC(F)(F)F)c1] | (ESI, m/z): 580 [M + H]$^+$ |

TABLE 17-5-continued
| Example | Structural formula | Mass spectrum |
| --- | --- | --- |
| Example 37-(a) | 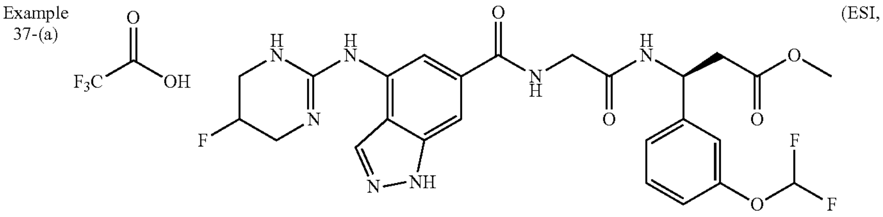 | (ESI, m/z): 562 [M + H]$^+$ |
| Example 38-(a) | 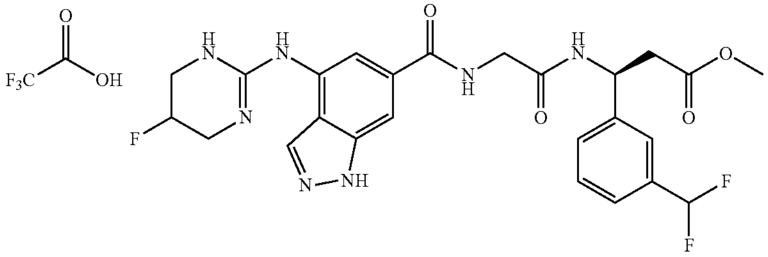 [SMILES: O=C(O)C(F)(F)F ; COC(=O)C[C@H](NC(=O)CNC(=O)c1cc(NC2=NCC(F)CN2)c2cn[nH]c2c1)c1cccc(C(F)F)c1] | (ESI, m/z): 546 [M + H]$^+$ |
| Example 39-(a) | 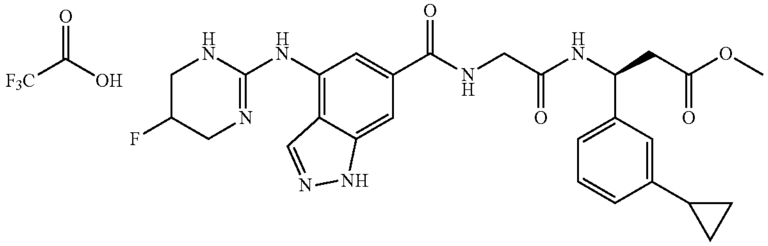 [SMILES: O=C(O)C(F)(F)F ; COC(=O)C[C@H](NC(=O)CNC(=O)c1cc(NC2=NCC(F)CN2)c2cn[nH]c2c1)c1cccc(C2CC2)c1] | (ESI, m/z): 536 [M + H]$^+$ |
| Example 40-(a) | 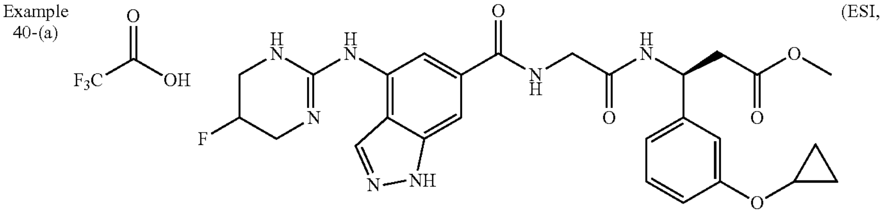 | (ESI, m/z): 552 [M + H]$^+$ |
| Example 41-(a) | 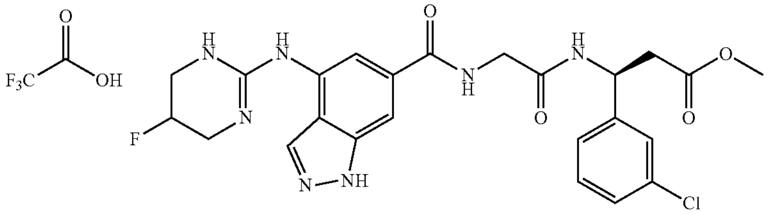 [SMILES: O=C(O)C(F)(F)F ; COC(=O)C[C@H](NC(=O)CNC(=O)c1cc(NC2=NCC(F)CN2)c2cn[nH]c2c1)c1cccc(Cl)c1] | (ESI, m/z): 530 [M + H]$^+$ |
TABLE 17-6
| Example | Structural formula | Mass spectrum |
| --- | --- | --- |
| Example 42-(a) | 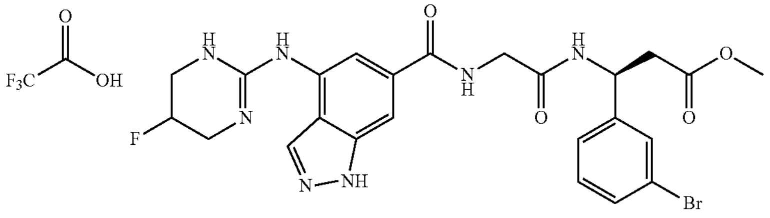 [SMILES: O=C(O)C(F)(F)F ; COC(=O)C[C@H](NC(=O)CNC(=O)c1cc(NC2=NCC(F)CN2)c2cn[nH]c2c1)c1cccc(Br)c1] | (ESI, m/z): 574, 576 [M + H]$^+$ |

TABLE 17-6-continued
| Example | Structural formula | Mass spectrum |
|---|---|---|
| Example 43-(a) | 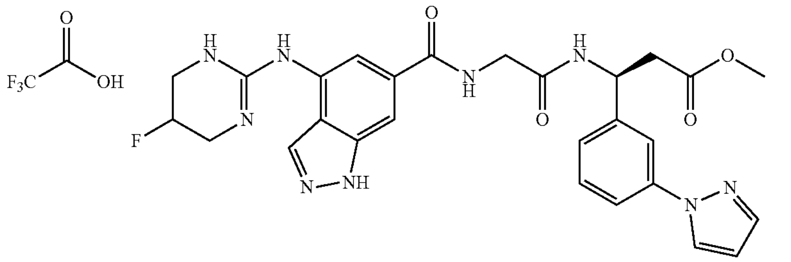 [SMILES: O=C(O)C(F)(F)F ; COC(=O)C[C@H](NC(=O)CNC(=O)c1cc(NC2=NCC(F)CN2)c2cn[nH]c2c1)c1cccc(-n2cccn2)c1] | (ESI, m/z): 562 [M + H]+ |
| Example 44-(a) | 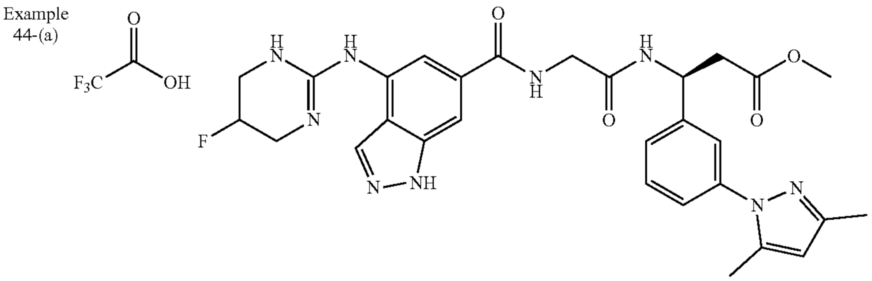 | (ESI, m/z): 590 [M + H]+ |
| Example 45-(a) | 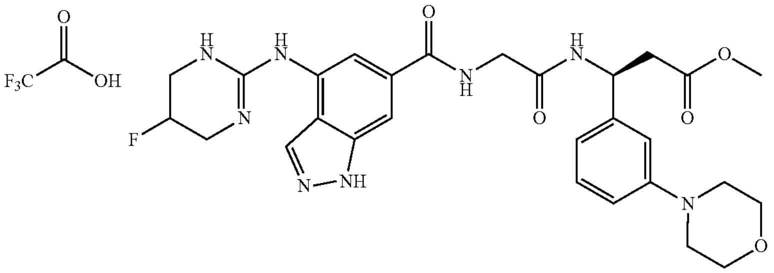 [SMILES: O=C(O)C(F)(F)F ; COC(=O)C[C@H](NC(=O)CNC(=O)c1cc(NC2=NCC(F)CN2)c2cn[nH]c2c1)c1cccc(N2CCOCC2)c1] | (ESI, m/z): 581 [M + H]+ |
| Example 46-(a) | 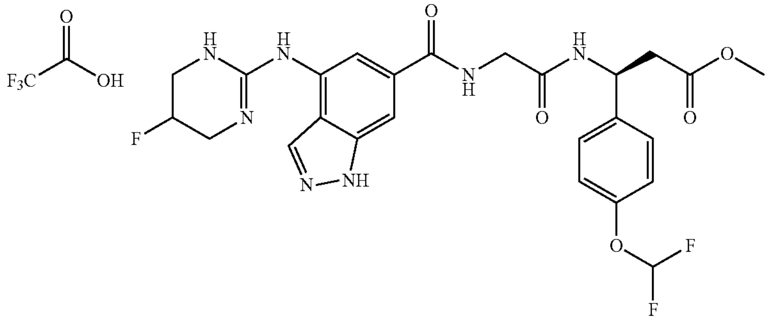 [SMILES: O=C(O)C(F)(F)F ; COC(=O)C[C@H](NC(=O)CNC(=O)c1cc(NC2=NCC(F)CN2)c2cn[nH]c2c1)c1ccc(OC(F)F)cc1] | (ESI, m/z): 562 [M + H]+ |
| Example 47-(a) | 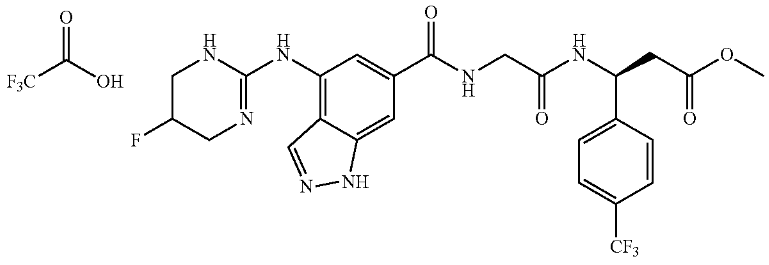 [SMILES: O=C(O)C(F)(F)F ; COC(=O)C[C@H](NC(=O)CNC(=O)c1cc(NC2=NCC(F)CN2)c2cn[nH]c2c1)c1ccc(C(F)(F)F)cc1] | (ESI, m/z): 564 [M + H]+ |

TABLE 17-6-continued
| Example | Structural formula | Mass spectrum |
|---|---|---|
| Example 48-(a) | 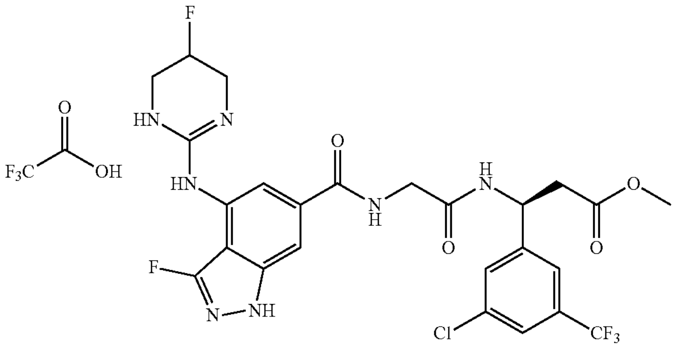 [SMILES: O=C(O)C(F)(F)F ; COC(=O)C[C@H](NC(=O)CNC(=O)c1cc(NC2=NCC(F)CN2)c2c(F)n[nH]c2c1)c1cc(Cl)cc(C(F)(F)F)c1] | (ESI, m/z): 616 [M + H]+ |
TABLE 17-7
| Example | Structural formula | Mass spectrum |
|---|---|---|
| Example 49-(a) | 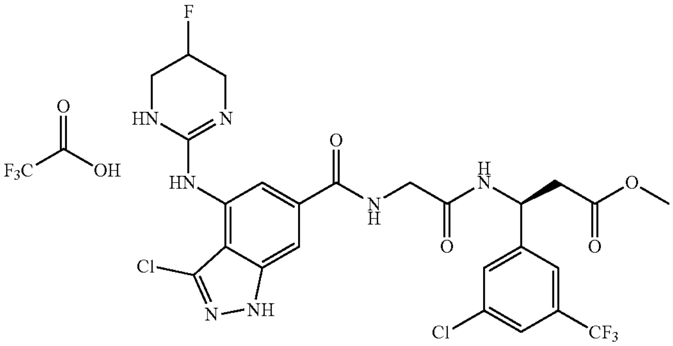 [SMILES: O=C(O)C(F)(F)F ; COC(=O)C[C@H](NC(=O)CNC(=O)c1cc(NC2=NCC(F)CN2)c2c(Cl)n[nH]c2c1)c1cc(Cl)cc(C(F)(F)F)c1] | (ESI, m/z): 632 [M + H]+ |
| Example 50-(a) | 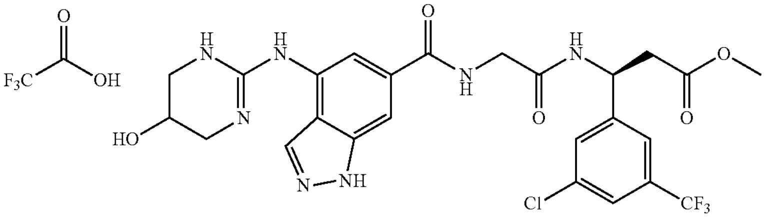 [SMILES: O=C(O)C(F)(F)F ; COC(=O)C[C@H](NC(=O)CNC(=O)c1cc(NC2=NCC(O)CN2)c2cn[nH]c2c1)c1cc(Cl)cc(C(F)(F)F)c1] | (ESI, m/z): 596 [M + H]+ |
| Example 51-(a) | 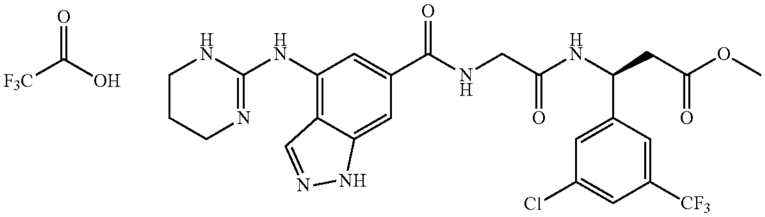 [SMILES: O=C(O)C(F)(F)F ; COC(=O)C[C@H](NC(=O)CNC(=O)c1cc(NC2=NCCCN2)c2cn[nH]c2c1)c1cc(Cl)cc(C(F)(F)F)c1] | (ESI, m/z): 580 [M + H]+ |
| Example 52-(a) | 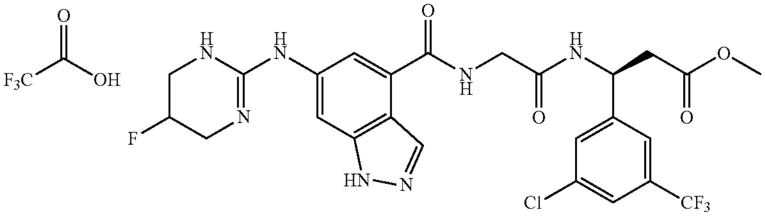 [SMILES: O=C(O)C(F)(F)F ; COC(=O)C[C@H](NC(=O)CNC(=O)c1cc(NC2=NCC(F)CN2)cc2[nH]ncc12)c1cc(Cl)cc(C(F)(F)F)c1] | (ESI, m/z): 598 [M + H]+ |

TABLE 17-7-continued

| Example | Structural formula | Mass spectrum |
|---|---|---|
| Example 53-(a) | 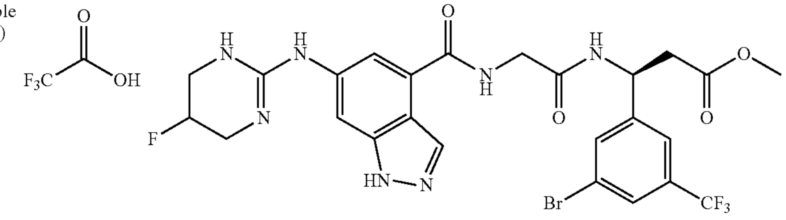 | (ESI, m/z): 642, 644 [M + H]$^+$ |
| Example 54-(a) | 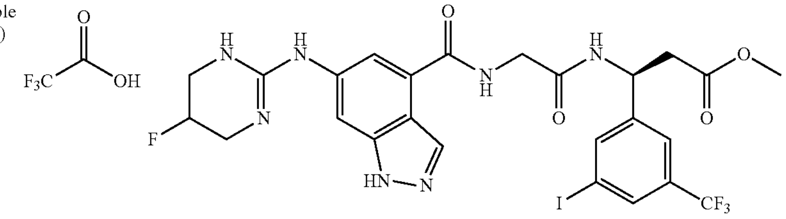 | (ESI, m/z): 690 [M + H]$^+$ |
| Example 55-(a) | 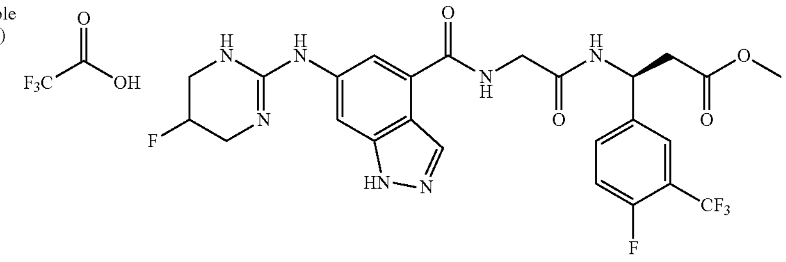 | (ESI, m/z): 582 [M + H]$^+$ |
| Example 56-(a) | 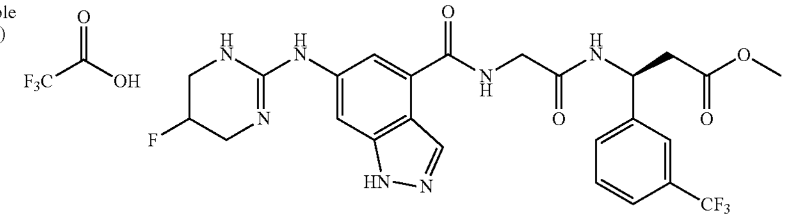 | (ESI, m/z): 564 [M + H]$^+$ |

Example 1-(b)

Production of (3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid

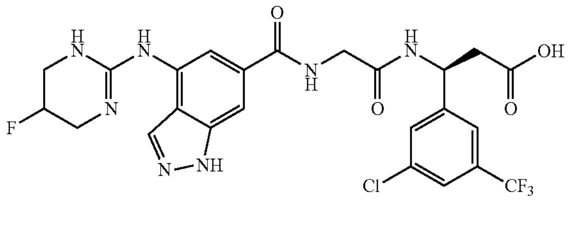 [SMILES: O=C(O)C[C@H](NC(=O)CNC(=O)c1cc(NC2=NCC(F)CN2)c2cn[nH]c2c1)c1cc(Cl)cc(C(F)(F)F)c1]

To a suspension of 130 mg of methyl (3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 1-(a) in acetonitrile (1.5 ml) and water (1.5 ml), 22 mg of lithium hydroxide was added at room temperature under a stream of argon, and the mixture was stirred at room temperature for 1 hour.

After the completion of reaction, the reaction mixture was filtered. The filtrate was adjusted to pH 5.2 by the addition of 1 N hydrochloric acid, and the mixture was stirred at room temperature for 2 hours. A deposited solid was collected by filtration, washed with water, and then dried under reduced pressure at 60 °C to obtain 58 mg of the title compound as a white solid.

Mass spectrum (ESI, m/z): 584 [M+H]$^+$.

$^1$H-NMR spectrum (400 MHz, $CD_3OD$) δ: 8.09-8.06 (m, 2H), 7.70-7.67 (m, 1H), 7.66-7.63 (m, 1H), 7.54-7.50 (m, 2H), 5.30-5.13 (m, 2H), 4.18-4.05 (m, 2H), 3.72-3.45 (m, 4H), 2.74-2.60 (m, 2H).

Example 2-(b)

Production of (3S)-3-(3-bromo-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid

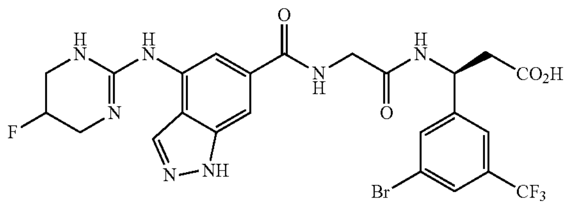

To a solution of 193 mg of methyl (3S)-3-(3-bromo-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 2-(a) in acetonitrile (3 ml) and water (3 ml), 31 mg of lithium hydroxide was added at room temperature under a stream of argon, and the mixture was stirred at room temperature for 3 hours. Subsequently, 36 mg of lithium hydroxide was further added thereto at room temperature, and the mixture was stirred at room temperature for 1 hour.

After the completion of reaction, the reaction mixture was adjusted to pH 5.8 by the addition of 1 N hydrochloric acid, and the mixture was stirred at room temperature for 16 hours. A deposited solid was collected by filtration, washed with water, and then dried under reduced pressure at 60 °C to obtain 107 mg of the title compound as a white solid.

Mass spectrum (ESI, m/z): 628, 630 $[M+H]^+$.

$^1$H-NMR spectrum (400 MHz, $CD_3OD$) δ: 8.10-8.05 (m, 2H), 7.86-7.81 (m, 1H), 7.71-7.64 (m, 2H), 7.51 (d, J=1.1 Hz, 1H), 5.31-5.12 (m, 2H), 4.18-4.05 (m, 2H), 3.73-3.43 (m, 4H), 2.73-2.60 (m, 2H).

Example 3-(b)

Production of (3S)-3-(2-(4-((5-fluoro-1,4,5,6-tetrahydropyrimidin-2-yl)amino)-1H-indazole-6-carboxamido)acetamido)-3-(3-iodo-5-(trifluoromethyl)phenyl)propanoic acid

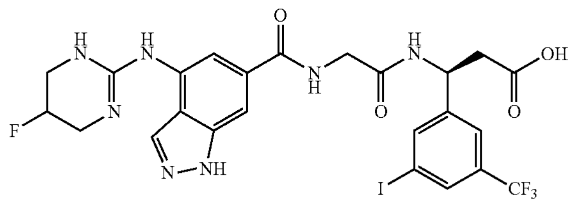 [SMILES: O=C(O)C[C@H](NC(=O)CNC(=O)c1cc(NC2=NCC(F)CN2)c2cn[nH]c2c1)c1cc(I)cc(C(F)(F)F)c1]

To a solution of 79 mg of methyl (3S)-3-(2-(4-((5-fluoro-1,4,5,6-tetrahydropyrimidin-2-yl)amino)-1H-indazole-6-carboxamido)acetamido)-3-(3-iodo-5-(trifluoromethyl)phenyl)propanoate trifluoroacetate synthesized in Example 3-(a) in acetonitrile (1.5 ml) and water (1.5 ml), 12 mg of lithium hydroxide was added at room temperature under a stream of argon, and the mixture was stirred at room temperature for 1.5 hours.

After the completion of reaction, the reaction mixture was adjusted to pH 5.4 by the addition of 1 N hydrochloric acid, and the mixture was stirred at room temperature for 1 hour. A deposited solid was collected by filtration, washed with water, and then dried under reduced pressure at 60 °C to obtain 35 mg of the title compound as a white solid.

Mass spectrum (ESI, m/z): 676 $[M+H]^+$.

$^1$H-NMR spectrum (400 MHz, $CD_3OD$) δ: 8.09-8.05 (m, 2H), 8.03-8.00 (m, 1H), 7.84-7.81 (m, 1H), 7.72-7.69 (m, 1H), 7.52-7.49 (m, 1H), 5.29-5.13 (m, 2H), 4.18-4.04 (m, 2H), 3.71-3.44 (m, 4H), 2.73-2.57 (m, 2H).

Example 4-(b)

Production of (3S)-3-(2-(4-((5-fluoro-1,4,5,6-tetrahydropyrimidin-2-yl)amino)-1H-indazole-6-carboxamido)acetamido)-3-(3-methyl-5-(trifluoromethyl)phenyl)propanoic acid

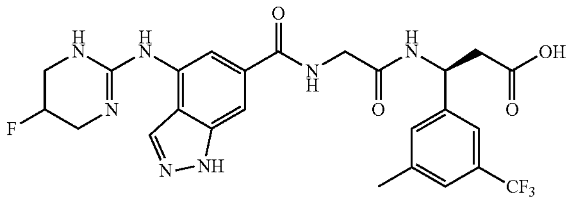 [SMILES: Cc1cc([C@H](CC(=O)O)NC(=O)CNC(=O)c2cc(NC3=NCC(F)CN3)c3cn[nH]c3c2)cc(C(F)(F)F)c1]

To a solution of 97 mg of methyl (3S)-3-(2-(4-((5-fluoro-1,4,5,6-tetrahydropyrimidin-2-yl)amino)-1H-indazole-6-carboxamido)acetamido)-3-(3-methyl-5-(trifluoromethyl)phenyl)propanoate trifluoroacetate synthesized in Example 4-(a) in acetonitrile (1 ml) and water (1 ml), 17 mg of lithium hydroxide was added at room temperature under a stream of argon, and the mixture was stirred at room temperature for 1.5 hours.

After the completion of reaction, the reaction mixture was adjusted to pH 5.8 by the addition of 1 N hydrochloric acid, and the mixture was filtered. The filtrate was stirred at room temperature for 17 hours, and a deposited solid was collected by filtration, washed with water, and then dried under reduced pressure at 60 °C to obtain 46 mg of the title compound as a white solid.

Mass spectrum (ESI, m/z): 564 $[M+H]^+$.

$^1$H-NMR spectrum (400 MHz, $CD_3OD$) δ: 8.09 (d, J=0.9 Hz, 1H), 8.08-8.06 (m, 1H), 7.51 (d, J=1.3 Hz, 1H), 7.49-7.45 (m, 2H), 7.33-7.30 (m, 1H), 5.30-5.14 (m, 2H), 4.19-4.04 (m, 2H), 3.73-3.45 (m, 4H), 2.75-2.63 (m, 2H), 2.39 (s, 3H).

Example 5-(b)

Production of (3S)-3-(2-(4-((5-fluoro-1,4,5,6-tetrahydropyrimidin-2-yl)amino)-1H-indazole-6-carboxamido)acetamido)-3-(3-methoxy-5-(trifluoromethyl)phenyl)propanoic acid

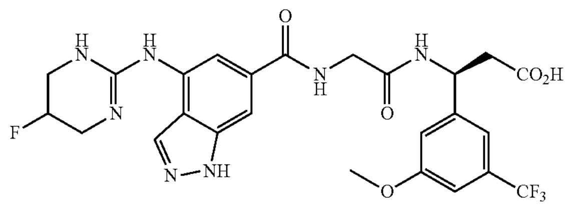 [SMILES: COc1cc([C@H](CC(=O)O)NC(=O)CNC(=O)c2cc(NC3=NCC(F)CN3)c3cn[nH]c3c2)cc(C(F)(F)F)c1]

To a solution of 183 mg of methyl (3S)-3-(2-(4-((5-fluoro-1,4,5,6-tetrahydropyrimidin-2-yl)amino)-1H-indazole-6-carboxamido)acetamido)-3-(3-methoxy-5-(trifluoromethyl)phenyl)propanoate trifluoroacetate synthesized in Example 5-(a) in acetonitrile (1 ml) and water (1 ml), 24 mg of lithium hydroxide was added at room temperature under a stream of argon, and the mixture was stirred at room temperature for 2 hours.

After the completion of reaction, the reaction mixture was filtered. The filtrate was adjusted to pH 5.5 by the addition of 1 N hydrochloric acid, and the mixture was stirred at room temperature for 2 hours. A deposited solid was collected by filtration, washed with water, and then dried under reduced pressure at 60 °C to obtain 44 mg of the title compound as a white solid.

Mass spectrum (ESI, m/z): 580 $[M+H]^+$.

$^1$H-NMR spectrum (400 MHz, $CD_3OD$) δ: 8.11-8.00 (m, 2H), 7.51-7.45 (m, 1H), 7.28-7.17 (m, 2H), 7.02-6.96 (m, 1H), 5.29-5.10 (m, 2H), 4.18 (d, J=16.8 Hz, 1H), 4.05 (d, J=16.8 Hz, 1H), 3.83 (s, 3H), 3.70-3.40 (m, 4H), 2.77-2.57 (m, 2H).

Example 6-(b)

Production of (3S)-3-(2-(4-((5-fluoro-1,4,5,6-tetrahydropyrimidin-2-yl)amino)-1H-indazole-6-carboxamido)acetamido)-3-(3-fluoro-5-(trifluoromethyl)phenyl)propanoic acid

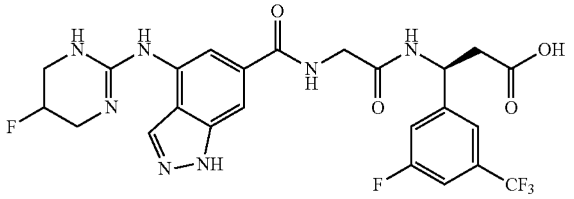

To a solution of 163 mg of methyl (3S)-3-(2-(4-((5-fluoro-1,4,5,6-tetrahydropyrimidin-2-yl)amino)-1H-indazole-6-carboxamido)acetamido)-3-(3-fluoro-5-(trifluoromethyl)phenyl)propanoate trifluoroacetate synthesized in Example 6-(a) in acetonitrile (1 ml) and water (1 ml), 28 mg of lithium hydroxide was added at room temperature under a stream of argon, and the mixture was stirred at room temperature for 3.5 hours.

After the completion of reaction, 1 ml of water was added to the reaction mixture. The reaction mixture was adjusted to pH 5.6 by the addition of 1 N hydrochloric acid, and the mixture was stirred at room temperature for 15 hours. A deposited solid was collected by filtration, washed with water, and then dried under reduced pressure at 60 °C to obtain 66 mg of the title compound as a white solid.

Mass spectrum (ESI, m/z): 568 $[M+H]^+$.

$^1$H-NMR spectrum (400 MHz, $CD_3OD$) δ: 8.09-8.05 (m, 2H), 7.56-7.53 (m, 1H), 7.50 (d, J=1.1 Hz, 1H), 7.46-7.41 (m, 1H), 7.29-7.24 (m, 1H), 5.30-5.12 (m, 2H), 4.18-4.05 (m, 2H), 3.70-3.45 (m, 4H), 2.75-2.60 (m, 2H).

Example 7-(b)

Production of (3S)-3-(3,5-bis(trifluoromethyl)phenyl)-3-(2-(4-((5-fluoro-1,4,5,6-tetrahydropyrimidin-2-yl)amino)-1H-indazole-6-carboxamido)acetamido)propanoic acid

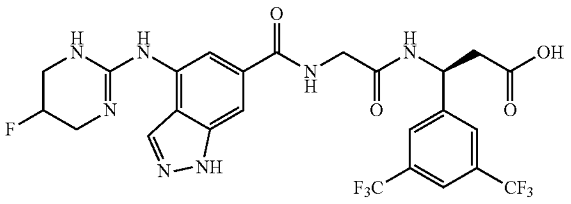 [SMILES: O=C(O)C[C@H](NC(=O)CNC(=O)c1cc(NC2=NCC(F)CN2)c2cn[nH]c2c1)c1cc(C(F)(F)F)cc(C(F)(F)F)c1]

To a solution of 130 mg of methyl (3S)-3-(3,5-bis(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 7-(a) in acetonitrile (1 ml) and water (1 ml), 21 mg of lithium hydroxide was added at room temperature under a stream of argon, and the mixture was stirred at room temperature for 2.5 hours.

After the completion of reaction, 1 ml of water was added to the reaction mixture. The reaction mixture was adjusted to pH 5.6 by the addition of 1 N hydrochloric acid, and the mixture was stirred at room temperature for 20 hours. A deposited solid was collected by filtration, washed with water, and then dried under reduced pressure at 60 °C to obtain 87 mg of the title compound as a gray solid.

Mass spectrum (ESI, m/z): 618 $[M+H]^+$.

$^1$H-NMR spectrum (400 MHz, $CD_3OD$) δ: 8.09-8.05 (m, 2H), 8.01-7.98 (m, 2H), 7.81-7.78 (m, 1H), 7.52-7.49 (m, 1H), 5.35 (t, J=5.3 Hz, 1H), 5.30-5.12 (m, 1H), 4.16 (d, J=16.8 Hz, 1H), 4.07 (d, J=16.8 Hz, 1H), 3.70-3.45 (m, 4H), 2.78-2.63 (m, 2H).

Example 8-(b)

Production of (3S)-3-(3-(1H-pyrazol-1-yl)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid

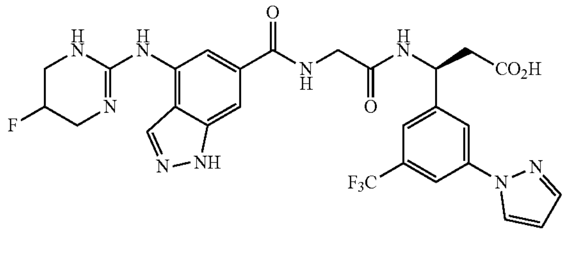 [SMILES: O=C(O)C[C@H](NC(=O)CNC(=O)c1cc(NC2=NCC(F)CN2)c2cn[nH]c2c1)c1cc(-n2cccn2)cc(C(F)(F)F)c1]

To a solution of 150 mg of methyl (3S)-3-(3-(1H-pyrazol-1-yl)-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 8-(a) in acetonitrile (1 ml) and water (1 ml), 34 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration, washed with water, and then dried under reduced pressure at 60 °C to obtain 45 mg of the title compound as a white solid.

Mass spectrum (ESI, m/z): 616 $[M+H]^+$.

$^1$H-NMR spectrum (400 MHz, $CD_3OD$) δ: 8.48 (d, J=2.4 Hz, 1H), 8.12-8.06 (m, 2H), 8.04-8.00 (m, 1H), 8.00-7.95 (m, 1H), 7.73 (d, J=1.6 Hz, 1H), 7.66-7.62 (m, 1H), 7.54 (d, J=1.0 Hz, 1H), 6.56-6.52 (m, 1H), 5.39-5.34 (m, 1H), 5.29-5.10 (m, 1H), 4.20-4.05 (m, 2H), 3.72-3.40 (m, 4H), 2.84-2.66 (m, 2H).

Example 9-(b)

Production of (3S)-3-(2-(4-((5-fluoro-1,4,5,6-tetrahydropyrimidin-2-yl)amino)-1H-indazole-6-carboxamido)acetamido)-3-(2-fluoro-3-(trifluoromethyl)phenyl)propanoic acid

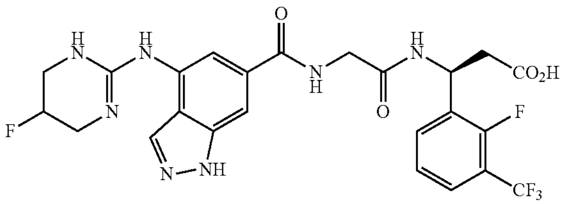 [SMILES: O=C(O)C[C@H](NC(=O)CNC(=O)c1cc(NC2=NCC(F)CN2)c2cn[nH]c2c1)c1cccc(C(F)(F)F)c1F]

To a suspension of 88 mg of methyl (3S)-3-(2-(4-((5-fluoro-1,4,5,6-tetrahydropyrimidin-2-yl)amino)-1H-indazole-6-carboxamido)acetamido)-3-(2-fluoro-3-(trifluoromethyl)phenyl)propanoate trifluoroacetate synthesized in Example 9-(a) in acetonitrile (1 ml) and water (1 ml), 16 mg of lithium hydroxide was added at room temperature under a stream of argon, and the mixture was stirred at room temperature for 1.5 hours.

After the completion of reaction, the reaction mixture was filtered. The filtrate was adjusted to pH 5.4 by the addition of 1 N hydrochloric acid, and the mixture was stirred at room temperature for 7.5 hours. A deposited solid was collected by filtration, washed with water, and then dried under reduced pressure at 60 °C to obtain 46 mg of the title compound as a white solid.

Mass spectrum (ESI, m/z): 568 $[M+H]^+$.

$^1$H-NMR spectrum (400 MHz, $CD_3OD$) δ: 8.11 (d, J=1.0 Hz, 1H), 8.08-8.06 (m, 1H), 7.74-7.69 (m, 1H), 7.56-7.51 (m, 2H), 7.27-7.22 (m, 1H), 5.49 (t, J=5.2 Hz, 1H), 5.30-5.13 (m, 1H), 4.16 (d, J=16.8 Hz, 1H), 4.05 (d, J=16.8 Hz, 1H), 3.70-3.45 (m, 4H), 2.76-2.58 (m, 2H).

Example 10-(b)

Production of (3S)-3-(2-chloro-3-(trifluoromethyl)phenyl)-3-(2-(4-((5-fluoro-1,4,5,6-tetrahydropyrimidin-2-yl)amino)-1H-indazole-6-carboxamido)acetamido)propanoic acid

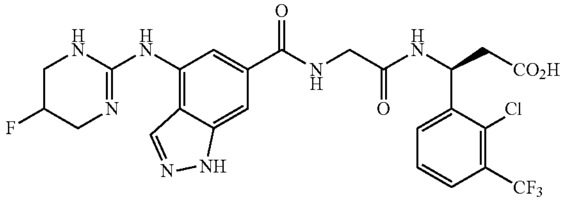 [SMILES: O=C(O)C[C@H](NC(=O)CNC(=O)c1cc(NC2=NCC(F)CN2)c2cn[nH]c2c1)c1cccc(C(F)(F)F)c1Cl]

To a suspension of 79 mg of methyl (3S)-3-(2-chloro-3-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 10-(a) in acetonitrile (1 ml) and water (1 ml), 14 mg of lithium hydroxide was added at room temperature under a stream of argon, and the mixture was stirred at room temperature for 1.5 hours.

After the completion of reaction, the reaction mixture was filtered. The filtrate was adjusted to pH 5.4 by the addition of 1 N hydrochloric acid, and the mixture was stirred at room temperature for 3 hours. A deposited solid was collected by filtration, washed with water, and then dried under reduced pressure at 60 °C to obtain 58 mg of the title compound as a white solid.

Mass spectrum (ESI, m/z): 584 $[M+H]^+$.

$^1$H-NMR spectrum (400 MHz, $CD_3OD$) δ: 8.11 (d, J=0.9 Hz, 1H), 8.10-8.07 (m, 1H), 7.77-7.73 (m, 1H), 7.66-7.62 (m, 1H), 7.56 (d, J=1.3 Hz, 1H), 7.42-7.36 (m, 1H), 5.61 (t, J=5.1 Hz, 1H), 5.29-5.13 (m, 1H), 4.17-4.03 (m, 2H), 3.70-3.45 (m, 4H), 2.75-2.58 (m, 2H).

Example 11-(b)

Production of (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethyl)phenyl)propanoic acid

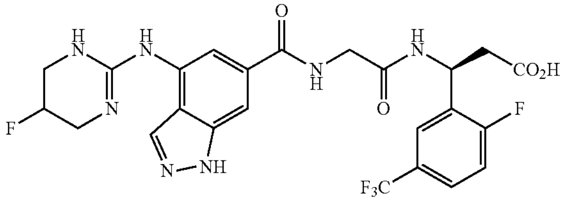 [SMILES: O=C(O)C[C@H](NC(=O)CNC(=O)c1cc(NC2=NCC(F)CN2)c2cn[nH]c2c1)c1cc(C(F)(F)F)ccc1F]

To a solution of 85 mg of methyl (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethyl)phenyl)propanoate trifluoroacetate synthesized in Example 11-(a) in acetonitrile (1 ml) and water (1 ml), 15 mg of lithium hydroxide was added at room temperature under a stream of argon, and the mixture was stirred at room temperature for 3.5 hours.

After the completion of reaction, the reaction mixture was filtered. The filtrate was adjusted to pH 5.5 by the addition of 1 N hydrochloric acid, and the mixture was stirred at room temperature for 18 hours. A deposited solid was collected by filtration, washed with water, and then dried under reduced pressure at 60 °C to obtain 23 mg of the title compound as a pale yellow solid.

Mass spectrum (ESI, m/z): 568 $[M+H]^+$.

$^1$H-NMR spectrum (400 MHz, $CD_3OD$) δ: 8.10-8.06 (m, 2H), 7.80-7.76 (m, 1H), 7.61-7.55 (m, 1H), 7.52 (d, J=1.0 Hz, 1H), 7.29-7.23 (m, 1H), 5.50 (t, J=5.4 Hz, 1H), 5.30-5.14 (m, 1H), 4.16 (d, J=16.8 Hz, 1H), 4.06 (d, J=16.8 Hz, 1H), 3.71-3.45 (m, 4H), 2.78-2.61 (m, 2H).

Example 12-(b)

Production of (3S)-3-(2-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid

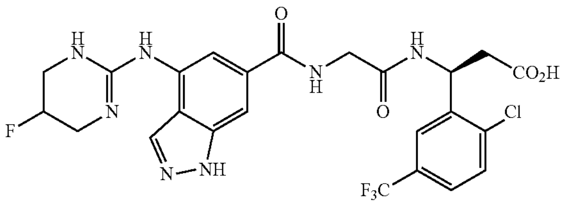 [SMILES: O=C(O)C[C@H](NC(=O)CNC(=O)c1cc(NC2=NCC(F)CN2)c2cn[nH]c2c1)c1cc(C(F)(F)F)ccc1Cl]

To a solution of 127 mg of methyl (3S)-3-(2-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 12-(a) in acetonitrile (1 ml) and water (1 ml), 22 mg of lithium hydroxide was added at room temperature under a stream of argon, and the mixture was stirred at room temperature for 1 hour.

After the completion of reaction, the reaction mixture was filtered. The filtrate was adjusted to pH 5.3 by the addition of 1 N hydrochloric acid, and the mixture was stirred at room temperature for 16 hours. A deposited solid was collected by filtration, washed with water, and then dried under reduced pressure at 60 °C to obtain 58 mg of the title compound as a gray solid.

Mass spectrum (ESI, m/z): 584 $[M+H]^+$.

$^1$H-NMR spectrum (400 MHz, $CD_3OD$) δ: 8.12-8.06 (m, 2H), 7.80 (d, J=1.6 Hz, 1H), 7.59-7.50 (m, 3H), 5.58 (t, J=5.3 Hz, 1H), 5.30-5.14 (m, 1H), 4.16 (d, J=16.8 Hz, 1H), 4.07 (d, J=16.8 Hz, 1H), 3.72-3.45 (m, 4H), 2.76-2.62 (m, 2H).

Example 13-(b)

Production of (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethyl)phenyl)propanoic acid

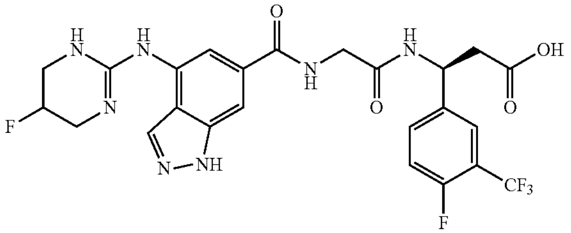

To a solution of 114 mg of methyl (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethyl)phenyl)propanoate trifluoroacetate synthesized in Example 1-(a) in acetonitrile (1 ml) and water (1 ml), 20 mg of lithium hydroxide was added at room temperature under a stream of argon, and the mixture was stirred at room temperature for 1 hour.

After the completion of reaction, the reaction mixture was filtered. The filtrate was adjusted to pH 5.3 by the addition of 1 N hydrochloric acid, and the mixture was stirred at room temperature for 4 hours. A deposited solid was collected by filtration, washed with water, and then dried under reduced pressure at 60 °C to obtain 62 mg of the title compound as a pale yellow solid.

Mass spectrum (ESI, m/z): 568 $[M+H]^+$.

$^1$H-NMR spectrum (400 MHz, $CD_3OD$) δ: 8.10-8.05 (m, 2H), 7.72-7.64 (m, 2H), 7.51 (d, J=1.1 Hz, 1H), 7.26-7.20 (m, 1H), 5.31-5.14 (m, 2H), 4.17-4.02 (m, 2H), 3.73-3.46 (m, 4H), 2.73-2.60 (m, 2H).

Example 14-(b)

Production of (3S)-3-(2-(4-((5-fluoro-1,4,5,6-tetrahydropyrimidin-2-yl)amino)-1H-indazole-6-carboxamido)acetamido)-3-(4-methyl-3-(trifluoromethyl)phenyl)propanoic acid

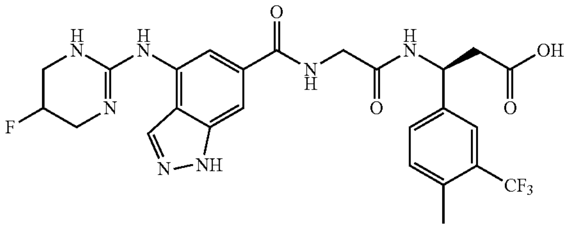 [SMILES: Cc1ccc([C@H](CC(=O)O)NC(=O)CNC(=O)c2cc(NC3=NCC(F)CN3)c3cn[nH]c3c2)cc1C(F)(F)F]

To a solution of 115 mg of methyl (3S)-3-(2-(4-((5-fluoro-1,4,5,6-tetrahydropyrimidin-2-yl)amino)-1H-indazole-6-carboxamido)acetamido)-3-(4-methyl-3-(trifluoromethyl)phenyl)propanoate trifluoroacetate synthesized in Example 14-(a) in acetonitrile (1 ml) and water (1 ml), 20 mg of lithium hydroxide was added at room temperature under a stream of argon, and the mixture was stirred at room temperature for 1 hour.

After the completion of reaction, the reaction mixture was filtered. The filtrate was adjusted to pH 5.4 by the addition of 1 N hydrochloric acid, and the mixture was stirred at room temperature for 3 hours. A deposited solid was collected by filtration, washed with water, and then dried under reduced pressure at 60 °C to obtain 46 mg of the title compound as a white solid.

Mass spectrum (ESI, m/z): 564 $[M+H]^+$.

$^1$H-NMR spectrum (400 MHz, $CD_3OD$) δ: 8.09-8.03 (m, 2H), 7.66-7.62 (m, 1H), 7.51-7.46 (m, 2H), 7.26 (d, J=8.0 Hz, 1H), 5.28-5.12 (m, 2H), 4.16 (d, J=16.8 Hz, 1H), 4.05 (d, J=16.8 Hz, 1H), 3.71-3.43 (m, 4H), 2.72-2.59 (m, 2H), 2.43-2.38 (m, 3H).

Example 15-(b)

Production of (3S)-3-(3-chloro-4-fluoro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid

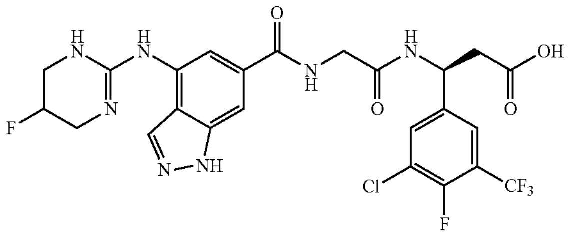 [SMILES: O=C(O)C[C@H](NC(=O)CNC(=O)c1cc(NC2=NCC(F)CN2)c2cn[nH]c2c1)c1cc(Cl)c(F)c(C(F)(F)F)c1]

To a solution of 90 mg of methyl (3S)-3-(3-chloro-4-fluoro-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 15-(a) in acetonitrile (1 ml) and water (1 ml), 15 mg of lithium hydroxide was added at room temperature under a stream of argon, and the mixture was stirred at room temperature for 1 hour.

After the completion of reaction, 1 ml of water was added to the reaction mixture, and the mixture was filtered. The filtrate was adjusted to pH 5.5 by the addition of 1 N hydrochloric acid. 1 ml of water and 1 ml of acetonitrile were added thereto, and the mixture was stirred at room temperature for 10 minutes. A deposited solid was collected by filtration, washed with water, and then dried under reduced pressure at 60 °C to obtain 51 mg of the title compound as a white solid.

Mass spectrum (ESI, m/z): 602 $[M+H]^+$.

$^1$H-NMR spectrum (400 MHz, $CD_3OD$) δ: 8.11-8.07 (m, 2H), 7.80 (dd, J=2.2, 6.6 Hz, 1H), 7.66 (dd, J=2.2, 6.0 Hz, 1H), 7.52 (d, J=1.1 Hz, 1H), 5.30-5.16 (m, 2H), 4.17-4.02 (m, 2H), 3.73-3.46 (m, 4H), 2.74-2.60 (m, 2H).

Example 16-(b)

Production of (3S)-3-(3-bromo-4-methoxyphenyl)-3-(2-(4-((5-fluoro-1,4,5,6-tetrahydropyrimidin-2-yl)amino)-1H-indazole-6-carboxamido)acetamido)propanoic acid

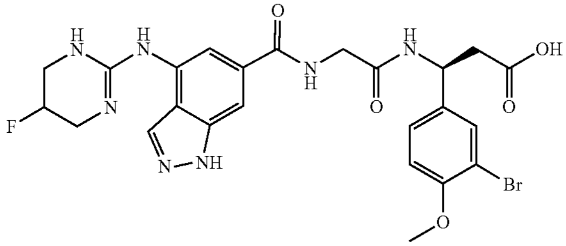 [SMILES: COc1ccc([C@H](CC(=O)O)NC(=O)CNC(=O)c2cc(NC3=NCC(F)CN3)c3cn[nH]c3c2)cc1Br]

To a solution of 110 mg of methyl (3S)-3-(3-bromo-4-methoxyphenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 16-(a) in acetonitrile (1 ml) and water (1 ml), 19 mg of lithium hydroxide was added at room temperature under a stream of argon, and the mixture was stirred at room temperature for 1.5 hours.

After the completion of reaction, the reaction mixture was filtered. The filtrate was adjusted to pH 5.2 by the addition of 1 N hydrochloric acid, and the mixture was stirred at room temperature for 16 hours. A deposited solid was collected by filtration, washed with water, and then dried under reduced pressure at 60 °C to obtain 62 mg of the title compound as a white solid.

Mass spectrum (ESI, m/z): 590, 592 $[M+H]^+$.

$^1$H-NMR spectrum (400 MHz, $CD_3OD$) δ: 8.06-8.01 (m, 2H), 7.55 (d, J=2.1 Hz, 1H), 7.45 (d, J=1.1 Hz, 1H), 7.30 (dd, J=2.1, 8.7 Hz, 1H), 6.90 (d, J=8.7 Hz, 1H), 5.29-5.11 (m, 2H), 4.16 (d, J=16.8 Hz, 1H), 4.05 (d, J=16.8 Hz, 1H), 3.80 (s, 3H), 3.67-3.42 (m, 4H), 2.70-2.57 (m, 2H).

Example 17-(b)

Production of (3S)-3-(3,5-dichlorophenyl)-3-(2-(4-((5-fluoro-1,4,5,6-tetrahydropyrimidin-2-yl)amino)-1H-indazole-6-carboxamido)acetamido)propanoic acid

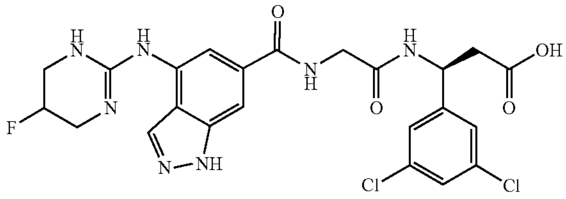 [SMILES: O=C(O)C[C@H](NC(=O)CNC(=O)c1cc(NC2=NCC(F)CN2)c2cn[nH]c2c1)c1cc(Cl)cc(Cl)c1]

To a suspension of 120 mg of methyl (3S)-3-(3,5-dichlorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 17-(a) in acetonitrile (1 ml) and water (1 ml), 22 mg of lithium hydroxide was added at room temperature under a stream of argon, and the mixture was stirred at room temperature for 3.5 hours.

After the completion of reaction, the reaction mixture was adjusted to pH 5.3 by the addition of 1 N hydrochloric acid, and the mixture was stirred at room temperature for 2.5 hours. A deposited solid was collected by filtration, washed with water, and then dried under reduced pressure at 60 °C to obtain 76 mg of the title compound as a pale yellow solid.

Mass spectrum (ESI, m/z): 550 $[M+H]^+$.

$^1$H-NMR spectrum (400 MHz, $CD_3OD$) δ: 8.08-8.05 (m, 2H), 7.51-7.47 (m, 1H), 7.37-7.34 (m, 2H), 7.25 (t, J=1.9 Hz, 1H), 5.30-5.13 (m, 2H), 4.17-4.05 (m, 2H), 3.71-3.44 (m, 4H), 2.70-2.57 (m, 2H).

Example 18-(b)

Production of (3S)-3-(3-bromo-5-chlorophenyl)-3-(2-(4-((5-fluoro-1,4,5,6-tetrahydropyrimidin-2-yl)amino)-1H-indazole-6-carboxamido)acetamido)propanoic acid

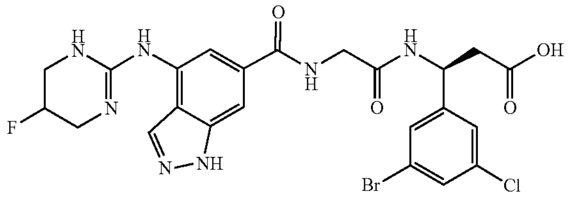 [SMILES: O=C(O)C[C@H](NC(=O)CNC(=O)c1cc(NC2=NCC(F)CN2)c2cn[nH]c2c1)c1cc(Cl)cc(Br)c1]

To a solution of 125 mg of methyl (3S)-3-(3-bromo-5-chlorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 18-(a) in acetonitrile (1 ml) and water (1 ml), 21 mg of lithium hydroxide was added at room temperature under a stream of argon, and the mixture was stirred at room temperature for 2.5 hours.

After the completion of reaction, 2 ml of water and 0.5 ml of acetonitrile were added to the reaction mixture, and the mixture was filtered. The filtrate was adjusted to pH 5.8 by the addition of 1 N hydrochloric acid, and the mixture was stirred at room temperature for 22 hours. A deposited solid was collected by filtration, washed with water, and then dried under reduced pressure at 60 °C to obtain 85 mg of the title compound as a white solid.

Mass spectrum (ESI, m/z): 594, 596 $[M+H]^+$.

$^1$H-NMR spectrum (400 MHz, $CD_3OD$) δ: 8.08-8.05 (m, 2H), 7.52-7.48 (m, 2H), 7.41-7.38 (m, 2H), 5.30-5.13 (m, 2H), 4.17-4.05 (m, 2H), 3.71-3.45 (m, 4H), 2.70-2.56 (m, 2H).

Example 19-(b)

Production of (3S)-3-(3,5-dibromophenyl)-3-(2-(4-((5-fluoro-1,4,5,6-tetrahydropyrimidin-2-yl)amino)-1H-indazole-6-carboxamido)acetamido)propanoic acid

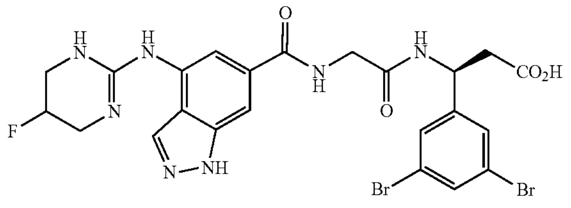 [SMILES: O=C(O)C[C@H](NC(=O)CNC(=O)c1cc(NC2=NCC(F)CN2)c2cn[nH]c2c1)c1cc(Br)cc(Br)c1]

To a suspension of 48 mg of methyl (3S)-3-(3,5-dibromophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 19-(a) in acetonitrile (0.5 ml) and water (0.5 ml), 13 mg of lithium hydroxide monohydrate was added at room temperature under a stream of argon, and the mixture was stirred at room temperature for 1 hour.

After the completion of reaction, the reaction mixture was adjusted to pH 5.9 by the addition of 1 M hydrochloric acid, and the mixture was stirred overnight at room temperature. A deposited solid was collected by filtration, washed with water, and then dried under reduced pressure at 50 °C to obtain 34 mg of the title compound as a white solid.

Mass spectrum (ESI, m/z): 640 $[M+H]^+$.

$^1$H-NMR spectrum (400 MHz, $CD_3OD$) δ: 8.10-8.07 (m, 2H), 7.56-7.53 (m, 3H), 7.52 (d, J=1.1 Hz, 1H), 5.31-5.10 (m, 2H), 4.18-4.03 (m, 2H), 3.71-3.45 (m, 4H), 2.71-2.54 (m, 2H).

Example 20-(b)

Production of (3S)-3-(3-bromo-5-iodophenyl)-3-(2-(4-((5-fluoro-1,4,5,6-tetrahydropyrimidin-2-yl)amino)-1H-indazole-6-carboxamido)acetamido)propanoic acid

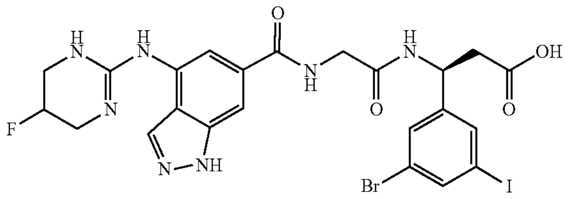 [SMILES: O=C(O)C[C@H](NC(=O)CNC(=O)c1cc(NC2=NCC(F)CN2)c2cn[nH]c2c1)c1cc(Br)cc(I)c1]

To a suspension of 140 mg of methyl (3S)-3-(3-bromo-5-iodophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 20-(a) in acetonitrile (1 ml) and water (1 ml), 21 mg of lithium hydroxide was added at room temperature under a stream of argon, and the mixture was stirred at room temperature for 3.5 hours.

After the completion of reaction, the reaction mixture was adjusted to pH 5.5 by the addition of 1 N hydrochloric acid, and the mixture was stirred at room temperature for 16 hours. A deposited solid was collected by filtration, washed with water, and then dried under reduced pressure at 60 °C to obtain 88 mg of the title compound as a light brown solid.

Mass spectrum (ESI, m/z): 686, 688 $[M+H]^+$.

$^1$H-NMR spectrum (400 MHz, $CD_3OD$) δ: 8.11-8.05 (m, 2H), 7.74-7.70 (m, 2H), 7.57-7.54 (m, 1H), 7.52 (d, J=1.1 Hz, 1H), 5.33-5.15 (m, 1H), 5.13 (t, J=5.3 Hz, 1H), 4.17-4.04 (m, 2H), 3.72-3.45 (m, 4H), 2.69-2.55 (m, 2H).

Example 21-(b)

Production of (3S)-3-(3-chloro-5-iodophenyl)-3-(2-(4-((5-fluoro-1,4,5,6-tetrahydropyrimidin-2-yl)amino)-1H-indazole-6-carboxamido)acetamido)propanoic acid

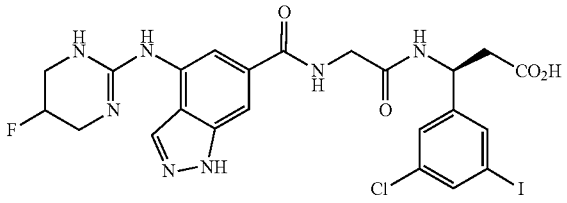 [SMILES: O=C(O)C[C@H](NC(=O)CNC(=O)c1cc(NC2=NCC(F)CN2)c2cn[nH]c2c1)c1cc(Cl)cc(I)c1]

To a suspension of 48 mg of methyl (3S)-3-(3-chloro-5-iodophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 21-(a) in acetonitrile (0.5 ml) and water (0.5 ml), 13 mg of lithium hydroxide monohydrate was added at room temperature under a stream of argon, and the mixture was stirred at room temperature for 1 hour.

After the completion of reaction, the reaction mixture was adjusted to pH 5.9 by the addition of 1 M hydrochloric acid, and the mixture was stirred overnight at room temperature. A deposited solid was collected by filtration, washed with water, and then dried under reduced pressure at 50 °C to obtain 38 mg of the title compound as a white solid.

Mass spectrum (ESI, m/z): 642 $[M+H]^+$.

$^1$H-NMR spectrum (400 MHz, $CD_3OD$) δ: 8.13-8.05 (m, 2H), 7.71-7.65 (m, 1H), 7.61-7.56 (m, 1H), 7.53 (d, J=1.1 Hz, 1H), 7.44-7.39 (m, 1H), 5.31-5.11 (m, 2H), 4.18-4.03 (m, 2H), 3.73-3.45 (m, 4H), 2.71-2.54 (m, 2H).

Example 22-(b)

Production of (3S)-3-(5-chloro-2-fluorophenyl)-3-(2-(4-((5-fluoro-1,4,5,6-tetrahydropyrimidin-2-yl)amino)-1H-indazole-6-carboxamido)acetamido)propanoic acid

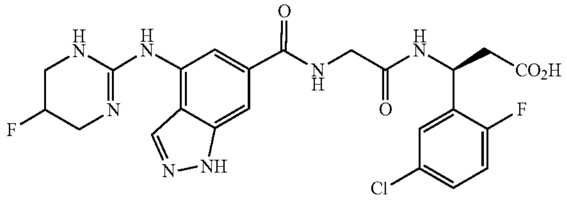 [SMILES: O=C(O)C[C@H](NC(=O)CNC(=O)c1cc(NC2=NCC(F)CN2)c2cn[nH]c2c1)c1cc(Cl)ccc1F]

To a solution of 203 mg of methyl (3S)-3-(5-chloro-2-fluorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 22-(a) in acetonitrile (1 ml) and water (1 ml), 49 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration. Acetonitrile/methanol=1/9 (v/v) (0.74 ml) was added to the obtained solid, and the mixture was stirred at 80 °C. Acetonitrile/methanol=1/9 (v/v) (0.74 ml) was further added thereto, and the mixture was stirred at room temperature for 30 minutes. A deposited solid was collected by filtration, washed with water, and then dried under reduced pressure at 60 °C to obtain 46 mg of the title compound as a white solid.

Mass spectrum (ESI, m/z): 534 $[M+H]^+$.

$^1$H-NMR spectrum (400 MHz, $CD_3OD$) δ: 8.09-8.04 (m, 2H), 7.51 (d, J=1.0 Hz, 1H), 7.44 (dd, J=2.7, 6.5 Hz, 1H), 7.22 (ddd, J=2.7, 4.3, 8.8 Hz, 1H), 7.05 (dd, J=8.8, 9.9 Hz, 1H), 5.45-5.40 (m, 1H), 5.28-5.10 (m, 1H), 4.19-4.05 (m, 2H), 3.71-3.41 (m, 4H), 2.75-2.57 (m, 2H).

Example 23-(b)

Production of (3S)-3-(5-bromo-2-fluorophenyl)-3-(2-(4-((5-fluoro-1,4,5,6-tetrahydropyrimidin-2-yl)amino)-1H-indazole-6-carboxamido)acetamido)propanoic acid

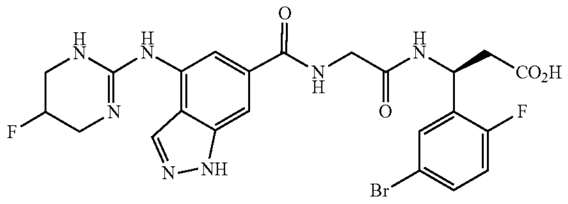 [SMILES: O=C(O)C[C@H](NC(=O)CNC(=O)c1cc(NC2=NCC(F)CN2)c2cn[nH]c2c1)c1cc(Br)ccc1F]

To a solution of 145 mg of methyl (3S)-3-(5-bromo-2-fluorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 23-(a) in acetonitrile (1 ml) and water (1 ml), 48 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration, washed with water, and then dried under reduced pressure at 60 °C to obtain 50 mg of the title compound as a white solid.

Mass spectrum (ESI, m/z): 578, 580 $[M+H]^+$.

$^1$H-NMR spectrum (400 MHz, $CD_3OD$) δ: 8.11-8.06 (m, 2H), 7.58 (dd, J=2.6, 6.7 Hz, 1H), 7.54 (d, J=1.1 Hz, 1H), 7.37 (ddd, J=2.6, 4.5, 8.7 Hz, 1H), 7.00 (dd, J=8.7, 10.1 Hz, 1H), 5.45-5.40 (m, 1H), 5.30-5.11 (m, 1H), 4.18-4.05 (m, 2H), 3.73-3.43 (m, 4H), 2.76-2.57 (m, 2H).

Example 24-(b)

Production of (3S)-3-(3-(difluoromethoxy)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid

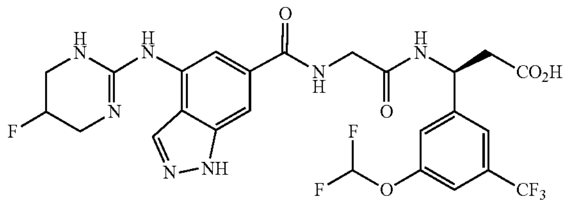 [SMILES: O=C(O)C[C@H](NC(=O)CNC(=O)c1cc(NC2=NCC(F)CN2)c2cn[nH]c2c1)c1cc(OC(F)F)cc(C(F)(F)F)c1]

To a solution of 118 mg of methyl (3S)-3-(3-(difluoromethoxy)-5-(trifluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 24-(a) in acetonitrile (1 ml) and water (1 ml), 19 mg of lithium hydroxide was added at room temperature under a stream of argon, and the mixture was stirred at room temperature for 2 hours.

After the completion of reaction, the reaction mixture was filtered. The filtrate was adjusted to pH 5.5 by the addition of 1 N hydrochloric acid, and the mixture was stirred at room temperature for 15 hours. A deposited solid was collected by filtration, washed with water, and then dried under reduced pressure at 60 °C to obtain 77 mg of the title compound as a white solid.

Mass spectrum (ESI, m/z): 616 $[M+H]^+$.

$^1$H-NMR spectrum (400 MHz, $CD_3OD$) δ: 8.10-8.05 (m, 2H), 7.59-7.56 (m, 1H), 7.51 (d, J=0.9 Hz, 1H), 7.46-7.42 (m, 1H), 7.27-7.24 (m, 1H), 6.97 (t, J=73.5 Hz, 1H), 5.32-5.11 (m, 2H), 4.15 (d, J=16.8 Hz, 1H), 4.06 (d, J=16.8 Hz, 1H), 3.71-3.42 (m, 4H), 2.75-2.60 (m, 2H).

Example 25-(b)

Production of (3S)-3-(3-chloro-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid

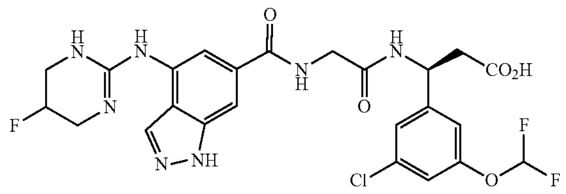 [SMILES: O=C(O)C[C@H](NC(=O)CNC(=O)c1cc(NC2=NCC(F)CN2)c2cn[nH]c2c1)c1cc(Cl)cc(OC(F)F)c1]

To a solution of 135 mg of methyl (3S)-3-(3-chloro-5-(difluoromethoxy)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 25-(a) in acetonitrile (1 ml) and water (1 ml), 23 mg of lithium hydroxide was added at room temperature under a stream of argon, and the mixture was stirred at room temperature for 1 hour.

After the completion of reaction, the reaction mixture was filtered. The filtrate was adjusted to pH 5.5 by the addition of 1 N hydrochloric acid, and the mixture was stirred at room temperature for 15 hours. A deposited solid was collected by filtration, washed with water, and then dried under reduced pressure at 60 °C to obtain 55 mg of the title compound as a pale yellow solid.

Mass spectrum (ESI, m/z): 582 $[M+H]^+$.

$^1$H-NMR spectrum (400 MHz, $CD_3OD$) δ: 8.11-8.06 (m, 2H), 7.51 (d, J=1.1 Hz, 1H), 7.30-7.27 (m, 1H), 7.14-7.10 (m, 1H), 7.06-7.04 (m, 1H), 6.90 (t, J=73.5 Hz, 1H), 5.32-5.13 (m, 2H), 4.15-4.06 (m, 2H), 3.74-3.45 (m, 4H), 2.78-2.70 (m, 2H).

Example 26-(b)

Production of (3S)-3-(3-bromo-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid

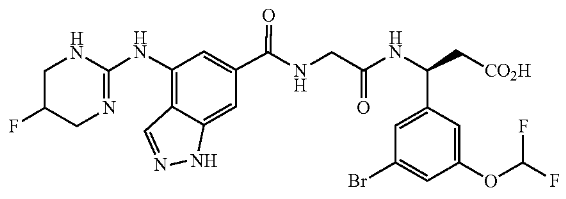 [SMILES: O=C(O)C[C@H](NC(=O)CNC(=O)c1cc(NC2=NCC(F)CN2)c2cn[nH]c2c1)c1cc(Br)cc(OC(F)F)c1]

To a solution of 177 mg of methyl (3S)-3-(3-bromo-5-(difluoromethoxy)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 26-(a) in acetonitrile (1 ml) and water (1 ml), 25 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration, washed with water, and then dried under reduced pressure at 60 °C to obtain 88 mg of the title compound as a light brown solid.

Mass spectrum (ESI, m/z): 626, 628 $[M+H]^+$.

$^1$H-NMR spectrum (400 MHz, $CD_3OD$) δ: 8.11-8.05 (m, 2H), 7.52 (d, J=1.1 Hz, 1H), 7.45-7.41 (m, 1H), 7.20-7.14 (m, 2H), 6.90 (t, J=73.5 Hz, 1H), 5.32-5.15 (m, 2H), 4.16-4.04 (m, 2H), 3.73-3.44 (m, 4H), 2.76-2.61 (m, 2H).

Example 27-(b)

Production of (3S)-3-(3-(difluoromethoxy)-4-fluorophenyl)-3-(2-(4-((5-fluoro-1,4,5,6-tetrahydropyrimidin-2-yl)amino)-1H-indazole-6-carboxamido)acetamido)propanoic acid

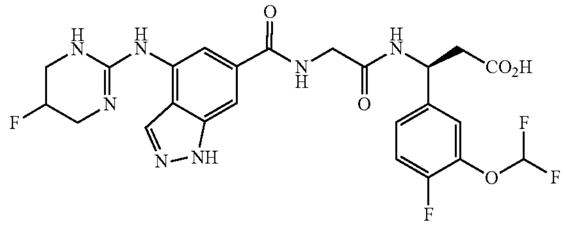 [SMILES: O=C(O)C[C@H](NC(=O)CNC(=O)c1cc(NC2=NCC(F)CN2)c2cn[nH]c2c1)c1ccc(F)c(OC(F)F)c1]

To a solution of 150 mg of methyl (3S)-3-(3-(difluoromethoxy)-4-fluorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 27-(a) in acetonitrile (1 ml) and water (1 ml), 49 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration, washed with water, and then dried under reduced pressure at 60 °C to obtain 40 mg of the title compound as a white solid.

Mass spectrum (ESI, m/z): 566 $[M+H]^+$.

$^1$H-NMR spectrum (400 MHz, $CD_3OD$) δ: 8.11-8.04 (m, 2H), 7.51 (d, J=1.1 Hz, 1H), 7.31 (dd, J=2.1, 7.4 Hz, 1H), 7.25 (ddd, J=2.1, 4.4, 8.6 Hz, 1H), 7.14 (dd, J=8.6, 10.4 Hz, 1H), 6.86 (t, J=73.8 Hz, 1H), 5.30-5.14 (m, 2H), 4.14 (d, J=16.8 Hz, 1H), 4.04 (d, J=16.8 Hz, 1H), 3.73-3.42 (m, 4H), 2.72-2.58 (m, 2H).

Example 28-(b)

Production of (3S)-3-(5-(difluoromethoxy)-2-fluorophenyl)-3-(2-(4-((5-fluoro-1,4,5,6-tetrahydropyrimidin-2-yl)amino)-1H-indazole-6-carboxamido)acetamido)propanoic acid

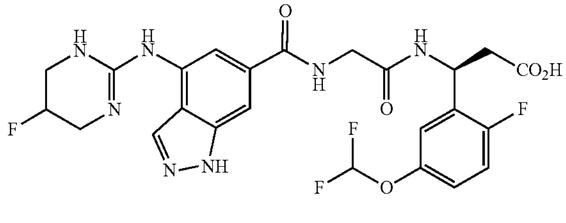 [SMILES: O=C(O)C[C@H](NC(=O)CNC(=O)c1cc(NC2=NCC(F)CN2)c2cn[nH]c2c1)c1cc(OC(F)F)ccc1F]

To a solution of 152 mg of methyl (3S)-3-(5-(difluoromethoxy)-2-fluorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 28-(a) in acetonitrile (1 ml) and water (1 ml), 49 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration, washed with water, and then dried under reduced pressure at 60 °C to obtain 70 mg of the title compound as a white solid.

Mass spectrum (ESI, m/z): 566 $[M+H]^+$.

$^1$H-NMR spectrum (400 MHz, $CD_3OD$) δ: 8.11-8.06 (m, 2H), 7.53 (d, J=1.1 Hz, 1H), 7.22 (dd, J=2.9, 6.1 Hz, 1H), 7.11-6.98 (m, 2H), 6.81 (t, J=74.3 Hz, 1H), 5.47-5.42 (m, 1H), 5.30-5.12 (m, 1H), 4.17-4.03 (m, 2H), 3.71-3.43 (m, 4H), 2.76-2.61 (m, 2H).

Example 29-(b)

Production of (3S)-3-(3-(difluoromethoxy)-5-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid

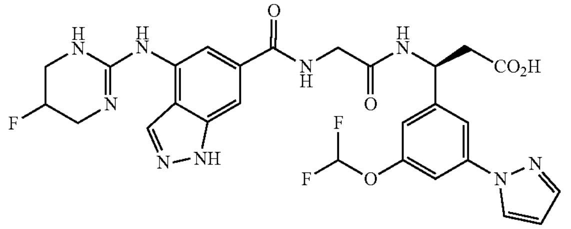 [SMILES: O=C(O)C[C@H](NC(=O)CNC(=O)c1cc(NC2=NCC(F)CN2)c2cn[nH]c2c1)c1cc(OC(F)F)cc(-n2cccn2)c1]

To a solution of 162 mg of methyl (3S)-3-(3-(difluoromethoxy)-5-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 29-(a) in acetonitrile (1 ml) and water (1 ml), 48 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid. 3 ml of water was added thereto, and the mixture was stirred at room temperature for 15 hours. A deposited solid was collected by filtration, washed with water, and then dried under reduced pressure at 60 °C to obtain 65 mg of the title compound as a pale yellow solid.

Mass spectrum (ESI, m/z): 614 $[M+H]^+$.

$^1$H-NMR spectrum (400 MHz, $CD_3OD$) δ: 8.38 (d, J=2.4 Hz, 1H), 8.11-8.06 (m, 2H), 7.69 (d, J=1.6 Hz, 1H), 7.62-7.59 (m, 1H), 7.55 (d, J=1.0 Hz, 1H), 7.46-7.43 (m, 1H), 7.13-7.10 (m, 1H), 6.95 (t, J=73.9 Hz, 1H), 6.53-6.49 (m, 1H), 5.30-5.10 (m, 2H), 4.17 (d, J=16.7 Hz, 1H), 4.08 (d, J=16.7 Hz, 1H), 3.70-3.40 (m, 4H), 2.81-2.64 (m, 2H).

Example 30-(b)

Production of (3S)-3-(3,5-bis(difluoromethoxy)phenyl)-3-(2-(4-((5-fluoro-1,4,5,6-tetrahydropyrimidin-2-yl)amino)-1H-indazole-6-carboxamido)acetamido) propanoic acid

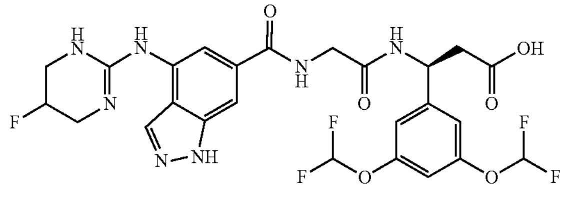 [SMILES: O=C(O)C[C@H](NC(=O)CNC(=O)c1cc(NC2=NCC(F)CN2)c2cn[nH]c2c1)c1cc(OC(F)F)cc(OC(F)F)c1]

To a suspension of 51 mg of methyl (3S)-3-(3,5-bis (difluoromethoxy)phenyl)-3-(2-(4-((5-fluoro-1,4,5,6-tetrahydropyrimidin-2-yl)amino)-1H-indazole-6-carboxamido) acetamido)propanoate trifluoroacetate synthesized in Example 30-(a) in acetonitrile (0.5 ml) and water (0.5 ml), 15 mg of lithium hydroxide monohydrate was added at room temperature under a stream of argon, and the mixture was stirred at room temperature for 1 hour.

After the completion of reaction, the reaction mixture was adjusted to pH 5.9 by the addition of 1 M hydrochloric acid, and the mixture was stirred overnight at room temperature. A deposited solid was collected by filtration, washed with water, and then dried under reduced pressure at 50 °C to obtain 44 mg of the title compound as a brown solid.

Mass spectrum (ESI, m/z): 614 $[M+H]^+$.

$^1$H-NMR spectrum (400 MHz, $CD_3OD$) δ: 8.10-8.03 (m, 2H), 7.54-7.48 (m, 1H), 7.06-7.00 (m, 2H), 6.90 (t, J=73.9 Hz, 2H), 6.77-6.74 (m, 1H), 5.30-5.12 (m, 2H), 4.19-3.99 (m, 2H), 3.72-3.43 (m, 4H), 2.71-2.57 (m, 2H).

Example 31-(b)

Production of (3S)-3-(3-chloro-5-(trifluoromethoxy) phenyl)-3-(2-(4-((5-fluoro-1,4,5,6-tetrahydropyrimidin-2-yl)amino)-1H-indazole-6-carboxamido)acetamido)propanoic acid

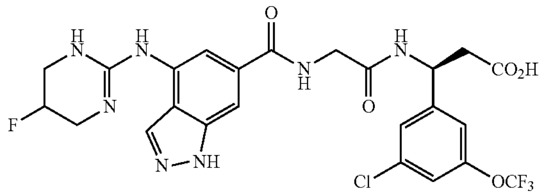 [SMILES: O=C(O)C[C@H](NC(=O)CNC(=O)c1cc(NC2=NCC(F)CN2)c2cn[nH]c2c1)c1cc(Cl)cc(OC(F)(F)F)c1]

To a suspension of 70 mg of methyl (3S)-3-(3-chloro-5-(trifluoromethoxy)phenyl)-3-(2-(4-((5-fluoro-1,4,5,6-tetrahydropyrimidin-2-yl)amino)-1H-indazole-6-carboxamido) acetamido)propanoate trifluoroacetate synthesized in Example 31-(a) in acetonitrile (0.5 ml) and water (0.5 ml), 21 mg of lithium hydroxide monohydrate was added at room temperature under a stream of argon, and the mixture was stirred at room temperature for 1 hour.

After the completion of reaction, the reaction mixture was adjusted to pH 5.9 by the addition of 1 M hydrochloric acid, and the mixture was stirred overnight at room temperature. A deposited solid was collected by filtration, washed with water, and then dried under reduced pressure at 50 °C to obtain 52 mg of the title compound as a white solid.

Mass spectrum (ESI, m/z): 600 $[M+H]^+$.

$^1$H-NMR spectrum (400 MHz, $CD_3OD$) δ: 8.13-8.05 (m, 2H), 7.52 (d, J=1.3 Hz, 1H), 7.46-7.42 (m, 1H), 7.29-7.25 (m, 1H), 7.21-7.18 (m, 1H), 5.34-5.13 (m, 2H), 4.17-4.05 (m, 2H), 3.78-3.45 (m, 4H), 2.77-2.65 (m, 2H).

Example 32-(b)

Production of (3S)-3-(3-bromo-5-(trifluoromethoxy) phenyl)-3-(2-(4-((5-fluoro-1,4,5,6-tetrahydropyrimidin-2-yl)amino)-1H-indazole-6-carboxamido)acetamido)propanoic acid

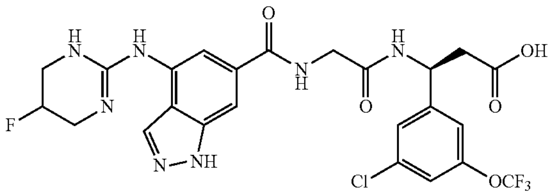 [SMILES: O=C(O)C[C@H](NC(=O)CNC(=O)c1cc(NC2=NCC(F)CN2)c2cn[nH]c2c1)c1cc(Cl)cc(OC(F)(F)F)c1]

To a solution of 321 mg of methyl (3S)-3-(3-bromo-5-(trifluoromethoxy)phenyl)-3-(2-(4-((5-fluoro-1,4,5,6-tetrahydropyrimidin-2-yl)amino)-1H-indazole-6-carboxamido) acetamido)propanoate trifluoroacetate synthesized in Example 32-(a) in acetonitrile (2.5 ml) and water (2.5 ml), 50 mg of lithium hydroxide was added at room temperature under a stream of argon, and the mixture was stirred at room temperature for 3.5 hours.

After the completion of reaction, 2.5 ml of water was added to the reaction mixture. The reaction mixture was adjusted to pH 5.0 by the addition of 1 N hydrochloric acid, and the mixture was stirred at room temperature for 20 hours. A deposited solid was collected by filtration, washed with water, and then dried under reduced pressure at 60 °C to obtain 244 mg of the title compound as a white solid.

Mass spectrum (ESI, m/z): 644, 646 $[M+H]^+$.

$^1$H-NMR spectrum (400 MHz, $CD_3OD$) δ: 8.12-8.06 (m, 2H), 7.61-7.58 (m, 1H), 7.51 (d, J=1.1 Hz, 1H), 7.36-7.33 (m, 1H), 7.33-7.30 (m, 1H), 5.33-5.16 (m, 2H), 4.16-4.05 (m, 2H), 3.73-3.49 (m, 4H), 2.76 (d, J=6.4 Hz, 2H).

Example 33-(b)

Production of (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethoxy) phenyl)propanoic acid

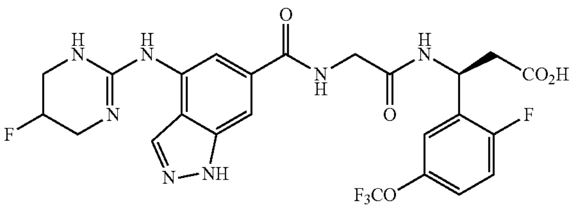

To a solution of 270 mg of methyl (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethoxy)phenyl)propanoate trifluoroacetate synthesized in Example 33-(a) in acetonitrile (2 ml) and water (2 ml), 45 mg of lithium hydroxide was added at room temperature under a stream of argon, and the mixture was stirred at room temperature for 1 hour.

After the completion of reaction, the reaction mixture was adjusted to pH 5.2 by the addition of 1 N hydrochloric acid. 4 ml of water was added thereto, and the mixture was stirred at room temperature for 16 hours. A deposited solid was collected by filtration, washed with water, and then dried under reduced pressure at 60 °C to obtain 169 mg of the title compound as a white solid.

Mass spectrum (ESI, m/z): 584 $[M+H]^+$.

$^1$H-NMR spectrum (400 MHz, $CD_3OD$) δ: 8.08-8.05 (m, 2H), 7.50-7.48 (m, 1H), 7.38-7.34 (m, 1H), 7.20-7.12 (m, 2H), 5.49-5.44 (m, 1H), 5.30-5.14 (m, 1H), 4.18-4.04 (m, 2H), 3.73-3.41 (m, 4H), 2.78-2.61 (m, 2H).

Example 34-(b)

Production of (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethoxy)phenyl)propanoic acid

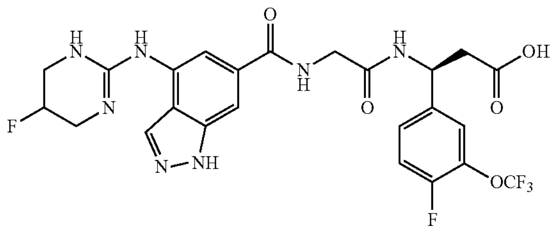 [SMILES: O=C(O)C[C@H](NC(=O)CNC(=O)c1cc(NC2=NCC(F)CN2)c2cn[nH]c2c1)c1ccc(F)c(OC(F)(F)F)c1]

To a solution of 93 mg of methyl (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethoxy)phenyl)propanoate trifluoroacetate synthesized in Example 34-(a) in acetonitrile (1 ml) and water (1 ml), 16 mg of lithium hydroxide was added at room temperature under a stream of argon, and the mixture was stirred at room temperature for 2.5 hours.

After the completion of reaction, 1 ml of water was added to the reaction mixture, and the mixture was filtered. The filtrate was adjusted to pH 5.6 by the addition of 1 N hydrochloric acid, and the mixture was stirred at room temperature for 18 hours. A deposited solid was collected by filtration, washed with water, and then dried under reduced pressure at 60 °C to obtain 63 mg of the title compound as a white solid.

Mass spectrum (ESI, m/z): 584 $[M+H]^+$.

$^1$H-NMR spectrum (400 MHz, $CD_3OD$) δ: 8.08 (d, J=1.0 Hz, 1H), 8.07-8.05 (m, 1H), 7.50 (d, J=1.1 Hz, 1H), 7.46-7.37 (m, 2H), 7.22 (dd, J=8.6, 10.1 Hz, 1H), 5.31-5.14 (m, 2H), 4.15 (d, J=16.8 Hz, 1H), 4.05 (d, J=16.8 Hz, 1H), 3.72-3.46 (m, 4H), 2.71-2.58 (m, 2H).

Example 35-(b)

Production of (3S)-3-(2-(4-((5-fluoro-1,4,5,6-tetrahydropyrimidin-2-yl)amino)-1H-indazole-6-carboxamido)acetamido)-3-(3-(trifluoromethyl)phenyl)propanoic acid

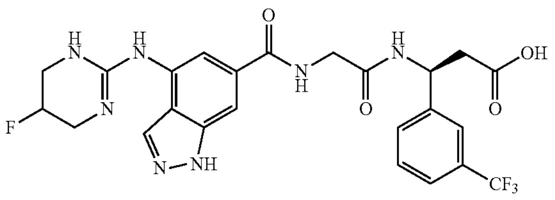

To a solution of 142 mg of methyl (3S)-3-(2-(4-((5-fluoro-1,4,5,6-tetrahydropyrimidin-2-yl)amino)-1H-indazole-6-carboxamido)acetamido)-3-(3-(trifluoromethyl)phenyl)propanoate trifluoroacetate synthesized in Example 35-(a) in acetonitrile (1.5 ml) and water (1.5 ml), 26 mg of lithium hydroxide was added at room temperature under a stream of argon, and the mixture was stirred at room temperature for 1 hour.

After the completion of reaction, the reaction mixture was filtered. The filtrate was adjusted to pH 5.4 by the addition of 1 N hydrochloric acid, and the mixture was stirred at room temperature for 16 hours. The reaction mixture was concentrated under reduced pressure, and acetonitrile was distilled off under reduced pressure. The residue was stirred at room temperature for 3 hours. A deposited solid was collected by filtration, washed with water, and then dried under reduced pressure at 60 °C to obtain 63 mg of the title compound as a pale yellow solid.

Mass spectrum (ESI, m/z): 550 $[M+H]^+$.

$^1$H-NMR spectrum (400 MHz, $CD_3OD$) δ: 8.10-8.04 (m, 2H), 7.73-7.67 (m, 1H), 7.67-7.61 (m, 1H), 7.53-7.45 (m, 3H), 5.31 (t, J=5.5 Hz, 1H), 5.29-5.13 (m, 1H), 4.20-4.04 (m, 2H), 3.72-3.44 (m, 4H), 2.77-2.64 (m, 2H).

Example 36-(b)

Production of (3S)-3-(2-(4-((5-fluoro-1,4,5,6-tetrahydropyrimidin-2-yl)amino)-1H-indazole-6-carboxamido)acetamido)-3-(3-(trifluoromethoxy)phenyl)propanoic acid

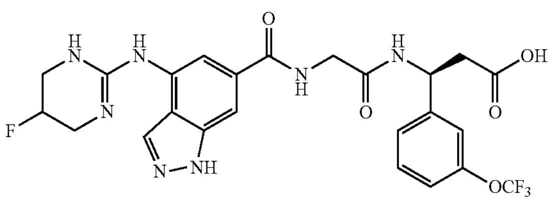 [SMILES: O=C(O)C[C@H](NC(=O)CNC(=O)c1cc(NC2=NCC(F)CN2)c2cn[nH]c2c1)c1cccc(OC(F)(F)F)c1]

To a solution of 104 mg of methyl (3S)-3-(2-(4-((5-fluoro-1,4,5,6-tetrahydropyrimidin-2-yl)amino)-1H-indazole-6-carboxamido)acetamido)-3-(3-(trifluoromethoxy)phenyl)propanoate trifluoroacetate synthesized in Example 36-(a) in acetonitrile (1 ml) and water (1 ml), 18 mg of lithium hydroxide was added at room temperature under a stream of argon, and the mixture was stirred at room temperature for 1 hour.

After the completion of reaction, the reaction mixture was filtered. The filtrate was adjusted to pH 5.2 by the addition of 1 N hydrochloric acid. The reaction mixture was concentrated under reduced pressure, and acetonitrile was distilled off under reduced pressure. The residue was stirred at room temperature for 2 hours. A deposited solid was collected by filtration, washed with water, and then dried under reduced pressure at 60 °C to obtain 50 mg of the title compound as a pale yellow solid.

Mass spectrum (ESI, m/z): 566 $[M+H]^+$.

$^1$H-NMR spectrum (400 MHz, $CD_3OD$) δ: 8.08 (d, J=0.9 Hz, 1H), 8.06-8.04 (m, 1H), 7.48 (d, J=1.1 Hz, 1H), 7.41-7.36 (m, 2H), 7.32-7.28 (m, 1H), 7.15-7.09 (m, 1H), 5.33-5.14 (m, 2H), 4.18-4.04 (m, 2H), 3.71-3.45 (m, 4H), 2.78-2.66 (m, 2H).

Example 37-(b)

Production of (3S)-3-(3-(difluoromethoxy)phenyl)-3-(2-(4-((5-fluoro-1,4,5,6-tetrahydropyrimidin-2-yl)amino)-1H-indazole-6-carboxamido)acetamido)propanoic acid

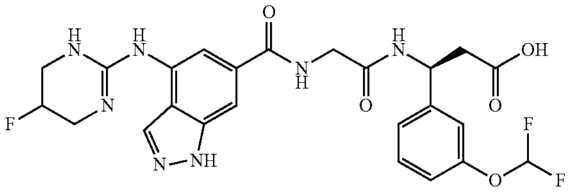 [SMILES: O=C(O)C[C@H](NC(=O)CNC(=O)c1cc(NC2=NCC(F)CN2)c2cn[nH]c2c1)c1cccc(OC(F)F)c1]

To a solution of 110 mg of methyl (3S)-3-(3-(difluoromethoxy)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 37-(a) in acetonitrile (1 ml) and water (1 ml), 20 mg of lithium hydroxide was added at room temperature under a stream of argon, and the mixture was stirred at room temperature for 1 hour.

After the completion of reaction, the reaction mixture was filtered. The filtrate was adjusted to pH 5.5 by the addition of 1 N hydrochloric acid. The reaction mixture was concentrated under reduced pressure, and acetonitrile was distilled off under reduced pressure. The residue was stirred at room temperature for 2.5 hours. A deposited solid was collected by filtration, washed with water, and then dried under reduced pressure at 60 °C to obtain 50 mg of the title compound as a beige solid.

Mass spectrum (ESI, m/z): 548 $[M+H]^+$.

$^1$H-NMR spectrum (400 MHz, $CD_3OD$) δ: 8.10-8.03 (m, 2H), 7.50 (d, J=1.1 Hz, 1H), 7.32-7.27 (m, 1H), 7.26-7.21 (m, 1H), 7.18-7.15 (m, 1H), 6.98-6.93 (m, 1H), 6.83 (t, J=74.3 Hz, 1H), 5.29-5.12 (m, 2H), 4.19-4.02 (m, 2H), 3.70-3.43 (m, 4H), 2.72-2.60 (m, 2H).

Example 38-(b)

Production of (3S)-3-(3-(difluoromethyl)phenyl)-3-(2-(4-((5-fluoro-1,4,5,6-tetrahydropyrimidin-2-yl)amino)-1H-indazole-6-carboxamido)acetamido)propanoic acid

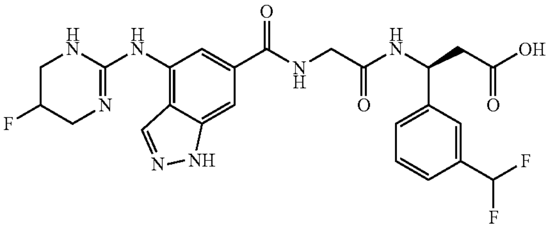 [SMILES: O=C(O)C[C@H](NC(=O)CNC(=O)c1cc(NC2=NCC(F)CN2)c2cn[nH]c2c1)c1cccc(C(F)F)c1]

To a solution of 150 mg of methyl (3S)-3-(3-(difluoromethyl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 38-(a) in acetonitrile (1 ml) and water (1 ml), 28 mg of lithium hydroxide was added at room temperature under a stream of argon, and the mixture was stirred at room temperature for 2.5 hours.

After the completion of reaction, the reaction mixture was filtered. The filtrate was adjusted to pH 5.3 by the addition of 1 N hydrochloric acid, and the mixture was stirred at room temperature for 18 hours. A deposited solid was collected by filtration, washed with water, and then dried under reduced pressure at 60 °C to obtain 60 mg of the title compound as a white solid.

Mass spectrum (ESI, m/z): 532 $[M+H]^+$.

$^1$H-NMR spectrum (400 MHz, $CD_3OD$) δ: 8.06 (d, J=1.0 Hz, 1H), 8.05-8.02 (m, 1H), 7.57-7.51 (m, 2H), 7.47 (d, J=1.3 Hz, 1H), 7.42-7.35 (m, 2H), 6.71 (t, J=56.2 Hz, 1H), 5.30-5.11 (m, 2H), 4.17 (d, J=16.8 Hz, 1H), 4.06 (d, J=16.8 Hz, 1H), 3.68-3.41 (m, 4H), 2.75-2.63 (m, 2H).

Example 39-(b)

Production of (3S)-3-(3-cyclopropylphenyl)-3-(2-(4-((5-fluoro-1,4,5,6-tetrahydropyrimidin-2-yl)amino)-1H-indazole-6-carboxamido)acetamido)propanoic acid

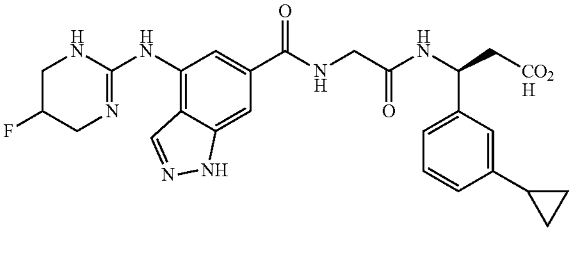 [SMILES: O=C(O)C[C@H](NC(=O)CNC(=O)c1cc(NC2=NCC(F)CN2)c2cn[nH]c2c1)c1cccc(C2CC2)c1]

To a solution of 149 mg of methyl (3S)-3-(3-cyclopropylphenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 39-(a) in acetonitrile (1 ml) and water (1 ml), 25 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. A deposited solid was collected by filtration, washed with water, and then dried under reduced pressure at 60 °C to obtain 66 mg of the title compound as a white solid.

Mass spectrum (ESI, m/z): 522 $[M+H]^+$.

$^1$H-NMR spectrum (400 MHz, $CD_3OD$) δ: 8.06 (d, J=1.0 Hz, 1H), 8.03 (dd, J=1.0, 1.1 Hz, 1H), 7.47 (d, J=1.1 Hz, 1H), 7.14-7.07 (m, 3H), 6.89-6.85 (m, 1H), 5.27-5.11 (m, 2H), 4.19 (d, J=16.7 Hz, 1H), 4.03 (d, J=16.7 Hz, 1H), 3.70-3.38 (m, 4H), 2.71-2.58 (m, 2H), 1.88-1.79 (m, 1H), 0.93-0.83 (m, 2H), 0.70-0.59 (m, 2H).

Example 40-(b)

Production of (3S)-3-(3-cyclopropoxyphenyl)-3-(2-(4-((5-fluoro-1,4,5,6-tetrahydropyrimidin-2-yl)amino)-1H-indazole-6-carboxamido)acetamido)propanoic acid

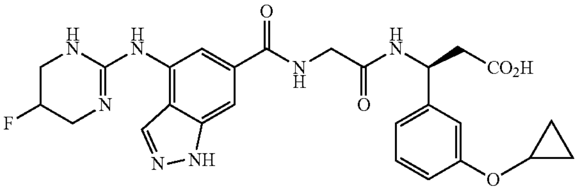 [SMILES: O=C(O)C[C@H](NC(=O)CNC(=O)c1cc(NC2=NCC(F)CN2)c2cn[nH]c2c1)c1cccc(OC2CC2)c1]

To a solution of 155 mg of methyl (3S)-3-(3-cyclopropoxyphenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 40-(a) in acetonitrile (1 ml) and water (1 ml), 25 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 15 hours. A deposited solid was collected by filtration, washed with water, and then dried under reduced pressure at 60 °C to obtain 51 mg of the title compound as a white solid.

Mass spectrum (ESI, m/z): 538 $[M+H]^+$.

$^1$H-NMR spectrum (400 MHz, $CD_3OD$) δ: 8.06 (d, J=0.9 Hz, 1H), 8.02 (dd, J=0.9, 1.1 Hz, 1H), 7.45 (d, J=1.1 Hz, 1H), 7.16 (dd, J=7.7, 7.8 Hz, 1H), 7.06 (dd, J=1.9, 2.1 Hz, 1H), 6.98-6.94 (m, 1H), 6.87 (dd, J=2.1, 7.8 Hz, 1H), 5.27-5.11 (m, 2H), 4.19 (d, J=16.8 Hz, 1H), 4.04 (d, J=16.8 Hz, 1H), 3.73 (tt, J=3.0, 6.0 Hz, 1H), 3.68-3.40 (m, 4H), 2.72-2.60 (m, 2H), 0.79-0.55 (m, 4H).

Example 41-(b)

Production of (3S)-3-(3-chlorophenyl)-3-(2-(4-((5-fluoro-1,4,5,6-tetrahydropyrimidin-2-yl)amino)-1H-indazole-6-carboxamido)acetamido)propanoic acid

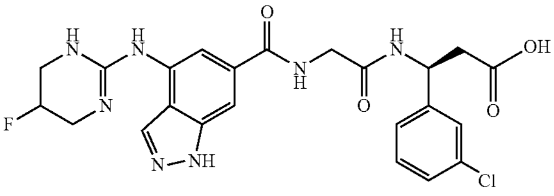 [SMILES: O=C(O)C[C@H](NC(=O)CNC(=O)c1cc(NC2=NCC(F)CN2)c2cn[nH]c2c1)c1cccc(Cl)c1]

To a solution of 99 mg of methyl (3S)-3-(3-chlorophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 41-(a) in acetonitrile (1 ml) and water (1 ml), 19 mg of lithium hydroxide was added at room temperature under a stream of argon, and the mixture was stirred at room temperature for 4 hours.

After the completion of reaction, 1 ml of water was added to the reaction mixture, and the mixture was filtered. The filtrate was adjusted to pH 5.4 by the addition of 1 N hydrochloric acid, and the mixture was stirred at room temperature for 4 hours. A deposited solid was collected by filtration, washed with water, and then dried under reduced pressure at 60 °C to obtain 33 mg of the title compound as a white solid.

Mass spectrum (ESI, m/z): 516 $[M+H]^+$.

$^1$H-NMR spectrum (400 MHz, $CD_3OD$) δ: 8.08 (d, J=1.0 Hz, 1H), 8.07-8.06 (m, 1H), 7.50 (d, J=1.3 Hz, 1H), 7.42-7.39 (m, 1H), 7.32-7.28 (m, 1H), 7.25 (t, J=7.7 Hz, 1H), 7.21-7.17 (m, 1H), 5.29-5.13 (m, 2H), 4.18-4.04 (m, 2H), 3.71-3.44 (m, 4H), 2.71-2.59 (m, 2H).

Example 42-(b)

Production of (3S)-3-(3-bromophenyl)-3-(2-(4-((5-fluoro-1,4,5,6-tetrahydropyrimidin-2-yl)amino)-1H-indazole-6-carboxamido)acetamido)propanoic acid

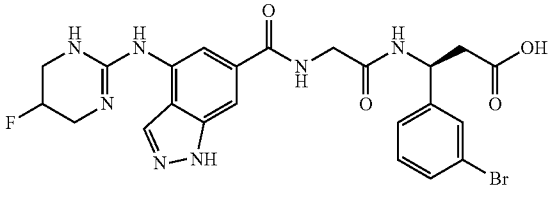 [SMILES: O=C(O)C[C@H](NC(=O)CNC(=O)c1cc(NC2=NCC(F)CN2)c2cn[nH]c2c1)c1cccc(Br)c1]

To a suspension of 122 mg of methyl (3S)-3-(3-bromophenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 42-(a) in acetonitrile (1 ml) and water (1 ml), 22 mg of lithium hydroxide was added at room temperature under a stream of argon, and the mixture was stirred at room temperature for 2 hours.

After the completion of reaction, 1 ml of water was added to the reaction mixture, and the mixture was filtered. The filtrate was adjusted to pH 5.3 by the addition of 1 N hydrochloric acid, and the mixture was stirred at room temperature for 2 hours. A deposited solid was collected by filtration, washed with water, and then dried under reduced pressure at 60 °C to obtain 66 mg of the title compound as a white solid.

Mass spectrum (ESI, m/z): 560, 562 $[M+H]^+$.

$^1$H-NMR spectrum (400 MHz, $CD_3OD$) δ: 8.09-8.06 (m, 2H), 7.56 (t, J=1.7 Hz, 1H), 7.52 (d, J=1.1 Hz, 1H), 7.36-7.32 (m, 2H), 7.22-7.17 (m, 1H), 5.30-5.14 (m, 2H), 4.18-4.04 (m, 2H), 3.71-3.45 (m, 4H), 2.70-2.57 (m, 2H).

Example 43-(b)

Production of (3S)-3-(3-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid

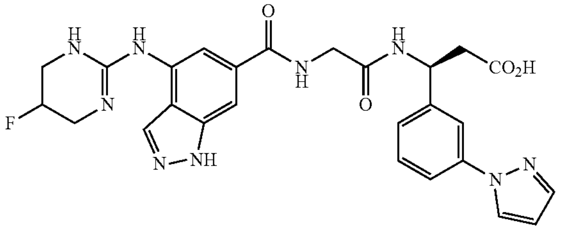 [SMILES: O=C(O)C[C@H](NC(=O)CNC(=O)c1cc(NC2=NCC(F)CN2)c2cn[nH]c2c1)c1cccc(-n2cccn2)c1]

To a solution of 123 mg of methyl (3S)-3-(3-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 43-(a) in acetonitrile (1 ml) and water (1 ml), 25 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. The reaction mixture was purified by BondElut (eluting solvent: water:acetonitrile:methanol) to obtain 49 mg of the title compound as a white solid.

Mass spectrum (ESI, m/z): 548 $[M+H]^+$.

$^1$H-NMR spectrum (400 MHz, $CD_3OD$) δ: 8.30 (dd, J=0.5, 2.5 Hz, 1H), 8.08 (d, J=0.8 Hz, 1H), 8.06 (dd, J=0.8, 1.3 Hz, 1H), 7.74-7.70 (m, 1H), 7.68-7.67 (m, 1H), 7.61-7.55 (m, 1H), 7.52 (d, J=1.3 Hz, 1H), 7.44-7.31 (m, 2H), 6.49 (dd, J=1.9, 2.5 Hz, 1H), 5.33-5.28 (m, 1H), 5.25-5.07 (m, 1H), 4.21-4.06 (m, 2H), 3.66-3.37 (m, 4H), 2.84-2.65 (m, 2H).

Example 44-(b)

Production of (3S)-3-(3-(3,5-dimethyl-1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid

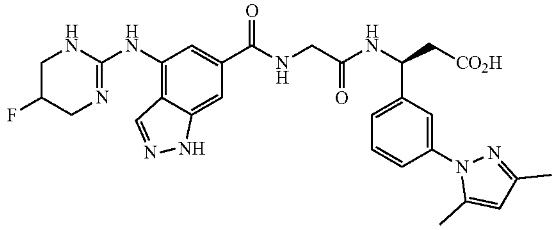 [SMILES: Cc1cc(C)n(-c2cccc([C@H](CC(=O)O)NC(=O)CNC(=O)c3cc(NC4=NCC(F)CN4)c4cn[nH]c4c3)c2)n1]

To a solution of 120 mg of methyl (3S)-3-(3-(3,5-dimethyl-1H-pyrazol-1-yl)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 44-(a) in acetonitrile (1 ml) and water (1 ml), 41 mg of lithium hydroxide was added at room temperature under a stream of argon, and the mixture was stirred at room temperature for 1 hour.

After the completion of reaction, the reaction mixture was adjusted to pH 5.0 by the addition of 1 N hydrochloric acid, and the mixture was stirred at room temperature for 1 hour. The reaction mixture was concentrated under reduced pressure, and acetonitrile was distilled off under reduced pressure. 300 μl of acetonitrile was added to the residue, and the mixture was stirred at room temperature for 1 hour. A deposited solid was collected by filtration, washed with water, and then dried under reduced pressure at 60 °C to obtain 35 mg of the title compound as a white solid.

Mass spectrum (ESI, m/z): 576 $[M+H]^+$.

$^1$H-NMR spectrum (400 MHz, $CD_3OD$) δ: 8.03 (d, J=0.9 Hz, 1H), 8.00-7.98 (m, 1H), 7.47-7.39 (m, 4H), 7.29-7.22 (m, 1H), 6.00 (s, 1H), 5.33-5.28 (m, 1H), 5.26-5.08 (m, 1H), 4.17 (d, J=16.8 Hz, 1H), 4.06 (d, J=16.8 Hz, 1H), 3.66-3.38 (m, 4H), 2.82-2.60 (m, 2H), 2.23 (s, 3H), 2.19 (s, 3H).

Example 45-(b)

Production of (3S)-3-(2-(4-((5-fluoro-1,4,5,6-tetrahydropyrimidin-2-yl)amino)-1H-indazole-6-carboxamido)acetamido)-3-(3-morpholinophenyl)propanoic acid

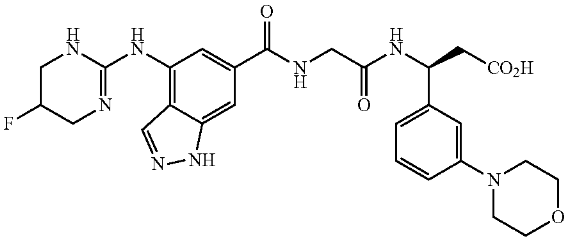 [SMILES: O=C(O)C[C@H](NC(=O)CNC(=O)c1cc(NC2=NCC(F)CN2)c2cn[nH]c2c1)c1cccc(N2CCOCC2)c1]

To a solution of 78 mg of methyl (3S)-3-(2-(4-((5-fluoro-1,4,5,6-tetrahydropyrimidin-2-yl)amino)-1H-indazole-6-carboxamido)acetamido)-3-(3-morpholinophenyl)propanoate trifluoroacetate synthesized in Example 45-(a) in acetonitrile (1 ml) and water (1 ml), 27 mg of lithium hydroxide was added at room temperature under a stream of argon, and the mixture was stirred at room temperature for 30 minutes.

After the completion of reaction, the reaction mixture was adjusted to pH 5.5 by the addition of 1 N hydrochloric acid, and the mixture was stirred at room temperature for 19 hours. The reaction mixture was purified by BondElut (eluting solvent: water:acetonitrile:methanol) to obtain 44 mg of the title compound as a white solid.

Mass spectrum (ESI, m/z): 567 $[M+H]^+$.

$^1$H-NMR spectrum (400 MHz, $CD_3OD$) δ: 8.08 (d, J=0.9 Hz, 1H), 8.03 (dd, J=0.9, 1.1 Hz, 1H), 7.48 (d, J=1.1 Hz, 1H), 7.18-7.12 (m, 1H), 6.99-6.96 (m, 1H), 6.89-6.85 (m, 1H), 6.80-6.76 (m, 1H), 5.28-5.11 (m, 2H), 4.20 (d, J=16.7 Hz, 1H), 4.01 (d, J=16.7 Hz, 1H), 3.80-3.74 (m, 4H), 3.69-3.39 (m, 4H), 3.14-3.06 (m, 4H), 2.79-2.57 (m, 2H).

Example 46-(b)

Production of (3S)-3-(4-(difluoromethoxy)phenyl)-3-(2-(4-((5-fluoro-1,4,5,6-tetrahydropyrimidin-2-yl)amino)-1H-indazole-6-carboxamido)acetamido)propanoic acid

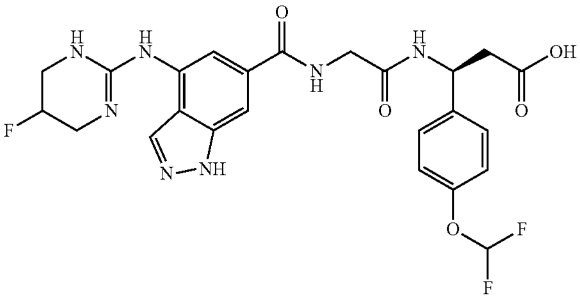 [SMILES: O=C(O)C[C@H](NC(=O)CNC(=O)c1cc(NC2=NCC(F)CN2)c2cn[nH]c2c1)c1ccc(OC(F)F)cc1]

To a solution of 126 mg of methyl (3S)-3-(4-(difluoromethoxy)phenyl)-3-(2-(4-((5-fluoro-1,4,5,6-tetrahydropyrimidin-2-yl)amino)-1H-indazole-6-carboxamido)acetamido)propanoate trifluoroacetate synthesized in Example 46-(a) in acetonitrile (1 ml) and water (1 ml), 23 mg of lithium hydroxide was added at room temperature under a stream of argon, and the mixture was stirred at room temperature for 1 hour.

After the completion of reaction, 1 ml of water was added to the reaction mixture, and the mixture was filtered. The filtrate was adjusted to pH 5.5 by the addition of 1 N hydrochloric acid, and the mixture was stirred at room temperature for 17 hours. A deposited solid was collected by filtration, washed with water, and then dried under reduced pressure at 60 °C to obtain 69 mg of the title compound as a white solid.

Mass spectrum (ESI, m/z): 548 $[M+H]^+$.

$^1$H-NMR spectrum (400 MHz, $CD_3OD$) δ: 8.09 (d, J=1.0 Hz, 1H), 8.06-8.04 (m, 1H), 7.50 (d, J=1.3 Hz, 1H), 7.42-7.38 (m, 2H), 7.06-7.02 (m, 2H), 6.73 (t, J=74.3 Hz, 1H), 5.28-5.13 (m, 2H), 4.19-4.01 (m, 2H), 3.70-3.42 (m, 4H), 2.71-2.59 (m, 2H).

Example 47-(b)

Production of (3S)-3-(2-(4-((5-fluoro-1,4,5,6-tetrahydropyrimidin-2-yl)amino)-1H-indazole-6-carboxamido)acetamido)-3-(4-(trifluoromethyl)phenyl)propanoic acid

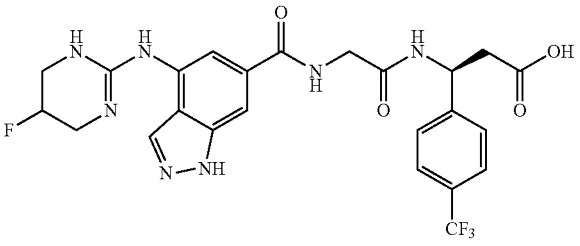 [SMILES: O=C(O)C[C@H](NC(=O)CNC(=O)c1cc(NC2=NCC(F)CN2)c2cn[nH]c2c1)c1ccc(C(F)(F)F)cc1]

To a solution of 125 mg of methyl (3S)-3-(2-(4-((5-fluoro-1,4,5,6-tetrahydropyrimidin-2-yl)amino)-1H-indazole-6-carboxamido)acetamido)-3-(4-(trifluoromethyl)phenyl)propanoate trifluoroacetate synthesized in Example 47-(a) in acetonitrile (1 ml) and water (1 ml), 23 mg of lithium hydroxide was added at room temperature under a stream of argon, and the mixture was stirred at room temperature for 2.5 hours.

After the completion of reaction, 1 ml of water was added to the reaction mixture, and the mixture was filtered. The filtrate was adjusted to pH 5.4 by the addition of 1 N hydrochloric acid, and the mixture was stirred at room temperature for 4 hours. A deposited solid was collected by filtration, washed with water, and then dried under reduced pressure at 60 °C to obtain 70 mg of the title compound as a white solid.

Mass spectrum (ESI, m/z): 550 $[M+H]^+$.

$^1$H-NMR spectrum (400 MHz, $CD_3OD$) δ: 8.09 (d, J=1.0 Hz, 1H), 8.07-8.05 (m, 1H), 7.56 (s, 4H), 7.52 (d, J=1.1 Hz, 1H), 5.30-5.13 (m, 2H), 4.17 (d, J=16.8 Hz, 1H), 4.07 (d, J=16.8 Hz, 1H), 3.71-3.43 (m, 4H), 2.74-2.62 (m, 2H).

Example 48-(b)

Production of (3S)-3-(3-chloro-5-(trifluoromethyl)phenyl)-3-(2-(3-fluoro-4-((5-fluoro-1,4,5,6-tetrahydropyrimidin-2-yl)amino)-1H-indazole-6-carboxamido)acetamido)propanoic acid

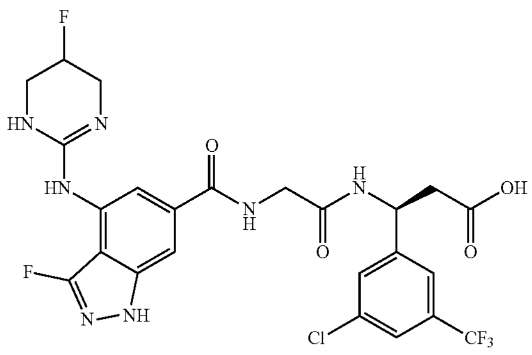 [SMILES: O=C(O)C[C@H](NC(=O)CNC(=O)c1cc(NC2=NCC(F)CN2)c2c(F)n[nH]c2c1)c1cc(Cl)cc(C(F)(F)F)c1]

To a solution of 65 mg of methyl (3S)-3-(3-chloro-5-(trifluoromethyl)phenyl)-3-(2-(3-fluoro-4-((5-fluoro-1,4,5, 6-tetrahydropyrimidin-2-yl)amino)-1H-indazole-6-carboxamido)acetamido)propanoate trifluoroacetate synthesized in Example 48-(a) in acetonitrile (0.8 ml) and water (0.8 ml), 10 mg of lithium hydroxide was added at room temperature under a stream of argon, and the mixture was stirred at room temperature for 30 minutes. Subsequently, 10 mg of lithium hydroxide was further added thereto at room temperature, and the mixture was stirred at room temperature for 30 minutes.

After the completion of reaction, the reaction mixture was adjusted to pH 5.6 by the addition of 1 N hydrochloric acid. 1.6 ml of water was added thereto, and the mixture was stirred at room temperature for 16 hours. A deposited solid was collected by filtration, washed with water, and then dried under reduced pressure at 60 °C to obtain 38 mg of the title compound as a white solid.

Mass spectrum (ESI, m/z): 602 $[M+H]^+$.

$^1$H-NMR spectrum (400 MHz, $CD_3OD$) δ: 8.01-7.94 (m, 1H), 7.70-7.61 (m, 2H), 7.55-7.49 (m, 1H), 7.46-7.41 (m, 1H), 5.31-5.08 (m, 2H), 4.18-4.03 (m, 2H), 3.70-3.41 (m, 4H), 2.79-2.56 (m, 2H).

Example 49-(b)

Production of (3S)-3-(2-(3-chloro-4-((5-fluoro-1,4,5,6-tetrahydropyrimidin-2-yl)amino)-1H-indazole-6-carboxamido)acetamido)-3-(3-chloro-5-(trifluoromethyl)phenyl)propanoic acid

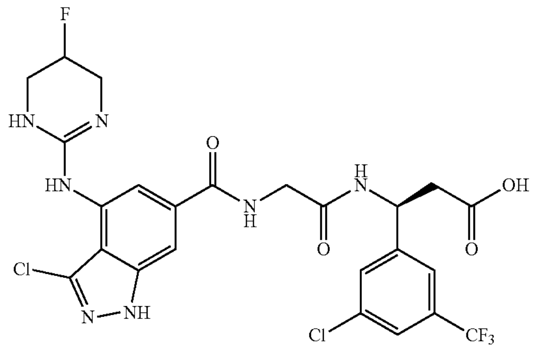 [SMILES: O=C(O)C[C@H](NC(=O)CNC(=O)c1cc(NC2=NCC(F)CN2)c2c(Cl)n[nH]c2c1)c1cc(Cl)cc(C(F)(F)F)c1]

To a solution of 54 mg of methyl (3S)-3-(2-(3-chloro-4-((5-fluoro-1,4,5,6-tetrahydropyrimidin-2-yl)amino)-1H-indazole-6-carboxamido)acetamido)-3-(3-chloro-5-(trifluoromethyl)phenyl)propanoate trifluoroacetate synthesized in Example 49-(a) in acetonitrile (0.5 ml) and water (0.5 ml), 10 mg of lithium hydroxide was added at room temperature under a stream of argon, and the mixture was stirred at room temperature for 1 hour.

After the completion of reaction, 1 ml of water was added to the reaction mixture. The reaction mixture was adjusted to pH 5.6 by the addition of 1 N hydrochloric acid, and the mixture was stirred at room temperature for 22 hours. A deposited solid was collected by filtration, washed with water, and then dried under reduced pressure at 60 °C to obtain 36 mg of the title compound as a white solid.

Mass spectrum (ESI, m/z): 618 $[M+H]^+$.

$^1$H-NMR spectrum (400 MHz, $CD_3OD$) δ: 8.14 (d, J=1.3 Hz, 1H), 7.69-7.67 (m, 1H), 7.65-7.62 (m, 1H), 7.56 (d, J=1.1 Hz, 1H), 7.54-7.51 (m, 1H), 5.27-5.10 (m, 2H), 4.17-4.04 (m, 2H), 3.68-3.44 (m, 4H), 2.73-2.59 (m, 2H).

Example 50-(b)

Production of (3S)-3-(3-chloro-5-(trifluoromethyl)phenyl)-3-(2-(4-((5-hydroxy-1,4,5,6-tetrahydropyrimidin-2-yl)amino)-1H-indazole-6-carboxamido)acetamido)propanoic acid

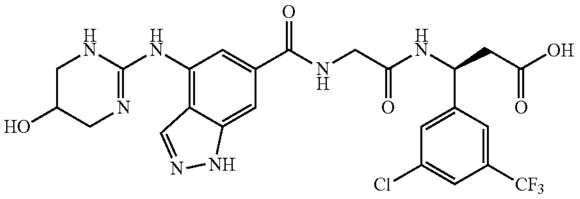 [SMILES: O=C(O)C[C@H](NC(=O)CNC(=O)c1cc(NC2=NCC(O)CN2)c2cn[nH]c2c1)c1cc(Cl)cc(C(F)(F)F)c1]

To a solution of 115 mg of methyl (3S)-3-(3-chloro-5-(trifluoromethyl)phenyl)-3-(2-(4-((5-hydroxy-1,4,5,6-tetrahydropyrimidin-2-yl)amino)-1H-indazole-6-carboxamido)acetamido)propanoate trifluoroacetate synthesized in Example 50-(a) in acetonitrile (1 ml) and water (1 ml), 20 mg of lithium hydroxide was added at room temperature under a stream of argon, and the mixture was stirred at room temperature for 1.5 hours.

After the completion of reaction, the reaction mixture was filtered. The filtrate was adjusted to pH 5.6 by the addition of 1 N hydrochloric acid, and the mixture was stirred at room temperature for 4 hours. A deposited solid was collected by filtration, washed with water, and then dried under reduced pressure at 60 °C to obtain 72 mg of the title compound as a white solid.

Mass spectrum (ESI, m/z): 582 $[M+H]^+$.

$^1$H-NMR spectrum (400 MHz, $CD_3OD$) δ: 8.16 (d, J=1.0 Hz, 1H), 8.06-8.04 (m, 1H), 7.70-7.67 (m, 1H), 7.66-7.63 (m, 1H), 7.53-7.51 (m, 1H), 7.50 (d, J=1.1 Hz, 1H), 5.26 (t, J=5.3 Hz, 1H), 4.24 (quin, J=3.1 Hz, 1H), 4.18-4.05 (m, 2H), 3.49-3.38 (m, 2H), 3.36-3.29 (m, 2H), 2.74-2.60 (m, 2H).

Example 51-(b)

Production of (S)-3-(3-chloro-5-(trifluoromethyl)phenyl)-3-(2-(4-((1,4,5,6-tetrahydropyrimidin-2-yl)amino)-1H-indazole-6-carboxamido)acetamido)propanoic acid

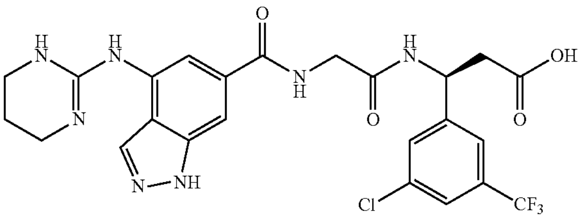 [SMILES: O=C(O)C[C@H](NC(=O)CNC(=O)c1cc(NC2=NCCCN2)c2cn[nH]c2c1)c1cc(Cl)cc(C(F)(F)F)c1]

To a suspension of 117 mg of methyl (S)-3-(3-chloro-5-(trifluoromethyl)phenyl)-3-(2-(4-((1,4,5,6-tetrahydropyrimidin-2-yl)amino)-1H-indazole-6-carboxamido)acetamido)propanoate trifluoroacetate synthesized in Example 51-(a) in acetonitrile (1 ml) and water (1 ml), 21 mg of lithium hydroxide was added at room temperature under a stream of argon, and the mixture was stirred at room temperature for 1 hour.

After the completion of reaction, the reaction mixture was filtered. The filtrate was adjusted to pH 5.6 by the addition of 1 N hydrochloric acid, and the mixture was stirred at room temperature for 2 hours. A deposited solid was collected by filtration, washed with water, and then dried under reduced pressure at 60 °C to obtain 47 mg of the title compound as a white solid.

Mass spectrum (ESI, m/z): 566 $[M+H]^+$.

$^1$H-NMR spectrum (400 MHz, $CD_3OD$) δ: 8.12 (d, J=1.0 Hz, 1H), 8.04-8.02 (m, 1H), 7.71-7.68 (m, 1H), 7.67-7.64 (m, 1H), 7.54-7.51 (m, 1H), 7.49 (d, J=1.1 Hz, 1H), 5.26 (t, J=5.2 Hz, 1H), 4.16 (d, J=16.8 Hz, 1H), 4.06 (d, J=16.8 Hz, 1H), 3.40-3.26 (m, 4H), 2.75-2.59 (m, 2H), 2.00-1.90 (m, 2H).

Example 52-(b)

Production of (3S)-3-(3-chloro-5-(trifluoromethyl) phenyl)-3-(2-(6-((5-fluoro-1,4,5,6-tetrahydropyrimidin-2-yl)amino)-1H-indazole-4-carboxamido)acetamido)propanoic acid

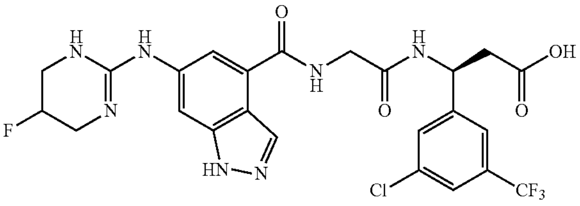

To a suspension of 152 mg of methyl (3S)-3-(3-chloro-5-(trifluoromethyl)phenyl)-3-(2-(6-((5-fluoro-1,4,5,6-tetrahydropyrimidin-2-yl)amino)-1H-indazole-4-carboxamido) acetamido)propanoate trifluoroacetate synthesized in Example 52-(a) in acetonitrile (2 ml) and water (2 ml), 26 mg of lithium hydroxide was added at room temperature under a stream of argon, and the mixture was stirred at room temperature for 2 hours.

After the completion of reaction, the reaction mixture was filtered. The filtrate was adjusted to pH 5.8 by the addition of 1 N hydrochloric acid, and the mixture was stirred at room temperature for 4 hours. A deposited solid was collected by filtration, washed with water, and then dried under reduced pressure at 60 °C to obtain 86 mg of the title compound as a white solid.

Mass spectrum (ESI, m/z): 584 $[M+H]^+$.

$^1$H-NMR spectrum (400 MHz, $CD_3OD$) δ: 8.48-8.45 (m, 1H), 7.71-7.68 (m, 1H), 7.66-7.64 (m, 1H), 7.62 (d, J=1.6 Hz, 1H), 7.61-7.58 (m, 1H), 7.54-7.51 (m, 1H), 5.29-5.12 (m, 2H), 4.19-4.10 (m, 2H), 3.72-3.46 (m, 4H), 2.72-2.59 (m, 2H).

Example 53-(b)

Production of (3S)-3-(3-bromo-5-(trifluoromethyl) phenyl)-3-(2-(6-((5-fluoro-1,4,5,6-tetrahydropyrimidin-2-yl)amino)-1H-indazole-4-carboxamido)acetamido)propanoic acid

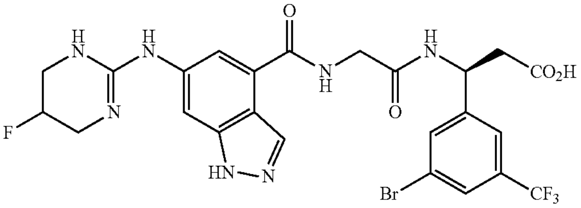 [SMILES: O=C(O)C[C@H](NC(=O)CNC(=O)c1cc(NC2=NCC(F)CN2)cc2[nH]ncc12)c1cc(Br)cc(C(F)(F)F)c1]

To a solution of 192 mg of methyl (3S)-3-(3-bromo-5-(trifluoromethyl)phenyl)-3-(2-(6-((5-fluoro-1,4,5,6-tetrahydropyrimidin-2-yl)amino)-1H-indazole-4-carboxamido)acetamido)propanoate trifluoroacetate synthesized in Example 53-(a) in acetonitrile (3 ml) and water (3 ml), 30 mg of lithium hydroxide was added at room temperature under a stream of argon, and the mixture was stirred at room temperature for 30 minutes.

After the completion of reaction, the reaction mixture was adjusted to pH 5.8 by the addition of 1 N hydrochloric acid, and the mixture was stirred at room temperature for 2 hours. A deposited solid was collected by filtration, washed with water, and then dried under reduced pressure at 60 °C to obtain 84 mg of the title compound as a white solid.

Mass spectrum (ESI, m/z): 628, 630 $[M+H]^+$.

$^1$H-NMR spectrum (400 MHz, DMSO-$d_6$+$D_2O$) δ: 8.35-8.31 (m, 1H), 7.86-7.83 (m, 1H), 7.79-7.67 (m, 2H), 7.54-7.49 (m, 1H), 7.44-7.40 (m, 1H), 5.32-5.06 (m, 2H), 4.07-3.89 (m, 2H), 3.60-3.29 (m, 4H), 2.62-2.40 (m, 2H).

Example 54-(b)

Production of (3S)-3-(2-(6-((5-fluoro-1,4,5,6-tetrahydropyrimidin-2-yl)amino)-1H-indazole-4-carboxamido)acetamido)-3-(3-iodo-5-(trifluoromethyl)phenyl)propanoic acid

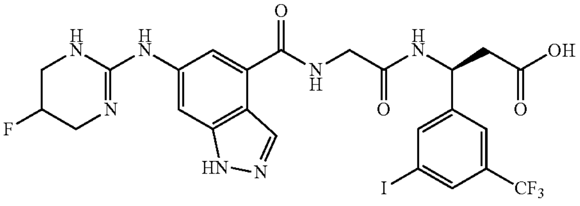 [SMILES: O=C(O)C[C@H](NC(=O)CNC(=O)c1cc(NC2=NCC(F)CN2)cc2[nH]ncc12)c1cc(I)cc(C(F)(F)F)c1]

To a solution of 85 mg of methyl (3S)-3-(2-(6-((5-fluoro-1,4,5,6-tetrahydropyrimidin-2-yl)amino)-1H-indazole-4-carboxamido)acetamido)-3-(3-iodo-5-(trifluoromethyl)phenyl)propanoate trifluoroacetate synthesized in Example 54-(a) in acetonitrile (1 ml) and water (1 ml), 13 mg of lithium hydroxide was added at room temperature under a stream of argon, and the mixture was stirred at room temperature for 1 hour.

After the completion of reaction, the reaction mixture was adjusted to pH 5.4 by the addition of 1 N hydrochloric acid, and the mixture was filtered. The filtrate was concentrated under reduced pressure, and acetonitrile was distilled off under reduced pressure. The residue was stirred at room temperature for 5 hours. A deposited solid was collected by filtration, washed with water, and then dried under reduced pressure at 60 °C to obtain 38 mg of the title compound as a white solid.

Mass spectrum (ESI, m/z): 676 $[M+H]^+$.

$^1$H-NMR spectrum (400 MHz, $CD_3OD$) δ: 8.48-8.47 (m, 1H), 8.03-8.01 (m, 1H), 7.84-7.82 (m, 1H), 7.72-7.69 (m, 1H), 7.62 (d, J=1.6 Hz, 1H), 7.60-7.58 (m, 1H), 5.27-5.12 (m, 2H), 4.20-4.08 (m, 2H), 3.72-3.46 (m, 4H), 2.71-2.57 (m, 2H).

Example 55-(b)

Production of (3S)-3-(2-(6-((5-fluoro-1,4,5,6-tetrahydropyrimidin-2-yl)amino)-1H-indazole-4-carboxamido)acetamido)-3-(4-fluoro-3-(trifluoromethyl)phenyl)propanoic acid

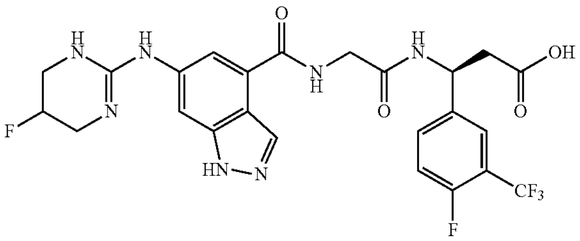 [SMILES: O=C(O)C[C@H](NC(=O)CNC(=O)c1cc(NC2=NCC(F)CN2)cc2[nH]ncc12)c1ccc(F)c(C(F)(F)F)c1]

To a suspension of 142 mg of methyl (3S)-3-(2-(6-((5-fluoro-1,4,5,6-tetrahydropyrimidin-2-yl)amino)-1H-indazole-4-carboxamido)acetamido)-3-(4-fluoro-3-(trifluoromethyl)phenyl)propanoate trifluoroacetate synthesized in Example 55-(a) in acetonitrile (1.5 ml) and water (1.5 ml), 25 mg of lithium hydroxide was added at room temperature under a stream of argon, and the mixture was stirred at room temperature for 1.5 hours.

After the completion of reaction, the reaction mixture was filtered. The filtrate was adjusted to pH 5.5 by the addition of 1 N hydrochloric acid, and the mixture was stirred at room temperature for 2 hours. A deposited solid was collected by filtration, washed with water, and then dried under reduced pressure at 60 °C to obtain 77 mg of the title compound as a white solid.

Mass spectrum (ESI, m/z): 568 $[M+H]^+$.

$^1$H-NMR spectrum (400 MHz, $CD_3OD$) δ: 8.45-8.43 (m, 1H), 7.73-7.64 (m, 2H), 7.62-7.59 (m, 2H), 7.27-7.20 (m, 1H), 5.28-5.13 (m, 2H), 4.20-4.08 (m, 2H), 3.72-3.46 (m, 4H), 2.71-2.57 (m, 2H).

Example 56-(b)

Production of (3S)-3-(2-(6-((5-fluoro-1,4,5,6-tetrahydropyrimidin-2-yl)amino)-1H-indazole-4-carboxamido)acetamido)-3-(3-(trifluoromethyl)phenyl)propanoic acid

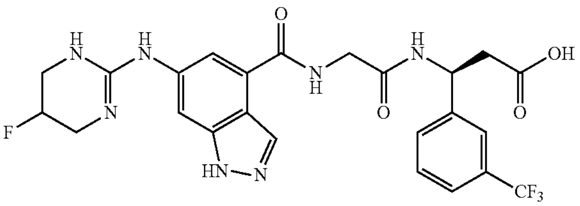

To a suspension of 161 mg of methyl (3S)-3-(2-(6-((5-fluoro-1,4,5,6-tetrahydropyrimidin-2-yl)amino)-1H-indazole-4-carboxamido)acetamido)-3-(3-(trifluoromethyl)phenyl)propanoate trifluoroacetate synthesized in Example 56-(a) in acetonitrile (1.5 ml) and water (1.5 ml), 28 mg of lithium hydroxide was added at room temperature under a stream of argon, and the mixture was stirred at room temperature for 1 hour.

After the completion of reaction, the reaction mixture was filtered. The filtrate was adjusted to pH 5.8 by the addition of 1 N hydrochloric acid, and the mixture was stirred at room temperature for 3 hours. A deposited solid was collected by filtration, washed with water, and then dried under reduced pressure at 60 °C to obtain 96 mg of the title compound as a white solid.

Mass spectrum (ESI, m/z): 550 $[M+H]^+$.

$^1$H-NMR spectrum (400 MHz, $CD_3OD$) δ: 8.45-8.43 (m, 1H), 7.72-7.68 (m, 1H), 7.67-7.63 (m, 1H), 7.62 (d, J=1.6 Hz, 1H), 7.60-7.58 (m, 1H), 7.50-7.46 (m, 2H), 5.32-5.27 (m, 1H), 5.27-5.11 (m, 1H), 4.21-4.09 (m, 2H), 3.71-3.46 (m, 4H), 2.73-2.60 (m, 2H).

(Test Example 1) αvβ1 Cell Adhesion Inhibition Test

Test Example 1 was performed by partially modifying the method of Reed et al. (Sci Transl Med., 7 (288), 288ra79, 2015).

Human fibronectin (manufactured by Sigma-Aldrich Co. LLC, F0895) was prepared at 1.25 μg/mL with phosphate buffered saline (PBS), dispensed at 100 μL/well to a 96-well plate, and left standing overnight. The plate was washed with Hanks' balanced salt solution (HBSS), then subjected to blocking treatment with Dulbecco's modified Eagle medium (DMEM) containing 1% bovine serum-derived albumin (BSA) (FUJIFILM Wako Pure Chemical Corp., for cell culture, 017-22231), and used as a coated plate in the adhesion test.

αv-transfected cells (CHO cells deficient in α5 gene and transfected with αv gene) cultured in Ham's F-12 medium (FUJIFILM Wako Pure Chemical Corp., 087-08335) containing 10% fetal bovine serum (FBS), 1% penicillin/streptomycin/amphotericin B (manufactured by Thermo Fisher Scientific, Inc., 15240), 1 mM GlutaMAX Supplement (manufactured by Thermo Fisher Scientific, Inc., 35050), and 400 μg/mL hygromycin B (FUJIFILM Wako Pure Chemical Corp., 080-07683) were recovered and suspended in DMEM containing 1 mM $MnCl_2$ (manufactured by Sigma-Aldrich Co. LLC, M1787) to prepare a cell suspension. A test compound dissolved in DMSO was added thereto.

The cell suspension of $1\times10^6$ cells/mL containing the test compound was added at 100 μL/well to the coated plate and left standing for 1 hour in a 5% $CO_2$ incubator (37 °C.). One hour later, the supernatant was removed, and the plate was washed with HBSS. The cells that adhered to each well in the plate were stained with crystal violet, and the cells were lysed, followed by absorbance measurement. Inhibition without substrate coating was defined as 100% inhibition, and inhibition when DMSO was added instead of the test compound was defined as 0% inhibition. The rate of inhibition of cell adhesion by the test compound was calculated according to the following expression.

Rate of inhibition of cell adhesion(%)=[1−{(Absorbance in the case of adding the test compound)−(Absorbance without substrate coating)}/{(Absorbance in the case of adding DMSO)−(Absorbance without substrate coating)}]×100

An $IC_{50}$ value was calculated from the rate of inhibition of cell adhesion by the test compound. The results about each test compound in this test are shown in Table 18 below. A: $IC_{50}$<3 nM, B: 3 nM≤$IC_{50}$<10 nM, C: 10 nM≤$IC_{50}$<30 nM, D: 30 nM≤$IC_{50}$<100 nM, or E: $IC_{50}$≥100 nM.

TABLE 18

Results of αvβ1 cell adhesion inhibition test about compound of Example

| Example No. | $IC_{50}$ |
|---|---|
| 1-(b) | A |
| 2-(b) | B |
| 3-(b) | B |
| 4-(b) | B |
| 5-(b) | A |
| 6-(b) | A |
| 7-(b) | A |
| 8-(b) | A |
| 9-(b) | B |
| 10-(b) | E |
| 11-(b) | B |
| 12-(b) | B |
| 13-(b) | A |
| 14-(b) | A |
| 15-(b) | A |
| 16-(b) | A |
| 17-(b) | A |
| 18-(b) | A |
| 19-(b) | A |
| 20-(b) | A |
| 21-(b) | A |
| 22-(b) | C |
| 23-(b) | A |
| 24-(b) | A |
| 25-(b) | A |
| 26-(b) | A |
| 27-(b) | A |
| 28-(b) | A |
| 29-(b) | A |
| 30-(b) | A |
| 31-(b) | B |
| 32-(b) | A |
| 33-(b) | A |
| 34-(b) | A |
| 35-(b) | B |
| 36-(b) | B |
| 37-(b) | B |
| 38-(b) | A |
| 39-(b) | A |
| 40-(b) | A |
| 41-(b) | B |

TABLE 18-continued

Results of αvβ1 cell adhesion inhibition test about compound of Example

| Example No. | $IC_{50}$ |
|---|---|
| 42-(b) | B |
| 43-(b) | B |
| 44-(b) | A |
| 45-(b) | A |
| 46-(b) | B |
| 47-(b) | B |
| 48-(b) | B |
| 49-(b) | A |
| 50-(b) | C |
| 51-(b) | D |
| 52-(b) | A |
| 53-(b) | A |
| 54-(b) | A |
| 55-(b) | A |
| 56-(b) | B |

(Test Example 2) αvβ6 Cell Adhesion Inhibition Test

Test Example 2 was performed by partially modifying the method of Henderson et al. (Nat Med., 19 (12), 1617-24, 2013). In Test Example 2, the same reagents as in Test Example 1 were used unless otherwise specified.

Recombinant human LAP protein (manufactured by R&D Systems, Inc., 246-LP-025) was prepared at 0.2 Jig/mL with PBS, dispensed at 100 μL/well to a 96-well plate, and left standing overnight. The plate was washed with HBSS, then subjected to blocking treatment with DMEM containing 1% BSA, and used as a coated plate in the adhesion test.

HT-29 cells cultured in McCoy's 5A medium (manufactured by Thermo Fisher Scientific, Inc., 16600) containing 10% FBS and 1% penicillin/streptomycin/amphotericin B were recovered and suspended in DMEM containing 0.1% BSA and 200 μM $MnCl_2$ to prepare a cell suspension. A test compound was added thereto.

The cell suspension of $5\times10^5$ cells/mL containing the test compound was added at 100 μL/well to the coated plate and left standing for 1 hour in a 5% $CO_2$ incubator (37 °C.). One hour later, the supernatant was removed, and the plate was washed with HBSS containing 200 μM $MnCl_2$. The cells that adhered to each well in the plate were stained with crystal violet, and the cells were lysed, followed by absorbance measurement. Inhibition without substrate coating was defined as 100% inhibition, and inhibition when DMSO was added instead of the test compound was defined as 0% inhibition. The rate of inhibition of cell adhesion by the test compound was calculated according to the following expression.

Rate of inhibition of cell adhesion(%)=[1−{(Absorbance in the case of adding the test compound)−(Absorbance without substrate coating)}/{(Absorbance in the case of adding DMS)−(Absorbance without substrate coating)}]×100

An $IC_{50}$ value was calculated from the rate of inhibition of cell adhesion by the test compound. The results about each test compound in this test are shown in Table 19 below. A: $IC_{50}$<3 nM, B: 3 nM≤$IC_{50}$<10 nM, C: 10 nM≤$IC_{50}$<30 nM, D: 30 nM≤$IC_{50}$<100 nM, or E: $IC_{50}$≥100 nM.

TABLE 19

Results of αvβ6 cell adhesion inhibition test about compound of Example

| Example No. | $IC_{50}$ |
|---|---|
| 1-(b) | A |
| 2-(b) | A |
| 3-(b) | A |
| 4-(b) | A |
| 5-(b) | A |
| 6-(b) | B |
| 7-(b) | A |
| 8-(b) | A |
| 9-(b) | A |
| 10-(b) | E |
| 11-(b) | A |
| 12-(b) | B |
| 13-(b) | A |
| 14-(b) | A |
| 15-(b) | A |
| 16-b) | A |
| 17-(b) | B |
| 18-(b) | A |
| 19-(b) | A |
| 20-(b) | A |
| 21-(b) | A |
| 22-(b) | B |
| 23-(b) | B |
| 24-(b) | A |
| 25-(b) | A |
| 26-(b) | A |
| 27-(b) | B |
| 28-(b) | A |
| 29-(b) | A |
| 30-(b) | A |
| 31-(b) | A |
| 32-(b) | A |
| 33-(b) | A |
| 34-(b) | A |
| 35-(b) | A |
| 36-(b) | A |
| 37-(b) | A |
| 38-(b) | A |
| 39-(b) | A |
| 40-(b) | A |
| 41-(b) | A |
| 42-(b) | A |
| 43-(b) | A |
| 44-(b) | A |
| 45-(b) | B |
| 46-(b) | B |
| 47-(b) | B |
| 48-(b) | A |
| 49-(b) | A |
| 50-(b) | C |
| 51-(b) | C |
| 52-(b) | A |
| 53-(b) | A |
| 54-(b) | A |
| 55-(b) | A |
| 56-(b) | B |

(Test Example 3) TGF-β Activation Inhibition Test

In Test Example 3, the inhibition of TGF-β activation by a compound was detected with the inhibition of SMAD3 phosphorylation as an index. In Test Example 3, the same reagents as in Test Example 1 were used unless otherwise specified.

Human fibronectin was prepared at 14 μg/mL with PBS and then dispensed at 50 μL/well to a 96-well plate. The plate was left standing at room temperature for 1 hour or longer, followed by the removal of the fibronectin solution. The plate was washed with PBS and used as a coated plate.

A test compound dissolved in DMSO was added to RPMI medium 1640 (manufactured by Thermo Fisher Scientific, Inc., 11875) containing 1% FBS and 1% penicillin/streptomycin/amphotericin B to prepare a medium containing the test compound having a concentration of two times the final concentration. This medium was added at 100 μL/well to the coated plate. TFK-1 cells (Cell Resource Center for Biomedical Research, Institute of Development, Aging and Cancer, Tohoku University) cultured in RPMI medium 1640 containing 10% FBS and 1% penicillin/streptomycin/amphotericin B were suspended in RPMI medium 1640 containing 1% FBS and 1% penicillin/streptomycin/amphotericin B to prepare a cell suspension of $1\times10^6$ cells/mL. The prepared cell suspension was further added at 100 μL/well and cultured for 2 days in a 5% $CO_2$ incubator (37 °C.).

Phosphorylated SMAD3 in the cells thus cultured for 2 days was measured using Phospho-SMAD3 (Ser423/425) cellular kit (manufactured by cisbio, 63ADK025), and a DeltaF value was calculated according to the calculation expression of the kit. Inhibition when 10 μM LY364947 (FUJIFILM Wako Pure Chemical Corp., 123-05981) was added instead of the test compound was defined as 100% inhibition, and inhibition when DMSO was added instead was defined as 0% inhibition. The rate of inhibition of phosphorylated SMAD3 by the test compound was calculated according to the following expression.

$$\text{Rate of inhibition of phosphorylated SMAD3(\%)} = [1-\{(\text{Delta}F \text{ value in the case of adding the test compound})-(\text{Delta}F \text{ value in the case of adding } 10\ \mu\text{M } LY364947)\}/\{(\text{Delta}F \text{ value in the case of adding DMSO})-(\text{Delta}F \text{ value in the case of adding } 10\ \mu\text{M } LY364947)\}]\times100$$

An $IC_{50}$ value was calculated from the rate of inhibition of phosphorylated SMAD3 by the test compound. The results about each test compound in this test are shown in Table 20 below. A: $IC_{50}$<10 nM, B: 10 nM≤$IC_{50}$<50 nM, C: 50 nM≤$IC_{50}$<100 nM, or D: $IC_{50}$≥100 nM.

TABLE 20

Results of TGF-β activation inhibition test about compound of Example

| Example No. | $IC_{50}$ |
|---|---|
| 1-(b) | A |
| 2-(6) | A |
| 3-(b) | A |
| 4-(b) | A |
| 5-(b) | B |
| 6-(b) | B |
| 7-(b) | A |
| 8-(b) | A |
| 9-(b) | C |
| 10-(b) | D |
| 11-(b) | A |
| 12-(b) | D |
| 13-(b) | B |
| 14-(b) | A |
| 15-(b) | A |
| 16-(b) | B |
| 17-(b) | A |
| 18-(b) | B |
| 19-(b) | A |
| 20-(b) | A |
| 21-(b) | A |
| 22-(b) | B |
| 23-(b) | B |
| 24-(b) | A |
| 25-(b) | A |
| 26-(b) | A |
| 27-(b) | A |

TABLE 20-continued

| Results of TGF-β activation inhibition test about compound of Example | |
|---|---|
| Example No. | $IC_{50}$ |
| 28-(b) | B |
| 29-(b) | A |
| 30-(b) | A |
| 31-(b) | A |
| 32-(b) | A |
| 33-(b) | A |
| 34-(b) | A |
| 35-(b) | B |
| 36-(b) | B |
| 37-(b) | A |
| 38-(b) | C |
| 39-(b) | A |
| 40-(b) | B |
| 41-(b) | A |
| 42-(b) | B |
| 43-(b) | A |
| 44-(b) | A |
| 45-(b) | B |
| 46-(b) | C |
| 47-(b) | B |
| 48-(b) | A |
| 49-(b) | A |
| 50-(b) | D |
| 51-(b) | C |
| 52-(b) | A |
| 53-(b) | A |
| 54-(b) | A |
| 55-(b) | A |
| 56-(b) | A |

(Test Example 4) Active Human Hepatic Stellate Cell Dedifferentiation Test

Human hepatic stellate cells (manufactured by ScienCell Research Laboratories, Inc., 5300) were suspended in DMEM containing 10% FBS and 1-0 penicillin/streptomycin/amphotericin B to prepare a cell suspension of $0.5\times10^5$ cells/mL, which was regarded as cells at the start of differentiation. The cells at the start of differentiation were dispensed at 1 mL/well to a 12-well plate and cultured, for differentiation, for 3 days in a 5% $CO_2$ incubator (37 °C.).

The culture solution in each well was removed, and DMEM containing 10% FBS and 1% penicillin/streptomycin/amphotericin B supplemented with a test compound dissolved in DMSO (final DMSO concentration: 0.1%) was added at 1 mL/well. The resultant was further cultured for 2 days in a 5% $CO_2$ incubator (37 °C.). In Test Example 4, the same reagents as in Test Example 1 were used unless otherwise specified.

RNA in the cultured cells was extracted using NucleoSpin® RNA (manufactured by Takara Bio Inc., U0955C), and cDNA was further synthesized from the extracted RNA using Prime Script™ RT reagent Kit with gDNA Eraser (manufactured by Takara Bio Inc., RR047A). Real time PCR was performed using the synthesized cDNA, various primers and TB Green® Premix Ex Taq™ II (manufactured by Takara Bio Inc., RR820A) and using PCR Thermal Cycler Dice Real Time (manufactured by Takara Bio Inc., System Code TP910, Model Code TP900). The primers used were actin alpha 2, smooth muscle (ACTA2) primer (manufactured by Takara Bio Inc., HA136273) and glyceraldehyde-3-phosphate dehydrogenase (GAPDH) primer (manufactured by Takara Bio Inc., HA067812).

The amplification curve of PCR was analyzed by the comparative Ct method. The expression level of ACTA2 mRNA was corrected with the expression level of GAPDH mRNA. An ACTA2 mRNA expression level when DMSO was added instead of the test compound was defined as 100%, and an ACTA2 mRNA expression level in the cells at the start of differentiation was defined as 0%. The rate of decrease in ACTA2 mRNA expression by the test compound was calculated according to the following expression.

Rate of decrease in ACTA2 mRNA expression(%)=[1−{(ACTA2 mRNA expression level in the case of adding the test compound)−(ACTA2 mRNA expression level in the cells at the start of differentiation)}/{(ACTA2 mRNA expression level in the case of adding DMSO)−(ACTA2 mRNA expression level in the cells at the start of differentiation)}]×100

An $IC_{50}$ value was calculated from the rate of decrease in ACTA2 mRNA expression by the test compound. The results about each test compound in this test are shown in Table 21 below. A: $IC_{50}<10$ nM, B: 10 nM$\leq IC_{50}<50$ nM, C: 50 nM$\leq IC_{50}<100$ nM, or D: $IC_{50}\geq100$ nM.

TABLE 21

| Results of active human hepatic stellate cell dedifferentiation test about compound of Example | |
|---|---|
| Example No. | $IC_{50}$ |
| 1-(b) | A |
| 2-(b) | B |
| 3-(b) | B |
| 4-(b) | B |
| 5-(b) | A |
| 6-(b) | B |
| 7-(b) | A |
| 8-(b) | C |
| 9-(b) | B |
| 10-(b) | D |
| 11-(b) | A |
| 12-(b) | B |
| 13-(b) | B |
| 14-(b) | A |
| 15-(b) | A |
| 16-(b) | A |
| 17-(b) | B |
| 18-(b) | A |
| 19-(b) | A |
| 20-(b) | A |
| 21-(b) | B |
| 24-(b) | A |
| 25-(b) | A |
| 26-(b) | A |
| 28-(b) | B |
| 30-(b) | A |
| 31-(b) | A |
| 32-(b) | B |
| 33-(b) | B |
| 34-(b) | B |
| 35-(b) | A |
| 36-(b) | B |
| 37-(b) | B |
| 38-(b) | A |
| 39-(b) | A |
| 40-(b) | B |
| 41-(b) | B |
| 42-(b) | B |
| 43-(b) | B |
| 48-(b) | A |
| 49-(b) | A |
| 52-(b) | B |
| 53-(b) | B |
| 54-(b) | B |
| 55-(b) | A |
| 56-(b) | A |

(Test Example 5) Hepatic Fibrosis Suppression Test in Hepatic Fibrosis (Non-Alcoholic Steatohepatitis: NASH) Model Test Example 5 was carried out by partially modifying the method of Matsumoto et al. (Int J Exp Pathol., 94 (2), 93-103 (2013)).

C57BL/6J mice (male, Japan SLC, Inc.) were fed with CDAHFD (choline-deficient amino acid-defined high fat diet, supplemented with 0.1% s methionine, 60 kcal % fat, manufactured by Research Diets Inc., A06071302) for 8 weeks to prepare hepatic fibrosis models. The start of feeding with CDAHFD was defined as week 0. A test compound or a vehicle was administered once a day during a period from weeks 0 to 8. The group given the test compound was used as a test compound administration group, and the group given the vehicle was used as a vehicle group.

Mice fed with CE-2 (CLEA Japan, Inc.) instead of CDAHFD were used as a non-fibrotic group. Eight weeks later, each mouse was euthanized by blood letting from the abdomen under inhalation anesthesia with isoflurane, and the liver was harvested.

Hydroxyproline (HYP) was quantified using a portion of the liver, and a hepatic HYP level per unit weight was calculated. The amount of increase in hepatic HYP level per unit weight of the vehicle group based on the hepatic HYP level of the non-fibrotic group was defined as 100%. The rate of suppression of increase in HYP in the test compound administration group was calculated.

As a result of testing compounds of Examples, the compounds of Examples suppressed increase in HYP.

(Test Example 6) Transcellular Transport Test Using Caco2 Cell

Caco2 cells (purchased from ATCC) were cultured in DMEM medium (Thermo Fisher Scientific, Inc., 11965) containing 10% FBS (Thermo Fisher Scientific, Inc., 10082) and 1% penicillin/streptomycin/amphotericin B (Thermo Fisher Scientific, Inc., 15240). A transcellular transport test was carried out in accordance with MultiScreen Caco2 Drug Transport Assembly in a 96-well system (Application Note AN1727EN, MultiScreen Caco-2 Assay System, Merck) by partially modifying it. The Caco2 cells were inoculated at a cell density of $4\times10^4$ cells/well onto a micropore polycarbonate insert of a 96-well plate (Merck, Millcell-96 culture insert plate 0.4 μm pore size, well membrane area=0.11 $cm^2$, PSHT004S5) and cultured for 20 to 22 days, and the resulting monolayer was used in the transcellular transport test. The medium of the inoculated cells was replaced with a fresh one every 3 to 4 days.

Apical-to-basolateral (A-to-B) transport in the Caco2 cell monolayer membrane was performed by using HBSS (Thermo Fisher Scientific, Inc., 14025) medium (pH=7.4) containing 20 mM HEPES (Thermo Fisher Scientific, Inc., 15630), and adding HEPES-containing HBSS medium containing 10 μM compound (a 10 mM solution of the compound in DMSO was added at a 1000-fold dilution; final DMSO concentration: 0.1%) at 75 μL/well to the apical side and HEPES-containing HBSS medium supplemented with no compound at 250 μL/well to the basolateral side, followed by culture at 37 °C for 90 minutes. After culture, a 100 μL aliquot was collected from the basolateral side, and the concentration of a permeated compound was measured by LC-MS/MS under measurement conditions mentioned later. Papp (apparent permeability; cm/sec) was calculated from the determined concentration. Papp was determined according to the expression given below by calculating the slope (dA/dt; nmol/sec) of a straight line drawn between two points 0 minutes and zero amount of the compound in a graph plotted with an assay time (90 min) on the abscissa against the amount of the compound in the solution on the permeated side on the ordinate. As for an assay concentration, the concentration in the compound in the HEPES-containing HBSS medium containing the added compound was measured by UV-HPLC under measurement conditions mentioned later.

$$P\text{app(cm/sec)}=C0\times S\times(\text{dA/dt})$$

C0: assay concentration, S: plate membrane area=0.11 $cm^2$

<Measurement Conditions of LC-MS/MS Analysis>

LC: LC20 or LC30 HPLC system manufactured by Shimadzu Corp.
Column: Phenomenex Kinetex C18 (50 mm×2.1 mm, 2.6 μm)
Column temperature: 40 °C.
Flow rate: 0.3 mL/min
Mobile phase A: 0.1% aqueous formic acid solution
Mobile phase B: 0.1% formic acid, 50% acetonitrile/methanol mixed solution
Gradient: 0-2 min; A/B=90/10 to 10/90, 2-3 min; A/B=10/90, 3-3.01 min; A/B=10/90 to 90/10
MS: Q-Trap3200 manufactured by AB Sciex Pte. Ltd.
Ionization: ESI
Mode: Positive <Measurement Conditions of UV-HPLC Analysis>

LC: LC20 or LC30 HPLC system manufactured by Shimadzu Corp.
Column: Phenomenex Kinetex C18 (100 mm×2.1 mm, 2.6 μm)
Column temperature: 40 °C.
Flow rate: 0.25 mL/min
Mobile phase A: 0.1% aqueous formic acid solution
Mobile phase B: 0.1% formic acid, 50% acetonitrile/methanol mixed solution
Gradient: 0-3 min; A/B=90/10, 3-11 min; A/B=90/10 to 5/95, 11-15 min; A/B=5/95, 15-15.1 min; A/B=5/95 to 90/10
UV detector: photodiode array detector The results about each test compound in this test are shown in Table 22 below. A: Papp>$1\times10^{-6}$ (cm/sec), B: $1\times10^{-6}$ (cm/sec)≥Papp>$5\times10^{-7}$ (cm/sec), C: $5\times10^{-7}$ (cm/sec)≥Papp>$1\times10^{-7}$ (cm/sec), or D: Papp≤$1\times10^{-7}$ (cm/sec).

TABLE 22

Results of transcellular transport test using Caco2 cell about compound of Example

| Example No. | Papp |
|---|---|
| 1-(b) | A |
| 2-(b) | B |
| 3-(b) | A |
| 4-(b) | A |
| 5-(b) | B |
| 6-(b) | A |
| 7-(b) | B |
| 8-(b) | B |
| 9-(b) | A |
| 10-(b) | A |
| 11-(b) | A |
| 12-(b) | A |
| 13-(b) | A |

TABLE 22-continued

Results of transcellular transport test using Caco2 cell about compound of Example

| Example No. | Papp |
|---|---|
| 14-(b) | A |
| 15-(b) | A |
| 16-(b) | A |
| 17-(b) | A |
| 18-(b) | A |
| 19-(b) | A |
| 20-(b) | A |
| 21-(b) | A |
| 22-(b) | A |
| 23-(b) | A |
| 24-(b) | B |
| 25-(b) | A |
| 26-(b) | A |
| 27-(b) | A |
| 28-(b) | A |
| 29-(b) | C |
| 30-(b) | B |
| 31-(b) | A |
| 32-(b) | A |
| 33-(b) | A |
| 34-(b) | A |
| 35-(b) | A |
| 36-(b) | A |
| 37-(b) | A |
| 38-(b) | A |
| 39-(b) | A |
| 40-(b) | A |
| 41-(b) | A |
| 42-(b) | A |
| 43-(b) | A |
| 44-(b) | B |
| 45-(b) | B |
| 46-(b) | A |
| 47-(b) | A |
| 48-(b) | A |
| 49-(b) | B |
| 50-(b) | A |
| 51-(b) | A |
| 52-(b) | C |
| 53-(b) | C |
| 54-(b) | C |
| 55-(b) | C |
| 56-(b) | C |

(Test Example 7) Dansyl Glutathione (dGSH) Trapping Assay

Among metabolites generated from a test compound through metabolism in liver microsomes, a metabolite that reacted with dansyl glutathione (dGSH) was detected and quantified as a method for detecting a reactive metabolite. The concentration of the metabolite-dGSH conjugate was measured using fluorescence detection UPLC system (manufactured by Shimadzu Corp.).

As a result of testing compounds of Examples, the compounds of Examples generated no or few dGSH adducts. This demonstrated the compound represented by the general formula (I) or (II) of the present invention or a pharmaceutically acceptable salt thereof is a compound excellent in safety that generates no or few reactive metabolites.

(Test Example 8) Hepatic Fibrosis Suppression Test in Carbon Tetrachloride-Induced Hepatic Fibrosis Model Carbon tetrachloride diluted 2-fold with olive oil was subcutaneously administered at 2 mL/kg twice a week up to the completion of a test to the back of C57BL/6J mice (female, Charles River Laboratories Japan, Inc.) under inhalation anesthesia with isoflurane to prepare carbon tetrachloride-induced hepatic fibrosis models. A test compound was orally administered once a day for 56 days from the start of model preparation. Then, the liver was collected, and HYP in the left lateral hepatic lobe was quantified.

As a result of testing compounds of Examples, the compounds of Examples suppressed increase in HYP.

(Test Example 9) Pulmonary Fibrosis Suppression Test in Bleomycin-Induced Idiopathic Pulmonary Fibrosis Model Bleomycin (manufactured by Nippon Kayaku Co., Ltd.) diluted with physiological saline was transtracheally administered once at 3.0 mg/kg (50 μL/animal) to C57BL/6J mice (female, Japan SLC, Inc.) under triple anesthesia (medetomidine hydrochloride/midazolam/butorphanol tartrate) using Microsprayer (manufactured by Penn-Century, Inc.) to prepare bleomycin-induced idiopathic pulmonary fibrosis models. A test compound was administered thereto for 14 days from 7 days after bleomycin administration. Then, the lung was collected, and HYP was quantified using the pulmonary left lobe.

As a result of testing compounds of Examples, the compounds of Examples suppressed increase in HYP.

(Test Example 10) Renal Fibrosis Suppression Test in Unilateral Ureteral Obstruction Model with Renal Fibrosis Test Example 10 was performed with reference to the method of Swaney et al. (The Journal of Pharmacology and Experimental Therapeutics 336 (3): 693-700 (2011)). The left ureter of C57BL/6J mice (male, Japan SLC, Inc.) was ligated with a suture thread under inhalation anesthesia with isoflurane to prepare unilateral ureteral obstruction models with renal fibrosis. A test compound was administered thereto for 10 days from model preparation. Then, the left kidney was collected, and HYP was quantified.

As a result of testing compounds of Examples, the compounds of Examples suppressed increase in HYP.

The invention claimed is:

1. A compound represented by the following general formula (I) or (II), or a pharmaceutically acceptable salt of any of the foregoing:

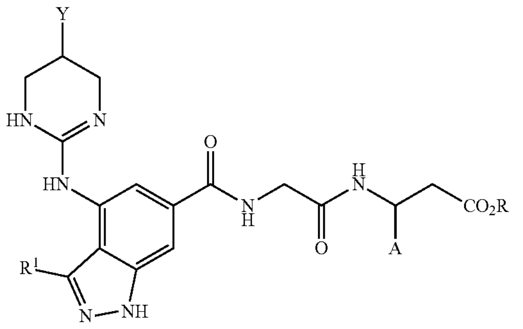

-continued

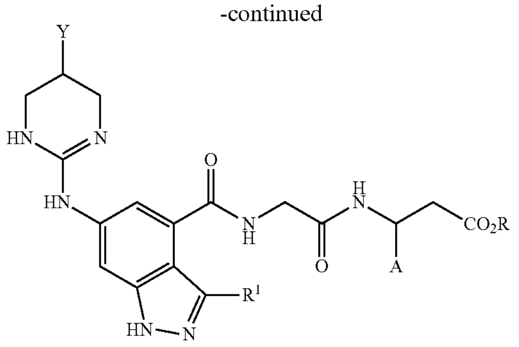

wherein:

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

2. The compound according to claim 1, wherein the compound is represented by the following general formula (I), or a pharmaceutically acceptable salt thereof:

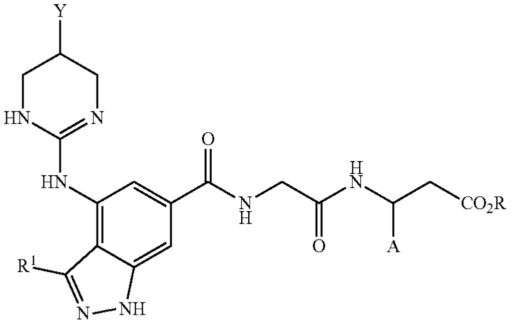

wherein:

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

3. The compound according to claim 1, wherein the compound is represented by the following general formula (II), or a pharmaceutically acceptable salt thereof:

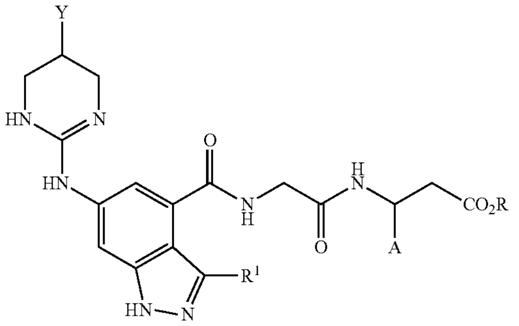

wherein:

A is a $C_6$-$C_{10}$ aryl group or a heteroaryl group, wherein at least one hydrogen atom of the aryl group or the heteroaryl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group, R is a hydrogen atom or a $C_1$-$C_6$ alkyl group, $R^1$ is a hydrogen atom or a halogen atom, and Y is a hydrogen atom, a fluorine atom or a hydroxy group.

4. The compound according to claim 1, or a pharmaceutically acceptable salt thereof, wherein A is a phenyl group, wherein at least one hydrogen atom of the phenyl group is optionally replaced with a substituent selected from the group consisting of a halogen atom, a hydroxy group, a $C_1$-$C_6$ alkyl group, a $C_1$-$C_6$ haloalkyl group, a $C_2$-$C_6$ alkenyl group, a $C_2$-$C_6$ alkynyl group, a $C_1$-$C_6$ alkoxy group, a $C_1$-$C_6$ haloalkoxy group, a $C_3$-$C_6$ cycloalkyl group, a $C_3$-$C_6$ cycloalkenyl group, a $C_3$-$C_6$ cycloalkoxy group, a heterocyclyl group, a heteroaryl group optionally substituted by a $C_1$-$C_6$ alkyl group, a cyano group, a carboxyl group, a carbamoyl group, a $C_1$-$C_6$ alkoxycarbonyl group, a $C_1$-$C_6$ alkylsulfanyl group, and a $C_1$-$C_6$ alkylsulfonyl group.

5. The compound according to claim 1, or a pharmaceutically acceptable salt thereof, wherein A is a phenyl group, wherein at least one hydrogen atom of the phenyl group is optionally replaced with a substituent selected from the group consisting of a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, and a heteroaryl group optionally substituted by a $C_1$-$C_6$ alkyl group.

6. The compound according to claim 1, or a pharmaceutically acceptable salt thereof, wherein Y is a fluorine atom.

7. The compound according to claim 1, or a pharmaceutically acceptable salt thereof, wherein A is a group represented by the following formula (i):

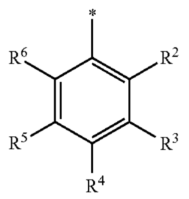

wherein:

$R^2$ is a hydrogen atom or a halogen atom, $R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, a $C_3$-$C_6$ cycloalkyl group, a $C_3$-$C_6$ cycloalkoxy group, a heterocyclyl group, or a heteroaryl group optionally substituted by a $C_1$-$C_6$ alkyl group, $R^4$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group, $R^5$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group, and $R^6$ is a hydrogen atom or a halogen atom.

8. The compound according to claim 7, or a pharmaceutically acceptable salt thereof, wherein:

$R^2$ is a hydrogen atom, $R^3$ is a hydrogen atom, a halogen atom, a $C_1$-$C_6$ alkyl group, a $C_1$-$C_6$ haloalkyl group, a $C_1$-$C_6$ alkoxy group, a $C_1$-$C_6$ haloalkoxy group, or a heteroaryl group optionally substituted by a $C_1$-$C_6$ alkyl group, $R^4$ is a hydrogen atom or a halogen atom, $R^5$ is a hydrogen atom, a halogen atom, a $C_1$-$C_6$ alkyl group, a $C_1$-$C_6$ haloalkyl group, a $C_1$-$C_6$ alkoxy group, or a $C_1$-$C_6$ haloalkoxy group, and $R^6$ is a hydrogen atom or a halogen atom.

9. The compound according to claim 1, or a pharmaceutically acceptable salt thereof, wherein the compound is selected from the group consisting of:

(3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(3-iodo-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-methyl-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-methoxy-5-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-fluoro-5-(trifluoromethyl)phenyl)propanoic acid, (3S)-3-(3,5-bis (trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(1H-pyrazol-1-yl)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-3-(trifluoromethyl)phenyl)propanoic acid, (3S)-3-(2-chloro-3-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethyl)phenyl)propanoic acid, (3S)-3-(2-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(4-methyl-3-(trifluoromethyl)phenyl)propanoic acid, (3S)-3-(3-chloro-4-fluoro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-4-methoxyphenyl)-3-(2-(4-((5-fluoro-1,4,5,6-tetrahydropyrimidin-2-yl)amino)-1H-indazole-6-carboxamido)acetamido)propanoic acid, (3S)-3-(3,5-dichlorophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-chlorophenyl)-3-(2-(4-((5-fluoro-1,4,5,6-tetrahydropyrimidin-2-yl)amino)-1H-indazole-6-carboxamido)acetamido)propanoic acid, (3S)-3-(3,5-dibromophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-iodophenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-iodophenyl)-3-(2-(4-((5-fluoro-1,4,5,6-tetrahydropyrimidin-2-yl)amino)-1H-indazole-6-carboxamido)acetamido)propanoic acid, (3S)-3-(5-chloro-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(5-bromo-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-4-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(5-(difluoromethoxy)-2-fluorophenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethoxy)-5-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(3,5-bis (difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-chloro-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-bromo-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(2-fluoro-5-(trifluoromethoxy)phenyl)propanoic acid, (3S)-3-(2-(4-((5-fluoro-1,4,5,6-tetrahydropyrimidin-2-yl)amino)-1H-indazole-6-carboxamido)acetamido)-3-(4-fluoro-3-(trifluoromethoxy)phenyl)propanoic acid, (3S)-3-(2-(4-((5-fluoro-1,4,5,6-tetrahydropyrimidin-2-yl)amino)-1H-indazole-6-carboxamido)acetamido)-3-(3-(trifluoromethyl)phenyl)propanoic acid, (3S)-3-(2-(4-((5-fluoro-1,4,5,6-tetrahydropyrimidin-2-yl)amino)-1H-indazole-6-carboxamido)acetamido)-3-(3-(trifluoromethoxy)phenyl)propanoic acid, (3S)-3-(3-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(difluoromethyl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-cyclopropylphenyl)-3-(2-(4-((5-fluoro-1,4,5,6-tetrahydropyrimidin-2-yl)amino)-1H-indazole-6-carboxamido)acetamido)propanoic acid, (3S)-3-(3-cyclopropoxyphenyl)-3-(2-(4-((5-fluoro-1,4,5,6-tetrahydropyrimidin-2-yl)amino)-1H-indazole-6-carboxamido)acetamido)propanoic acid, (3S)-3-(3-chlorophenyl)-3-(2-(4-((5-fluoro-1,4,5,6-tetrahydropyrimidin-2-yl)amino)-1H-indazole-6-carboxamido)acetamido)propanoic acid, (3S)-3-(3-bromophenyl)-3-(2-(4-((5-fluoro-1,4,5,6-tetrahydropyrimidin-2-yl)amino)-1H-indazole-6-carboxamido)acetamido)propanoic acid, (3S)-3-(3-(1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(3-(3,5-dimethyl-1H-pyrazol-1-yl)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(3-morpholinophenyl)propanoic acid, (3S)-3-(4-(difluoromethoxy)phenyl)-3-(2-(4-((5-fluoro-1,4,5,6-tetrahydropyrimidin-2-yl)amino)-1H-indazole-6-carboxamido)acetamido)propanoic acid, (3S)-3-(2-(4-((5-fluoro-1,4,5,6-tetrahydropyrimidin-2-yl)amino)-1H-indazole-6-carboxamido)acetamido)-3-(4-(trifluoromethyl)phenyl)propanoic acid, (3S)-3-(3-chloro-5-(trifluoromethyl)phenyl)-3-(2-(3-fluoro-4-((5-fluoro-1,4,5,6-tetrahydropyrimidin-2-yl)amino)-1H-indazole-6-carboxamido)acetamido)propanoic acid, (3S)-3-(2-(3-chloro-4-((5-fluoro-1,4,5,6-tetrahydropyrimidin-2-yl)amino)-1H-indazole-6-carboxamido)acetamido)-3-(3-chloro-5-(trifluoromethyl)phenyl)propanoic acid, (3S)-3-(3-chloro-5-(trifluoromethyl)phenyl)-3-(2-(4-((5-hydroxy-1,4,5,6-tetrahydropyrimidin-2-yl)amino)-1H-indazole-6-carboxamido)acetamido)propanoic acid, (S)-3-(3-chloro-5-(trifluoromethyl)phenyl)-3-(2-(4-((1,4,5,6-tetrahydropyrimidin-2-yl)amino)-1H-indazole-6-carboxamido)acetamido)propanoic acid, (3S)-3-(3-chloro-5-(trifluoromethyl)phenyl)-3-(2-(6-((5-fluoro-1,4,5,6-tetrahydropyrimidin-2-yl)amino)-1H-indazole-4-carboxamido)acetamido)propanoic acid, (3S)-3-(3-bromo-5-(trifluoromethyl)phenyl)-3-(2-(6-((5-fluoro-1,4,5,6-tetrahydropyrimidin-2-yl)amino)-1H-indazole-4-carboxamido)acetamido)propanoic acid, (3S)-3-(2-(6-((5-fluoro-1,4,5,6-tetrahydropyrimidin-2-yl)amino)-1H-indazole-4-carboxamido)acetamido)-3-(3-iodo-5-(trifluoromethyl)phenyl)propanoic acid, (3S)-3-(2-(6-((5-fluoro-1,4,5,6-tetrahydropyrimidin-2-yl)amino)-1H-indazole-4-carboxamido)acetamido)-3-(4-fluoro-3-(trifluoromethyl)phenyl)propanoic acid, and (3S)-3-(2-(6-((5-fluoro-1,4,5,6-tetrahydropyrimidin-2-yl)amino)-1H-indazole-4-carboxamido)acetamido)-3-(3-(trifluoromethyl)phenyl)propanoic acid, or a pharmaceutically acceptable salt of any of the foregoing.

10. The compound according to claim 1, or a pharmaceutically acceptable salt thereof, wherein the compound is (3S)-3-(3-chloro-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid.

11. The compound according to claim 1, or a pharmaceutically acceptable salt thereof, wherein the compound is (3S)-3-(3,5-dichlorophenyl)-3-(2-(4-((5-fluoro-1,4,5,6-tetrahydropyrimidin-2-yl)amino)-1H-indazole-6-carboxamido)acetamido)propanoic acid.

12. The compound according to claim 1, or a pharmaceutically acceptable salt thereof, wherein the compound is (3S)-3-(3,5-dibromophenyl)-3-(2-(4-((5-fluoro-1,4,5,6-tetrahydropyrimidin-2-yl)amino)-1H-indazole-6-carboxamido)acetamido)propanoic acid.

13. The compound according to claim 1, or a pharmaceutically acceptable salt thereof, wherein the compound is (3S)-3-(3-(difluoromethoxy)-5-(trifluoromethyl)phenyl)-3-(2-(4-((5-fluoro-1,4,5,6-tetrahydropyrimidin-2-yl)amino)-1H-indazole-6-carboxamido)acetamido)propanoic acid.

14. The compound according to claim 1, or a pharmaceutically acceptable salt thereof, wherein the compound is (3S)-3-(3-chloro-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid.

15. The compound according to claim 1, or a pharmaceutically acceptable salt thereof, wherein the compound is (3S)-3-(3-bromo-5-(trifluoromethoxy)phenyl)-3-(2-(4-((5-fluoro-1,4,5,6-tetrahydropyrimidin-2-yl)amino)-1H-indazole-6-carboxamido)acetamido)propanoic acid.

16. A pharmaceutical composition comprising a compound according to claim 1, or a pharmaceutically acceptable salt thereof, and a pharmaceutically acceptable carrier.

17. A method for alleviating and/or treating a disease, comprising administering an effective amount of the compound according to claim 1, or a pharmaceutically acceptable salt thereof, to a subject suffering from the disease, wherein the disease is related to integrin av or wherein the disease is improved by inhibiting integrin αv, and wherein the disease is selected from the group consisting of fibrosis, eye disease, osteoporosis, and osteogenesis imperfecta.

18. A method for treating fibrosis, comprising administering an effective amount the compound according to claim 1, or a pharmaceutically acceptable salt thereof, to a subject suffering from fibrosis.

* * * * *